United States Patent
Kruegel et al.

(10) Patent No.: US 11,787,772 B2
(45) Date of Patent: Oct. 17, 2023

(54) CARBOXYLIC DIARYTHIAZEPINEAMINES AS MIXED MU- AND DELTA-OPIOID RECEPTOR AGONISTS

(71) Applicants: Andrew Kruegel, New York, NY (US); Dalibor Sames, New York, NY (US); Jonathan A. Javitch, Dobbs Ferry, NY (US)

(72) Inventors: Andrew Kruegel, New York, NY (US); Dalibor Sames, New York, NY (US); Jonathan A. Javitch, Dobbs Ferry, NY (US)

(73) Assignee: THE TRUSTEES OF COLUMBIA UNIVERSITY IN THE CITY OF NEW YORK, New York, NY (US)

( * ) Notice: Subject to any disclaimer, the term of this patent is extended or adjusted under 35 U.S.C. 154(b) by 867 days.

(21) Appl. No.: 16/493,992

(22) PCT Filed: Mar. 15, 2018

(86) PCT No.: PCT/US2018/022650
§ 371 (c)(1),
(2) Date: Sep. 13, 2019

(87) PCT Pub. No.: WO2018/170275
PCT Pub. Date: Sep. 20, 2018

(65) Prior Publication Data
US 2020/0079745 A1   Mar. 12, 2020

Related U.S. Application Data

(60) Provisional application No. 62/471,745, filed on Mar. 15, 2017.

(51) Int. Cl.
| | | |
|---|---|---|
| *C07D 281/02* | (2006.01) | |
| *A61K 31/485* | (2006.01) | |
| *A61K 31/55* | (2006.01) | |
| *A61K 45/06* | (2006.01) | |

(52) U.S. Cl.
CPC .......... *C07D 281/02* (2013.01); *A61K 31/485* (2013.01); *A61K 31/55* (2013.01); *A61K 45/06* (2013.01)

(58) Field of Classification Search
CPC .................................................. C07D 281/02
See application file for complete search history.

(56) References Cited

U.S. PATENT DOCUMENTS

| | | |
|---|---|---|
| 2001/0037021 A1 | 11/2001 | Blanchard et al. |
| 2009/0209474 A1 | 8/2009 | Roegel et al. |

FOREIGN PATENT DOCUMENTS

| | | |
|---|---|---|
| WO | WO 2015/138791 | 9/2015 |

OTHER PUBLICATIONS

American Chemical Society, Chemical Abstract Service, RN: 118409-30-6. First made available to the public Jan. 13, 1989 (Year: 1989).*
International Search Report dated Jun. 28, 2018 in connection with PCT International Application No. PCT/US2018/022650.
Written Opinion of the International Searching Authority dated Jun. 28, 2018 in connection with PCT International Application No. PCT/US2018/022650.

* cited by examiner

Primary Examiner — John S Kenyon
Assistant Examiner — Gillian A Hutter
(74) Attorney, Agent, or Firm — Gary J. Gershik

(57) ABSTRACT

The present invention provides a compound having the structure:

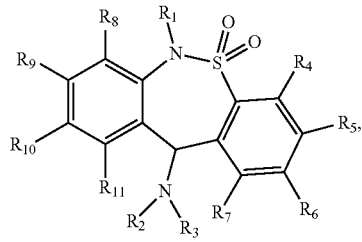

or a pharmaceutically acceptable salt or ester thereof, and a method of treating a subject afflicted with a pain, a depressive disorder, a mood disorder, an anxiety disorder, borderline personality disorder, opioid addiction, or opioid withdrawal symptoms by administering the compound to the subject.

23 Claims, 2 Drawing Sheets

CARBOXYLIC DIARYTHIAZEPINEAMINES AS MIXED MU- AND DELTA-OPIOID RECEPTOR AGONISTS

CROSS-REFERENCE TO RELATED APPLICATIONS

This application is a § 371 national stage of PCT International Application No. PCT/US2018/022650, filed Mar. 15, 2018, and claims the benefit of U.S. Provisional Application No. 62/471,745, filed Mar. 15, 2017, the contents of each of which are hereby incorporated by reference.

Throughout this application, certain publications are referenced in parentheses. Full citations for these publications may be found immediately preceding the claims. The disclosures of these publications in their entireties are hereby incorporated by reference into this application in order to describe more fully the state of the art to which this invention relates.

BACKGROUND OF THE INVENTION

The mu opioid receptor (MOR) has been the major molecular target for treatment of pain for several decades. However, the vast majority of MOR agonists used clinically today are structurally related to or derived from morphine (and other poppy alkaloids). These compounds suffer from many serious problems, including development of tolerance (increased dosing is required to achieve the same analgesic effects), high addiction liability, and other side effects (e.g. respiratory depression, nausea, and constipation) (Williams, J. T. et al. 2013). Therefore, there is a continuing interest in the development of new pain medications, including new MOR agonists with improved therapeutic profile (Corbett, A. D. et al. 2006).

There is also both historical and growing interest in the use of MOR agonists as medicaments for depression. Prior to the adoption of tricyclic antidepressants and electroshock therapy as favored treatments for depression, opioids were among the only options available, with the "opium cure" being an accepted treatment modality in the early 20th century (Berrocoso, E. et al. 2009). More recently, studies in both rodents (Besson, A. et al. 1996) and humans (Bodkin, J. A. et al. 1995) have suggested that MOR activation may lead to antidepressant and/or anxiolytic effects. The antidepressant tianeptine has also been reported to act as a full agonist of the MOR (Gassaway, M. M. et al. 2014). On the molecular level, MORs are extensively expressed in the hippocampus and have been shown to exert a variety of indirect modulatory effects on glutamatergic neurons in this brain region (Xie, C. W. et al. 1997; Svoboda, K. R. et al. 1999). Normalization and modulation of glutamate signaling has been strongly associated with the actions of antidepressants (Paul, I. A. and Skolnick, P. 2003) and indeed, the NMDA receptor antagonist ketamine, shows rapid and efficacious antidepressant activity in human clinical trials (Zarate, C. A. Jr et al. 2006). Further, agonists of the related delta opioid receptor (DOR) have been demonstrated to show robust antidepressant efficacy in animals (Jutkiewicz, E. M. 2006).

Opioid receptor dysfunction may also be associated with borderline personality disorder (BPD). Patients afflicted with BPD exhibit alterations in both basal MOR binding potential and endogenous opioid responses to negative stimuli (Prossin, A. R. et al. 2010). There is also a high prevalence of BPD among patients seeking buprenorphine treatment for opioid addiction (Sansone, R. A. et al. 2008). Accordingly, MOR modulators may be useful medicaments for BPD.

Long-acting prescription opioids may also be used as maintenance (replacement) therapies in the treatment of opioid addiction. In this case, a prescription opioid is provided to the patient chronically and under medical supervision to substitute for the use of illicit opioids (e.g. heroin), thus reducing cravings for, and abuse of, the illicit drug. Opioid maintenance therapy is considered a standard method of care for opioid addiction and is more successful than behavioral or antagonist interventions (Bart, G. 2012).

SUMMARY OF THE INVENTION

The present invention provides a compound having the structure:

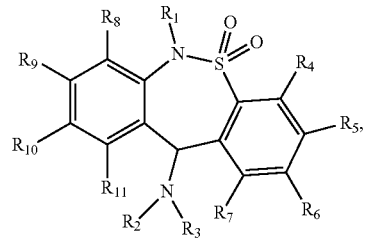

wherein $R_1$ is —H or -(alkyl);

$R_2$ is —($C_3$-$C_{20}$ alkyl)-$CO_2$H or —($C_3$-$C_{20}$ alkyl)-$CO_2$-(alkyl);

$R_3$ is —H or -(alkyl);

$R_4$, $R_5$, $R_6$ and $R_7$ are each independently —H, —Cl, —Br, —F, —I, —CN, —$CF_3$, —$OCF_3$, -(alkyl), -(alkenyl), -(alkynyl), -(aryl), —$NH_2$, —NH-(alkyl), —NH-(alkenyl), —NH-(alkynyl) —NH-(aryl), —NH-(heteroaryl), —OH, —OAc, —O—C(O)(alkyl), —O-(alkyl), —O-(alkylaryl), —O-(alkenyl), —O-(alkynyl), —O-(aryl), —O-(heteroaryl), —S-(alkyl), —S-(alkenyl), —S-(alkynyl), —S-(aryl), —S-(heteroaryl), —S(O)-(alkyl), —S(O)-(aryl), —S(O)-(heteroaryl), —$SO_2$-(alkyl), —$SO_2$-(aryl), or —$SO_2$-(heteroaryl);

$R_8$, $R_9$, $R_{10}$ and $R_{11}$ are each independently —H, —Cl, —Br, —F, —I, —CN, —$CF_3$, —$OCF_3$, -(alkyl), -(aryl), -(heteroaryl) -(alkenyl), -(alkynyl), —$NH_2$, —NH-(alkyl), —NH-(alkenyl), —NH-(alkynyl) —NH-(aryl), —NH-(heteroaryl), —OH, —OAc, —O—C(O)(alkyl), —O-(alkyl), —O-(alkenyl), —O-(alkynyl), —O-(aryl), —O-(heteroaryl), —S-(alkyl), —S-(alkenyl), —S-(alkynyl), —S-(aryl), —S-(heteroaryl), —S(O)-(alkyl), —S(O)-(aryl), —S(O)-(heteroaryl), —$SO_2$-(alkyl), —$SO_2$-(aryl), or —$SO_2$-(heteroaryl);

wherein when $R_2$ is —($C_{3-6}$ alkyl)-$CO_2$H, then one of $R_5$ or $R_6$ is -(alkynyl) or —S-(alkyl), or $R_5$ and $R_6$ are each independently —Cl, —Br, —F, or —I, wherein when $R_2$ is —($C_{3-6}$ alkyl)-$CO_2$-(alkyl), then one of $R_5$ or $R_6$ is -(alkynyl), or $R_5$ and $R_6$ are each independently —Cl, —Br, —F, or —I, wherein when $R_1$ is —$CH_3$, $R_3$, $R_4$, $R_6$, $R_7$, $R_8$, $R_9$, $R_{10}$ and $R_{11}$ are each —H, and $R_5$ is Cl, then $R_2$ is other than —($CH_2$)$_7$$CO_2$H, —($CH_2$)$_{10}$$CO_2$H, —CH($CH_3$)($CH_2$)$_5$$CO_2$H or —($CH_2$)$_2$CH($CH_3$)($CH_2$)$_3$$CO_2$H, and wherein when $R_1$ is —$CH_3$, $R_3$, $R_4$, $R_6$, $R_7$, $R_8$, $R_9$, $R_{10}$ and $R_{11}$ are each —H, and $R_5$ is $SCH_3$, then $R_2$ is other than —$(CH_2)_6CO_2H$, or a pharmaceutically acceptable salt or ester thereof.

DETAILED DESCRIPTION OF THE INVENTION

Figure 1:
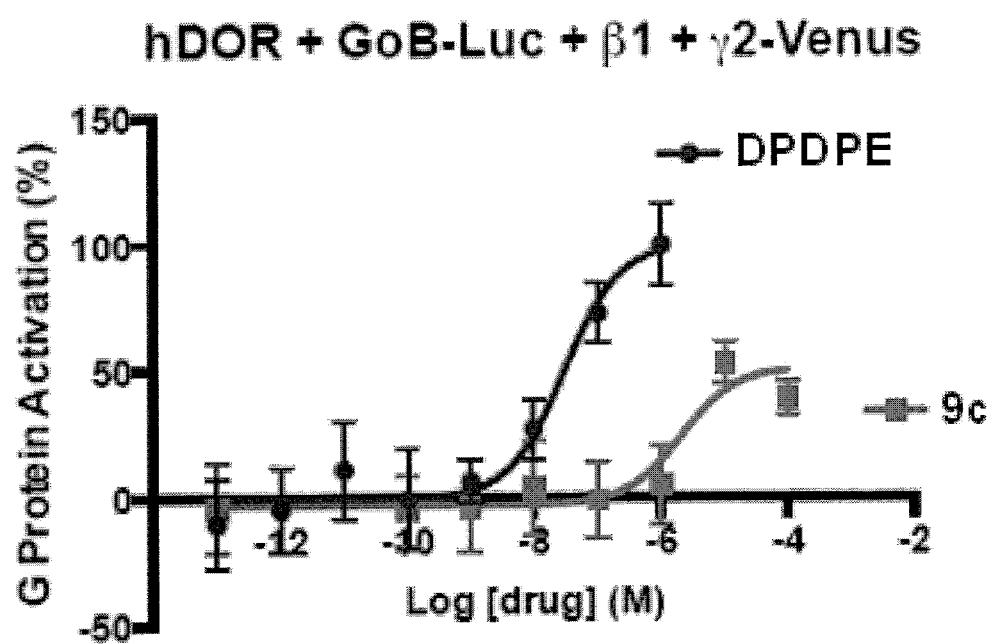
FIG. 1: Compound 9c activates DOR to a lesser $E_{max}$ than the control agonist DPDPE.

The present invention provides a compound having the structure:

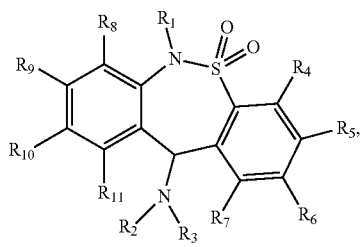

wherein $R_1$ is —H or -(alkyl);
$R_2$ is —$(C_3$-$C_{20}$ alkyl)-$CO_2H$ or —$(C_3$-$C_{20}$ alkyl)-$CO_2$-(alkyl);
$R_3$ is —H or -(alkyl);
$R_4$, $R_5$, $R_6$ and $R_7$ are each independently —H, —Cl, —Br, —F, —I, —CN, —$CF_3$, —$OCF_3$, -(alkyl), -(alkenyl), -(alkynyl), -(aryl), —$NH_2$, —NH-(alkyl), —NH-(alkenyl), —NH-(alkynyl) —NH-(aryl), —NH-(heteroaryl), —OH, —OAc, —O—C(O)(alkyl), —O-(alkyl), —O-(alkylaryl), —O-(alkenyl), —O-(alkynyl), —O-(aryl), —O-(heteroaryl), —S-(alkyl), —S-(alkenyl), —S-(alkynyl), —S-(aryl), —S-(heteroaryl), —S(O)-(alkyl), —S(O)-(aryl), —S(O)-(heteroaryl), —$SO_2$-(alkyl), —$SO_2$-(aryl), or —$SO_2$-(heteroaryl);
$R_8$, $R_9$, $R_{10}$ and $R_{11}$ are each independently —H, —Cl, —Br, —F, —I, —CN, —$CF_3$, —$OCF_3$, -(alkyl), -(aryl), -(heteroaryl) -(alkenyl), -(alkynyl), —$NH_2$, —NH-(alkyl), —NH-(alkenyl), —NH-(alkynyl) —NH-(aryl), —NH-(heteroaryl), —OH, —OAc, —O—C(O)(alkyl), —O-(alkyl), —O-(alkenyl), —O-(alkynyl), —O-(aryl), —O-(heteroaryl), —S-(alkyl), —S-(alkenyl), —S-(alkynyl), —S-(aryl), —S-(heteroaryl), —S(O)-(alkyl), —S(O)-(aryl), —S(O)-(heteroaryl), —$SO_2$-(alkyl), —$SO_2$-(aryl), or —$SO_2$-(heteroaryl);
wherein when $R_2$ is —$(C_{3-6}$ alkyl)-$CO_2H$, then one of $R_5$ or $R_6$ is -(alkynyl) or —S-(alkyl), or $R_5$ and $R_6$ are each independently —Cl, —Br, —F, or —I,
wherein when $R_2$ is —$(C_{3-6}$ alkyl)-$CO_2$-(alkyl), then one of $R_5$ or $R_6$ is -(alkynyl), or $R_5$ and $R_6$ are each independently —Cl, —Br, —F, or —I, and
wherein when $R_1$ is —$CH_3$, $R_3$, $R_4$, $R_6$, $R_7$, $R_8$, $R_9$, $R_{10}$ and $R_{11}$ are each —H, and $R_5$ is Cl, then $R_2$ is other than —$(CH_2)_7CO_2H$, —$(CH_2)_{10}CO_2H$, —$CH(CH_3)(CH_2)_5CO_2H$ or —$(CH_2)_2CH(CH_3)(CH_2)_3CO_2H$, and wherein when $R_1$ is —$CH_3$, $R_3$, $R_4$, $R_6$, $R_7$, $R_8$, $R_9$, $R_{10}$ and $R_{11}$ are each —H, and $R_5$ is $SCH_3$, then $R_2$ is other than —$(CH_2)_6CO_2H$, or a pharmaceutically acceptable salt or ester thereof.

In some embodiments, a compound having the structure:

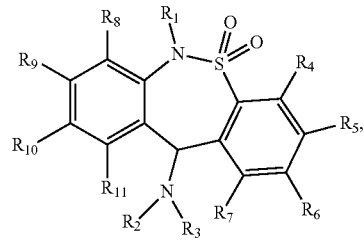

wherein $R_1$ is —H or -(alkyl);
$R_2$ is —$(C_6$-$C_{20}$ alkyl)-$CO_2H$ or —$(C_6$-$C_{20}$ alkyl)-$CO_2$-(alkyl);
$R_3$ is —H or -(alkyl);
$R_4$, $R_5$, $R_6$ and $R_7$ are each independently —H, —Cl, —Br, —F, —I, —CN, —$CF_3$, —$OCF_3$, -(alkyl), -(alkenyl), -(alkynyl), -(aryl), —$NH_2$, —NH-(alkyl), —NH-(alkenyl), —NH-(alkynyl) —NH-(aryl), —NH-(heteroaryl), —OH, —OAc, —O—C(O)(alkyl), —O-(alkyl), —O-(alkylaryl), —O-(alkenyl), —O-(alkynyl), —O-(aryl), —O-(heteroaryl), —S-(alkyl), —S-(alkenyl), —S-(alkynyl), —S-(aryl), —S-(heteroaryl), —S(O)-(alkyl), —S(O)-(aryl), —S(O)-(heteroaryl), —$SO_2$-(alkyl), —$SO_2$-(aryl), or —$SO_2$-(heteroaryl);
$R_8$, $R_9$, $R_{10}$ and $R_{11}$ are each independently —H, —Cl, —Br, —F, —I, —CN, —$CF_3$, —$OCF_3$, -(alkyl), -(aryl), -(heteroaryl) -(alkenyl), -(alkynyl), —$NH_2$, —NH-(alkyl), —NH-(alkenyl), —NH-(alkynyl) —NH-(aryl), —NH-(heteroaryl), —OH, —OAc, —O—C(O)(alkyl), —O-(alkyl), —O-(alkenyl), —O-(alkynyl), —O-(aryl), —O-(heteroaryl), —S-(alkyl), —S-(alkenyl), —S-(alkynyl), —S-(aryl), —S-(heteroaryl), —S(O)-(alkyl), —S(O)-(aryl), —S(O)-(heteroaryl), —$SO_2$-(alkyl), —$SO_2$-(aryl), or —$SO_2$-(heteroaryl);
wherein when $R_2$ is —$(C_6$ alkyl)-$CO_2H$, then one of $R_5$ or $R_6$ is -(alkynyl) or —S-(alkyl), or $R_5$ and $R_6$ are each independently —Cl, —Br, —F, or —I,
wherein when $R_1$ is —$CH_3$, $R_3$, $R_4$, $R_6$, $R_7$, $R_8$, $R_9$, $R_{10}$ and $R_{11}$ are each —H, and $R_5$ is Cl, then $R_2$ is other than —$(CH_2)_7CO_2H$, —$(CH_2)_{10}CO_2H$, —$CH(CH_3)(CH_2)_5CO_2H$ or —$(CH_2)_2CH(CH_3)(CH_2)_3CO_2H$, and
wherein when $R_1$ is —$CH_3$, $R_3$, $R_4$, $R_6$, $R_7$, $R_8$, $R_9$, $R_{10}$ and $R_{11}$ are each —H, and $R_5$ is $SCH_3$, then $R_2$ is other than —$(CH_2)_6CO_2H$, or a pharmaceutically acceptable salt or ester thereof.

In some embodiments, a compound having the structure:

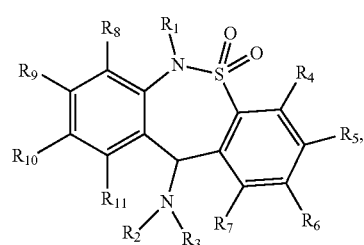

wherein

R$_1$ is —H or -(alkyl);

R$_2$ is —(C$_6$-C$_{20}$ alkyl)-CO$_2$H or —(C$_6$-C$_{20}$ alkyl)-CO$_2$-(alkyl);

R$_3$ is —H or -(alkyl);

R$_4$, R$_5$, R$_6$ and R$_7$ are each independently —H, —Cl, —Br, —F, —I, —CN, —CF$_3$, —OCF$_3$, -(alkyl), -(alkenyl), -(alkynyl), -(aryl), —NH$_2$, —NH-(alkyl), —NH-(alkenyl), —NH-(alkynyl) —NH-(aryl), —NH-(heteroaryl), —OH, —OAc, —O—C(O)(alkyl), —O-(alkyl), —O-(alkylaryl), —O-(alkenyl), —O-(alkynyl), —O-(aryl), —O-(heteroaryl), —S-(alkyl), —S-(alkenyl), —S-(alkynyl), —S-(aryl), —S-(heteroaryl), —S(O)-(alkyl), —S(O)-(aryl), —S(O)-(heteroaryl), —SO$_2$-(alkyl), —SO$_2$-(aryl), or —SO$_2$-(heteroaryl);

R$_8$, R$_9$, R$_{10}$ and R$_{11}$ are each independently —H, —Cl, —Br, —F, —I, —CN, —CF$_3$, —OCF$_3$, -(alkyl), -(aryl), -(heteroaryl) -(alkenyl), -(alkynyl), —NH$_2$, —NH-(alkyl), —NH-(alkenyl), —NH-(alkynyl) —NH-(aryl), —NH-(heteroaryl), —OH, —OAc, —O—C(O)(alkyl), —O-(alkyl), —O-(alkenyl), —O-(alkynyl), —O-(aryl), —O-(heteroaryl), —S-(alkyl), —S-(alkenyl), —S-(alkynyl), —S-(aryl), —S-(heteroaryl), —S(O)-(alkyl), —S(O)-(aryl), —S(O)-(heteroaryl), —SO$_2$-(alkyl), —SO$_2$-(aryl), or —SO$_2$-(heteroaryl);

wherein when R$_2$ is —(C$_6$ alkyl)-CO$_2$H, then one of R$_5$ or R$_6$ is -(alkynyl) or —S-(alkyl), or R$_5$ and R$_6$ are each independently —Cl, —Br, —F, or —I, wherein when R$_2$ is —(C$_6$ alkyl)-CO$_2$-(alkyl), then one of R$_5$ or R$_6$ is -(alkynyl), or R$_5$ and R$_6$ are each independently —Cl, —Br, —F, or —I, and wherein when R$_1$ is —CH$_3$, R$_3$, R$_4$, R$_6$, R$_7$, R$_8$, R$_9$, R$_{10}$ and R$_{11}$ are each —H, and R$_5$ is Cl, then R$_2$ is other than —(CH$_2$)$_7$CO$_2$H or —(CH$_2$)$_{10}$CO$_2$H, or a pharmaceutically acceptable salt or ester thereof.

In some embodiments, the compound wherein

R$_2$ is —(C$_6$ alkyl)-CO$_2$H); and one of R$_5$ or R$_6$ is -(alkynyl) or —S-(alkyl) and the other is —H, or R$_5$ and R$_6$ are each independently —Cl, —Br, —F, or —I.

In some embodiments, the compound wherein

R$_2$ is —(C$_6$ alkyl)-CO$_2$-(alkyl); and one of R$_5$ or R$_6$ is -(alkynyl) and the other is —H, or R$_5$ and R$_6$ are each independently —Cl, —Br, —F, or —I.

In some embodiments, the compound having the structure:

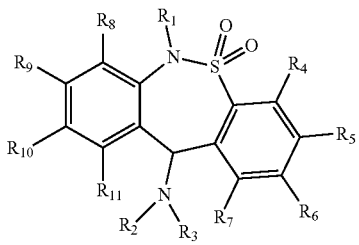

wherein

R$_1$ is —H or -(alkyl);

R$_2$ is —(C$_7$-C$_{20}$ alkyl)-CO$_2$H or —(C$_7$-C$_{20}$ alkyl)-CO$_2$-(alkyl);

R$_3$ is —H or -(alkyl);

R$_4$, R$_5$, R$_6$ and R$_7$ are each independently —H, —Cl, —Br, —F, —I, —CN, —CF$_3$, —OCF$_3$, -(alkyl), -(alkenyl), -(alkynyl), -(aryl), —NH$_2$, —NH-(alkyl), —NH-(alkenyl), —NH-(alkynyl) —NH-(aryl), —NH-(heteroaryl), —OH, —OAc, —O—C(O)(alkyl), —O-(alkyl), —O-(alkylaryl), —O-(alkenyl), —O-(alkynyl), —O-(aryl), —O-(heteroaryl), —S-(alkyl), —S-(alkenyl), —S-(alkynyl), —S-(aryl), —S-(heteroaryl), —S(O)-(alkyl), —S(O)-(aryl), —S(O)-(heteroaryl), —SO$_2$-(alkyl), —SO$_2$-(aryl), or —SO$_2$-(heteroaryl);

R$_8$, R$_9$, R$_{10}$ and R$_{11}$ are each independently —H, —Cl, —Br, —F, —I, —CN, —CF$_3$, —OCF$_3$, -(alkyl), -(aryl), -(heteroaryl) -(alkenyl), -(alkynyl), —NH$_2$, —NH-(alkyl), —NH-(alkenyl), —NH-(alkynyl) —NH-(aryl), —NH-(heteroaryl), —OH, —OAc, —O—C(O)(alkyl), —O-(alkyl), —O-(alkenyl), —O-(alkynyl), —O-(aryl), —O-(heteroaryl), —S-(alkyl), —S-(alkenyl), —S-(alkynyl), —S-(aryl), —S-(heteroaryl), —S(O)-(alkyl), —S(O)-(aryl), —S(O)-(heteroaryl), —SO$_2$-(alkyl), —SO$_2$-(aryl), or —SO$_2$-(heteroaryl);

wherein when R$_1$ is —CH$_3$, R$_3$, R$_4$, R$_6$, R$_7$, R$_8$, R$_9$, R$_{10}$ and R$_{11}$ are each —H, and R$_5$ is Cl, then R$_2$ is other than —(CH$_2$)$_7$CO$_2$H, —(CH$_2$)$_{10}$CO$_2$H, —CH(CH$_3$)(CH$_2$)CO$_2$H or —(CH$_2$)$_2$CH(CH$_3$)(CH$_2$)$_3$CO$_2$H, and or a pharmaceutically acceptable salt or ester thereof.

In some embodiments, the compound wherein

R$_2$ is —(C$_8$-C$_{20}$ alkyl)-CO$_2$H or —(C$_8$-C$_{20}$ alkyl)-CO$_2$-(alkyl).

In some embodiments, the compound wherein

R$_2$ is —(C$_9$-C$_{20}$ alkyl)-CO$_2$H or —(C$_9$-C$_{20}$ alkyl)-CO$_2$-(alkyl).

In some embodiments, the compound wherein

R$_2$ is —(C$_8$-C$_{20}$ alkyl)-CO$_2$H or —(C$_8$-C$_{20}$ alkyl)-CO$_2$CH$_3$.

In some embodiments, the compound wherein

R$_2$ is —(C$_9$-C$_{30}$ alkyl)-CO$_2$H or —(C$_9$-C$_{20}$ alkyl)-CO$_2$CH$_2$CH$_3$.

In some embodiments, the compound wherein

R$_5$ is —Br, —F, —I, —CN, —CF$_3$, —OCF$_3$, -(alkyl), -(alkenyl), -(alkynyl), -(aryl), —NH$_2$, —NH-(alkyl), —NH-(alkenyl), —NH-(alkynyl) —NH-(aryl), —NH-(heteroaryl), —OH, —OAc, —O—C(O)(alkyl), —O-(alkyl), —O-(alkylaryl), —O-(alkenyl), —O-(alkynyl), —O-(aryl), —O-(heteroaryl), —S-(alkyl), —S-(alkenyl), —S-(alkynyl), —S-(aryl), —S-(heteroaryl), —S(O)-(alkyl), —S(O)-(aryl), —S(O)-(heteroaryl), —SO$_2$-(alkyl), —SO$_2$-(aryl), or —SO$_2$-(heteroaryl).

In some embodiments, the compound wherein

R$_5$ is —Br, —I, -(alkenyl), -(alkynyl) or —S-(alkyl).

In some embodiments, the compound wherein

R$_5$ is —Br, —I, —(C$_2$ alkenyl), —(C$_2$ alkynyl) or —S—CH$_3$.

In some embodiments, the compound wherein one of R$_5$ or R$_6$ is -(alkynyl).

In some embodiments, the compound wherein one of R$_5$ or R$_6$ is —S-(alkyl).

In some embodiments, the compound wherein

R$_5$ and R$_6$ are each independently —Cl, —Br, —F, or —I.

In some embodiments, the compound wherein

R$_5$ and R$_6$ are each independently —Br, —F, or —I.

In some embodiments, the compound wherein

R$_5$ and R$_6$ are each independently —Br, —Cl, or —I.

In some embodiments, the compound wherein

R$_5$ and R$_6$ are each independently —Br or —I.

In some embodiments, the compound having the structure

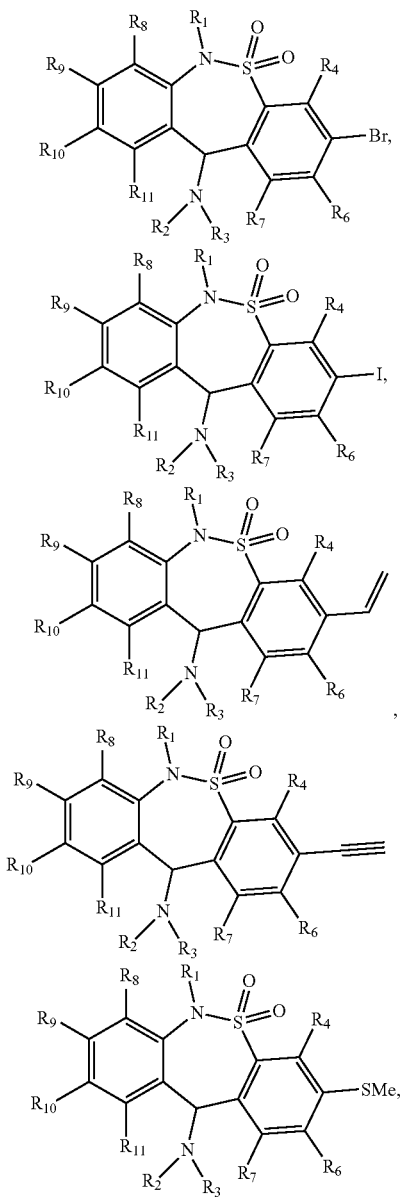

wherein
R₁ is —H or -(alkyl);
R₂ is —(C₇-C₂₀ alkyl)-CO₂H or —(C₇-C₂₀ alkyl)-CO₂-(alkyl);
R₃ is —H or -(alkyl);
R₄, R₆ and R₇ are each independently —H, —Cl, —Br, —F, —I, —CN, —CF₃, —OCF₃, -(alkyl), -(alkenyl), -(alkynyl), -(aryl), —NH₂, —NH-(alkyl), —NH-(alkenyl), —NH-(alkynyl) —NH-(aryl), —NH-(heteroaryl), —OH, —OAc, —O—C(O)(alkyl), —O-(alkyl), —O-(alkylaryl), —O-(alkenyl), —O-(alkynyl), —O-(aryl), —O-(heteroaryl), —S-(alkyl), —S-(alkenyl), —S-(alkynyl), —S-(aryl), —S-(heteroaryl), —S(O)-(alkyl), —S(O)-(aryl), —S(O)-(heteroaryl), —SO₂-(alkyl), —SO₂-(aryl), or —SO₂-(heteroaryl);
R₈, R₉, R₁₀ and R₁₁ are each independently —H, —Cl, —Br, —F, —I, —CN, —CF₃, —OCF₃, -(alkyl), -(aryl), -(heteroaryl) -(alkenyl), -(alkynyl), —NH₂, —NH-(alkyl), —NH-(alkenyl), —NH-(alkynyl) —NH-(aryl), —NH-(heteroaryl), —OH, —OAc, —O—C(O)(alkyl), —O-(alkyl), —O-(alkenyl), —O-(alkynyl), —O-(aryl), —O-(heteroaryl), —S-(alkyl), —S-(alkenyl), —S-(alkynyl), —S-(aryl), —S-(heteroaryl), —S(O)-(alkyl), —S(O)-(aryl), —S(O)-(heteroaryl), —SO₂-(alkyl), —SO₂-(aryl), or —SO₂-(heteroaryl).

In some embodiments, the compound having the structure

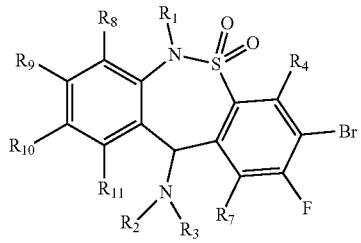

wherein
R₁ is —H or -(alkyl);
R₂ is —(C₇-C₂₀ alkyl)-CO₂H or —(C₇-C₂₀ alkyl)-CO₂-(alkyl);
R₃ is —H or -(alkyl);
R₄ and R₇ are each independently —H, —Cl, —Br, —F, —I, —CN, —CF₃, —OCF₃, -(alkyl), -(alkenyl), -(alkynyl), -(aryl), —NH₂, —NH-(alkyl), —NH-(alkenyl), —NH-(alkynyl) —NH-(aryl), —NH-(heteroaryl), —OH, —OAc, —O—C(O)(alkyl), —O-(alkyl), —O-(alkylaryl), —O-(alkenyl), —O-(alkynyl), —O-(aryl), —O-(heteroaryl), —S-(alkyl), —S-(alkenyl), —S-(alkynyl), —S-(aryl), —S-(heteroaryl), —S(O)-(alkyl), —S(O)-(aryl), —S(O)-(heteroaryl), —SO₂-(alkyl), —SO₂-(aryl), or —SO₂-(heteroaryl);
R₈, R₉, R₁₀ and R₁₁ are each independently —H, —Cl, —Br, —F, —I, —CN, —CF₃, —OCF₃, -(alkyl), -(aryl), -(heteroaryl) -(alkenyl), -(alkynyl), —NH₂, —NH-(alkyl), —NH-(alkenyl), —NH-(alkynyl) —NH-(aryl), —NH-(heteroaryl), —OH, —OAc, —O—C(O)(alkyl), —O-(alkyl), —O-(alkenyl), —O-(alkynyl), —O-(aryl), —O-(heteroaryl), —S-(alkyl), —S-(alkenyl), —S-(alkynyl), —S-(aryl), —S-(heteroaryl), —S(O)-(alkyl), —S(O)-(aryl), —S(O)-(heteroaryl), —SO₂-(alkyl), —SO₂-(aryl), or —SO₂-(heteroaryl).

In some embodiments, the compound having the structure

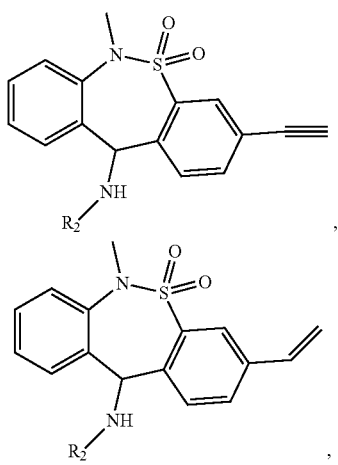

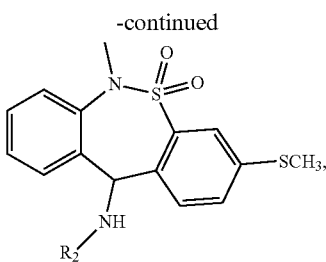
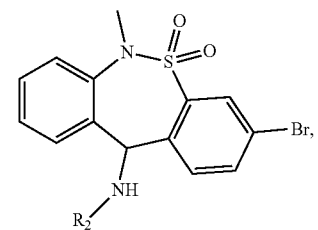
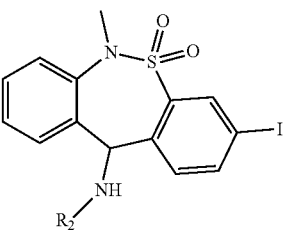
or
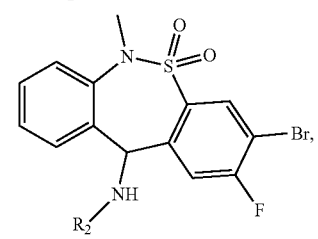
wherein
R$_2$ is —(C$_7$-C$_{20}$ alkyl)-CO$_2$H or —(C$_7$-C$_{20}$ alkyl)-CO$_2$-(alkyl),
or a pharmaceutically acceptable salt or ester thereof.
In some embodiments, the compound having the structure
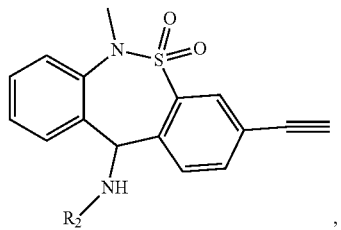
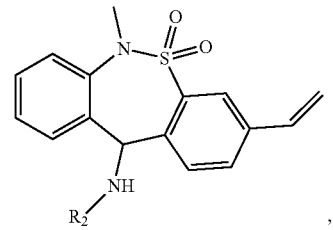
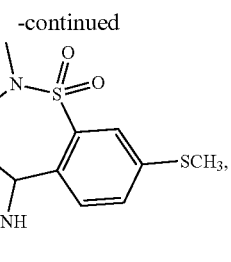
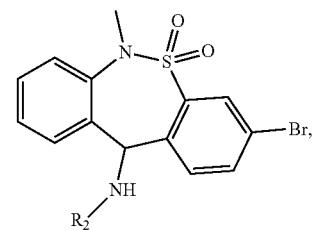
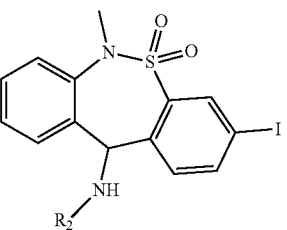
or
wherein
R$_2$ is —(C$_8$-C$_{20}$ alkyl)-CO$_2$H or —(C$_8$-C$_{20}$ alkyl)-CO$_2$-(alkyl),
or a pharmaceutically acceptable salt or ester thereof.
In some embodiments, the compound having the structure
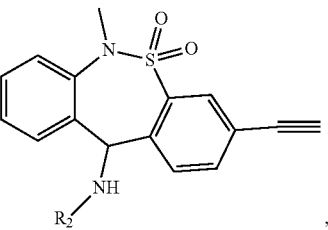
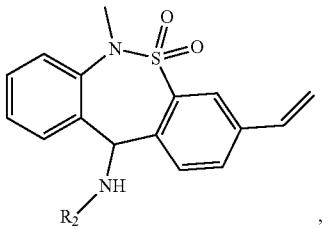

-continued

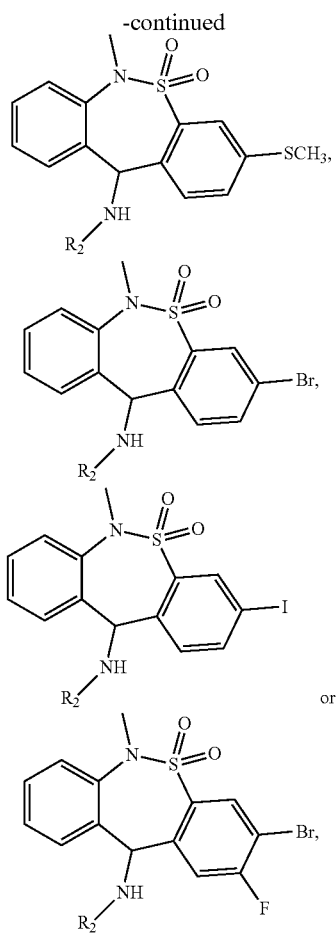

wherein
R₂ is —(C₉-C₂₀ alkyl)-CO₂H or —(C₉-C₂₀ alkyl)-CO₂-(alkyl),
or a pharmaceutically acceptable salt or ester thereof.

In some embodiments, the compound having the structure

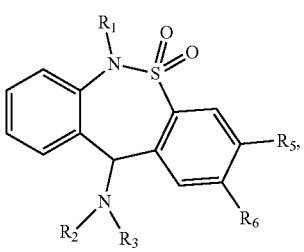

wherein
R₁ is —H or -(alkyl);
R₂ is —(C₇-C₂₀ alkyl)-CO₂H or —(C₇-C₂₀ alkyl)-CO₂-(alkyl);
R₃ is —H or -(alkyl);
R₅ is —Br, —I, -(alkenyl)-(alkynyl) or —S-(alkyl), and
R₆ is —H,
or R₅ and R₆ are each independently —Cl, —Br, —F, or —I;
or a pharmaceutically acceptable salt or ester thereof.

In some embodiments, the compound having the structure

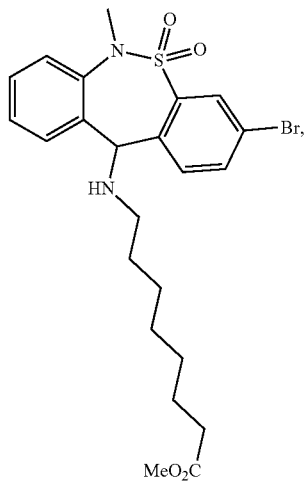

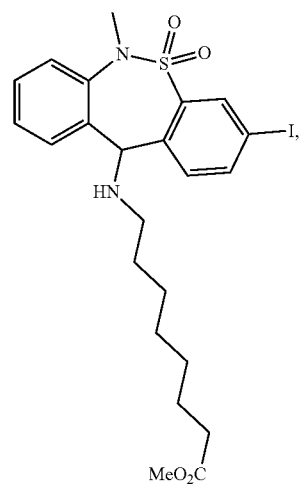

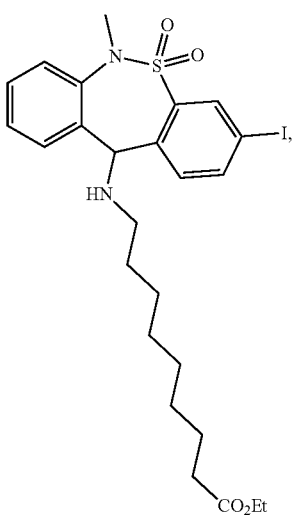

13
-continued
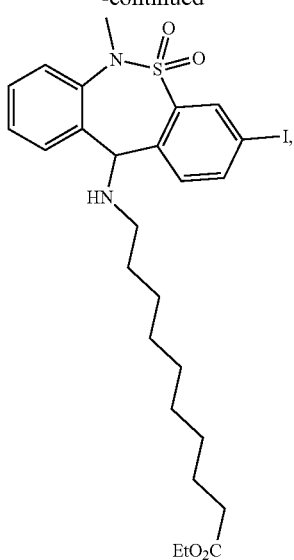
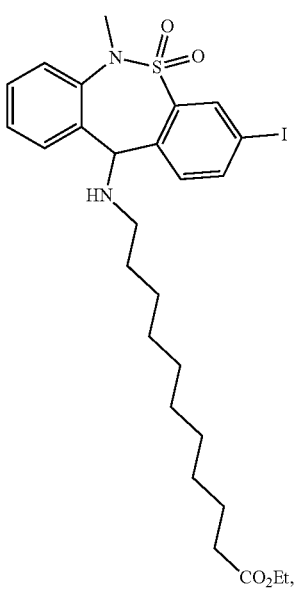
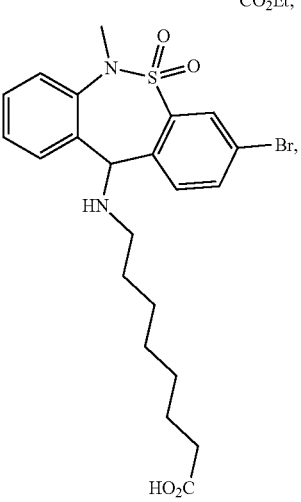
14
-continued
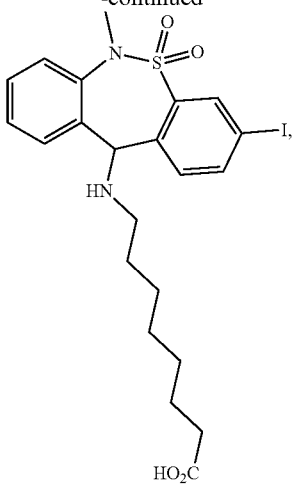
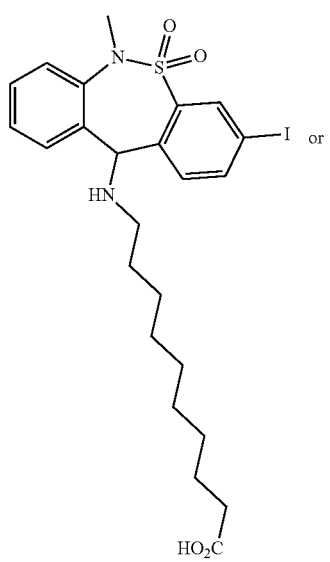

-continued
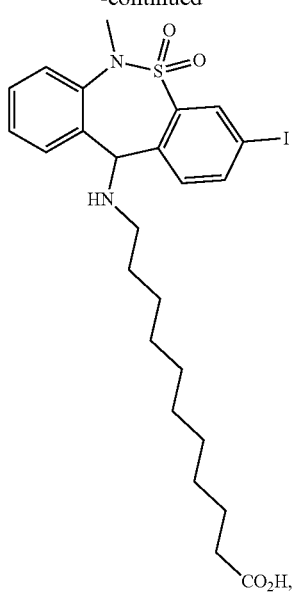
or a pharmaceutically acceptable salt or ester thereof.
In some embodiments, the compound having the structure
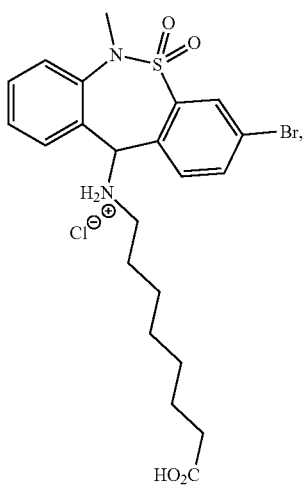
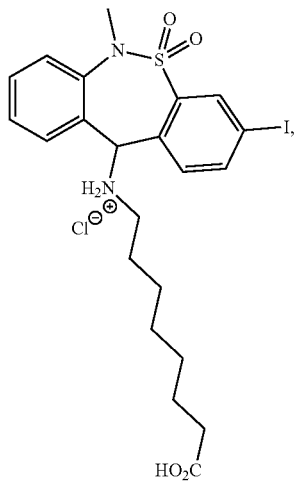
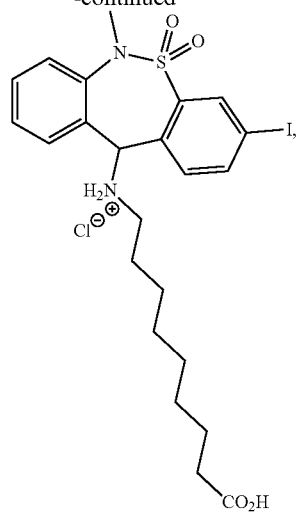
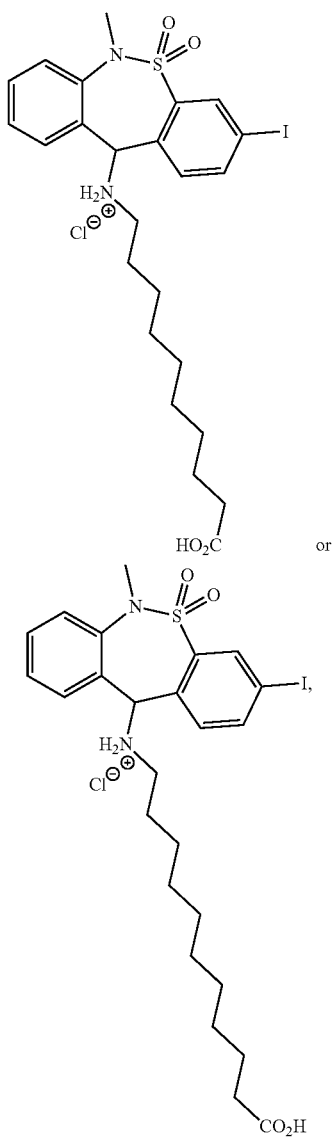
or an ester thereof.

In some embodiments, the compound having the structure:

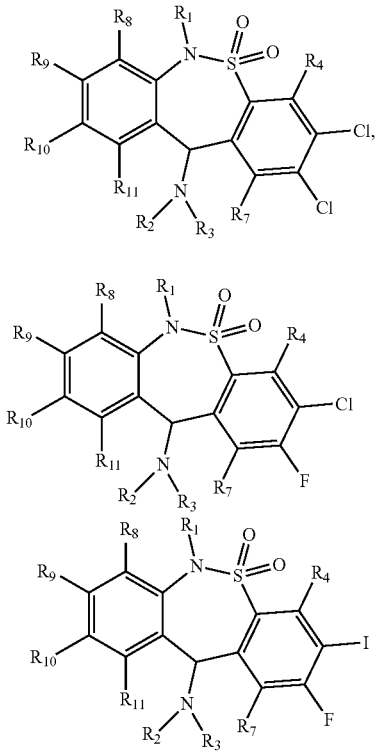

wherein

R₁ is —H or -(alkyl);

R₂ is —(C₇-C₂ alkyl)-CO₂H or —(C₇-C₂₀ alkyl)-CO₂-(alkyl);

R₃ is —H or -(alkyl);

R₄ and R₇ are each independently —H, —Cl, —Br, —F, —I, —CN, —CF₃, —OCF₃, -(alkyl), -(alkenyl), -(alkynyl), -(aryl), —NH₂, —NH-(alkyl), —NH-(alkenyl), —NH-(alkynyl) —NH-(aryl), —NH-(heteroaryl), —OH, —OAc, —O—C(O)(alkyl), —O-(alkyl), —O-(alkylaryl), —O-(alkenyl), —O-(alkynyl), —O-(aryl), —O-(heteroaryl), —S-(alkyl), —S-(alkenyl), —S-(alkynyl), —S-(aryl), —S-(heteroaryl), —S(O)-(alkyl), —S(O)-(aryl), —S(O)-(heteroaryl), —SO₂-(alkyl), —SO₂-(aryl), or —SO₂-(heteroaryl);

R₈, R₉, R₁₀ and R₁₁ are each independently —H, —Cl, —Br, —F, —I, —CN, —CF₃, —OCF₃, -(alkyl), -(aryl), -(heteroaryl) -(alkenyl), -(alkynyl), —NH₂, —NH-(alkyl), —NH-(alkenyl), —NH-(alkynyl) —NH-(aryl), —NH-(heteroaryl), —OH, —OAc, —O—C(O)(alkyl), —O-(alkenyl), —O-(alkynyl), —O-(aryl), —O-(heteroaryl), —S-(alkyl), —S-(alkenyl), —S-(alkynyl), —S-(aryl), —S-(heteroaryl), —S(O)-(alkyl), —S(O)-(aryl), —S(O)-(heteroaryl), —SO₂-(alkyl), —SO₂-(aryl), or —SO₂-(heteroaryl).

In some embodiments, the compound having the structure:

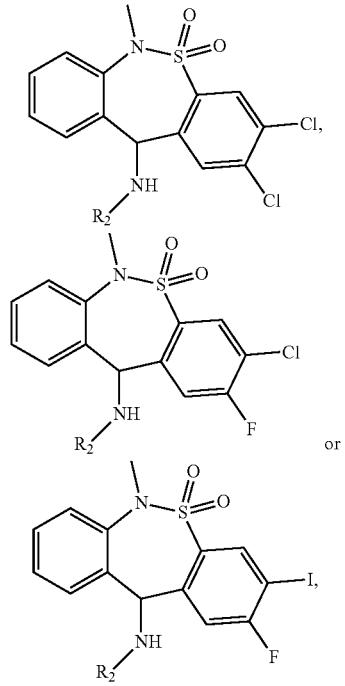

wherein

R₂ is —(C₇-C₂₀ alkyl)-CO₂H or —(C₇₋₂₀ alkyl)-CO₂-(alkyl), or a pharmaceutically acceptable salt or ester thereof.

In some embodiments, wherein R₂ is —(C₈-C₂₀ alkyl)-CO₂H or —(C₈-C₂₀ alkyl)-CO₂-(alkyl), or a pharmaceutically acceptable salt or ester thereof.

In some embodiments, wherein R₂ is —(C₉-C₂₀ alkyl)-CO₂H or —(C₉-C₂₀ alkyl)-CO₂-(alkyl), or a pharmaceutically acceptable salt or ester thereof.

In some embodiments, the compound having the structure:

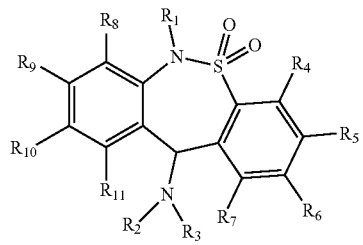

wherein

R₁ is —H or -(alkyl);

R₂ is —(C₆ alkyl)-CO₂H;

R₃ is —H or -(alkyl);

R₄, R₅, R₆ and R₇ are each independently —H, —Cl, —Br, —F, —I, —CN, —CF₃, —OCF₃, -(alkyl), -(alkenyl), -(alkynyl), -(aryl), —NH₂, —NH-(alkyl), —NH-(alkenyl), —NH-(alkynyl) —NH-(aryl), —NH-(heteroaryl), —OH, —OAc, —O—C(O)(alkyl), —O-(alkyl), —O-(alkylaryl), —O-(alkenyl), —O-(alkynyl), —O-(aryl), —O-(heteroaryl), —S-(alkyl), —S-(alkenyl), —S-(alkynyl), —S-(aryl), —S-(heteroaryl), —S(O)-(alkyl), —S(O)-(aryl), —S(O)-(heteroaryl), —SO₂-(alkyl), —SO₂-(aryl), or —SO₂-(heteroaryl);

$R_8$, $R_9$, $R_{10}$ and $R_{11}$ are each independently —H, —Cl, —Br, —F, —I, —CN, —CF₃, —OCF₃, -(alkyl), -(aryl), -(heteroaryl) -(alkenyl), -(alkynyl), —NH₂, —NH-(alkyl), —NH-(alkenyl), —NH-(alkynyl) —NH-(aryl), —NH-(heteroaryl), —OH, —OAc, —O—C(O)(alkyl), —O-(alkyl), —O-(alkenyl), —O-(alkynyl), —O-(aryl), —O-(heteroaryl), —S-(alkyl), —S-(alkenyl), —S-(alkynyl), —S-(aryl), —S-(heteroaryl), —S(O)-(alkyl), —S(O)-(aryl), —S(O)-(heteroaryl), —SO₂-(alkyl), —SO₂-(aryl), or —SO₂-(heteroaryl);

wherein one of $R_5$ or $R_6$ is -(alkynyl) or —S-(alkyl), or $R_5$ and $R_6$ are each independently —Cl, —Br, —F, or —I, wherein when $R_1$ is —CH₃, $R_3$, $R_4$, $R_6$, $R_7$, $R_8$, $R_9$, $R_{10}$ and $R_{11}$ are each —H, and $R_5$ is SCH₃, then $R_2$ is other than —(CH₂)₆CO₂H, or a pharmaceutically acceptable salt or ester thereof.

In some embodiments, the compound having the structure:

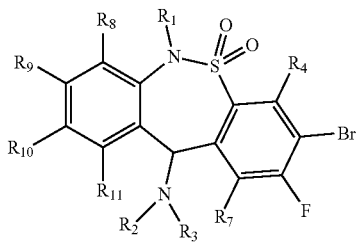

wherein
$R_1$ is —H or -(alkyl);
$R_2$ is —(C₆ alkyl)-CO₂H;
$R_3$ is —H or -(alkyl);
$R_4$ and $R_7$ are each independently —H, —Cl, —Br, —F, —I, —CN, —CF₃, —OCF₃, -(alkyl), -(alkenyl), -(alkynyl), -(aryl), —NH₂, —NH-(alkyl), —NH-(alkenyl), —NH-(alkynyl) —NH-(aryl), —NH-(heteroaryl), —OH, —OAc, —O—C(O)(alkyl), —O-(alkyl), —O-(alkylaryl), —O-(alkenyl), —O-(alkynyl), —O-(aryl), —O-(heteroaryl), —S-(alkyl), —S-(alkenyl), —S-(alkynyl), —S-(aryl), —S-(heteroaryl), —S(O)-(alkyl), —S(O)-(aryl), —S(O)-(heteroaryl), —SO₂-(alkyl), —SO₂-(aryl), or —SO₂-(heteroaryl);

$R_8$, $R_9$, $R_{10}$ and $R_{11}$ are each independently —H, —Cl, —Br, —F, —I, —CN, —CF₃, —OCF₃, -(alkyl), -(aryl), -(heteroaryl) -(alkenyl), -(alkynyl), —NH₂, —NH-(alkyl), —NH-(alkenyl), —NH-(alkynyl) —NH-(aryl), —NH-(heteroaryl), —OH, —OAc, —O—C(O)(alkyl), —O-(alkyl), —O-(alkenyl), —O-(alkynyl), —O-(aryl), —O-(heteroaryl), —S-(alkyl), —S-(alkenyl), —S-(alkynyl), —S-(aryl), —S (heteroaryl), —S(O)-(alkyl), —S(O)-(aryl), —S(O)-(heteroaryl), —SO₂-(alkyl), —SO₂-(aryl), or —SO₂-(heteroaryl), or a pharmaceutically acceptable salt or ester thereof.

In some embodiments, the compound having the structure:

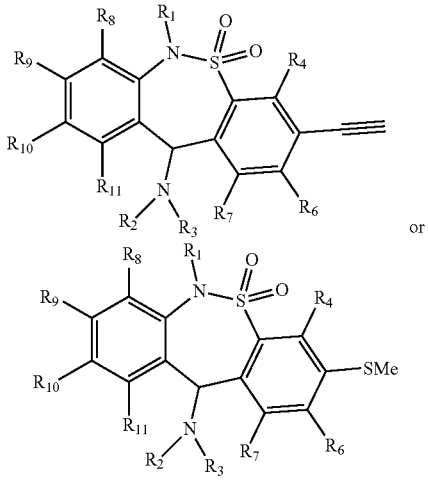

wherein
$R_1$ is —H or -(alkyl);
$R_2$ is —(C₆ alkyl)-CO₂H;
$R_3$ is —H or -(alkyl);
$R_4$, $R_6$ and $R_7$ are each independently —H, —Cl, —Br, —F, —I, —CN, —CF₃, —OCF₃, -(alkyl), -(alkenyl), -(alkynyl), -(aryl), —NH₂, —NH-(alkyl), —NH-(alkenyl), —NH-(alkynyl) —NH-(aryl), —NH-(heteroaryl), —OH, —OAc, —O—C(O)(alkyl), —O-(alkyl), —O-(alkylaryl), —O-(alkenyl), —O-(alkynyl), —O-(aryl), —O-(heteroaryl), —S-(alkyl), —S-(alkenyl), —S-(alkynyl), —S-(aryl), —S-(heteroaryl), —S(O)-(alkyl), —S(O)-(aryl), —S(O)-(heteroaryl), —SO₂-(alkyl), —SO₂-(aryl), or —SO₂-(heteroaryl);

$R_8$, $R_9$, $R_{10}$ and $R_{11}$ are each independently —H, —Cl, —Br, —F, —I, —CN, —CF₃, —OCF₃, -(alkyl), -(aryl), -(heteroaryl) -(alkenyl), -(alkynyl), —NH₂, —NH-(alkyl), —NH-(alkenyl), —NH-(alkynyl) —NH-(aryl), —NH-(heteroaryl), —OH, —OAc, —O—C(O)(alkyl), —O-(alkyl), —O-(alkenyl), —O-(alkynyl), —O-(aryl), —O-(heteroaryl), —S-(alkyl), —S-(alkenyl), —S-(alkynyl), —S-(aryl), —S-(heteroaryl), —S(O)-(alkyl), —S(O)-(aryl), —S(O)-(heteroaryl), —SO₂-(alkyl), —SO₂-(aryl), or —SO₂-(heteroaryl), or a pharmaceutically acceptable salt or ester thereof.

In some embodiments, the compound having the structure:

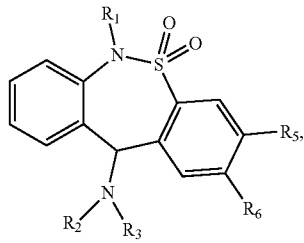

wherein
$R_1$ is —H or -(alkyl);
$R_2$ is —(C₆ alkyl)-CO₂H;
$R_3$ is —H or -(alkyl);

$R_5$ is -(alkynyl) or —S-(alkyl) and $R_6$ is H, or $R_5$ and $R_6$ are each independently —Cl, —Br, —F, or —I, or a pharmaceutically acceptable salt or ester thereof.

In some embodiments, the compound having the structure:

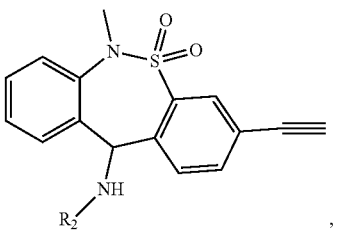

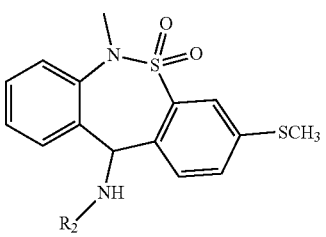

or

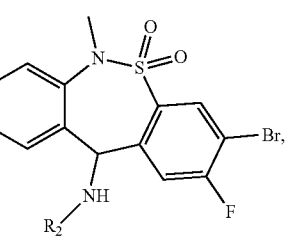

wherein $R_2$ is —($C_6$ alkyl)-$CO_2H$.

or a pharmaceutically acceptable salt or ester thereof.

In some embodiments, the compound having the structure:

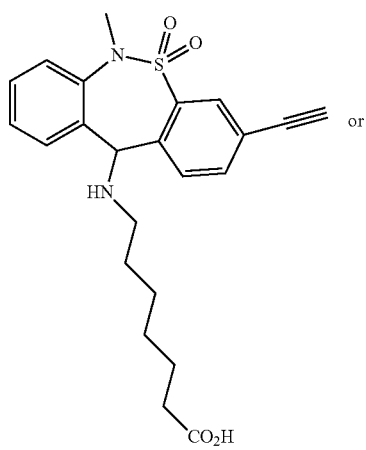 or

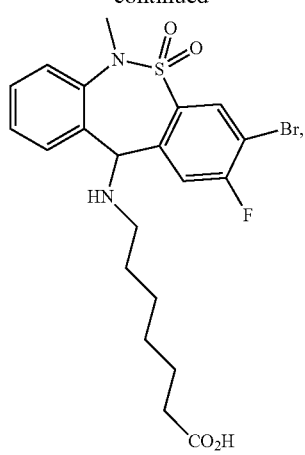

or a pharmaceutically acceptable salt or ester thereof.

In some embodiments, the compound having the structure:

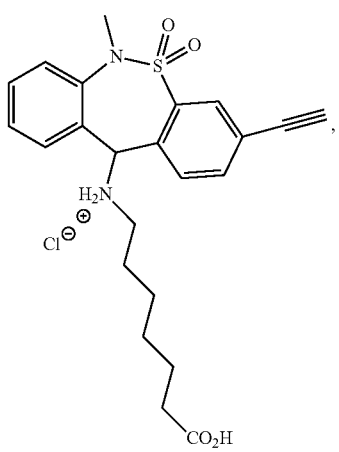

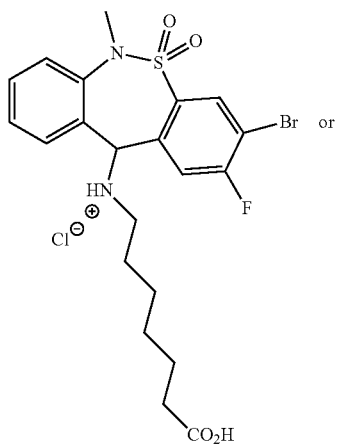

or

-continued

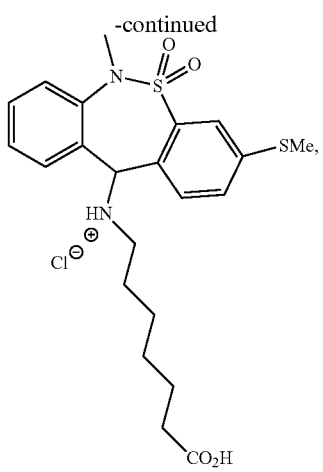

or an ester thereof.

In some embodiments, the compound having the structure

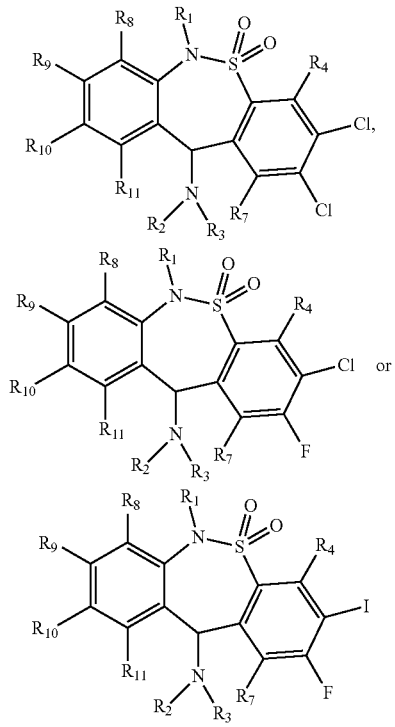

wherein
R₁ is —H or -(alkyl);
R₂ is —(C₆ alkyl)-CO₂H;
R₃ is —H or -(alkyl);
R₄ and R₇ are each independently —H, —Cl, —Br, —F, —I, —CN, —CF₃, —OCF₃, -(alkyl), -(alkenyl), -(alkynyl), -(aryl), —NH₂, —NH-(alkyl), —NH-(alkenyl), —NH-(alkynyl) —NH-(aryl), —NH-(heteroaryl), —OH, —OAc, —O—C(O)(alkyl), —O-(alkyl), —O-(alkylaryl), —O-(alkenyl), —O-(alkynyl), —O-(aryl), —O-(heteroaryl), —S-(alkyl), —S-(alkenyl), —S-(alkynyl), —S-(aryl), —S-(heteroaryl), —S(O)-(alkyl), —S(O)-(aryl), —S(O)-(heteroaryl), —SO₂-(alkyl), —SO₂-(aryl), or —SO₂-(heteroaryl);
R₈, R₉, R₁₀ and R₁₁ are each independently —H, —Cl, —Br, —F, —I, —CN, —CF₃, —OCF₃, -(alkyl), -(aryl), -(heteroaryl) -(alkenyl), -(alkynyl), —NH₂, —NH-(alkyl), —NH-(alkenyl), —NH-(alkynyl) —NH-(aryl), —NH-(heteroaryl), —OH, —OAc, —O—C(O)(alkyl), —O-(alkyl), —O-(alkenyl), —O-(alkynyl), —O-(aryl), —O-(heteroaryl), —S-(alkyl), —S-(alkenyl), —S-(alkynyl), —S-(aryl), —S-(heteroaryl), —S(O)-(alkyl), —S(O)-(aryl), —S(O)-(heteroaryl), —SO₂-(alkyl), —SO₂-(aryl), or —SO₂-(heteroaryl).

or a pharmaceutically acceptable salt or ester thereof.

In some embodiments, the compound having the structure:

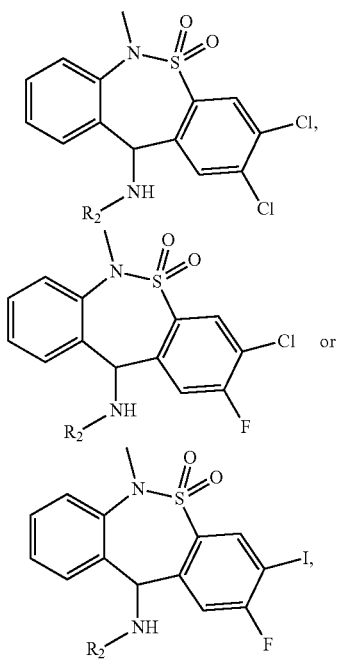

wherein
R₂ is —(C₆ alkyl)-CO₂H, or a pharmaceutically acceptable salt or ester thereof.

In some embodiments, the compound having the structure:

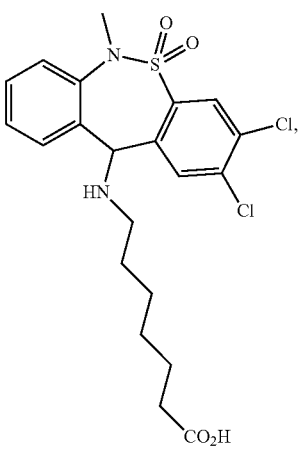

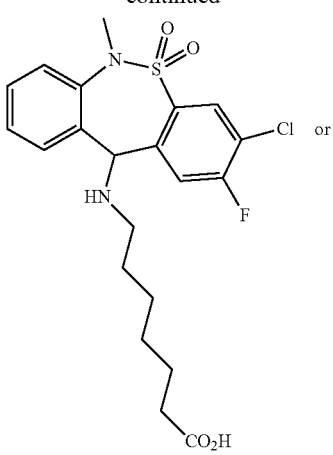

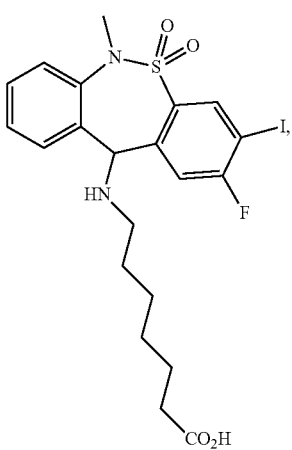

or an ester thereof.

In some embodiments, the compound having the structure:

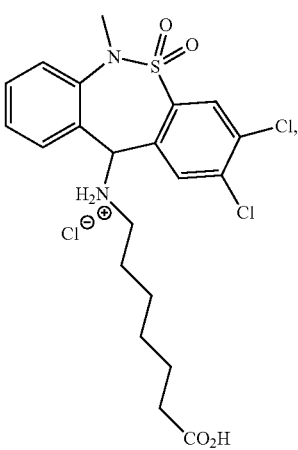

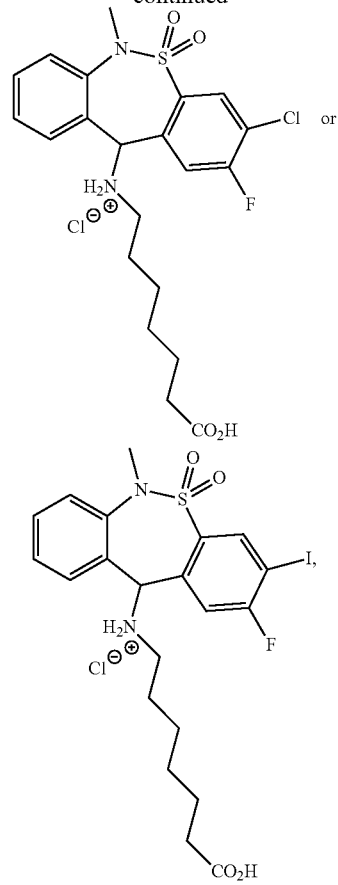

or an ester thereof.

In some embodiments, the compound having the structure:

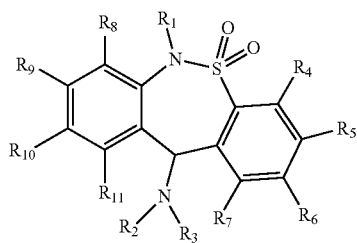

wherein $R_1$ is —H or -(alkyl);

$R_2$ is —($C_6$ alkyl)-$CO_2$-(alkyl);

$R_3$ is —H or -(alkyl);

$R_4$, $R_5$, $R_6$ and $R_7$ are each independently —H, —Cl, —Br, —F, —I, —CN, —$CF_3$, —$OCF_3$, -(alkyl), -(alkenyl), -(alkynyl), -(aryl), —$NH_2$, —NH-(alkyl), —NH-(alkenyl), —NH-(alkynyl) —NH-(aryl), —NH-(heteroaryl), —OH, —OAc, —O—C(O)(alkyl), —O-(alkyl), —O-(alkylaryl), —O-(alkenyl), —O-(alkynyl), —O-(aryl), —O-(heteroaryl), —S-(alkyl), —S-(alkenyl), —S-(alkynyl), —S-(aryl), —S-(heteroaryl), —S(O)-(alkyl), —S(O)-(aryl), —S(O)-(heteroaryl), —$SO_2$-(alkyl), —$SO_2$-(aryl), or —$SO_2$-(heteroaryl);

$R_8$, $R_9$, $R_{10}$ and $R_{11}$ are each independently —H, —Cl, —Br, —F, —I, —CN, —$CF_3$, —$OCF_3$, -(alkyl), -(aryl), -(heteroaryl) -(alkenyl), -(alkynyl), —NH₂, —NH-(alkyl), —NH-(alkenyl), —NH-(alkynyl) —NH-(aryl), —NH-(heteroaryl), —OH, —OAc, —O—C(O)(alkyl), —O-(alkyl), —O-(alkenyl), —O-(alkynyl), —O-(aryl), —O-(heteroaryl), —S-(alkyl), —S-(alkenyl), —S-(alkynyl), —S-(aryl), —S-(heteroaryl), —S(O)-(alkyl), —S(O)-(aryl), —S(O)-(heteroaryl), —SO₂-(alkyl), —SO₂-(aryl), or —SO₂-(heteroaryl);

wherein one of $R_5$ or $R_6$ is -(alkynyl) or —S-(alkyl), or $R_5$ and $R_6$ are each independently —Cl, —Br, —F, or —I, and or a pharmaceutically acceptable salt or ester thereof.

In some embodiments, the compound having the structure:

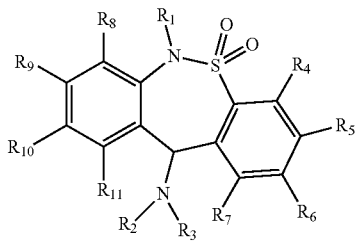

wherein
$R_1$ is —H or -(alkyl);
$R_2$ is —(C₆ alkyl)-CO₂-(alkyl);
$R_3$ is —H or -(alkyl);
$R_4$, $R_5$, $R_6$ and $R_7$ are each independently —H, —Cl, —Br, —F, —I, —CN, —CF₃, —OCF₃, -(alkyl), -(alkenyl), -(alkynyl), -(aryl), —NH₂, —NH-(alkyl), —NH-(alkenyl), —NH-(alkynyl) —NH-(aryl), —NH-(heteroaryl), —OH, —OAc, —O—C(O)(alkyl), —O-(alkyl), —O-(alkylaryl), —O-(alkenyl), —O-(alkynyl), —O-(aryl), —O-(heteroaryl), —S-(alkyl), —S-(alkenyl), —S-(alkynyl), —S-(aryl), —S-(heteroaryl), —S(O)-(alkyl), —S(O)-(aryl), —S(O)-(heteroaryl), —SO₂-(alkyl), —SO₂-(aryl), or —SO₂-(heteroaryl);

$R_8$, $R_9$, $R_{10}$ and $R_{11}$ are each independently —H, —Cl, —Br, —F, —I, —CN, —CF₃, —OCF₃, -(alkyl), -(aryl), -(heteroaryl) -(alkenyl), -(alkynyl), —NH₂, —NH-(alkyl), —NH-(alkenyl), —NH-(alkynyl) —NH-(aryl), —NH-(heteroaryl), —OH, —OAc, —O—C(O)(alkyl), —O-(alkyl), —O-(alkenyl), —O-(alkynyl), —O-(aryl), —O-(heteroaryl), —S-(alkyl), —S-(alkenyl), —S-(alkynyl), —S-(aryl), —S-(heteroaryl), —S(O)-(alkyl), —S(O)-(aryl), —S(O)-(heteroaryl), —SO₂-(alkyl), —SO₂-(aryl), or —SO₂-(heteroaryl);

wherein one of $R_5$ or $R_6$ is -(alkynyl), or $R_5$ and $R_6$ are each independently —Cl, —Br, —F, or —I, and or a pharmaceutically acceptable salt or ester thereof.

In some embodiments, the compound having the structure:

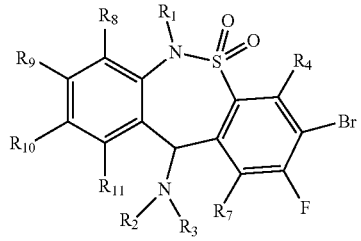

wherein
$R_1$ is —H or -(alkyl);
$R_2$ is —(C₆ alkyl)-CO₂-(alkyl);
$R_3$ is —H or -(alkyl);
$R_4$ and $R_7$ are each independently —H, —Cl, —Br, —F, —I, —CN, —CF₃, —OCF₃, -(alkyl), -(alkenyl), -(alkynyl), -(aryl), —NH₂, —NH-(alkyl), —NH-(alkenyl), —NH-(alkynyl) —NH-(aryl), —NH-(heteroaryl), —OH, —OAc, —O—C(O)(alkyl), —O-(alkyl), —O-(alkylaryl), —O-(alkenyl), —O-(alkynyl), —O-(aryl), —O-(heteroaryl), —S-(alkyl), —S-(alkenyl), —S-(alkynyl), —S-(aryl), —S-(heteroaryl), —S(O)-(alkyl), —S(O)-(aryl), —S(O)-(heteroaryl), —SO₂-(alkyl), —SO₂-(aryl), or —SO₂-(heteroaryl);

$R_8$, $R_9$, $R_{10}$ and $R_{11}$ are each independently —H, —Cl, —Br, —F, —I, —CN, —CF₃, —OCF₃, -(alkyl), -(aryl), -(heteroaryl) -(alkenyl), -(alkynyl), —NH₂, —NH-(alkyl), —NH-(alkenyl), —NH-(alkynyl) —NH-(aryl), —NH-(heteroaryl), —OH, —OAc, —O—C(O)(alkyl), —O-(alkyl), —O-(alkenyl), —O-(alkynyl), —O-(aryl), —O-(heteroaryl), —S-(alkyl), —S-(alkenyl), —S-(alkynyl), —S-(aryl), —S-(heteroaryl), —S(O)-(alkyl), —S(O)-(aryl), —S(O)-(heteroaryl), —SO₂-(alkyl), —SO₂-(aryl), or —SO₂-(heteroaryl), or a pharmaceutically acceptable salt or ester thereof.

In some embodiments, the compound having the structure:

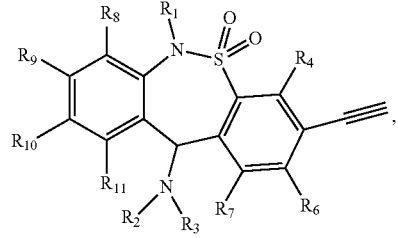

wherein
$R_1$ is —H or -(alkyl);
$R_2$ is —(C₆ alkyl)-CO₂-(alkyl);
$R_3$ is —H or -(alkyl);
$R_4$, $R_6$ and $R_7$ are each independently —H, —Cl, —Br, —F, —I, —CN, —CF₃, —OCF₃, -(alkyl), -(alkenyl), -(alkynyl), -(aryl), —NH₂, —NH-(alkyl), —NH-(alkenyl), —NH-(alkynyl) —NH-(aryl), —NH-(heteroaryl), —OH, —OAc, —O—C(O)(alkyl), —O-(alkyl), —O-(alkylaryl), —O-(alkenyl), —O-(alkynyl), —O-(aryl), —O-(heteroaryl), —S-(alkyl), —S-(alkenyl), —S-(alkynyl), —S-(aryl), —S-(heteroaryl), —S(O)-(alkyl), —S(O)-(aryl), —S(O)-(heteroaryl), —SO₂-(alkyl), —SO₂-(aryl), or —SO₂-(heteroaryl);

$R_8$, $R_9$, $R_{10}$ and $R_{11}$ are each independently —H, —Cl, —Br, —F, —I, —CN, —CF$_3$, —OCF$_3$, -(alkyl), -(aryl), -(heteroaryl) -(alkenyl), -(alkynyl), —NH$_2$, —NH-(alkyl), —NH-(alkenyl), —NH-(alkynyl) —NH-(aryl), —NH-(heteroaryl), —OH, —OAc, —O—C(O)(alkyl), —O-(alkyl), —O-(alkenyl), —O-(alkynyl), —O-(aryl), —O-(heteroaryl), —S-(alkyl), —S-(alkenyl), —S-(alkynyl), —S-(aryl), —S-(heteroaryl), —S(O)-(alkyl), —S(O)-(aryl), —S(O)-(heteroaryl), —SO$_2$-(alkyl), —SO$_2$-(aryl), or —SO$_2$-(heteroaryl), or a pharmaceutically acceptable salt or ester thereof.

In some embodiments, the compound having the structure:

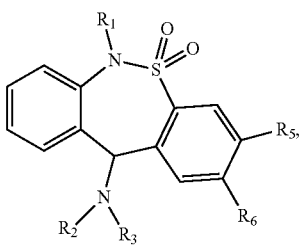

wherein $R_1$ is —H or -(alkyl);

$R_2$ is —(C$_6$ alkyl)-CO$_2$-(alkyl);

$R_3$ is —H or -(alkyl);

$R_5$ is -(alkynyl) and $R_6$ is H, or $R_5$ and $R_6$ are each independently —Cl, —Br, —F, or —I, or a pharmaceutically acceptable salt or ester thereof.

In some embodiments, the compound having the structure:

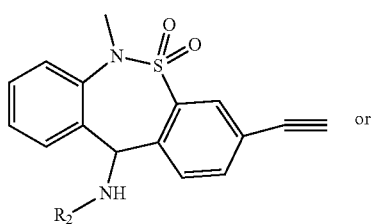

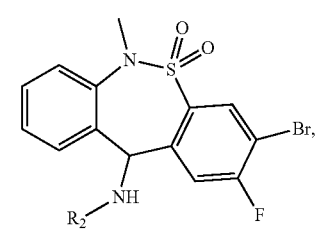

wherein $R_2$ is —(C$_6$ alkyl)-CO$_2$-(alkyl).

or a pharmaceutically acceptable salt or ester thereof.

In some embodiments, the compound having the structure:

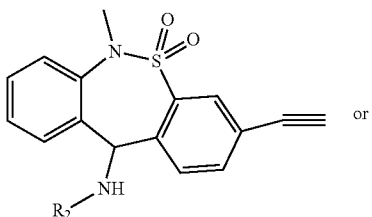

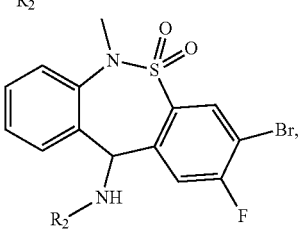

wherein $R_2$ is —(C$_6$ alkyl)-CO$_2$CH$_2$CH$_3$.

or a pharmaceutically acceptable salt or ester thereof.

In some embodiments, the compound having the structure:

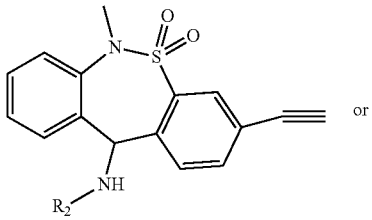

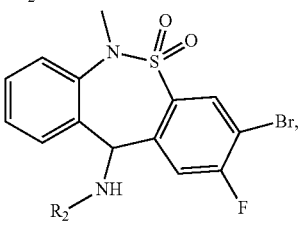

wherein $R_2$ is —(C$_6$ alkyl)-CO$_2$CH$_3$.

In some embodiments, the compound having the structure:

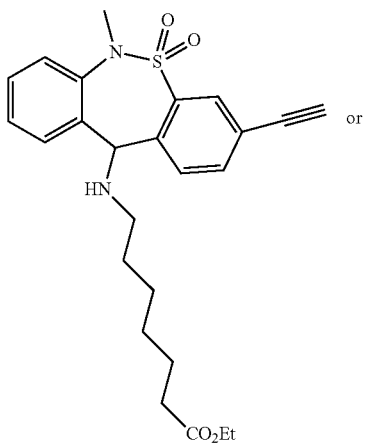

-continued

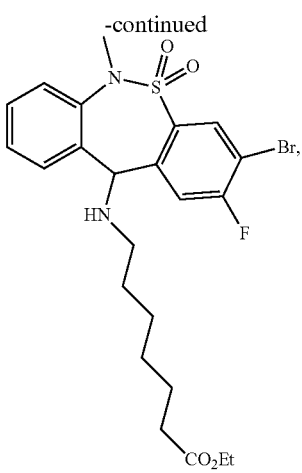

or a pharmaceutically acceptable salt or ester thereof.
In some embodiments, the compound having the structure:

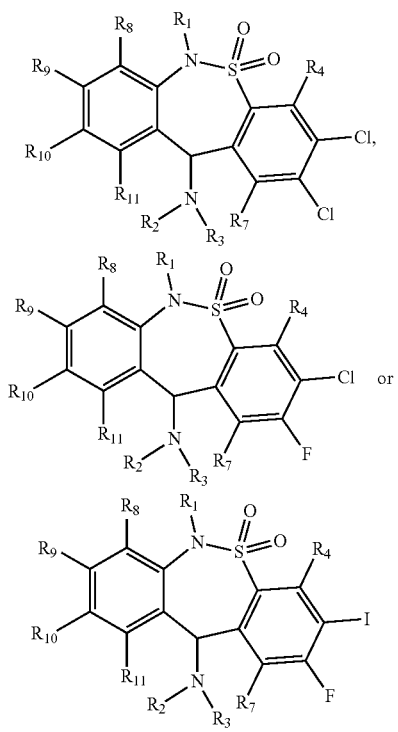

wherein
$R_1$ is —H or -(alkyl);
$R_2$ is —($C_6$ alkyl)-$CO_2$-(alkyl);
$R_3$ is —H or -(alkyl);
$R_4$ and $R_7$ are each independently —H, —Cl, —Br, —F, —I, —CN, —$CF_3$, —$OCF_3$, -(alkyl), -(alkenyl), -(alkynyl), -(aryl), —$NH_2$, —NH-(alkyl), —NH-(alkenyl), —NH-(alkynyl) —NH-(aryl), —NH-(heteroaryl), —OH, —OAc, —O—C(O)(alkyl), —O-(alkyl), —O-(alkylaryl), —O-(alkenyl), —O-(alkynyl), —O-(aryl), —O-(heteroaryl), —S-(alkyl), —S-(alkenyl), —S-(alkynyl), —S-(aryl), —S-(heteroaryl), —S(O)-(alkyl), —S(O)-(aryl), —S(O)-(heteroaryl), —$SO_2$-(alkyl), —$SO_2$-(aryl), or —$SO_2$-(heteroaryl);

$R_8$, $R_9$, $R_{10}$ and $R_{11}$ are each independently —H, —Cl, —Br, —F, —I, —CN, —$CF_3$, —$OCF_3$, -(alkyl), -(aryl), -(heteroaryl) -(alkenyl), -(alkynyl), —$NH_2$, —NH-(alkyl), —NH-(alkenyl), —NH-(alkynyl) —NH-(aryl), —NH-(heteroaryl), —OH, —OAc, —O—C(O)(alkyl), —O-(alkyl), —O-(alkenyl), —O-(alkynyl), —O-(aryl), —O-(heteroaryl), —S-(alkyl), —S-(alkenyl), —S-(alkynyl), —S-(aryl), —S-(heteroaryl), —S(O)-(alkyl), —S(O)-(aryl), —S(O)-(heteroaryl), —$SO_2$-(alkyl), —$SO_2$-(aryl), or —$SO_2$-(heteroaryl),
or a pharmaceutically acceptable salt or ester thereof.
In some embodiments, the compound having the structure:

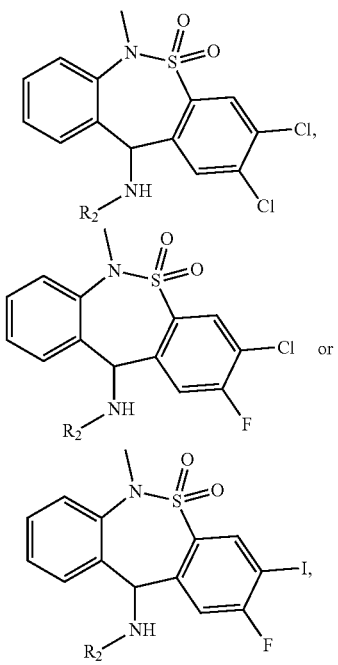

wherein
$R_2$ is —($C_6$ alkyl)-$CO_2CH_3$,
or a pharmaceutically acceptable salt or ester thereof.
In some embodiments, the compound having the structure:

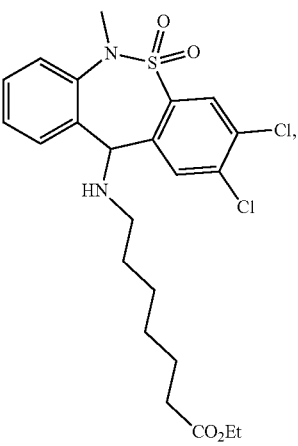

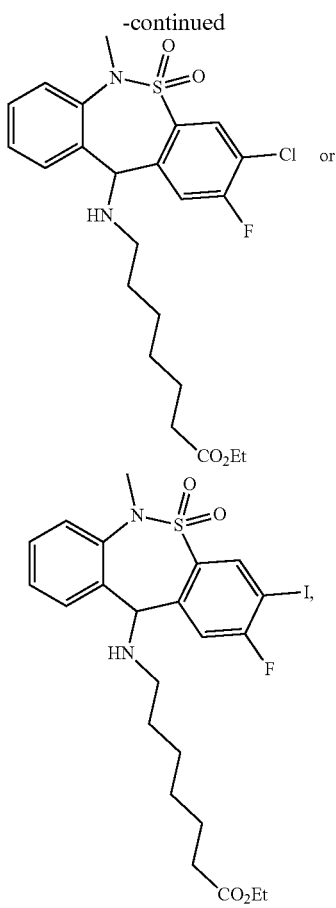

or a pharmaceutically acceptable salt thereof.

In some embodiments, the compound having the structure:

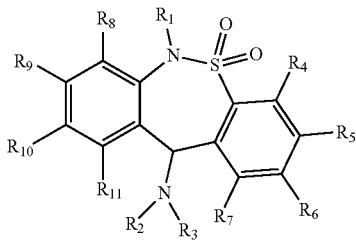

wherein
$R_1$ is —H or -(alkyl);
$R_2$ is —($C_{3-5}$ alkyl)-$CO_2H$ or —($C_{3-5}$ alkyl)-$CO_2$(alkyl);
$R_3$ is —H or -(alkyl);
$R_4$, $R_5$, $R_6$ and $R_7$ are each independently —H, —Cl, —Br, —F, —I, —CN, —$CF_3$, —$OCF_3$, -(alkyl), -(alkenyl), -(alkynyl), -(aryl), —$NH_2$, —NH-(alkyl), —NH-(alkenyl), —NH-(alkynyl) —NH-(aryl), —NH-(heteroaryl), —OH, —OAc, —O—C(O)(alkyl), —O-(alkyl), —O-(alkylaryl), —O-(alkenyl), —O-(alkynyl), —O-(aryl), —O-(heteroaryl), —S-(alkyl), —S-(alkenyl), —S-(alkynyl), —S-(aryl), —S-(heteroaryl), —S(O)-(alkyl), —S(O)-(aryl), —S(O)-(heteroaryl), —$SO_2$-(alkyl), —$SO_2$-(aryl), or —$SO_2$-(heteroaryl);
$R_8$, $R_9$, $R_{10}$ and $R_{11}$ are each independently —H, —Cl, —Br, —F, —I, —CN, —$CF_3$, —$OCF_3$, -(alkyl), -(aryl), -(heteroaryl) -(alkenyl), -(alkynyl), —$NH_2$, —NH-(alkyl), —NH-(alkenyl), —NH-(alkynyl) —NH-(aryl), —NH-(heteroaryl), —OH, —OAc, —O—C(O)(alkyl), —O-(alkyl), —O-(alkenyl), —O-(alkynyl), —O-(aryl), —O-(heteroaryl), —S-(alkyl), —S-(alkenyl), —S-(alkynyl), —S-(aryl), —S-(heteroaryl), —S(O)-(alkyl), —S(O)-(aryl), —S(O)-(heteroaryl), —$SO_2$-(alkyl), —$SO_2$-(aryl), or —$SO_2$-(heteroaryl);
wherein $R_5$ and $R_6$ are each independently —Cl, —Br, —F, or —I,
or a pharmaceutically acceptable salt or ester thereof.

In some embodiments, the compound having the structure:

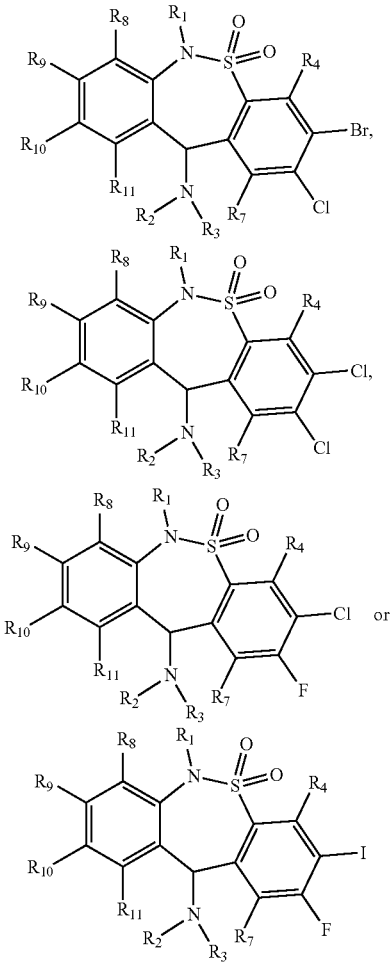

wherein
$R_1$ is —H or -(alkyl);
$R_2$ is —($C_{3-5}$ alkyl)-$CO_2H$ or —($C_{3-5}$ alkyl)-$CO_2$(alkyl);
$R_3$ is —H or -(alkyl);
$R_4$ and $R_7$ are each independently —H, —Cl, —Br, —F, —I, —CN, —$CF_3$, —$OCF_3$, -(alkyl), -(alkenyl), -(alkynyl), -(aryl), —$NH_2$, —NH-(alkyl), —NH-(alkenyl), —NH-(alkynyl) —NH-(aryl), —NH-(heteroaryl), —OH, —OAc, —O—C(O)(alkyl), —O-(alkyl), —O-(alkylaryl), —O-(alkenyl), —O-(alkynyl), —O-(aryl), —O-(heteroaryl), —S-(alkyl), —S-(alkenyl), —S-(alkynyl), —S-(aryl), —S-(heteroaryl), —S(O)-(alkyl), —S(O)-(aryl), —S(O)-(heteroaryl), —$SO_2$-(alkyl), —$SO_2$-(aryl), or —$SO_2$-(heteroaryl);

$R_8$, $R_9$, $R_{10}$ and $R_{11}$ are each independently —H, —Cl, —Br, —F, —I, —CN, —CF$_3$, —OCF$_3$, -(alkyl), -(aryl), -(heteroaryl) -(alkenyl), -(alkynyl), —NH$_2$, —NH-(alkyl), —NH-(alkenyl), —NH-(alkynyl) —NH-(aryl), —NH-(heteroaryl), —OH, —OAc, —O—C(O)(alkyl), —O-(alkyl), —O-(alkenyl), —O-(alkynyl), —O-(aryl), —O-(heteroaryl), —S-(alkyl), —S-(alkenyl), —S-(alkynyl), —S-(aryl), —S-(heteroaryl), —S(O)-(alkyl), —S(O)-(aryl), —S(O)-(heteroaryl), —SO$_2$-(alkyl), —SO$_2$-(aryl), or —SO$_2$-(heteroaryl), or a pharmaceutically acceptable salt or ester thereof.

In some embodiments, the compound having the structure:

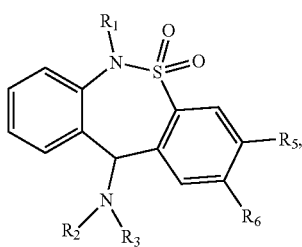

wherein
$R_1$ is —H or -(alkyl);
$R_2$ is —(C$_{3-5}$ alkyl)-CO$_2$H or —(C$_{3-5}$ alkyl)-CO$_2$(alkyl);
$R_3$ is —H or -(alkyl); and
$R_5$ and $R_6$ are each independently —Cl, —Br, —F, or —I, or a pharmaceutically acceptable salt or ester thereof.

In some embodiments, wherein $R_2$ is —(C$_4$ alkyl)-CO$_2$H, or —(C$_4$ alkyl)-CO$_2$CH$_3$ or —(C$_4$ alkyl)-CO$_2$CH$_2$CH$_3$, or a pharmaceutically acceptable salt or ester thereof.

In some embodiments, the compound having the structure:

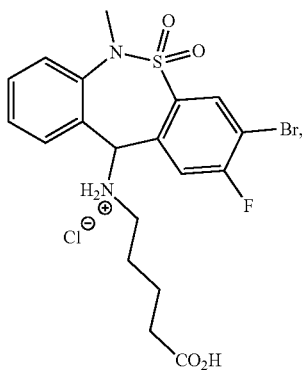

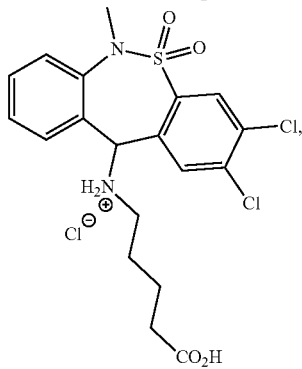

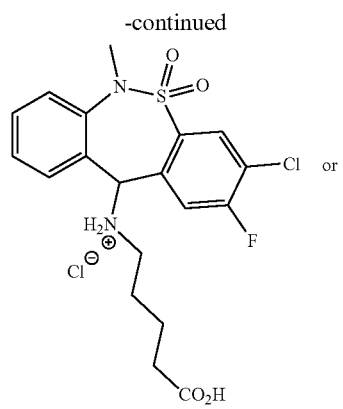

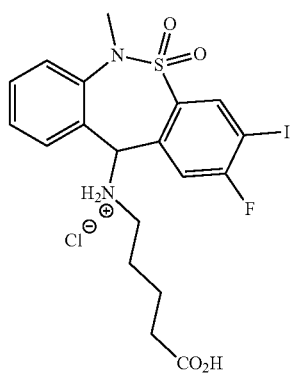

or an ester thereof.

In some embodiments, the compound having the structure:

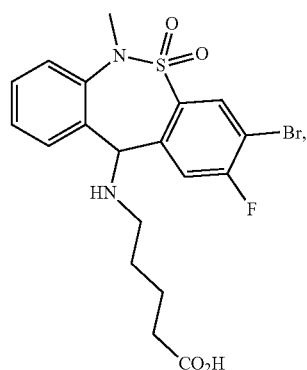

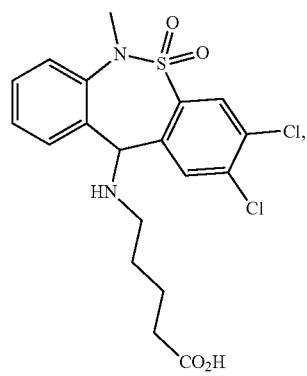

-continued

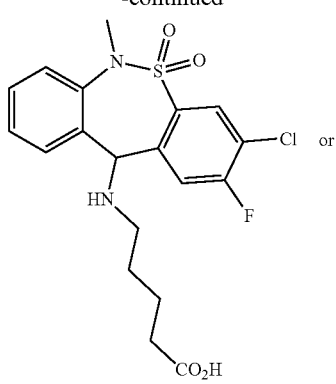

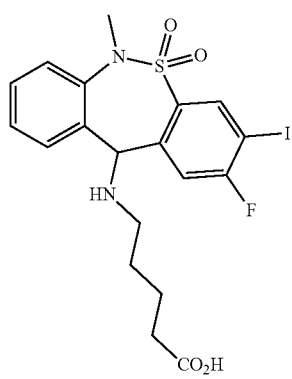

or a pharmaceutically acceptable salt or ester thereof.

In some embodiments, the compound having the structure:

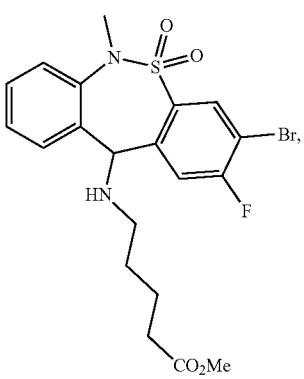

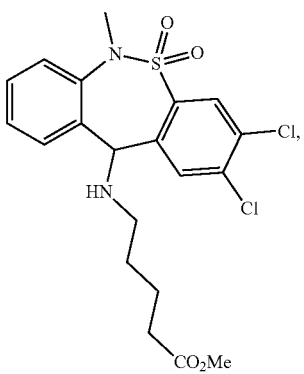

-continued

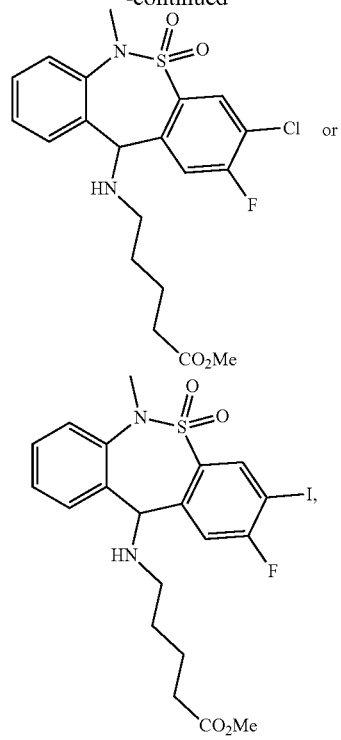

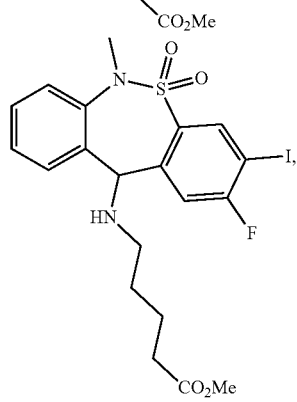

or a pharmaceutically acceptable salt thereof.

The present invention provides a pharmaceutical composition comprising the compound of the present invention and a pharmaceutically acceptable carrier.

In some embodiments, a pharmaceutical composition comprising the compound the present invention, an NMDA receptor antagonist, an NMDA receptor partial agonist, a neurokinin 1 receptor antagonist, a neurokinin 2 receptor antagonist, a neurokinin 3 receptor antagonist, a DOR agonist, naloxone or methylnaltrexone, and a pharmaceutically acceptable carrier.

In some embodiments, a method of activating a mu-opioid receptor or delta-opioid receptor comprising contacting the mu-opioid receptor or delta-opioid receptor with the compound of the present invention.

In some embodiments, a method of treating a subject afflicted with a depressive disorder or a mood disorder comprising administering an effective amount of the compound of the present invention to the subject so as to treat the subject afflicted with the depressive disorder or the mood disorder.

In some embodiments, a method of treating a subject afflicted with pain, an anxiety disorder, or borderline personality disorder, comprising administering an effective amount of the compound of the present invention to the subject so as to treat the subject afflicted with pain, the anxiety disorder, or borderline personality disorder In some embodiments, a method of treating a subject afflicted with opioid addiction or opioid withdrawal symptoms comprising administering an effective amount of the compound of the present invention to the subject so as to treat the subject afflicted with the opioid addiction or opioid withdrawal symptoms.

In some embodiments, a method of treating a subject afflicted with, a depressive disorder or a mood disorder comprising administering to the subject an effective amount of an NMDA receptor antagonist, an NMDA receptor partial agonist, a neurokinin 1 receptor antagonist, a neurokinin 2 receptor antagonist, a neurokinin 3 receptor antagonist or a DOR agonist and an effective amount of the compound of the present invention so as to thereby treat the subject afflicted with the depressive disorder or the mood disorder.

In some embodiments, a method of treating a subject afflicted with pain, an anxiety disorder, or borderline personality disorder comprising administering to the subject an effective amount of an NMDA receptor antagonist, an NMDA receptor partial agonist, a neurokinin 1 receptor antagonist, or a DOR agonist and an effective amount of the compound of the present invention so as to thereby treat the subject afflicted with pain, the anxiety disorder, or borderline personality disorder.

In some embodiments, a method of treating a subject afflicted with opioid addiction or opioid withdrawal symptoms comprising administering to the subject an effective amount of an NMDA receptor antagonist, an NMDA receptor partial agonist or a neurokinin 1 receptor antagonist and an effective amount of the compound of the present invention so as to thereby treat the subject afflicted with the opioid addiction or opioid withdrawal symptoms.

In some embodiments, a method of treating a subject afflicted with opioid addiction or opioid withdrawal symptoms comprising administering to the subject an effective amount of naloxone or methylnaltrexone and an effective amount of the compound of the present invention so as to thereby treat the subject afflicted with the opioid addiction or opioid withdrawal symptoms.

In some embodiments, a method of treating a subject afflicted with pain, a depressive disorder, a mood disorder, an anxiety disorder, or borderline personality disorder, comprising administering to the subject an effective amount of naloxone or methylnaltrexone and an effective amount of the compound of the present invention so as to thereby treat the subject afflicted with pain, the depressive disorder, the mood disorder, the anxiety disorder, or borderline personality disorder.

In some embodiments, a pharmaceutical composition comprising the compound of the present invention, a selective serotonin reuptake inhibitor or a serotonin-norepinephrine reuptake inhibitor, and a pharmaceutically acceptable carrier.

In some embodiments, a method of treating a subject afflicted with a depressive disorder, a mood disorder, an anxiety disorder, or borderline personality disorder, comprising administering to the subject an effective amount of a selective serotonin reuptake inhibitor or a serotonin-norepinephrine reuptake inhibitor and an effective amount of the compound of the present invention so as to thereby treat the subject afflicted with the depressive disorder, mood disorder, anxiety disorder, or borderline personality disorder.

In some embodiments, a method of activating a mu-opioid receptor comprising contacting the mu-opioid receptor with the compound of the present invention.

In some embodiments, a method of activating a delta-opioid receptor comprising contacting the delta-opioid receptor with the compound of the present invention.

In some embodiments, a method of activating a mu-opioid receptor and delta-opioid receptor comprising contacting the mu-opioid receptor and delta-opioid receptor with the compound of the present invention.

In some embodiments, a method of treating a subject afflicted with pain comprising administering an effective amount of the compound of the present invention to the subject so as to treat the subject afflicted with pain.

In some embodiments, a method of treating a subject afflicted with a depressive disorder comprising administering an effective amount of the compound of the present invention to the subject so as to treat the subject afflicted with the depressive disorder.

In some embodiments, a method of treating a subject afflicted with a mood disorder comprising administering an effective amount of the compound of the present invention to the subject so as to treat the subject afflicted with the mood disorder.

In some embodiments, a method of treating a subject afflicted with an anxiety disorder comprising administering an effective amount of the compound of the present invention to the subject so as to treat the subject afflicted with the anxiety disorder.

In some embodiments, a method of treating a subject afflicted with borderline personality disorder comprising administering an effective amount of the compound of the present invention to the subject so as to treat the subject afflicted with borderline personality disorder.

In some embodiments, a method of treating a subject afflicted with opioid addiction comprising administering an effective amount of the compound of the present invention to the subject so as to treat the subject afflicted with the opioid addiction.

In some embodiments, a method of treating a subject afflicted with opioid withdrawal symptoms comprising administering an effective amount of the compound of the present invention to the subject so as to treat the subject afflicted with the opioid withdrawal symptoms.

In some embodiments, a method of treating a subject afflicted with a pain comprising administering to the subject an effective amount of an NMDA receptor antagonist, an NMDA receptor partial agonist, a neurokinin 1 receptor antagonist or a DOR agonist and an effective amount of the compound of the present invention so as to thereby treat the subject afflicted with pain.

In some embodiments, a method of treating a subject afflicted with a depressive disorder comprising administering to the subject an effective amount of a NMDA receptor antagonist, an NMDA receptor partial agonist, a neurokinin 1 receptor antagonist, a neurokinin 2 receptor antagonist, a neurokinin 3 receptor antagonist or a DOR agonist and an effective amount of the compound of the present invention so as to thereby treat the subject afflicted with the depressive disorder.

In some embodiments, a method of treating a subject afflicted with a mood disorder comprising administering to the subject an effective amount of a NMDA receptor antagonist, an NMDA receptor partial agonist, a neurokinin 1 receptor antagonist, a neurokinin 2 receptor antagonist, a neurokinin 3 receptor antagonist or a DOR agonist and an effective amount of the compound of the present invention so as to thereby treat the subject afflicted with the mood disorder.

In some embodiments, a method of treating a subject afflicted with an anxiety disorder comprising administering to the subject an effective amount of an NMDA receptor antagonist, an NMDA receptor partial agonist, a neurokinin 1 receptor antagonist, or a DOR agonist and an effective amount of the compound of the present invention or a salt or ester thereof, so as to thereby treat the subject afflicted with the anxiety disorder.

In some embodiments, a method of treating a subject: afflicted with borderline personality disorder comprising administering to the subject an effective amount of an NMDA receptor antagonist, an NMDA receptor partial agonist, a neurokinin 1 receptor antagonist or a DOR agonist and an effective amount of the compound of the present invention or a salt or ester thereof, so as to thereby treat the subject afflicted with borderline personality disorder.

In some embodiments, a method of treating a subject afflicted with opioid addiction comprising administering to the subject an effective amount of an NMDA receptor antagonist, an NMDA receptor partial agonist or a neurokinin 1 receptor antagonist and an effective amount of the compound of the present invention or a salt or ester thereof, so as to thereby treat the subject afflicted with the opioid addiction.

In some embodiments, a method of treating a subject afflicted with opioid withdrawal symptoms comprising administering to the subject an effective amount of an NMDA receptor antagonist, an NMDA receptor partial agonist or a neurokinin 1 receptor antagonist and an effective amount of the compound of the present invention or a salt or ester thereof, so as to thereby treat the subject afflicted with the opioid withdrawal symptoms.

In some embodiments, a method of treating a subject afflicted with opioid addiction or opioid withdrawal symptoms comprising administering to the subject an effective amount of naloxone or methylnaltrexone and an effective amount of a compound of the present invention or a salt or ester thereof, so as to thereby treat the subject afflicted with the opioid addiction or opioid withdrawal symptoms.

In some embodiments, a method of treating a subject afflicted with pain, a depressive disorder, a mood disorder, an anxiety disorder or borderline personality disorder comprising administering to the subject an effective amount of naloxone or methylnaltrexone and an effective amount of the compound of the present invention or a salt or ester thereof, so as to thereby treat the subject afflicted with pain, the depressive disorder, the mood disorder, the anxiety disorder or borderline personality disorder.

In one embodiment of any of the compounds disclosed herein $R_2$ is —($C_{7-20}$ alkyl)-$CO_2H$ or any combination or range within the $C_{7-20}$ alkyl. The $C_{7-20}$ alkyl may be linear or branched.

In one embodiment of any of the compounds disclosed herein $R_2$ is —($C_{7-20}$ alkyl)-$CO_2$-(alkyl) or any combination or range within the $C_{7-20}$ alkyl. The $C_{7-20}$ alkyl may be linear or branched.

In one embodiment of any of the compounds disclosed herein $R_2$ is —($C_{7-20}$ alkyl)-$CO_2H$ or any combination of any of —($C_7$ alkyl)-$CO_2H$, —($C_8$ alkyl)-$CO_2H$, —($C_9$ alkyl)-$CO_2H$, —($C_{10}$ alkyl)-$CO_2H$, —($C_{11}$ alkyl)-$CO_2H$, —($C_{12}$ alkyl)-$CO_2H$, —($C_9$ alkyl)-$CO_2H$, —($C_{13}$ alkyl)-$CO_2H$, —($C_{14}$ alkyl)-$CO_2H$, —($C_8$ alkyl)-$CO_2H$, —($C_{15}$ alkyl)-$CO_2H$, —($C_{16}$ alkyl)-$CO_2H$, —($C_{17}$ alkyl)-$CO_2H$, —($C_{18}$ alkyl)-$CO_2H$, —($C_{19}$ alkyl)-$CO_2H$ or —($C_{20}$ alkyl)-$CO_2H$.

In one embodiment of any of the compounds disclosed herein $R_2$ is —($C_{7-20}$ alkyl)-$CO_2$-(alkyl) or any combination of any of —($C_7$ alkyl)-$CO_2$-(alkyl), —($C_8$ alkyl)-$CO_2$-(alkyl), —($C_9$ alkyl)-$CO_2$-(alkyl), —($C_{10}$ alkyl)-$CO_2$-(alkyl), —($C_{11}$ alkyl)-$CO_2$-(alkyl), —($C_{12}$ alkyl)-$CO_2$-(alkyl), —($C_9$ alkyl)-$CO_2$-(alkyl), —($C_{13}$ alkyl)-$CO_2$-(alkyl), —($C_{14}$ alkyl)-$CO_2$-(alkyl), —($C_8$ alkyl)-$CO_2$-(alkyl), —($C_{15}$ alkyl)-$CO_2$-(alkyl), —($C_{16}$ alkyl)-$CO_2$-(alkyl), —($C_{17}$ alkyl)-$CO_2$-(alkyl), —($C_{18}$ alkyl)-$CO_2$-(alkyl), —($C_{19}$ alkyl)-$CO_2$-(alkyl) or —($C_{20}$ alkyl)-$CO_2$-(alkyl).

In one embodiment of any of the compounds disclosed herein, $R_5$ is other than Cl, or other than $SCH_3$.

The present invention provides a pharmaceutical composition comprising the compound of the present invention and a pharmaceutically acceptable carrier.

The present invention provides a pharmaceutical composition comprising the compound of the present invention and an NMDA receptor antagonist, an NMDA receptor partial agonist, a neurokinin 1 receptor antagonist, a neurokinin 2 receptor antagonist, a neurokinin 3 receptor antagonist, a DOR agonist, naloxone or methylnaltrexone and a pharmaceutically acceptable carrier.

The present invention provides a method of activating the mu-opioid receptor comprising contacting the mu-opioid receptor with the compound of the present invention.

The present invention provides a method of activating the delta-opioid receptor comprising contacting the delta-opioid receptor with the compound of the present invention.

The present invention provides a method of treating a subject afflicted with depression comprising administering an effective amount of the compound of the present invention to the subject so as to treat the subject afflicted with the depression.

The present invention provides a method of treating a subject afflicted with pain comprising administering an effective amount of the compound of the present invention to the subject so as to treat the subject afflicted with pain.

The present invention provides a method of treating a subject afflicted with an anxiety disorder comprising administering an effective amount of the compound of the present invention to the subject so as to treat the subject afflicted with the anxiety disorder.

The present invention provides a method of treating a subject afflicted with borderline personality disorder comprising administering an effective amount of the compound of the present invention to the subject so as to treat the subject afflicted with borderline personality disorder.

The present invention provides a method of treating a subject afflicted with a depressive disorder comprising administering an effective amount of the compound of the present invention to the subject so as to treat the subject afflicted with the depressive disorder.

The present invention provides a method of treating a subject afflicted with a mood disorder comprising administering an effective amount of the compound of the present invention to the subject so as to treat the subject afflicted with the mood disorder.

The present invention provides a method of treating a subject afflicted with opioid addiction comprising administering an effective amount of the compound of the present invention to the subject so as to treat the subject afflicted with the opioid addiction.

The present invention provides a method of treating a subject afflicted with opioid withdrawal symptoms comprising administering an effective amount of the compound of the present invention to the subject so as to treat the subject afflicted with the opioid withdrawal symptoms.

In some embodiments, the mu-opioid receptors or delta-opioid receptors are in a human subject.

The present invention also provides a compound of the present invention, or a salt or ester thereof, for use as an add-on therapy or in combination with an NMDA receptor antagonist, an NMDA receptor partial agonist, a neurokinin 1 receptor antagonist, a neurokinin 2 receptor antagonist, a neurokinin 3 receptor antagonist, or a DOR agonist in treating a subject afflicted with depression.

The present invention also provides a compound of the present invention, or a salt or ester thereof, for use as an add-on therapy or in combination with an NMDA receptor antagonist, an NMDA receptor partial agonist, a neurokinin 1 receptor antagonist or a DOR agonist in treating a subject afflicted with pain.

The present invention also provides a compound of the present invention, or a salt or ester thereof, for use as an add-on therapy or in combination with an NMDA receptor antagonist, an NMDA receptor partial agonist, a neurokinin 1 receptor antagonist, a neurokinin 2 receptor antagonist, a neurokinin 3 receptor antagonist, or a DOR agonist in treating a subject afflicted with a depressive disorder or mood disorder.

The present invention also provides a compound of the present invention, or a salt or ester thereof, for use as an add-on therapy or in combination with an NMDA receptor antagonist, an NMDA receptor partial agonist, a neurokinin 1 receptor antagonist, or a DOR agonist in treating a subject afflicted with an anxiety disorder.

The present invention also provides a compound of the present invention, or a salt or ester thereof, for use as an add-on therapy or in combination with an NMDA receptor antagonist, an NMDA receptor partial agonist, a neurokinin 1 receptor antagonist or a DOR agonist in treating a subject afflicted with borderline personality disorder.

The present invention also provides a compound of the present invention, or a salt or ester thereof, for use as an add-on therapy or in combination with an NMDA receptor antagonist, an NMDA receptor partial agonist or a neurokinin 1 receptor antagonist in treating a subject afflicted with opioid addiction or opioid withdrawal symptoms.

The present invention further provides a pharmaceutical composition comprising an amount of a compound of the present invention, or a salt or ester thereof, and an amount of a NMDA receptor antagonist, an NMDA receptor partial agonist, a neurokinin 1 receptor antagonist, a neurokinin 2 receptor antagonist, a neurokinin 3 receptor antagonist, or a DOR agonist for use in treating a subject afflicted with depression.

The present invention further provides a pharmaceutical composition comprising an amount of a compound of the present invention, or a salt or ester thereof, and an amount of a NMDA receptor antagonist, an NMDA receptor partial agonist, a neurokinin 1 receptor antagonist or a DOR agonist for use in treating a subject afflicted with pain.

The present invention further provides a pharmaceutical composition comprising an amount of a compound of the present invention, or a salt or ester thereof, and an amount of a NMDA receptor antagonist, an NMDA receptor partial agonist, a neurokinin 1 receptor antagonist, a neurokinin 2 receptor antagonist, a neurokinin 3 receptor antagonist, or a DOR agonist for use in treating a subject afflicted with a depressive disorder or mood disorder.

The present invention further provides a pharmaceutical composition comprising an amount of a compound of the present invention, or a salt or ester thereof, and an amount of a NMDA receptor antagonist, an NMDA receptor partial agonist, a neurokinin 1 receptor antagonist, or a DOR agonist for use in treating a subject afflicted with an anxiety disorder.

The present invention further provides a pharmaceutical composition comprising an amount of a compound of the present invention, or a salt or ester thereof, and an amount of a NMDA receptor antagonist, an NMDA receptor partial agonist, a neurokinin 1 receptor antagonist or a DOR agonist in treating a subject afflicted with borderline personality disorder.

The present invention further provides a pharmaceutical composition comprising an amount of a compound of the present invention, or a salt or ester thereof, and an amount of an NMDA receptor antagonist, an NMDA receptor partial agonist or a neurokinin 1 receptor antagonist in treating a subject afflicted with opioid addiction or opioid withdrawal symptoms.

The present invention also provides a compound of the present invention, or a salt or ester thereof, for use as an add-on therapy or in combination with an SSRI or an SNRI in treating a subject afflicted with a depressive disorder, a mood disorder, or borderline personality disorder.

The present invention also provides a compound of the present invention, or a salt or ester thereof, for use as an add-on therapy or in combination with an SSRI or an SNRI in treating a subject afflicted with an anxiety disorder.

The present invention also provides a compound of the present invention, or a salt or ester thereof, and an amount of an SSRI or an SNRI in treating a subject afflicted with a depressive disorder, a mood disorder, or borderline personality disorder.

The present invention also provides compound of the present invention, or a salt or ester thereof, and an amount of an SSRI or an SNRI in treating a subject afflicted with an anxiety disorder.

In some embodiments, a package comprising:
a) a first pharmaceutical composition comprising an amount of an NMDA receptor antagonist, an NMDA receptor partial agonist, a neurokinin 1 receptor antagonist or a DOR agonist and a pharmaceutically acceptable carrier;
b) a second pharmaceutical composition comprising an amount of any compound of the present invention, or a salt or ester thereof; and
c) instructions for use of the first and second pharmaceutical compositions together to treat a subject afflicted with pain.

In some embodiments, a package comprising:
a) a first pharmaceutical composition comprising an amount of an NMDA receptor antagonist, an NMDA receptor partial agonist, a neurokinin 1 receptor antagonist, a neurokinin 2 receptor antagonist, a neurokinin 3 receptor antagonist or a DOR agonist and a pharmaceutically acceptable carrier;
b) a second pharmaceutical composition comprising an amount of any compound of the present invention, or a salt or ester thereof; and
c) instructions for use of the first and second pharmaceutical compositions together to treat a subject afflicted with depression.

In some embodiments, a package comprising:
a) a first pharmaceutical composition comprising an amount of an NMDA receptor antagonist, an NMDA receptor partial agonist, a neurokinin 1 receptor antagonist, a neurokinin 2 receptor antagonist, a neurokinin 3 receptor antagonist, or a DOR agonist and a pharmaceutically acceptable carrier;
b) a second pharmaceutical composition comprising an amount of any compound of the present invention, or a salt or ester thereof; and
c) instructions for use of the first and second pharmaceutical compositions together to treat a subject afflicted with a depressive disorder or mood disorder.

In some embodiments, a package comprising:
a) a first pharmaceutical composition comprising an amount of an NMDA receptor antagonist, an NMDA receptor partial agonist, a neurokinin 1 receptor antagonist or a DOR agonist and a pharmaceutically acceptable carrier;

b) a second pharmaceutical composition comprising an amount of any compound of the present invention, or a salt or ester thereof; and
c) instructions for use of the first and second pharmaceutical compositions together to treat a subject afflicted with an anxiety disorder.

In some embodiments, a package comprising:
a) a first pharmaceutical composition comprising an amount of an NMDA receptor antagonist, an NMDA receptor partial agonist, a neurokinin 1 receptor antagonist or a DOR agonist and a pharmaceutically acceptable carrier;
b) a second pharmaceutical composition comprising an amount of any compound of the present invention, or a salt or ester thereof; and
c) instructions for use of the first and second pharmaceutical compositions together to treat a subject afflicted with borderline personality disorder.

In some embodiments, a package comprising:
a) a first pharmaceutical composition comprising an amount of an NMDA receptor antagonist, an NMDA receptor partial agonist or a neurokinin 1 receptor antagonist and a pharmaceutically acceptable carrier;
b) a second pharmaceutical composition comprising an amount of any compound of the present invention, or a salt or ester thereof; and
c) instructions for use of the first and second pharmaceutical compositions together to treat a subject afflicted with opioid addiction or opioid withdrawal symptoms.

The therapeutic package of the above embodiment, wherein the respective amounts of said compound and said agonist or antagonist in said unit dose when taken together is more effective to treat the subject than when compared to the administration of said compound in the absence of said agonist or antagonist or the administration of said agonist or antagonist in the absence of said compound.

In some embodiments, a therapeutic package for dispensing to, or for use in dispensing to, a subject afflicted with pain, which comprises:
a) one or more unit doses, each such unit dose comprising:
(i) an amount of any compound of the present invention, or a salt or ester thereof; and
(ii) an amount of an NMDA receptor antagonist, an NMDA receptor partial agonist, a neurokinin 1 receptor antagonist or a DOR agonist,
wherein the respective amounts of said compound and said agonist or antagonist in said unit dose are effective, upon concomitant administration to said subject, to treat the subject, and
(b) a finished pharmaceutical container therefor, said container containing said unit dose or unit doses, said container further containing or comprising labeling directing the use of said package in the treatment of said subject.

In some embodiments, a therapeutic package for dispensing to, or for use in dispensing to, a subject afflicted with depression, which comprises:
a) one or more unit doses, each such unit dose comprising:
(i) an amount of any compound of the present invention, or a salt or ester thereof; and
(ii) an amount of an NMDA receptor antagonist, an NMDA receptor partial agonist, a neurokinin 1 receptor antagonist, a neurokinin 2 receptor antagonist, a neurokinin 3 receptor antagonist, or a DOR agonist,
wherein the respective amounts of said compound and said agonist or antagonist in said unit dose are effective, upon concomitant administration to said subject, to treat the subject, and
(b) a finished pharmaceutical container therefor, said container containing said unit dose or unit doses, said container further containing or comprising labeling directing the use of said package in the treatment of said subject.

In some embodiments, a therapeutic package for dispensing to, or for use in dispensing to, a subject afflicted with a depressive disorder or mood disorder, which comprises:
a) one or more unit doses, each such unit dose comprising:
(i) an amount of any compound of the present invention, or a salt or ester thereof; and
(ii) an amount of an NMDA receptor antagonist, an NMDA receptor partial agonist, a neurokinin 1 receptor antagonist, a neurokinin 2 receptor antagonist, a neurokinin 3 receptor antagonist, or a DOR agonist,
wherein the respective amounts of said compound and said agonist or antagonist in said unit dose are effective, upon concomitant administration to said subject, to treat the subject, and
(b) a finished pharmaceutical container therefor, said container containing said unit dose or unit doses, said container further containing or comprising labeling directing the use of said package in the treatment of said subject.

In some embodiments, a therapeutic package for dispensing to, or for use in dispensing to, a subject afflicted with an anxiety disorder, which comprises:
a) one or more unit doses, each such unit dose comprising:
(i) an amount of any compound of the present invention, or a salt or ester thereof; and
(ii) an amount of an NMDA receptor antagonist, an NMDA receptor partial agonist, a neurokinin 1 receptor antagonist, or a DOR agonist,
wherein the respective amounts of said compound and said agonist or antagonist in said unit dose are effective, upon concomitant administration to said subject, to treat the subject, and
(b) a finished pharmaceutical container therefor, said container containing said unit dose or unit doses, said container further containing or comprising labeling directing the use of said package in the treatment of said subject.

In some embodiments, a therapeutic package for dispensing to, or for use in dispensing to, a subject afflicted with borderline personality disorder, which comprises:
a) one or more unit doses, each such unit dose comprising:
(i) an amount of any compound of the present invention, or a salt or ester thereof; and
(ii) an amount of an NMDA receptor antagonist, an NMDA receptor partial agonist, a neurokinin 1 receptor antagonist or a DOR agonist
wherein the respective amounts of said compound and said agonist or antagonist in said unit dose are effective, upon concomitant administration to said subject, to treat the subject, and
(b) a finished pharmaceutical container therefor, said container containing said unit dose or unit doses, said container further containing or comprising labeling directing the use of said package in the treatment of said subject.

In some embodiments, a therapeutic package for dispensing to, or for use in dispensing to, a subject afflicted with opioid addiction or opioid withdrawal symptoms, which comprises:

a) one or more unit doses, each such unit dose comprising:
  (i) an amount of any compound of the present invention, or a salt or ester thereof; and
  (ii) an amount of an NMDA receptor antagonist, an NMDA receptor partial agonist or a neurokinin 1 receptor antagonist,
  wherein the respective amounts of said compound and said agonist or antagonist in said unit dose are effective, upon concomitant administration to said subject, to treat the subject, and
b) a finished pharmaceutical container therefor, said container containing said unit dose or unit doses, said container further containing or comprising labeling directing the use of said package in the treatment of said subject.

The therapeutic package of the above embodiment, wherein the respective amounts of said compound and said agonist or antagonist in said unit dose when taken together is more effective to treat the subject than when compared to the administration of said compound in the absence of said agonist or antagonist or the administration of said agonist or antagonist in the absence of said compound.

[A1]

A pharmaceutical composition in unit dosage form, useful in treating a subject afflicted with pain, which comprises:
  (i) an amount of any compound of the present invention, or a salt or ester thereof; and
  (ii) an amount of an NMDA receptor antagonist, an NMDA receptor partial agonist, a neurokinin 1 receptor antagonist, or a DOR agonist,
  wherein the respective amounts of said compound and said agonist or antagonist in said composition are effective, upon concomitant administration to said subject of one or more of said unit dosage forms of said composition, to treat the subject.

A pharmaceutical composition in unit dosage form, useful in treating a subject afflicted with depression, which comprises:
  (i) an amount of any compound of the present invention, or a salt or ester thereof; and
  (ii) an amount of an NMDA receptor antagonist, an NMDA receptor partial agonist, a neurokinin 1 receptor antagonist, a neurokinin 2 receptor antagonist, a neurokinin 3 receptor antagonist, or a DOR agonist,
  wherein the respective amounts of said compound and said agonist or antagonist in said composition are effective, upon concomitant administration to said subject of one or more of said unit dosage forms of said composition, to treat the subject.

A pharmaceutical composition in unit dosage form, useful in treating a subject afflicted with a depressive disorder or mood disorder, which comprises:
  (i) an amount of any compound of the present invention, or a salt or ester thereof; and
  (ii) an amount of an NMDA receptor antagonist, an NMDA receptor partial agonist, a neurokinin 1 receptor antagonist, a neurokinin 2 receptor antagonist, a neurokinin 3 receptor antagonist, or a DOR agonist,
  wherein the respective amounts of said compound and said agonist or antagonist in said composition are effective, upon concomitant administration to said subject of one or more of said unit dosage forms of said composition, to treat the subject.

A pharmaceutical composition in unit dosage form, useful in treating a subject afflicted with an anxiety disorder, which comprises:
  (i) an amount of any compound of the present invention, or a salt or ester thereof; and
  (ii) an amount of an NMDA receptor antagonist, an NMDA receptor partial agonist, a neurokinin 1 receptor antagonist, or a DOR agonist,
  wherein the respective amounts of said compound and said agonist or antagonist in said composition are effective, upon concomitant administration to said subject of one or more of said unit dosage forms of said composition, to treat the subject.

A pharmaceutical composition in unit dosage form, useful in treating a subject afflicted with borderline personality disorder, which comprises:
  (i) an amount of any compound of the present invention, or a salt or ester thereof; and
  (ii) an amount of an NMDA receptor antagonist, an NMDA receptor partial agonist, a neurokinin 1 receptor antagonist or a DOR agonist,
  wherein the respective amounts of said compound and said agonist or antagonist in said composition are effective, upon concomitant administration to said subject of one or more of said unit dosage forms of said composition, to treat the subject.

A pharmaceutical composition in unit dosage form, useful in treating a subject afflicted with opioid addiction or opioid withdrawal symptoms, which comprises:
  (i) an amount of any compound of the present invention, or a salt or ester thereof; and
  (ii) an amount of an NMDA receptor antagonist, an NMDA receptor partial agonist or a neurokinin 1 receptor antagonist,
  wherein the respective amounts of said compound and said agonist or antagonist in said composition are effective, upon concomitant administration to said subject of one or more of said unit dosage forms of said composition, to treat the subject.

The pharmaceutical composition of the above embodiment, wherein the respective amounts of said compound and said agonist or antagonist in said unit dose when taken together is more effective to treat the subject than when compared to the administration of said compound in the absence of said agonist or antagonist or the administration of said agonist or antagonist in the absence of said compound.

The present invention also provides a method of treating a subject afflicted with pain, a depressive disorder, a mood disorder, or borderline personality disorder comprising administering to the subject an effective amount of an SSRI or an SNRI and an effective amount of any compound of the present invention, or a salt or ester thereof, so as to thereby treat the subject.

The present invention also provides a method of treating a subject afflicted with an anxiety disorder comprising administering to the subject an effective amount of an SSRI or an SNRI and an effective amount of any compound of the present invention, or a salt or ester thereof, so as to thereby treat the subject.

The present invention further provides a pharmaceutical composition comprising an amount of any of the compounds of the present invention, or a salt or ester thereof, and an amount of an SSRI or an SNRI for use in treating a subject afflicted with pain, a depressive disorder, a mood disorder, or borderline personality disorder.

The present invention further provides a pharmaceutical composition comprising an amount of any of the compounds of the present invention, or a salt or ester thereof, and an amount of an SSRI or an SNRI for use in treating a subject afflicted with an anxiety disorder.

The present invention also provides a method of treating a subject afflicted with a depressive disorder or mood disorder comprising administering to the subject an effective amount of an NMDA receptor antagonist and an effective amount of any compound of the present invention, or a salt or ester thereof, so as to thereby treat the subject.

The present invention also provides a compound of the present invention or a salt or ester thereof, for use as an add-on therapy or in combination with an NMDA receptor antagonist, in treating a subject afflicted with a depressive disorder or mood disorder.

The present invention further provides a pharmaceutical composition comprising an amount of any of the compounds of the present invention, or a salt or ester thereof, and an amount of an NMDA receptor antagonist, for use in treating a subject afflicted with a depressive disorder or mood disorder.

The present invention also provides a method of treating a subject afflicted with a depressive disorder or mood disorder comprising administering to the subject an effective amount of an NMDA receptor partial agonist, and an effective amount of any compound of the present invention, or a salt or ester thereof, so as to thereby treat the subject.

The present invention also provides a compound of the present invention or a salt or ester thereof, for use as an add-on therapy or in combination with an NMDA receptor partial agonist in treating a subject afflicted with a depressive disorder or mood disorder.

The present invention further provides a pharmaceutical composition comprising an amount of any of the compounds of the present invention, or a salt or ester thereof, and an amount of an NMDA receptor partial agonist, for use in treating a subject afflicted with a depressive disorder or mood disorder.

The present invention also provides a method of treating a subject afflicted with a depressive disorder or mood disorder comprising administering to the subject an effective amount of a neurokinin 1 receptor antagonist and an effective amount of any compound of the present invention, or a salt or ester thereof, so as to thereby treat the subject.

The present invention also provides a compound of the present invention or a salt or ester thereof, for use as an add-on therapy or in combination with a neurokinin 1 receptor antagonist in treating a subject afflicted with a depressive disorder or mood disorder.

The present invention further provides a pharmaceutical composition comprising an amount of any of the compounds of the present invention, or a salt or ester thereof, and an amount of a neurokinin 1 receptor antagonist for use in treating a subject afflicted with a depressive disorder or mood disorder.

The present invention also provides a method of treating a subject afflicted with a depressive disorder or mood disorder comprising administering to the subject an effective amount of a neurokinin 2 receptor antagonist and an effective amount of any compound of the present invention, or a salt or ester thereof, so as to thereby treat the subject.

The present invention also provides a compound of the present invention or a salt or ester thereof, for use as an add-on therapy or in combination with a neurokinin 2 receptor antagonist in treating a subject afflicted with a depressive disorder or mood disorder.

The present invention further provides a pharmaceutical composition comprising an amount of any of the compounds of the present invention, or a salt or ester thereof, and an amount of a neurokinin 2 receptor antagonist for use in treating a subject afflicted with a depressive disorder or mood disorder.

The present invention also provides a method of treating a subject afflicted with a depressive disorder or mood disorder comprising administering to the subject an effective amount of a neurokinin 3 receptor antagonist and an effective amount of any compound of the present invention, or a salt or ester thereof, so as to thereby treat the subject.

The present invention also provides a compound of the present invention or a salt or ester thereof, for use as an add-on therapy or in combination with a neurokinin 3 receptor antagonist in treating a subject afflicted with a depressive disorder or mood disorder.

The present invention further provides a pharmaceutical composition comprising an amount of any of the compounds of the present invention, or a salt or ester thereof, and an amount of a neurokinin 3 receptor antagonist for use in treating a subject afflicted with a depressive disorder or mood disorder.

The present invention also provides a method of treating a subject afflicted with a depressive disorder or mood disorder comprising administering to the subject an effective amount of a DOR agonist and an effective amount of any compound of the present invention, or a salt or ester thereof, so as to thereby treat the subject.

The present invention also provides a compound of the present invention or a salt or ester thereof, for use as an add-on therapy or in combination with a DOR agonist in treating a subject afflicted with a depressive disorder or mood disorder.

The present invention further provides a pharmaceutical composition comprising an amount of any of the compounds of the present invention, or a salt or ester thereof, and an amount of a DOR agonist for use in treating a subject afflicted with a depressive disorder or mood disorder.

The present invention also provides a method of treating a subject afflicted with pain comprising administering to the subject an effective amount of an NMDA receptor antagonist and an effective amount of any compound of the present invention, or a salt or ester thereof, so as to thereby treat the subject.

The present invention also provides a compound of the present invention or a salt or ester thereof, for use as an add-on therapy or in combination with an NMDA receptor antagonist, in treating a subject afflicted with pain.

The present invention further provides a pharmaceutical composition comprising an amount of any of the compounds of the present invention, or a salt or ester thereof, and an amount of an NMDA receptor antagonist, for use in treating a subject afflicted with pain.

The present invention also provides a method of treating a subject afflicted with pain comprising administering to the subject an effective amount of an NMDA receptor partial agonist, and an effective amount of any compound of the present invention, or a salt or ester thereof, so as to thereby treat the subject.

The present invention also provides a compound of the present invention or a salt or ester thereof, for use as an add-on therapy or in combination with an NMDA receptor partial agonist in treating a subject afflicted with pain.

The present invention further provides a pharmaceutical composition comprising an amount of any of the compounds of the present invention, or a salt or ester thereof, and an amount of an NMDA receptor partial agonist, for use in treating a subject afflicted with pain.

The present invention also provides a method of treating a subject afflicted with pain comprising administering to the subject an effective amount of a neurokinin 1 receptor antagonist and an effective amount of any compound of the present invention, or a salt or ester thereof, so as to thereby treat the subject.

The present invention also provides a compound of the present invention or a salt or ester thereof, for use as an add-on therapy or in combination with a neurokinin 1 receptor antagonist in treating a subject afflicted with pain.

The present invention further provides a pharmaceutical composition comprising an amount of any of the compounds of the present invention, or a salt or ester thereof, and an amount of a neurokinin 1 receptor antagonist for use in treating a subject afflicted with pain.

The present invention also provides a method of treating a subject afflicted with pain comprising administering to the subject an effective amount of a DOR agonist and an effective amount of any compound of the present invention, or a salt or ester thereof, so as to thereby treat the subject.

The present invention also provides a compound of the present invention or a salt or ester thereof, for use as an add-on therapy or in combination with a DOR agonist in treating a subject afflicted with pain.

The present invention further provides a pharmaceutical composition comprising an amount of any of the compounds of the present invention, or a salt or ester thereof, and an amount of a DOR agonist for use in treating a subject afflicted with pain.

In any of the embodiments of the present method, compound, package, use or pharmaceutical composition the subject is afflicted with pain, depression, a depressive or mood disorder, an anxiety disorder, borderline personality disorder, opioid addiction or opioid withdrawal symptoms.

In some embodiments of the present method, compound, package, use or pharmaceutical composition, the compound has the structure:

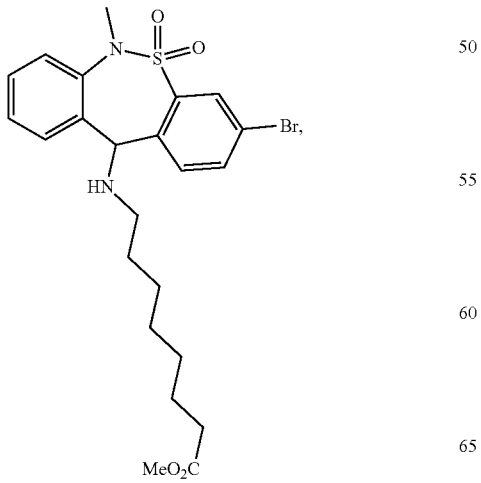

-continued

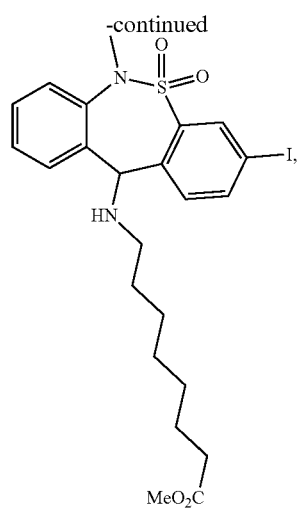

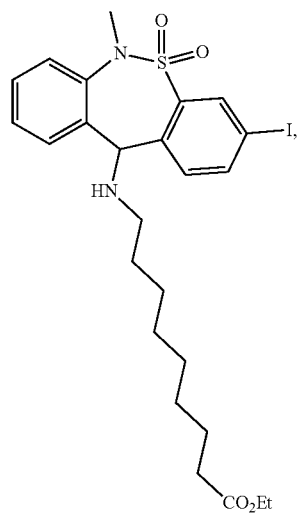

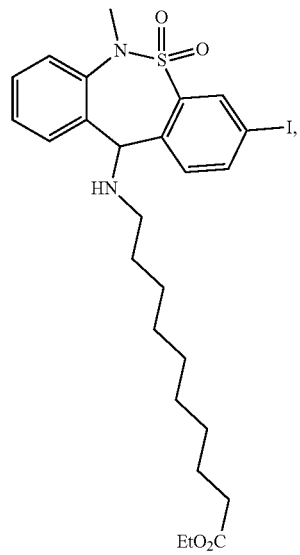

53
-continued
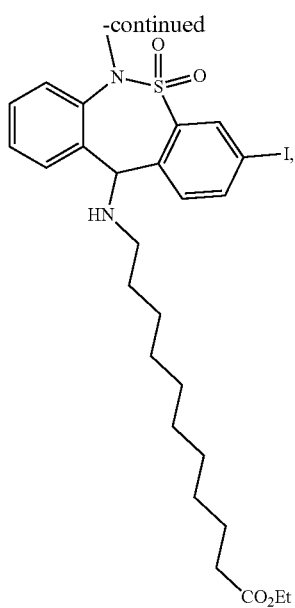
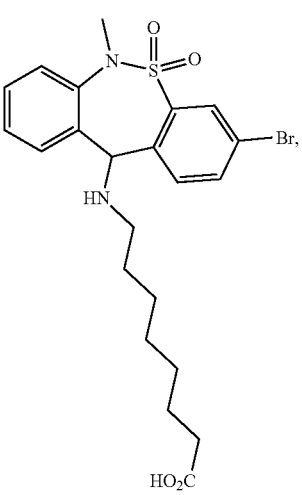
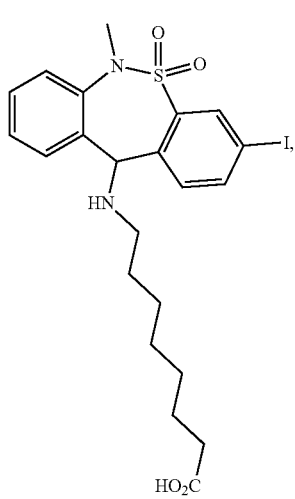
54
-continued
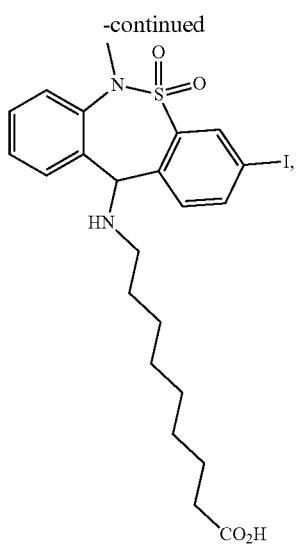
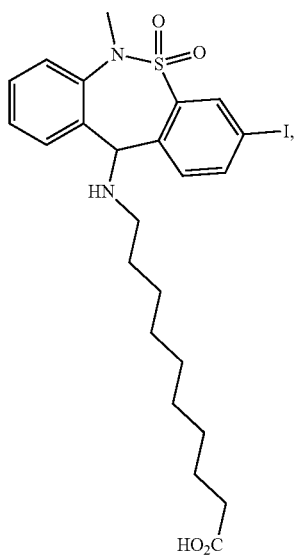
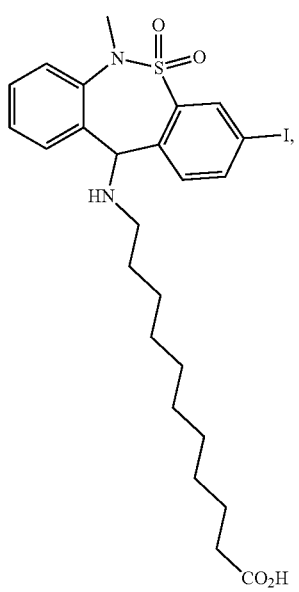

55
-continued
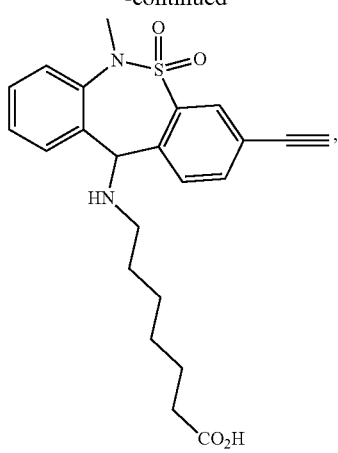
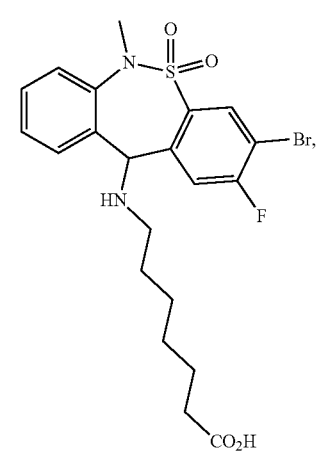
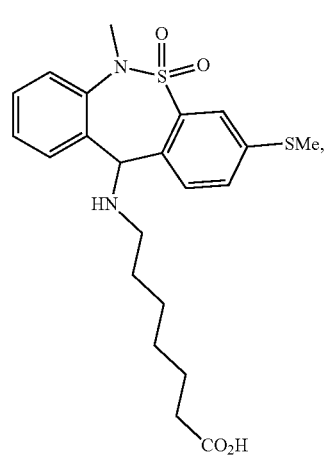
56
-continued
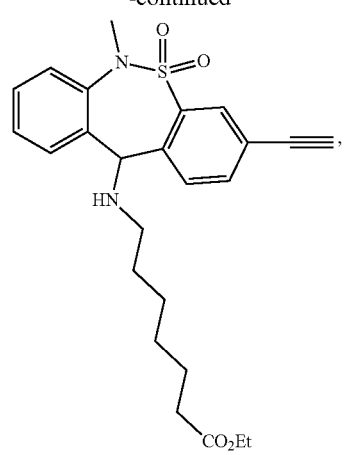
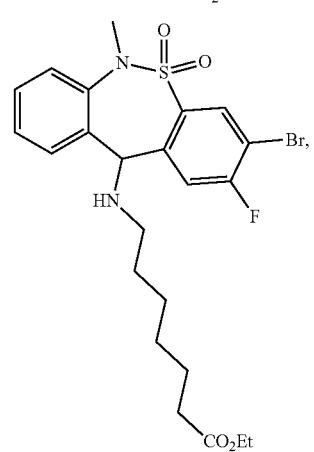
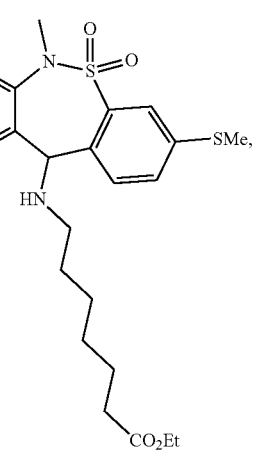
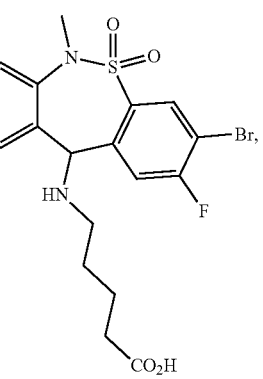

-continued
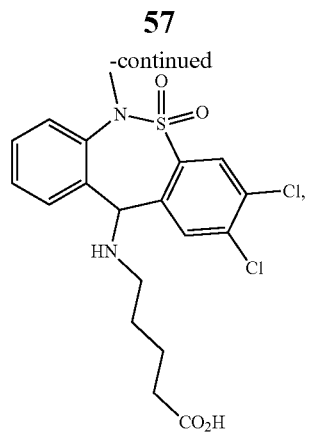
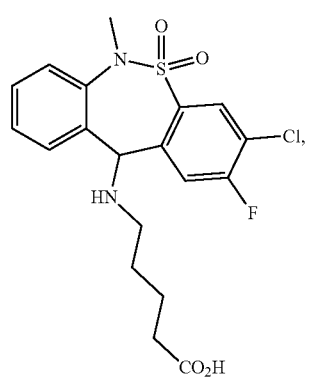
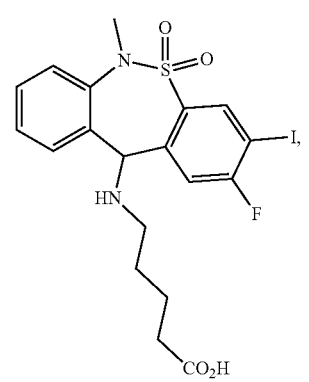
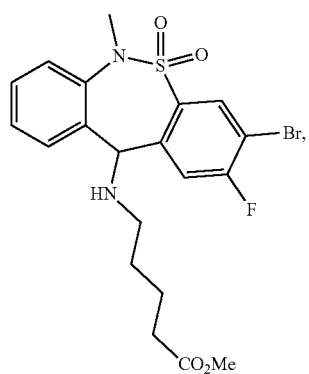
-continued
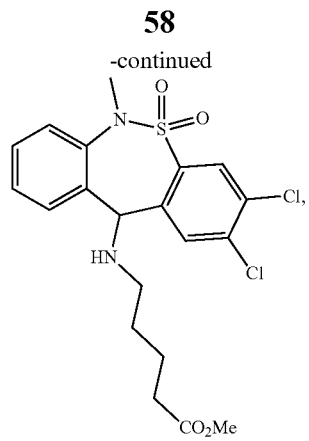
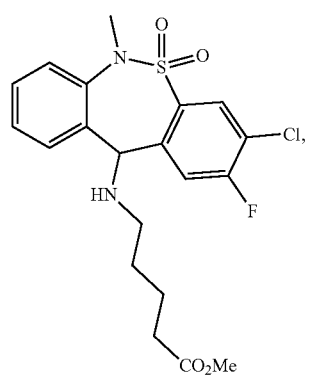
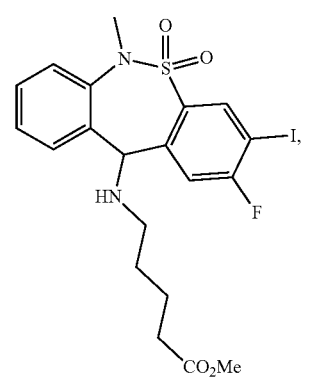
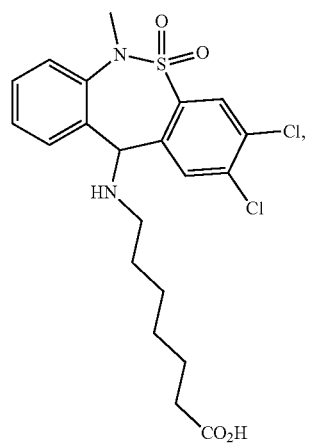

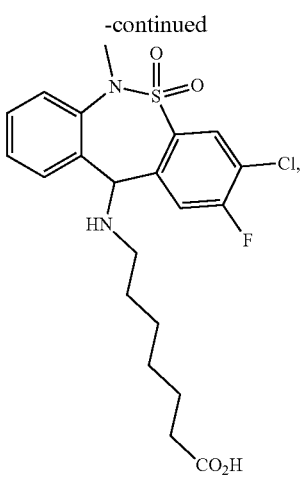
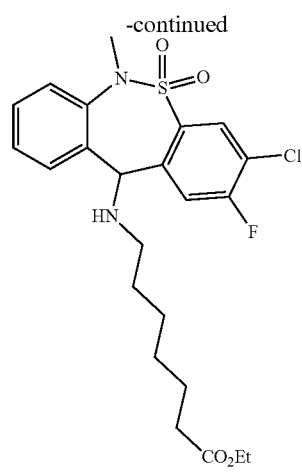
or
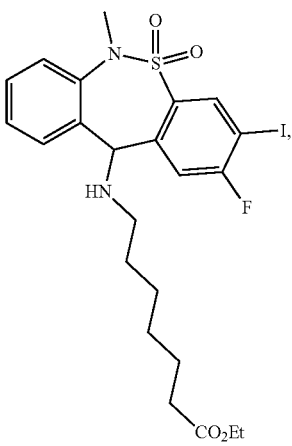
or a pharmaceutically acceptable salt or ester thereof.
In some embodiments of the present method, compound, package, use or pharmaceutical composition, the compound has the structure:
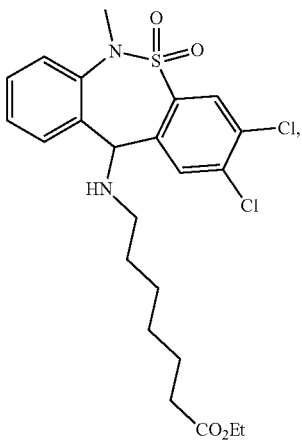
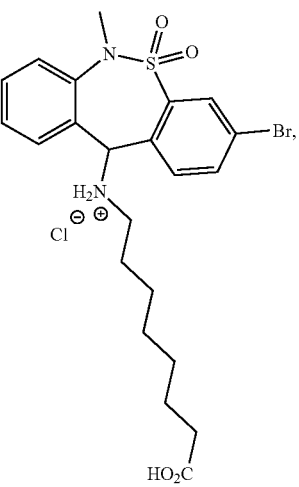

61
-continued
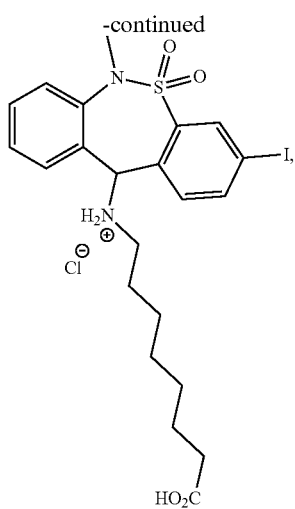
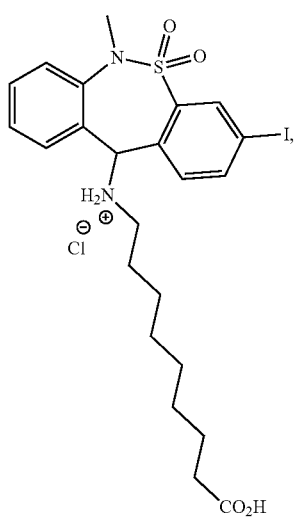
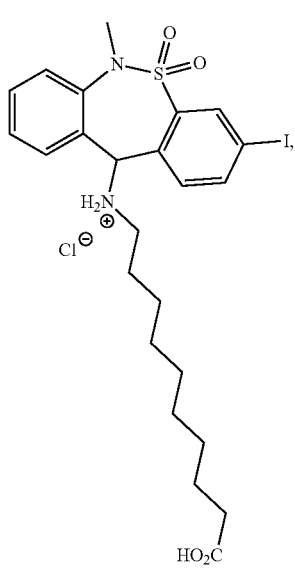
62
-continued
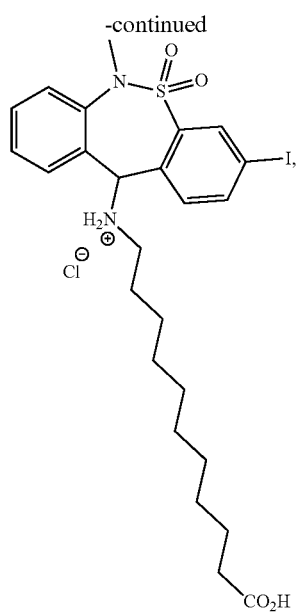
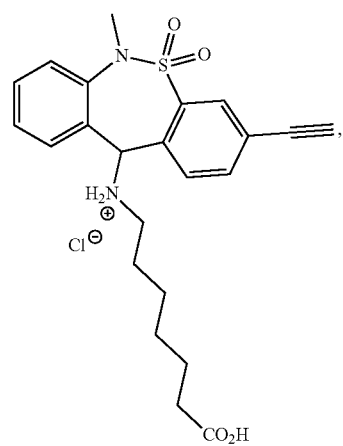
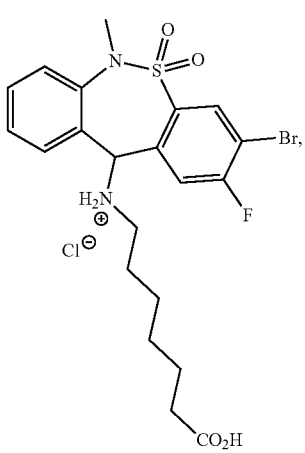

-continued
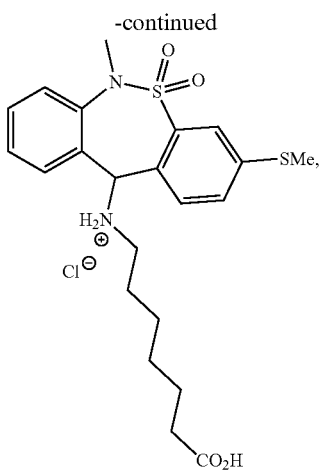
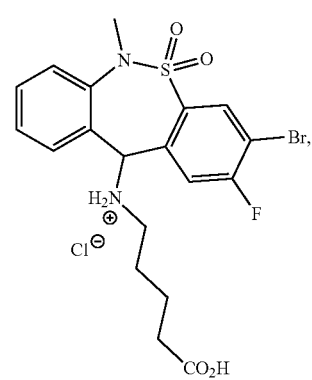
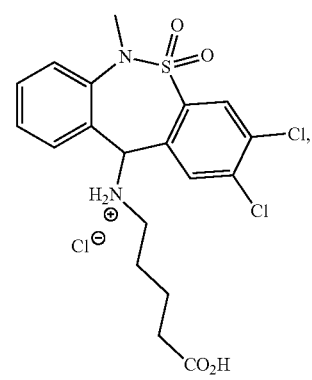
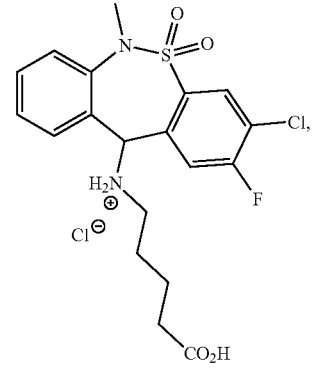
-continued
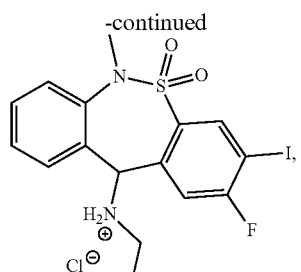
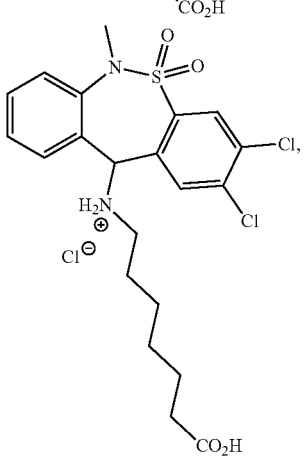
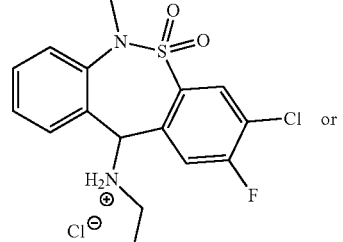
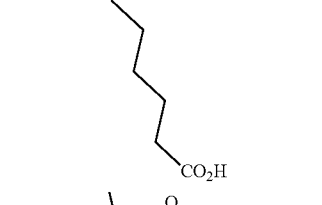 or
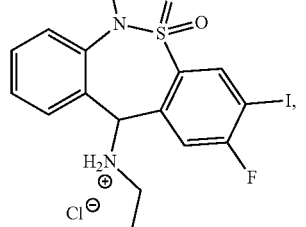
or an ester thereof.

In some embodiments, a pharmaceutically acceptable salt of any of the above compounds of the present invention.

In some embodiments, a salt of the compound of the present invention is used in any of the above methods, uses, packages or compositions.

In some embodiments, a pharmaceutically acceptable salt of the compound of the present invention is used in any of the above methods, uses, packages or compositions.

In some embodiments, an ester of the compound of the present invention is used in any of the above methods, uses, packages or compositions.

Any of the above compounds may be used in any of the disclosed methods, uses, packages or pharmaceutical compositions.

Any of the compounds used in the disclosed methods, uses, packages or pharmaceutical compositions may be replaced with any other compound disclosed in the present invention.

Any of the above generic compounds may be used in any of the disclosed methods, uses, packages or compositions.

In some embodiments, the methods, uses, packages or pharmaceutical compositions of the present invention wherein the depressive disorder includes, but is not limited to, depression, major depression, dysthymia, postpartum depression, seasonal affective disorder, atypical depression, psychotic depression, bipolar disorder, premenstrual dysphoric disorder, situational depression or adjustment disorder with depressed mood. Depressive disorders can also include other mood disorders and is not limited to the above list.

In some embodiments, the methods, uses, packages or pharmaceutical compositions of the present invention wherein the depressive disorder is cyclothymia.

In some embodiments, the methods, uses, packages or pharmaceutical compositions of the present invention wherein the anxiety disorder includes, but is not limited to, anxiety, post-traumatic stress disorder (PTSD), acute stress disorder, generalized anxiety disorder (GAD), obsessive-compulsive disorder (OCD), panic disorder, social phobia or social anxiety disorder.

In some embodiments, the methods, uses, packages or pharmaceutical compositions of the present invention wherein the pain includes, but is not limited to, chronic pain or acute pain.

In some embodiments, the methods, uses, packages or pharmaceutical compositions wherein the opioid addiction includes, but is not limited to, addiction to codeine, hydrocodone, morphine, oxycodone, hydromorphone, oxymorphone, fentanyl or heroin.

In some embodiments, the methods, uses, packages or pharmaceutical compositions wherein the opioid withdrawal symptoms include, but are not limited to, agitation, anxiety, muscle aches, increased tearing, insomnia, runny nose, sweating, yawning, abdominal cramping, diarrhea, dilated pupils, goose bumps, nausea or vomiting.

In some embodiments, the NMDA receptor antagonist is an arylcyclohexylamine, dextromorphinan or adamantane.

In some embodiments, the NMDA receptor antagonist is dextromethorphan, dextrorphan, dextrallorphan, memantine, amantadine, rimantadine, nitromemantine (YQW-36), ketamine (and its analogs, e.g. tiletamine), phencyclidine (and its analogs, e.g. tenocyclidine, eticyclidine, rolicyclidine), methoxetamine (and its analogs), gacyclidine (GK-11), neramexane, lanicemine (AZD6765), diphenidine, dizocilpine (MK-801), 8a-phenyldecahydroquinoline (8A-PDHQ), remacemide, ifenprodil, traxoprodil (CP-101,606), eliprodil (SL-82.0715), etoxadrol (CL-1848C), dexoxadrol, WMS-2539, NEFA, delucemine (NPS-1506), aptiganel (Cerestat; CNS-1102), midafotel (CPPene; SDZ EAA 494), dexanabinol (HU-211 or ETS2101), selfotel (CGS-19755), 7-chlorokynurenic acid (7-CKA), 5,7-dichlorokynurenic acid (5,7-DCKA), L-683344, L-689560, L-701324, GV150526A, GV196771A, CERC-301 (formerly MK-0657), atomoxetine, LY-235959, CGP 61594, CGP 37849, CGP 40116 (active enantiomer of CG 37849), LY-233536, PEAQX (NVP-AAM077), ibogaine, noribogaine, Ro 25-6981, GW468816, EVT-101, indantadol, perzinfotel (EAA-090), SSR240600, 2-MDP (U-23807A) or AP-7.

In some embodiments, the NMDA receptor partial agonist is NRX-1074 or rapastinel (GLYX-13).

In some embodiments, the neurokinin 1 receptor antagonist is aprepitant, fosaprepitant, casopitant, maropitant, vestipitant, vofopitant, lanepitant, orvepitant, ezlopitant, netupitant, rolapitant, L-733060, L-703606, L-759274, L-822429, L-760735, L-741671, L-742694, L-732138, CP-122721, RPR-100893, CP-96345, CP-99994, TAK-637, T-2328, CJ-11974, RP 67580, NKP608, VPD-737, GR 205171, LY686017, AV608, SR140333B, SSR240600C, FK 888 or GR 82334.

In some embodiments, the neurokinin 2 receptor antagonist is saredutant, ibodutant, nepadutant, GR-159897 or MEN-10376.

In some embodiments, the neurokinin 3 receptor antagonist is osanetant, talnetant, SB-222200 or SB-218795.

In some embodiments, the DOR agonist is tianeptine, (+)BW373U86, SNC-80, SNC-121, SNC-162, DPI-287, DPI-3290, DPI-221, TAN-67, KN-127, AZD2327, JNJ-20788560, NIH11082, RWJ-394674, ADL5747, ADL5859, UFP-512, AR-M100390, SB-235863 or 7-spiroindanyloxymorphone.

The term "MOR agonist" is intended to mean any compound or substance that activates the mu-opioid receptor (MOR). The agonist may be a partial, full or super agonist.

The term "DOR agonist" is intended to mean any compound or substance that activates the delta-opioid receptor (DOR). The agonist may be a partial, full or super agonist.

The term "super agonist" is intended to mean a compound or substance that activates a receptor with a greater maximal response (higher $E_{max}$) than said receptor's primary endogenous ligand.

In some embodiments, the compound is prepared by the following process:

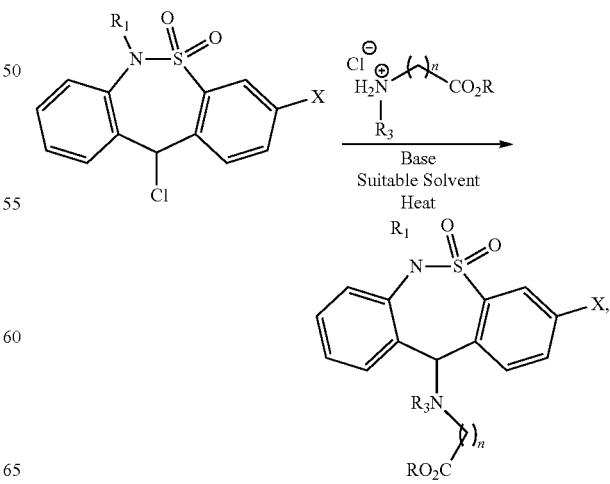

wherein R is -(alkyl); $R_1$ is —H or -(alkyl); $R_3$ is —H or -(alkyl); X=Br, I, —SMe, —CH=$CH_2$, or —C≡CH; and n=7-20.

In some embodiments, the compound is prepared by the following process:

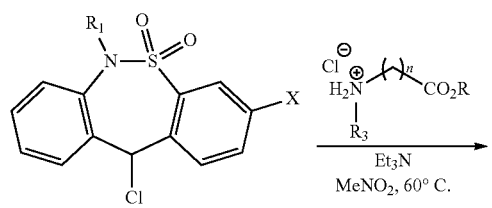

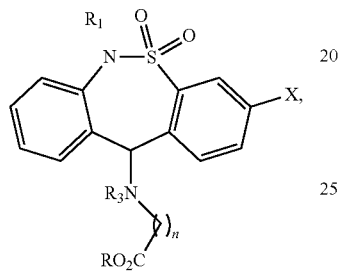

wherein R is -(alkyl); $R_1$ is —H or -(alkyl); $R_3$ is —H or -(alkyl); X=Br, I, —SMe, —CH=$CH_2$, or —C≡CH; and n=7-20.

In some embodiments, the compound is prepared by the following process:

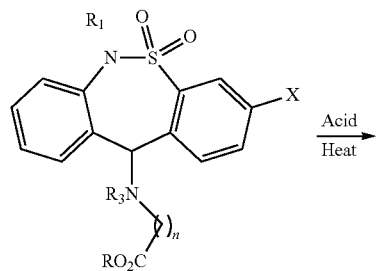

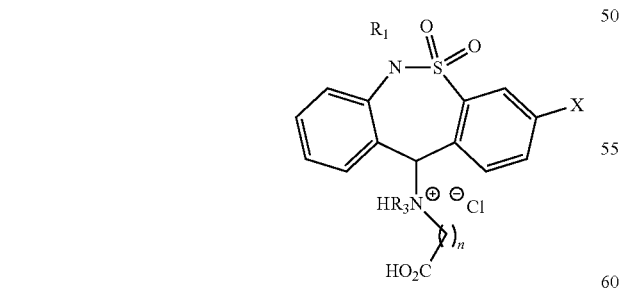

wherein R is -(alkyl); $R_1$ is —H or -(alkyl); $R_3$ is —H or -(alkyl); X=Br, I, —SMe, —CH=$CH_2$, or —C≡CH; and n=7-20.

In one embodiment of the above process, the acid is aqueous acid.

In some embodiments, the compound is prepared by the following process:

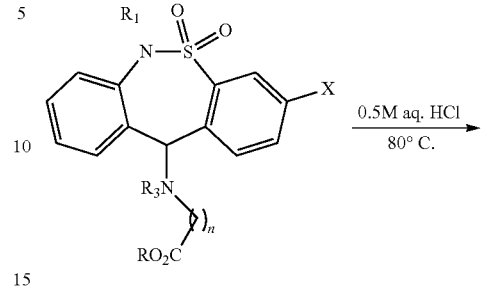

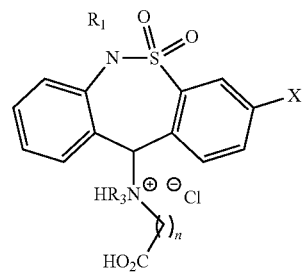

wherein R is -(alkyl); $R_1$ is —H or -(alkyl); $R_3$ is —H or -(alkyl); X=Br, I, —SMe, —CH=$CH_2$, or —C≡CH; and n=7-20.

In some embodiments, the compound is prepared by the following process:

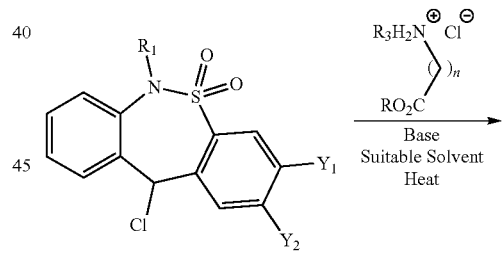

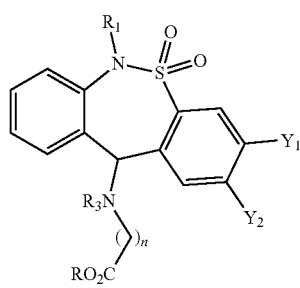

wherein R is -(alkyl); $R_1$ is —H or -(alkyl); $Y_1$=Cl, Br or I; $Y_2$=F, Cl, Br or I; and n=7-20.

In some embodiments, the compound is prepared by the following process:

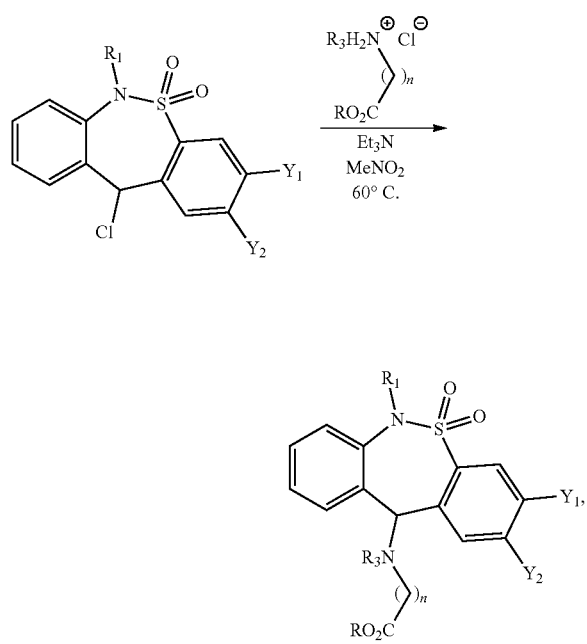

wherein R is -(alkyl); $R_1$ is —H or -(alkyl); $R_3$ is —H or -(alkyl); $Y_1$=Cl, Br or I; $Y_2$=F, Cl, Br or I; and n=7-20.

In some embodiments, the compound is prepared by the following process:

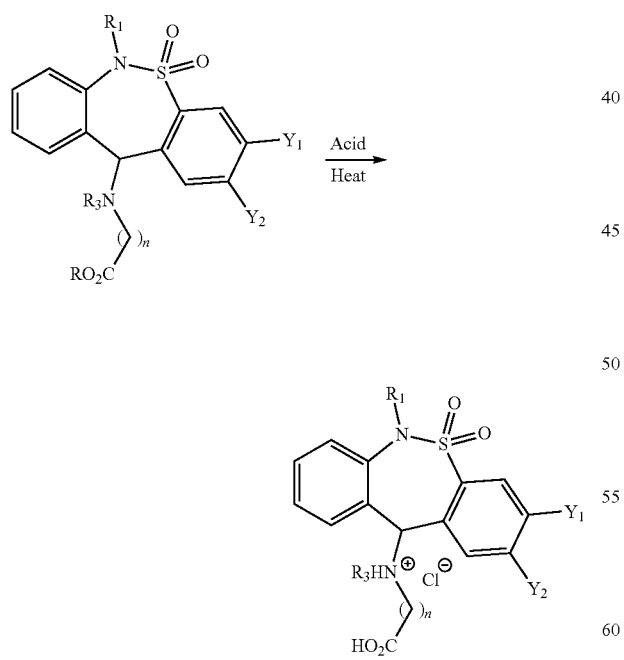

wherein R is -(alkyl); $R_1$ is —H or -(alkyl); $R_3$ is —H or -(alkyl); $Y_1$=Cl, Br or I; $Y_2$=F, Cl, Br or I; and n=7-20.

In one embodiment of the above process, the acid is aqueous acid.

In some embodiments, the compound is prepared by the following process:

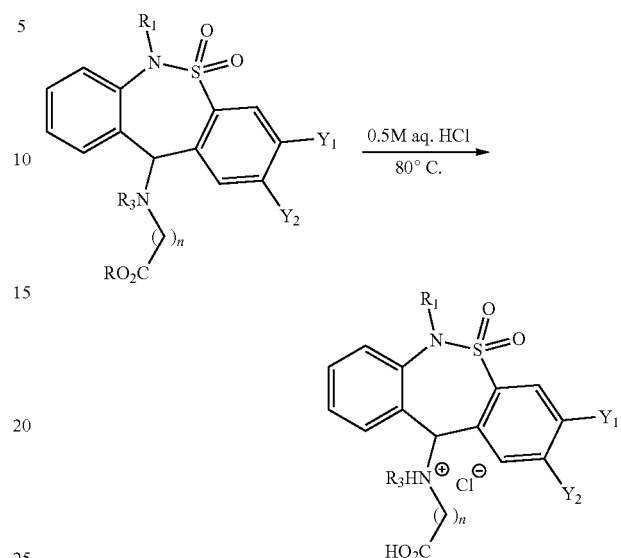

wherein R is -(alkyl); $R_1$ is —H or -(alkyl); $R_3$ is —H or -(alkyl); $Y_1$=Cl, Br or I; $Y_2$=F, Cl, Br or I; and n=7-20.

In one embodiment, wherein when F is present in the compound, the F is $^{18}$F.

In one embodiment, wherein when F is present in the compound at $R_6$, the F is $^{18}$F.

In some embodiments, the compound having the structure,

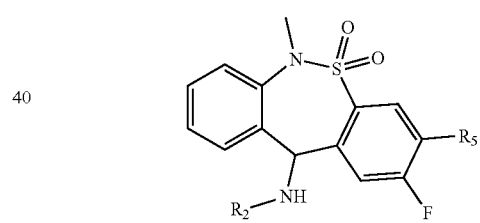

wherein
$R_5$ is Cl, Br, I, SMe or —C≡CH,
$R_2$ is —($C_{3-5}$ alkyl)-$CO_2H$ or —($C_{3-5}$ alkyl)-$CO_2$(alkyl),
wherein the F is $^{18}$F.

In some embodiments, the compound having the structure,

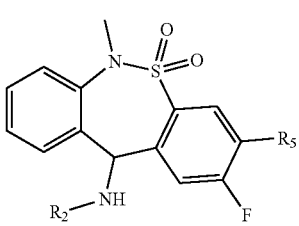

wherein
$R_5$ is Cl, Br, I, SMe or —C≡CH,
$R_2$ is —($C_6$ alkyl)-$CO_2H$ or —($C_6$ alkyl)-$CO_2$(alkyl),
wherein the F is $^{18}$F.

In some embodiments, the compound having the structure,
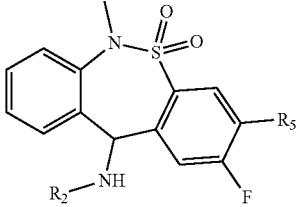
wherein
$R_5$ is Cl, Br, I, SMe or —C≡CH,
$R_2$ is —($C_{7-10}$ alkyl)-$CO_2H$ or —($C_{7-10}$ alkyl)-$CO_2$(alkyl),
wherein the F is $^{18}F$.
In some embodiments, the compound having the structure,
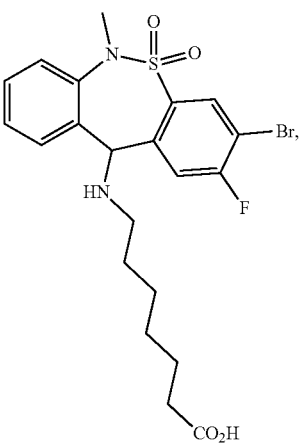
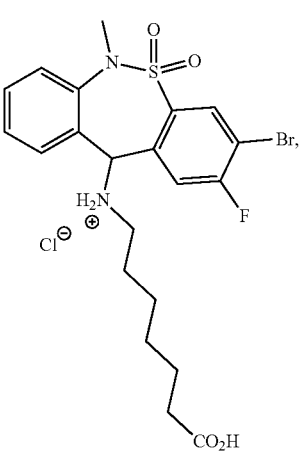
-continued
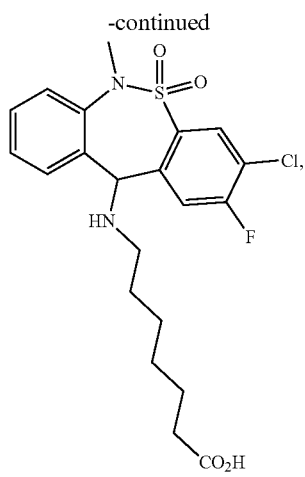
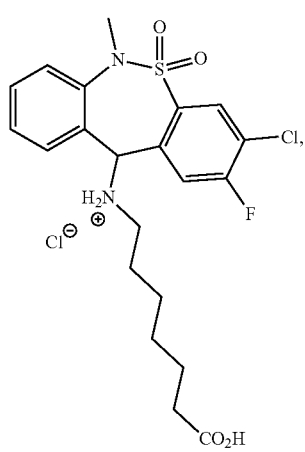
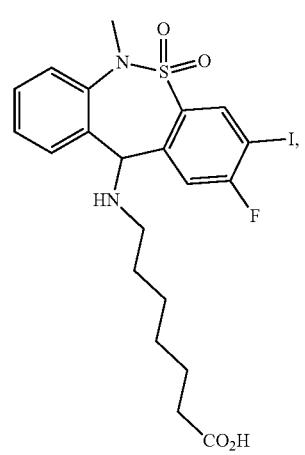

-continued
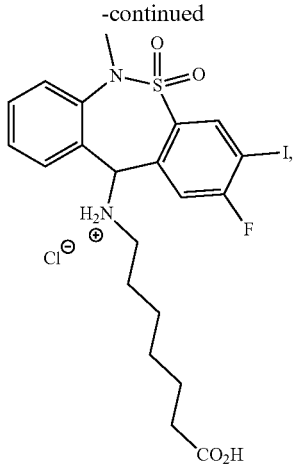
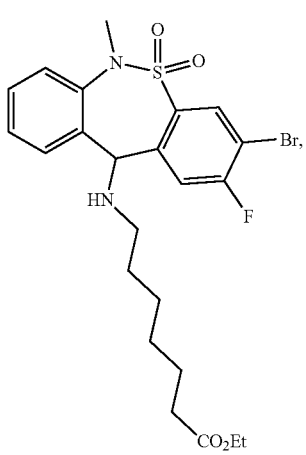
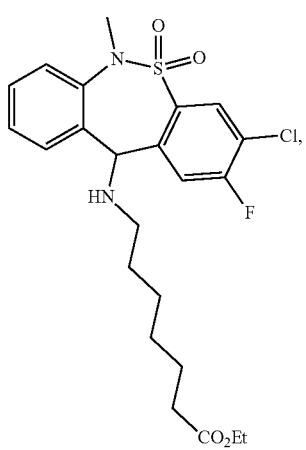
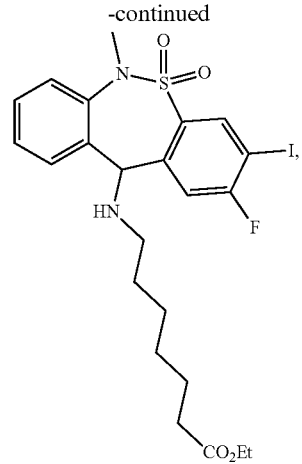
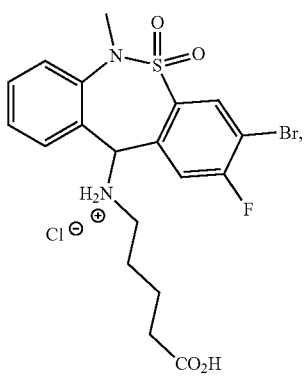
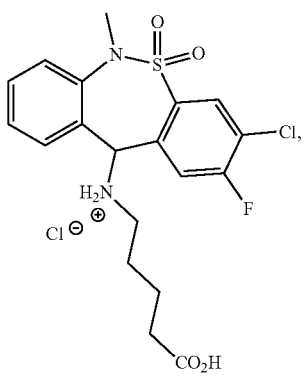
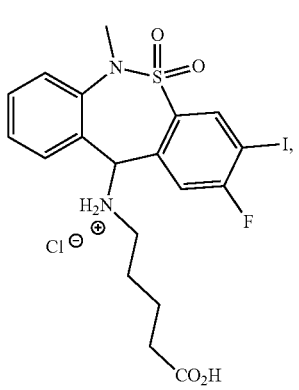

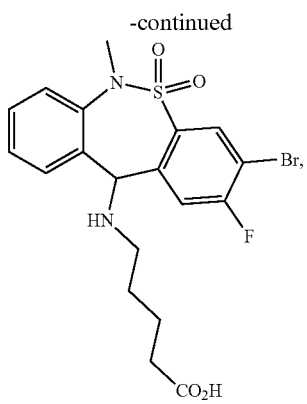

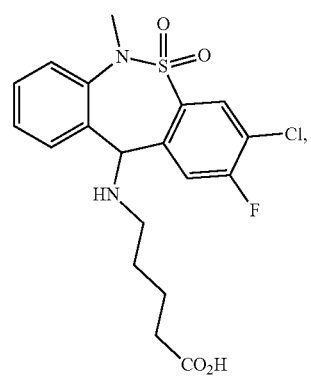

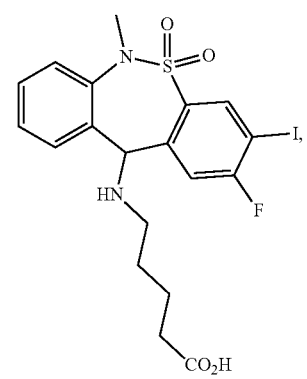

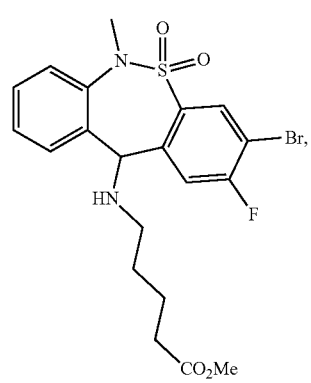

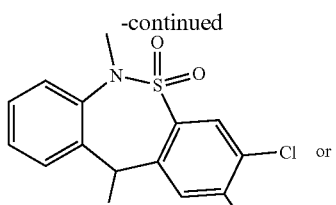

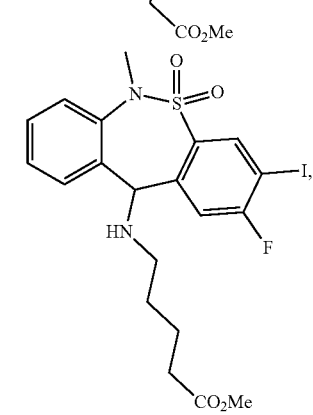

wherein the F is $^{18}$F.

In some embodiments, a pharmaceutical composition comprising the compound of the present invention containing an $^{18}$F and a pharmaceutically acceptable carrier.

In some embodiments, a pharmaceutical composition comprising the compound of the present invention containing an F, the same compound of the present invention containing an $^{18}$F, and a pharmaceutically acceptable carrier.

In some embodiments, a method of detecting the presence of mu-opioid receptors in the brain of a subject which comprises determining if an amount of the compound of the present invention containing an $^{18}$F is present in the brain of the subject at a period of time after administration of the compound or salt thereof to the subject, thereby detecting the presence of the mu-opioid receptors based on the amount of the compound determined to be present in the brain of the subject.

In some embodiments, a method of detecting the location of mu-opioid receptors in the brain of a subject which comprises determining where an amount of the compound of the present invention containing an $^{18}$F is present in the subject at a period of time after administration of the compound or salt thereof to the subject, thereby detecting the location of the mu-opioid receptors based on the location of the compound determined to be present in the subject.

In some embodiments, a method of quantifying the occupancy of mu-opioid receptors by a compound of the present invention or another compound binding to mu-opioid receptors in the brain of a subject, which comprises determining the binding competition between said compound and a second compound of the present invention containing an $^{18}$F at a period of time after administration of the compounds or salts thereof to the subject, thereby detecting the occupancy of the mu-opioid receptors based on the displacement of the compound containing $^{18}$F by the other compound.

In some embodiments, a method of quantifying the occupancy of mu-opioid receptors by endogenous opioid peptides in the brain of a subject, which comprises determining the binding competition between said endogenous opioid peptides and a compound of the present invention containing an $^{18}$F at a period of time after administration of the compound to the subject, thereby detecting the occupancy of the mu-opioid receptors based on the displacement of the compound containing $^{18}$F by the endogenous opioid peptides.

In some embodiments, the method wherein the compound binding to mu-opioid receptors in the brain of a subject is the compound of the present invention.

In some embodiments, the method wherein the compound binding to mu-opioid receptors in the brain of a subject is the compound of the present invention containing an $^{18}$F.

In some embodiments, the method further comprising quantifying the amount of the compound containing $^{18}$F in the subject and comparing the quantity to a predetermined control.

In some embodiments, the method wherein the determining is performed by a Positron Emission Tomography (PET) device.

In some embodiments, the method further comprising determining whether the subject is afflicted with a disease associated with dysregulation, up-regulation or down-regulation of mu-opioid receptor based on the amount of the compound containing $^{18}$F in the subject or its location in the subject.

In some embodiments, the method further comprising determining whether the subject is afflicted with a disease associated with dysregulation, up-regulation or down-regulation of release of endogenous opioid peptides based on displacement of the compound containing $^{18}$F from mu-opioid receptors in the subject.

In some embodiments, the method further comprising determining whether the subject is afflicted with a disease associated with dysregulation, up-regulation or down-regulation of release of endogenous opioid peptides based on displacement of the compound containing $^{18}$F from mu-opioid receptors in the subject.

In some embodiments, the method wherein the disease is a depressive disorder, a mood disorder, pain, an anxiety disorder or borderline personality disorder.

Additional synthetic methods for preparation of the disclosed compounds are found in PCT International Application No. PCT/US2015/020273, filed Mar. 12, 2015, the contents of which are hereby incorporated by reference.

Except where otherwise specified, the structure of a compound of this invention includes an asymmetric carbon atom, it is understood that the compound occurs as a racemate, racemic mixture, and isolated single enantiomer. All such isomeric forms of these compounds are expressly included in this invention. Except where otherwise specified, each stereogenic carbon may be of the R or S configuration. It is to be understood accordingly that the isomers arising from such asymmetry (e.g., all enantiomers and diastereomers) are included within the scope of this invention, unless indicated otherwise. Such isomers can be obtained in substantially pure form by classical separation techniques and by stereochemically controlled synthesis, such as those described in "Enantiomers, Racemates and Resolutions" by J. Jacques, A. Collet and S. Wilen, Pub. John Wiley & Sons, NY, 1981. For example, the resolution may be carried out by preparative chromatography on a chiral column.

The subject invention is also intended to include all isotopes of atoms occurring on the compounds disclosed herein. Isotopes include those atoms having the same atomic number but different mass numbers. By way of general example and without limitation, isotopes of hydrogen include tritium and deuterium. Isotopes of carbon include C-13 and C-14.

It will be noted that any notation of a carbon in structures throughout this application, when used without further notation, are intended to represent all isotopes of carbon, such as $^{12}$C, $^{13}$C, or $^{14}$C. Furthermore, any compounds containing $^{13}$C or $^{14}$C may specifically have the structure of any of the compounds disclosed herein.

It will also be noted that any notation of a hydrogen in structures throughout this application, when used without further notation, are intended to represent all isotopes of hydrogen, such as $^{1}$H, $^{2}$H, or $^{3}$H. Furthermore, any compounds containing $^{2}$H or $^{3}$H may specifically have the structure of any of the compounds disclosed herein.

Isotopically-labeled compounds can generally be prepared by conventional techniques known to those skilled in the art using appropriate isotopically-labeled reagents in place of the non-labeled reagents employed.

In the compounds used in the method of the present invention, the substituents may be substituted or unsubstituted, unless specifically defined otherwise.

In the compounds used in the method of the present invention, alkyl, heteroalkyl, monocycle, bicycle, aryl, heteroaryl and heterocycle groups can be further substituted by replacing one or more hydrogen atoms with alternative non-hydrogen groups. These include, but are not limited to, halo, hydroxy, mercapto, amino, carboxy, cyano and carbamoyl.

It is understood that substituents and substitution patterns on the compounds used in the method of the present invention can be selected by one of ordinary skill in the art to provide compounds that are chemically stable and that can be readily synthesized by techniques known in the art from readily available starting materials. If a substituent is itself substituted with more than one group, it is understood that these multiple groups may be on the same carbon or on different carbons, so long as a stable structure results.

In choosing the compounds used in the method of the present invention, one of ordinary skill in the art will recognize that the various substituents, i.e. $R_1$, $R_2$, etc. are to be chosen in conformity with well-known principles of chemical structure connectivity.

As used herein, "alkyl" is intended to include both branched and straight-chain saturated aliphatic hydrocarbon groups having the specified number of carbon atoms. Thus, $C_1$-$C_n$ as in "$C_1$-$C_n$ alkyl" is defined to include groups having 1, 2 . . . , n–1 or n carbons in a linear or branched arrangement, and specifically includes methyl, ethyl, propyl, butyl, pentyl, hexyl, heptyl, isopropyl, isobutyl, sec-butyl and so on. An embodiment can be $C_1$-$C_{12}$ alkyl, $C_2$-$C_{12}$ alkyl, $C_3$-$C_{12}$ alkyl, $C_4$-$C_{12}$ alkyl and so on. An embodiment can be $C_1$-$C_8$ alkyl, $C_2$-$C_8$ alkyl, $C_3$-$C_8$ alkyl, $C_4$-$C_8$ alkyl and so on. "Alkoxy" represents an alkyl group as described above attached through an oxygen bridge.

The term "alkenyl" refers to a non-aromatic hydrocarbon radical, straight or branched, containing at least 1 carbon to carbon double bond, and up to the maximum possible number of non-aromatic carbon-carbon double bonds may be present. Thus, $C_2$-$C_n$ alkenyl is defined to include groups having 1, 2 . . . , n–1 or n carbons. For example, "$C_2$-$C_6$ alkenyl" means an alkenyl radical having 2, 3, 4, 5, or 6 carbon atoms, and at least 1 carbon-carbon double bond, and up to, for example, 3 carbon-carbon double bonds in the case of a $C_6$ alkenyl, respectively. Alkenyl groups include ethenyl, propenyl, butenyl and cyclohexenyl. As described above with respect to alkyl, the straight, branched or cyclic portion of the alkenyl group may contain double bonds and may be substituted if a substituted alkenyl group is indicated. An embodiment can be $C_2$-$C_{12}$ alkenyl or $C_2$-$C_8$ alkenyl.

The term "alkynyl" refers to a hydrocarbon radical straight or branched, containing at least 1 carbon to carbon triple bond, and up to the maximum possible number of non-aromatic carbon-carbon triple bonds may be present. Thus, $C_2$-$C_n$ alkynyl is defined to include groups having 1, 2 . . . , n–1 or n carbons. For example, "$C_2$-$C_6$ alkynyl" means an alkynyl radical having 2 or 3 carbon atoms, and 1 carbon-carbon triple bond, or having 4 or 5 carbon atoms, and up to 2 carbon-carbon triple bonds, or having 6 carbon atoms, and up to 3 carbon-carbon triple bonds. Alkynyl groups include ethynyl, propynyl and butynyl. As described above with respect to alkyl, the straight or branched portion of the alkynyl group may contain triple bonds and may be substituted if a substituted alkynyl group is indicated. An embodiment can be a $C_2$-$C_n$ alkynyl. An embodiment can be $C_2$-$C_{12}$ alkynyl or $C_3$-$C_8$ alkynyl.

As used herein, "hydroxyalkyl" includes alkyl groups as described above wherein one or more bonds to hydrogen contained therein are replaced by a bond to an —OH group. In some embodiments, $C_1$-$C_{12}$ hydroxyalkyl or $C_1$-$C_5$ hydroxyalkyl. $C_1$-$C_n$ as in "$C_1$-$C_n$ alkyl" is defined to include groups having 1, 2, . . . , n–1 or n carbons in a linear or branched arrangement (e.g. $C_1$-$C_2$ hydroxyalkyl, $C_1$-$C_3$ hydroxyalkyl, $C_1$-$C_4$ hydroxyalkyl, $C_1$-$C_5$ hydroxyalkyl, or $C_1$-$C_6$ hydroxyalkyl) For example, $C_1$-$C_6$, as in "$C_1$-$C_6$ hydroxyalkyl" is defined to include groups having 1, 2, 3, 4, 5, or 6 carbons in a linear or branched alkyl arrangement wherein a hydrogen contained therein is replaced by a bond to an —OH group.

As used herein, "heteroalkyl" includes both branched and straight-chain saturated aliphatic hydrocarbon groups having the specified number of carbon atoms and at least 1 heteroatom within the chain or branch.

As used herein, "monocycle" includes any stable polyatomic carbon ring of up to 10 atoms and may be unsubstituted or substituted. Examples of such non-aromatic monocycle elements include but are not limited to: cyclobutyl, cyclopentyl, cyclohexyl, and cycloheptyl. Examples of such aromatic monocycle elements include but are not limited to: phenyl.

As used herein, "bicycle" includes any stable polyatomic carbon ring of up to 10 atoms that is fused to a polyatomic carbon ring of up to 10 atoms with each ring being independently unsubstituted or substituted. Examples of such non-aromatic bicycle elements include but are not limited to: decahydronaphthalene. Examples of such aromatic bicycle elements include but are not limited to: naphthalene.

As used herein, "aryl" is intended to mean any stable monocyclic, bicyclic or polycyclic carbon ring of up to 10 atoms in each ring, wherein at least one ring is aromatic, and may be unsubstituted or substituted. Examples of such aryl elements include but are not limited to: phenyl, p-toluenyl (4-methylphenyl), naphthyl, tetrahydro-naphthyl, indanyl, phenanthryl, anthryl or acenaphthyl. In cases where the aryl substituent is bicyclic and one ring is non-aromatic, it is understood that attachment is via the aromatic ring.

The term "heteroaryl", as used herein, represents a stable monocyclic, bicyclic or polycyclic ring of up to 10 atoms in each ring, wherein at least one ring is aromatic and contains from 1 to 4 heteroatoms selected from the group consisting of O, N and S. Bicyclic aromatic heteroaryl groups include phenyl, pyridine, pyrimidine or pyridazine rings that are (a) fused to a 6-membered aromatic (unsaturated) heterocyclic ring having one nitrogen atom; (b) fused to a 5- or 6-membered aromatic (unsaturated) heterocyclic ring having two nitrogen atoms; (c) fused to a 5-membered aromatic (unsaturated) heterocyclic ring having one nitrogen atom together with either one oxygen or one sulfur atom; or (d) fused to a 5-membered aromatic (unsaturated) heterocyclic ring having one heteroatom selected from O, N or S. Heteroaryl groups within the scope of this definition include but are not limited to: benzoimidazolyl, benzofuranyl, benzofurazanyl, benzopyrazolyl, benzotriazolyl, benzothiophenyl, benzoxazolyl, carbazolyl, carbolinyl, cinnolinyl, furanyl, indolinyl, indolyl, indolazinyl, indazolyl, isobenzofuranyl, isoindolyl, isoquinolyl, isothiazolyl, isoxazolyl, naphthpyridinyl, oxadiazolyl, oxazolyl, oxazoline, isoxazoline, oxetanyl, pyranyl, pyrazinyl, pyrazolyl, pyridazinyl, pyridopyridinyl, pyridazinyl, pyridyl, pyrimidyl, pyrrolyl, quinazolinyl, quinolyl, quinoxalinyl, tetrazolyl, tetrazolopyridyl, thiadiazolyl, thiazolyl, thienyl, triazolyl, azetidinyl, aziridinyl, 1,4-dioxanyl, hexahydroazepinyl, dihydrobenzoimidazolyl, dihydrobenzofuranyl, dihydrobenzothiophenyl, dihydrobenzoxazolyl, dihydrofuranyl, dihydroimidazolyl, dihydroindolyl, dihydroisooxazolyl, dihydroisothiazolyl, dihydrooxadiazolyl, dihydrooxazolyl, dihydropyrazinyl, dihydropyrazolyl, dihydropyridinyl, dihydropyrimidinyl, dihydropyrrolyl, dihydroquinolinyl, dihydrotetrazolyl, dihydrothiadiazolyl, dihydrothiazolyl, dihydrothienyl, dihydrotriazolyl, dihydroazetidinyl, methylenedioxybenzoyl, tetrahydrofuranyl, tetrahydrothienyl, acridinyl, carbazolyl, cinnolinyl, quinoxalinyl, pyrrazolyl, indolyl, benzotriazolyl, benzothiazolyl, benzoxazolyl, isoxazolyl, isothiazolyl, furanyl, thienyl, benzothienyl, benzofuranyl, quinolinyl, isoquinolinyl, oxazolyl, isoxazolyl, indolyl, pyrazinyl, pyridazinyl, pyridinyl, pyrimidinyl, pyrrolyl, tetra-hydroquinoline. In cases where the heteroaryl substituent is bicyclic and one ring is non-aromatic or contains no heteroatoms, it is understood that attachment is via the aromatic ring or via the heteroatom containing ring, respectively. If the heteroaryl contains nitrogen atoms, it is understood that the corresponding N-oxides thereof are also encompassed by this definition.

The term "heterocycle", "heterocyclyl" or "heterocyclic" refers to a mono- or poly-cyclic ring system which can be saturated or contains one or more degrees of unsaturation and contains one or more heteroatoms. Preferred heteroatoms include N, O, and/or S, including N-oxides, sulfur oxides, and dioxides. Preferably the ring is three to ten-membered and is either saturated or has one or more degrees of unsaturation. The heterocycle may be unsubstituted or substituted, with multiple degrees of substitution being allowed. Such rings may be optionally fused to one or more of another "heterocyclic" ring(s), heteroaryl ring(s), aryl ring(s), or cycloalkyl ring(s). Examples of heterocycles include, but are not limited to, tetrahydrofuran, pyran, 1,4-dioxane, 1,3-dioxane, piperidine, piperazine, pyrrolidine, morpholine, thiomorpholine, tetrahydrothiopyran, tetrahydrothiophene, 1,3-oxathiolane, and the like.

The term "ester" is intended to a mean an organic compound containing the R—O—CO—R' group.

The term "substitution", "substituted" and "substituent" refers to a functional group as described above in which one or more bonds to a hydrogen atom contained therein are replaced by a bond to non-hydrogen or non-carbon atoms, provided that normal valencies are maintained and that the substitution results in a stable compound. Substituted groups also include groups in which one or more bonds to a carbon(s) or hydrogen(s) atom are replaced by one or more bonds, including double or triple bonds, to a heteroatom.

Examples of substituent groups include the functional groups described above, and halogens (i.e., F, Cl, Br, and I); alkyl groups, such as methyl, ethyl, n-propyl, isopropryl, n-butyl, tert-butyl, and trifluoromethyl; hydroxyl; alkoxy groups, such as methoxy, ethoxy, n-propoxy, and isopropoxy; aryloxy groups, such as phenoxy; arylalkyloxy, such as benzyloxy (phenylmethoxy) and p-trifluoromethylbenzyloxy (4-trifluoromethylphenylmethoxy); heteroaryloxy groups; sulfonyl groups, such as trifluoromethanesulfonyl, methanesulfonyl, and p-toluenesulfonyl; nitro, nitrosyl; mercapto; sulfanyl groups, such as methylsulfanyl, ethylsulfanyl and propylsulfanyl; cyano; amino groups, such as amino, methylamino, dimethylamino, ethylamino, and diethylamino; and carboxyl. Where multiple substituent moieties are disclosed or claimed, the substituted compound can be independently substituted by one or more of the disclosed or claimed substituent moieties, singly or plurally. By independently substituted, it is meant that the (two or more) substituents can be the same or different.

The compounds used in the method of the present invention may be prepared by techniques well known in organic synthesis and familiar to a practitioner ordinarily skilled in the art. However, these may not be the only means by which to synthesize or obtain the desired compounds.

The compounds used in the method of the present invention may be prepared by techniques described in Vogel's Textbook of Practical Organic Chemistry, A. I. Vogel, A. R. Tatchell, B. S. Furnis, A. J. Hannaford, P. W. G. Smith, (Prentice Hall) $5^{th}$ Edition (1996), March's Advanced Organic Chemistry: Reactions, Mechanisms, and Structure, Michael B. Smith, Jerry March, (Wiley-Interscience) $5^{th}$ Edition (2007), and references therein, which are incorporated by reference herein. However, these may not be the only means by which to synthesize or obtain the desired compounds.

The various R groups attached to the aromatic rings of the compounds disclosed herein may be added to the rings by standard procedures, for example those set forth in Advanced Organic Chemistry: Part B: Reactions and Synthesis, Francis Carey and Richard Sundberg, (Springer) 5th ed. Edition. (2007), the content of which is hereby incorporated by reference.

Another aspect of the invention comprises a compound used in the method of the present invention as a pharmaceutical composition.

As used herein, the term "pharmaceutically active agent" means any substance or compound suitable for administration to a subject and furnishes biological activity or other direct effect in the treatment, cure, mitigation, diagnosis, or prevention of disease, or affects the structure or any function of the subject. Pharmaceutically active agents include, but are not limited to, substances and compounds described in the Physicians' Desk Reference (PDR Network, LLC; 64th edition; Nov. 15, 2009) and "Approved Drug Products with Therapeutic Equivalence Evaluations" (U.S. Department Of Health And Human Services, $30^{th}$ edition, 2010), which are hereby incorporated by reference. Pharmaceutically active agents which have pendant carboxylic acid groups may be modified in accordance with the present invention using standard esterification reactions and methods readily available and known to those having ordinary skill in the art of chemical synthesis. Where a pharmaceutically active agent does not possess a carboxylic acid group, the ordinarily skilled artisan will be able to design and incorporate a carboxylic acid group into the pharmaceutically active agent where esterification may subsequently be carried out so long as the modification does not interfere with the pharmaceutically active agent's biological activity or effect.

The compounds used in the method of the present invention may be in a salt form. As used herein, a "salt" is a salt of the instant compounds which has been modified by making acid or base salts of the compounds. In the case of compounds used to treat an infection or disease caused by a pathogen, the salt is pharmaceutically acceptable. Examples of pharmaceutically acceptable salts include, but are not limited to, mineral or organic acid salts of basic residues such as amines; alkali or organic salts of acidic residues such as phenols; alkali or organic salts of acidic residues such as carboxylic acids. The salts can be made using an organic or inorganic acid. Such acid salts are chlorides, bromides, sulfates, nitrates, phosphates, sulfonates, formates, tartrates, maleates, malates, citrates, benzoates, salicylates, ascorbates, and the like. Phenolate salts are the alkali metal salts, sodium, potassium or lithium. The salts can be made using an organic or inorganic base. Such basic salts are alkali metal salts, such as sodium, potassium or lithium and alkaline earth metal salts, such as magnesium and calcium.

The term "pharmaceutically acceptable salt" in this respect, refers to the relatively non-toxic, inorganic and organic acid or base addition salts of compounds of the present invention. These salts can be prepared in situ during the final isolation and purification of the compounds of the invention, or by separately reacting a purified compound of the invention in its free base or free acid form with a suitable organic or inorganic acid or base, and isolating the salt thus formed. Representative salts include the hydrobromide, hydrochloride, sulfate, bisulfate, phosphate, nitrate, acetate, valerate, oleate, palmitate, stearate, laurate, benzoate, lactate, phosphate, tosylate, citrate, maleate, fumarate, succinate, tartrate, napthylate, mesylate, glucoheptonate, lactobionate, and laurylsulphonate salts and the like. Representative salts also include the sodium, potassium, lithium, magnesium and calcium salts and the like. (See, e.g., Berge et al. (1977) "Pharmaceutical Salts", *J. Pharm. Sci.* 66:1-19).

As used herein, "treating" means preventing, slowing, halting, or reversing the progression of a disease or infection. Treating may also mean improving one or more symptoms of a disease or infection.

The compounds used in the method of the present invention may be administered in various forms, including those detailed herein. The treatment with the compound may be a component of a combination therapy or an adjunct therapy, i.e. the subject or patient in need of the drug is treated or given another drug for the disease in conjunction with one or more of the instant compounds. This combination therapy can be sequential therapy where the patient is treated first with one drug and then the other or the two drugs are given simultaneously. These can be administered independently by the same route or by two or more different routes of administration depending on the dosage forms employed.

As used herein, a "pharmaceutically acceptable carrier" is a pharmaceutically acceptable solvent, suspending agent or vehicle, for delivering the instant compounds to the animal or human. The carrier may be liquid or solid and is selected with the planned manner of administration in mind. Liposomes are also a pharmaceutically acceptable carrier.

The dosage of the compounds administered in treatment will vary depending upon factors such as the pharmacodynamic characteristics of a specific chemotherapeutic agent and its mode and route of administration; the age, sex, metabolic rate, absorptive efficiency, health and weight of the recipient; the nature and extent of the symptoms; the kind of concurrent treatment being administered; the frequency of treatment with; and the desired therapeutic effect.

A dosage unit of the compounds used in the method of the present invention may comprise a single compound or mixtures thereof with additional antibacterial agents. The compounds can be administered in oral dosage forms as tablets, capsules, pills, powders, granules, elixirs, tinctures, suspensions, syrups, and emulsions. The compounds may also be administered in intravenous (bolus or infusion), intraperitoneal, subcutaneous, or intramuscular form, or introduced directly, e.g. by injection, topical application, or other methods, into or onto a site of infection, all using dosage forms well known to those of ordinary skill in the pharmaceutical arts.

The compounds used in the method of the present invention can be administered in admixture with suitable pharmaceutical diluents, extenders, excipients, or carriers (collectively referred to herein as a pharmaceutically acceptable carrier) suitably selected with respect to the intended form of administration and as consistent with conventional pharmaceutical practices. The unit will be in a form suitable for oral, rectal, topical, intravenous or direct injection or parenteral administration. The compounds can be administered alone or mixed with a pharmaceutically acceptable carrier. This carrier can be a solid or liquid, and the type of carrier is generally chosen based on the type of administration being used. The active agent can be co-administered in the form of a tablet or capsule, liposome, as an agglomerated powder or in a liquid form. Examples of suitable solid carriers include lactose, sucrose, gelatin and agar. Capsule or tablets can be easily formulated and can be made easy to swallow or chew; other solid forms include granules, and bulk powders. Tablets may contain suitable binders, lubricants, diluents, disintegrating agents, coloring agents, flavoring agents, flow-inducing agents, and melting agents. Examples of suitable liquid dosage forms include solutions or suspensions in water, pharmaceutically acceptable fats and oils, alcohols or other organic solvents, including esters, emulsions, syrups or elixirs, suspensions, solutions and/or suspensions reconstituted from non-effervescent granules and effervescent preparations reconstituted from effervescent granules. Such liquid dosage forms may contain, for example, suitable solvents, preservatives, emulsifying agents, suspending agents, diluents, sweeteners, thickeners, and melting agents. Oral dosage forms optionally contain flavorants and coloring agents. Parenteral and intravenous forms may also include minerals and other materials to make them compatible with the type of injection or delivery system chosen.

Techniques and compositions for making dosage forms useful in the present invention are described in the following references: 7 Modern Pharmaceutics, Chapters 9 and 10 (Banker & Rhodes, Editors, 1979); Pharmaceutical Dosage Forms: Tablets (Lieberman et al., 1981); Ansel, Introduction to Pharmaceutical Dosage Forms 2nd Edition (1976); Remington's Pharmaceutical Sciences, 17th ed. (Mack Publishing Company, Easton, Pa., 1985); Advances in Pharmaceutical Sciences (David Ganderton, Trevor Jones, Eds., 1992); Advances in Pharmaceutical Sciences Vol. 7. (David Ganderton, Trevor Jones, James McGinity, Eds., 1995); Aqueous Polymeric Coatings for Pharmaceutical Dosage Forms (Drugs and the Pharmaceutical Sciences, Series 36 (James McGinity, Ed., 1989); Pharmaceutical Particulate Carriers: Therapeutic Applications: Drugs and the Pharmaceutical Sciences, Vol 61 (Alain Rolland, Ed., 1993); Drug Delivery to the Gastrointestinal Tract (Ellis Horwood Books in the Biological Sciences. Series in Pharmaceutical Technology; J. G. Hardy, S. S. Davis, Clive G. Wilson, Eds.); Modern Pharmaceutics Drugs and the Pharmaceutical Sciences, Vol 40 (Gilbert S. Banker, Christopher T. Rhodes, Eds.). All of the aforementioned publications are incorporated by reference herein.

Tablets may contain suitable binders, lubricants, disintegrating agents, coloring agents, flavoring agents, flow-inducing agents, and melting agents. For instance, for oral administration in the dosage unit form of a tablet or capsule, the active drug component can be combined with an oral, non-toxic, pharmaceutically acceptable, inert carrier such as lactose, gelatin, agar, starch, sucrose, glucose, methyl cellulose, magnesium stearate, dicalcium phosphate, calcium sulfate, mannitol, sorbitol and the like. Suitable binders include starch, gelatin, natural sugars such as glucose or beta-lactose, corn sweeteners, natural and synthetic gums such as acacia, tragacanth, or sodium alginate, carboxymethylcellulose, polyethylene glycol, waxes, and the like. Lubricants used in these dosage forms include sodium oleate, sodium stearate, magnesium stearate, sodium benzoate, sodium acetate, sodium chloride, and the like. Disintegrators include, without limitation, starch, methyl cellulose, agar, bentonite, xanthan gum, and the like.

The compounds used in the method of the present invention may also be administered in the form of liposome delivery systems, such as small unilamellar vesicles, large unilamallar vesicles, and multilamellar vesicles. Liposomes can be formed from a variety of phospholipids, such as cholesterol, stearylamine, or phosphatidylcholines. The compounds may be administered as components of tissue-targeted emulsions.

The compounds used in the method of the present invention may also be coupled to soluble polymers as targetable drug carriers or as a prodrug. Such polymers include polyvinylpyrrolidone, pyran copolymer, polyhydroxylpropyl-methacrylamide-phenol, polyhydroxyethylasparta-midephenol, or polyethyleneoxide-polylysine substituted with palmitoyl residues. Furthermore, the compounds may be coupled to a class of biodegradable polymers useful in achieving controlled release of a drug, for example, polylactic acid, polyglycolic acid, copolymers of polylactic and polyglycolic acid, polyepsilon caprolactone, polyhydroxy butyric acid, polyorthoesters, polyacetals, polydihydropyrans, polycyanoacylates, and crosslinked or amphipathic block copolymers of hydrogels.

Gelatin capsules may contain the active ingredient compounds and powdered carriers, such as lactose, starch, cellulose derivatives, magnesium stearate, stearic acid, and the like. Similar diluents can be used to make compressed tablets. Both tablets and capsules can be manufactured as immediate release products or as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract.

For oral administration in liquid dosage form, the oral drug components are combined with any oral, non-toxic, pharmaceutically acceptable inert carrier such as ethanol, glycerol, water, and the like. Examples of suitable liquid dosage forms include solutions or suspensions in water, pharmaceutically acceptable fats and oils, alcohols or other organic solvents, including esters, emulsions, syrups or elixirs, suspensions, solutions and/or suspensions reconstituted from non-effervescent granules and effervescent preparations reconstituted from effervescent granules. Such liquid dosage forms may contain, for example, suitable solvents, preservatives, emulsifying agents, suspending agents, diluents, sweeteners, thickeners, and melting agents.

Liquid dosage forms for oral administration can contain coloring and flavoring to increase patient acceptance. In general, water, a suitable oil, saline, aqueous dextrose (glucose), and related sugar solutions and glycols such as propylene glycol or polyethylene glycols are suitable carriers for parenteral solutions. Solutions for parenteral administration preferably contain a water-soluble salt of the active ingredient, suitable stabilizing agents, and if necessary, buffer substances. Antioxidizing agents such as sodium bisulfite, sodium sulfite, or ascorbic acid, either alone or combined, are suitable stabilizing agents. Also used are citric acid and its salts and sodium EDTA. In addition, parenteral solutions can contain preservatives, such as benzalkonium chloride, methyl- or propyl-paraben, and chlorobutanol. Suitable pharmaceutical carriers are described in Remington's Pharmaceutical Sciences, Mack Publishing Company, a standard reference text in this field.

The compounds used in the method of the present invention may also be administered in intranasal form via use of suitable intranasal vehicles, or via transdermal routes, using those forms of transdermal skin patches well known to those of ordinary skill in that art. To be administered in the form of a transdermal delivery system, the dosage administration will generally be continuous rather than intermittent throughout the dosage regimen. Parenteral and intravenous forms may also include minerals and other materials to make them compatible with the type of injection or delivery system chosen.

Each embodiment disclosed herein is contemplated as being applicable to each of the other disclosed embodiments. Thus, all combinations of the various elements described herein are within the scope of the invention.

This invention will be better understood by reference to the Experimental Details which follow, but those skilled in the art will readily appreciate that the specific experiments detailed are only illustrative of the invention as described more fully in the claims which follow thereafter.

EXPERIMENTAL DETAILS

Example 1. Preparation of Compounds

General Considerations.

Reagents and solvents were obtained from commercial sources and were used without further purification unless otherwise stated. All compounds were prepared in racemic form. All reactions were performed in flame-dried glassware under an argon atmosphere unless otherwise stated, and monitored by TLC using solvent mixtures appropriate to each reaction. All column chromatography was performed on silica gel (40-63 μm). Preparative TLC was conducted on 20×20 cm plates coated with a 1 mm silica layer. Nuclear magnetic resonance spectra were recorded on Bruker 400 or 500 MHz instruments as indicated. Chemical shifts are reported as δ values in ppm referenced to $CDCl_3$ ($^1$H NMR=7.26 and $^{13}$C NMR=77.16), MeOD ($^1$H NMR=3.31 and $^{13}$C NMR=49.00), or DMSO-$d_6$ ($^1$H NMR=2.50 and $^{13}$C NMR=39.52). Multiplicity is indicated as follows: s (singlet); d (doublet); t (triplet); q (quartet); p (pentet); dd (doublet of doublets); ddd (doublet of doublet of doublets); dt (doublet of triplets); td (triplet of doublets); m (multiplet); br (broad). All carbon peaks are rounded to one decimal place unless such rounding would cause two close peaks to become identical; in these cases, two decimal places are retained. Two carbon peaks joined by "and" in the peak list correspond to a single carbon atom but are split due to F—C coupling. Low-resolution mass spectra were recorded on a JEOL LCmate (ionization mode: APCI+). For compounds 4 and 5 mass spectra are reported for carbocations corresponding to loss of OH or Cl respectively.

Preparation of Diarylthiazepinones (3)

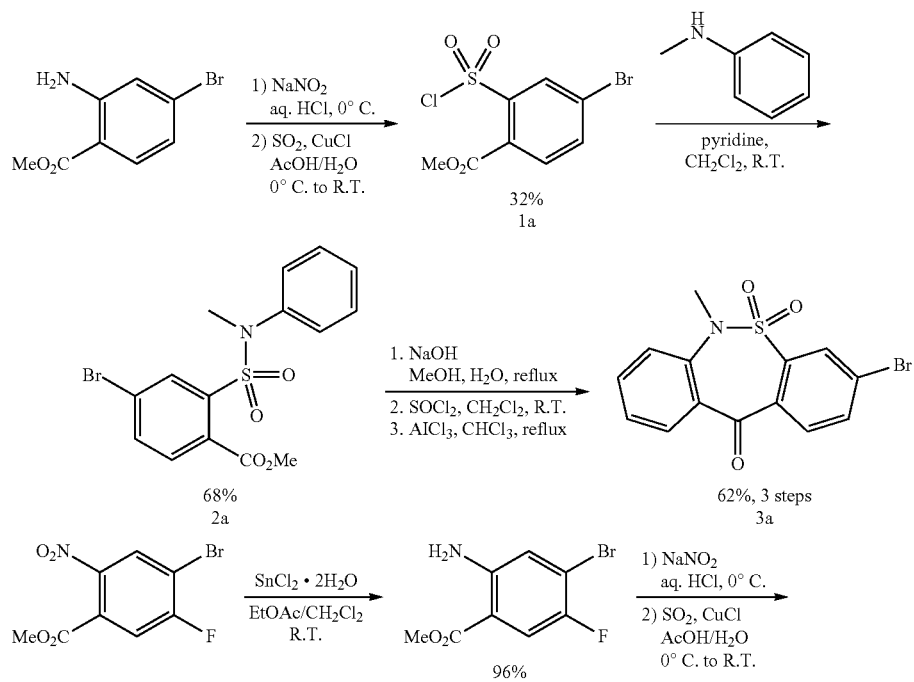

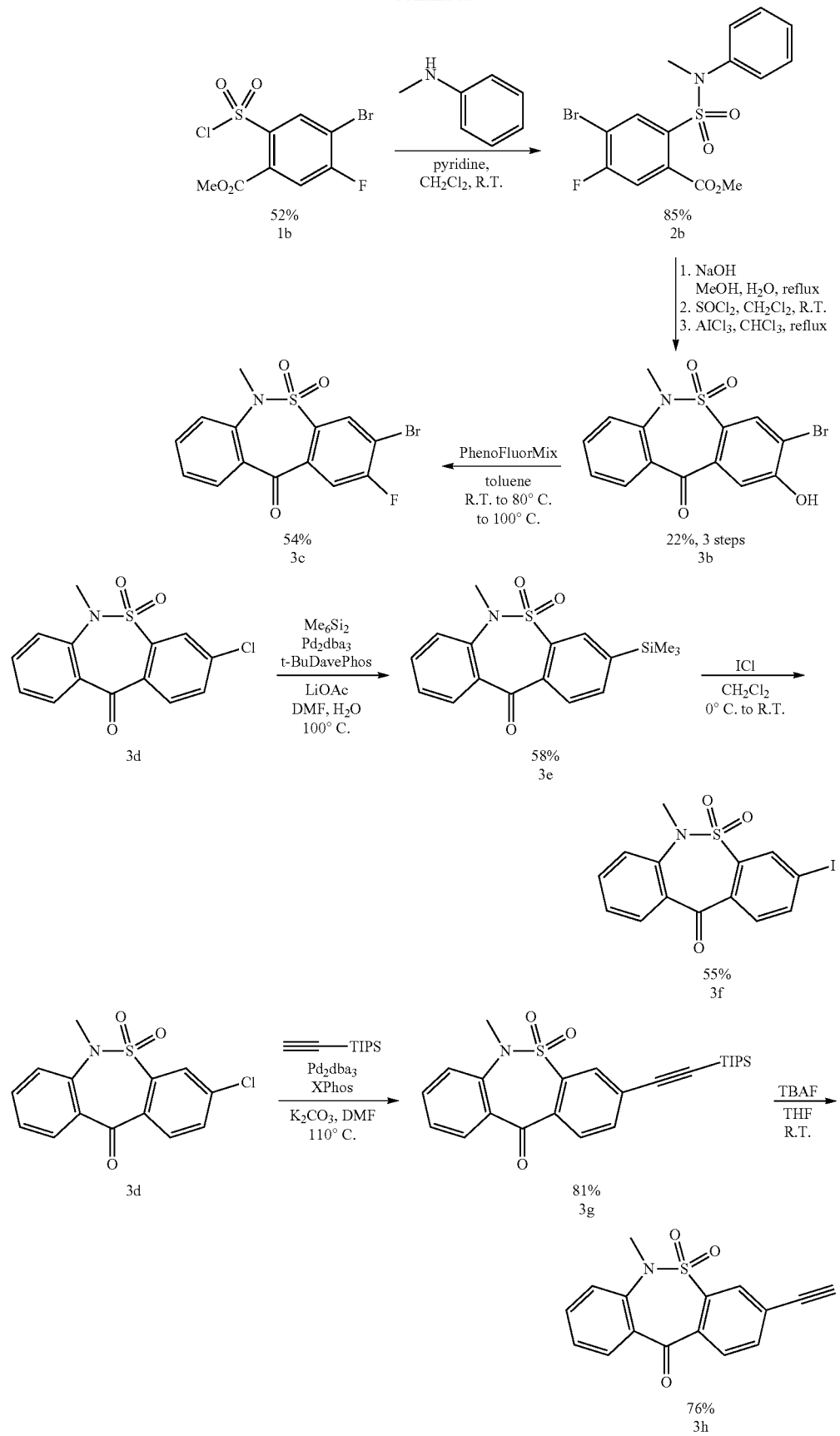

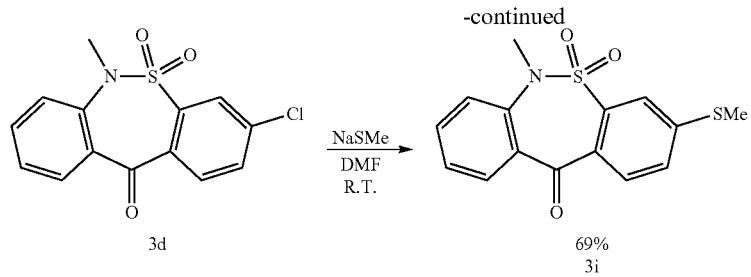

Methyl 4-bromo-2-(chlorosulfonyl)benzoate (1a)

A suspension of methyl 2-amino-4-bromobenzoate (10.35 g, 45.0 mmol) in 20% aqueous HCl (29 mL) was sonicated for several minutes and warmed slightly until all clumps were broken up and the mixture was a uniform suspension of fine particles. This mixture was cooled to 0° C., and a solution of NaNO$_2$ (3.11 g, 45.0 mmol) in water (7.5 mL) was added dropwise, maintaining the internal temperature below 5° C. The resulting mixture was then stirred for 2 h at 0° C. Simultaneously, a solution of SO$_2$ (23.1 g, 360 mmol) in AcOH (36.0 mL) and water (3.75 mL) was prepared by bubbling the gas though the mixed solvents at 0° C. until the mass had increased by the required amount. To this SO$_2$ solution was then added CuCl (1.11 g, 11.25 mmol) followed by the diazonium salt solution portionwise over 30 minutes at 0° C. The resulting mixture was then stirred for 1 h at 0° C. and 1 h at room temperature, poured into ice water (150 mL), and extracted with CH$_2$Cl$_2$ (3×50 mL). The combined organics were poured into saturated aqueous NaHCO$_3$ (75 mL), and solid NaHCO$_3$ was added carefully until effervescence ceased. The organic phase was then separated, washed with brine (50 mL), dried over Na$_2$SO$_4$, and concentrated to provide the crude sulfonyl chloride 1a as a waxy brown solid (6.11 g, 74 mass % product by NMR, 32% yield). This material was used in the next step without further purification.

Methyl 4-bromo-2-(N-methyl-N-phenylsulfamoyl)benzoate (2a)

To a solution of crude methyl 4-bromo-2-(chlorosulfonyl) benzoate 1a (6.04 g, 74% pure, 14.25 mmol) in anhydrous pyridine (10.7 mL) was added N-methylaniline (1.71 mL, 1.68 g, 15.68 mmol) at room temperature, and the resulting mixture was stirred for 1 h. The reaction mixture was then diluted with CH$_2$Cl$_2$ (100 mL) and washed with 7% aqueous HCl (2×100 mL), brine (100 mL), saturated aqueous NaHCO$_3$ (100 mL), and brine again (100 mL), dried over Na$_2$SO$_4$, and concentrated to give a yellow-brown oil. This material was purified by column chromatography (9:1 hexanes:EtOAc, 4 column volumes→8:2 hexanes:EtOAc, 4 column volumes) to provide pure sulfonamide 2a as a yellow oil (3.71 g, 68%) $^1$H NMR (500 MHz, CDCl$_3$) δ 7.69 (dd, J=8.2, 1.9 Hz, 1H), 7.52 (d, J=1.9 Hz, 1H), 7.38-7.29 (m, 4H), 7.21-7.17 (m, 2H), 3.82 (s, 3H), 3.30 (s, 3H); $^{13}$C NMR (126 MHz, CDCl$_3$) δ 167.7, 141.0, 137.1, 135.5, 132.8, 132.3, 129.8, 129.3, 128.0, 127.4, 123.9, 53.4, 39.0.

3-Bromo-6-methyldibenzo[c,f][1,2]thiazepin-11(6H)-one 5,5-dioxide (3a)

To a solution of sulfonamide 2a (3.69 g, 9.60 mmol) in MeOH (24 mL) was added water (12 mL) and NaOH (1.15 g, 28.80 mmol) and the mixture was refluxed for 1 h. Most of the MeOH was then removed in vacuo and the resulting clumpy white mixture was diluted with water (30 mL), acidified with 10% aqueous HCl (20 mL), and extracted with CH$_2$Cl$_2$ (50 mL, 2×20 mL). The combined organics were dried over Na$_2$SO$_4$ and concentrated to provide the carboxylic acid as a pale-pink glass (3.46 g), which was used in the next step without further purification. The carboxylic acid (3.43 g, 9.26 mmol) was dissolved in thionyl chloride (15 mL) and the solution was stirred for 13 h at room temperature. The volatiles were then removed to provide the crude acyl chloride as a yellow-orange oil. This material was dissolved in CHCl$_3$ (40 mL), aluminum chloride (3.95 g, 29.63 mmol) was added, and the mixture was refluxed for 1 h. The reaction was then cooled to room temperature, quenched with ice water (150 mL), and extracted with CH$_2$Cl$_2$ (3×50 mL). The combined organics were filtered through a silica plug, washing with additional CH$_2$Cl$_2$ until all of the product had passed through, and the filtrate was concentrated to provide an off-white solid. This material was recrystallized from MeOH (250 mL) to provide the pure ketone 3a as cream-colored needles (2.08 g, 62% over 3 steps). $^1$H NMR (500 MHz, CDCl$_3$) δ 8.30 (dd, J=8.1, 1.5 Hz, 1H), 8.11 (t, J=1.0 Hz, 1H), 7.84 (d, J=1.1 Hz, 2H), 7.68-7.62 (m, 1H), 7.41-7.37 (m, 1H), 7.35 (dd, J=8.1, 0.7 Hz, 1H), 3.36 (s, 3H); $^{13}$C NMR (126 MHz, CDCl$_3$) δ 189.8, 141.5, 138.5, 136.4, 135.1, 135.0, 133.4, 132.3, 131.0, 128.4, 126.9, 126.4, 124.8, 39.2; LR-MS calcd. for C$_{14}$H$_{11}$BrNO$_3$S [M+H]$^+$ 351.96, found 351.85.

Methyl 2-amino-4-bromo-5-fluorobenzoate

To a solution of methyl 4-bromo-5-fluoro-2-nitrobenzoate (2.50 g, 9.00 mmol) in EtOAc (67.5 mL) and CH$_2$Cl$_2$ (22.5 mL) was added SnCl$_2$·2H$_2$O (10.15 g, 45.00 mmol) and the white suspension was stirred for 15 h. The reaction mixture was then poured into saturated aqueous NaHCO$_3$ (200 mL), solid NaHCO$_3$ was added with stirring until bubbling stopped, and the mixture was extracted with EtOAc (3×200 mL). The combined organics were washed with water (200 mL) and brine (200 mL), dried over Na$_2$SO$_4$, and concentrated to provide methyl 2-amino-4-bromo-5-fluorobenzoate as a pale-tan crystalline solid (2.14 g, 96%). $^1$H NMR (500 MHz, CDCl$_3$) δ 7.58 (d, J=9.4 Hz, 1H), 6.88 (d, J=5.7 Hz, 1H), 5.62 (br s, 2H), 3.87 (s, 3H); $^{13}$C NMR (126 MHz, CDCl$_3$) δ 167.39 and 167.36, 151.4 and 149.5, 147.41 and 147.39, 120.7, 117.4 and 117.2, 116.5 and 116.3, 110.2 and 110.1, 52.1.

Methyl 4-bromo-2-(chlorosulfonyl)-5-fluorobenzoate (1b)

A suspension of methyl 2-amino-4-bromo-5-fluorobenzoate (4.18 g, 16.85 mmol) in 20% aqueous HCl (10.9 mL)

was sonicated for several minutes and warmed slightly until all clumps were broken up and the mixture was a uniform suspension of fine particles. This mixture was cooled to −5° C., and a solution of $NaNO_2$ (1.16 g, 16.85 mmol) in water (2.8 mL) was added dropwise over 10 minutes, maintaining the internal temperature below 0° C. The resulting mixture was then stirred for 30 minutes at −5° C., during which time, most solids dissolved to leave a cloudy yellow solution. Simultaneously, a solution of $SO_2$ (8.65 g, 135 mmol) in AcOH (13.5 mL) and water (1.4 mL) was prepared by bubbling the gas though the mixed solvents at 0° C. until the mass had increased by the required amount. To this $SO_2$ solution was then added CuCl (417 mg, 4.21 mmol) followed by the diazonium salt solution portionwise over 25 minutes at 0° C. The resulting mixture was then stirred for 1 h at 0° C. and 1 h at room temperature, poured into ice water (75 mL), and extracted with $CH_2Cl_2$ (3×30 mL). The combined organics were poured into saturated aqueous $NaHCO_3$ (100 mL) containing excess solid $NaHCO_3$ and the mixture was stirred until effervescence ceased. The organic phase was then separated, washed with brine (30 mL), dried over $Na_2SO_4$, and concentrated to provide the crude sulfonyl chloride 1b as a waxy tan solid (3.57 g, 82 mass % product by NMR, 52% yield). This material was used in the next step without further purification.

Methyl 4-bromo-5-fluoro-2-(N-methyl-N-phenylsulfamoyl)benzoate (2b)

To a solution of N-methylaniline (1.05 mL, 1.04 g, 9.66 mmol) in anhydrous $CH_2Cl_2$ (8.5 mL) at 0° C. was added anhydrous pyridine (6.4 mL) followed by a solution of crude methyl 4-bromo-2-(chlorosulfonyl)-5-fluorobenzoate 1b (3.54 g, 82% pure, 8.78 mmol) in anhydrous $CH_2Cl_2$ (8.5 mL) over 3 minutes. The resulting bright orange solution was then allowed to warm to room temperature and stirred for 1 h. The reaction mixture was then diluted with $CH_2Cl_2$ (100 mL) and washed with 3% aqueous HCl (2×50 mL), brine (50 mL), saturated aqueous $NaHCO_3$ (50 mL), and brine again (50 mL), dried over $Na_2SO_4$, and concentrated to give a viscous orange oil. This material was purified by column chromatography (9:1 hexanes:EtOAc, 4 column volumes→8:2 hexanes:EtOAc, 2 column volumes) to provide sulfonamide 2b as a viscous, pale-yellow oil that slowly crystallized to off-white crystals (3.00 g, 85%). $^1H$ NMR (500 MHz, $CDCl_3$) δ 7.58 (d, J=6.3 Hz, 1H), 7.39-7.29 (m, 3H), 7.25-7.16 (m, 3H), 3.83 (s, 3H), 3.30 (s, 3H); $^{13}C$ NMR (126 MHz, $CDCl_3$) δ 166.28 and 166.26, 161.9 and 159.9, 140.9, 135.84 and 135.83, 134.81 and 134.76, 132.59 and 132.55, 129.4, 128.1, 127.4, 116.6 and 116.41, 111.1 and 110.9, 53.6, 39.0.

3-Bromo-2-hydroxy-6-methyldibenzo[c,f][1,2]thiazepin-11(6H)-one 5,5-dioxide (3b)

To a solution of sulfonamide 2b (2.98 g, 7.41 mmol) in MeOH (19 mL) was added water (9.5 mL) and NaOH (889 mg, 22.23 mmol) and the mixture was refluxed for 50 minutes. The volatiles were removed in vacuo and the resulting white mass was triturated with water (50 mL) and 10% aqueous HCl (20 mL) and extracted with $CH_2Cl_2$ (250 mL, 150 mL, 50 mL; poor solubility). The combined organics were dried over $Na_2SO_4$ and concentrated to provide the carboxylic acid as a white solid (2.99 g), in which the fluoro substituent had been replaced with a methoxy group via nucleophilic aromatic substitution occurring concurrent with hydrolysis. This material was used in the next step without further purification. To the methoxy carboxylic acid (2.95 g, 7.37 mmol) was added thionyl chloride (11.9 mL) and the mixture was stirred for 2.5 h at room temperature (solids now dissolved). The volatiles were then removed to provide the crude acyl chloride as a white solid. This material was dissolved in anhydrous $CHCl_3$ (32 mL), aluminum chloride (3.14 g, 23.58 mmol) was added, and the mixture was refluxed for 1.25 h. The reaction was then cooled to room temperature, quenched with ice water (150 mL), diluted with $CH_2Cl_2$ (50 mL), and stirred until all black sludge had broken up. The mixture was then extracted with $CH_2Cl_2$ (3×50 mL) and the combined organics washed with water (100 mL), dried over $Na_2SO_4$, and concentrated to provide an olive solid. This material was purified by column chromatography (20:1 $CH_2Cl_2:Et_2O$, 2 column volumes→10:1 $CH_2Cl_2:Et_2O$, 2 column volumes) to give a pale-yellow solid still containing impurities (0.78 g). The crude product was washed 2 times with small portions of $CH_2Cl_2$, removing the supernatant by pipet each time. It was then dissolved in $CH_2Cl_2$, boiled down until most of the solvent was removed and the product had partially crystallized, cooled to 0° C., and the supernatant was again removed by pipet to provide the phenolic ketone 3b (O-demethylation occurs concomitant to cyclization) as a crystalline, pale-yellow solid (595 mg, 22% over 3 steps). $^1H$ NMR (500 MHz, DMSO-$d_6$) δ 11.92 (s, 1H), 8.12 (dd, J=8.1, 1.7 Hz, 1H), 7.96 (s, 1H), 7.79-7.73 (m, 1H), 7.58 (dd, J=8.2, 1.2 Hz, 1H), 7.44 (ddd, J=8.3, 7.2, 1.2 Hz, 1H), 7.38 (s, 1H), 3.28 (s, 3H); $^{13}C$ NMR (126 MHz, DMSO-$d_6$) δ 190.2, 158.9, 141.7, 136.8, 135.3, 131.1, 129.9, 129.7, 126.9, 125.9, 125.4, 117.6, 113.0, 39.0.

3-Bromo-2-fluoro-6-methyldibenzo[c,f][1,2]thiazepin-11(6H)-one 5,5-dioxide (3c)

PhenoFluorMix (230 mg; a mixture of N,N'-1,3-bis(2,6-diisopropylphenyl)chloroimidazolium chloride and CsF; Fujimoto, T. and Ritter, T. 2015) was dried under high vacuum at 140° C. in a vial for 1.5 h. After cooling to room temperature, phenolic ketone 3b (38.7 mg, 0.105 mmol) was added followed by anhydrous toluene (1.0 mL) and the mixture was stirred for 30 minutes at room temperature, 10 minutes at 80° C., and 45 minutes at 100° C. The supernatant was then removed from residual solids by pipet, the solids were washed 3 times with $CH_2Cl_2$, and the combined organics were concentrated to give a pale-yellow solid. This material was purified by repeated preparative TLC (Plate 1: 7:3 hexanes:EtOAc; Plate 2: $CH_2Cl_2$) to provide ketone 3c as a white, crystalline solid (21 mg, 54%). $^1H$ NMR (400 MHz, $CDCl_3$) δ 8.29 (dd, J=8.1, 1.7 Hz, 1H), 8.19 (d, J=6.2 Hz, 1H), 7.73 (d, J=8.5 Hz, 1H), 7.67 (ddd, J=8.1, 7.2, 1.7 Hz, 1H), 7.40 (ddd, J=8.3, 7.2, 1.2 Hz, 1H), 7.35 (dd, J=8.1, 1.2 Hz, 1H), 3.36 (s, 3H); 13C NMR (101 MHz, $CDCl_3$) δ 188.4, 163.2 and 160.6, 141.4, 137.62 and 137.55, 135.4, 134.25 and 134.21, 132.4, 131.4, 130.6, 126.5, 124.9, 120.0 and 119.8, 114.0 and 113.8, 39.2.

3-Chloro-6-methyldibenzo[c,f][1,2]thiazepin-11 (6H)-one 5,5-dioxide (3d)

Ketone 3d was purchased from Ark Pharm Inc. (Libertyville, IL) and used without further purification.

6-Methyl-3-(trimethylsilyl)dibenzo[c,f][1,2]thiazepin-11(6H)-one 5,5-dioxide (3e)

Ketone 3e was prepared from the aryl chloride utilizing the trimethylsilylation procedure of Buchwald (McNeill, E.

et al. 2007). Ketone 3d (462 mg, 1.50 mmol), $Pd_2dba_3$ (20.6 mg, 0.0225 mmol), t-BuDavePhos (2'-(Di-tert-butylphosphino)-N,N-dimethylbiphenyl-2-amine, 46.1 mg, 0.135 mmol), and LiOAc (495 mg, 7.50 mmol) were combined under argon. Anhydrous DMF (4.5 mL), water (54 μL, 3.00 mmol), and hexamethyldisilane (369 μL, 1.80 mmol) were then added, and the resulting orange-brown mixture was heated to 100° C. for 33 h. After cooling to room temperature, the reaction mixture was diluted with water (20 mL) and extracted with $Et_2O$ (3×10 mL). The combined organics were washed with water (10 mL), dried over $Na_2SO_4$, and concentrated to yield a yellow crystalline solid. This crude material was recrystallized from MeOH to obtain pure ketone 3e as fine yellow needles (301 mg, 58%). $^1H$ NMR (500 MHz, $CDCl_3$) δ 8.30 (dd, J=8.1, 1.6 Hz, 1H), 8.04 (d, J=0.8 Hz, 1H), 7.91 (d, J=7.5 Hz, 1H), 7.85 (dd, J=7.6, 1.1 Hz, 1H), 7.63 (ddd, J=8.1, 7.3, 1.7 Hz, 1H), 7.41-7.29 (m, 2H), 3.35 (s, 3H), 0.36 (s, 9H); $^{13}C$ NMR (126 MHz, $CDCl_3$) δ 191.2, 147.4, 141.9, 138.3, 136.6, 136.0, 134.8, 132.1, 131.2, 130.5, 129.7, 126.0, 124.6, 39.1, −1.2; LR-MS calcd. for $C_{17}H_{20}NO_3SSi$ $[M+H]^+$ 346.09, found 345.86.

3-Iodo-6-methyldibenzo[c,f][1,2]thiazepin-11(6H)-one 5,5-dioxide (3f)

To a solution of trimethylsilylketone 3e (108 mg, 0.313 mmol) in anhydrous $CH_2Cl_2$ (0.94 mL) at 0° C. was added a solution of iodine monochloride (173 mg, 1.06 mmol) in anhydrous $CH_2Cl_2$ (0.63 mL) dropwise over 3 min. The resulting dark-brown solution was allowed to warm to room temperature, stirred for 35 min (extended reaction times produce polyiodinated byproducts), and quenched with saturated aqueous $Na_2S_2O_3$ (3 mL). The resulting mixture was diluted with water (15 mL) and extracted with $CH_2Cl_2$ (2×15 mL). The combined organics were washed with water (15 mL), dried over $Na_2SO_4$, and concentrated to yield a yellow solid. This material was purified by column chromatography (1:1 $CH_2Cl_2$:hexanes) to yield impure product. This crude product was recrystallized from MeOH and the resulting fine-white needles were dissolved in $CH_2Cl_2$ and concentrated, causing a second crystallization to occur once most of the solvent had been removed. The powdery white crystals thus obtained were washed with ice-cold MeOH and dried to yield the pure ketone 3f (68.4 mg, 55%). $^1H$ NMR (400 MHz, $CDCl_3$) δ 8.32-8.27 (m, 2H), 8.06 (dd, J=8.1, 1.7 Hz, 1H), 7.69-7.62 (m, 2H), 7.38 (ddd, J=8.2, 7.3, 1.1 Hz, 1H), 7.34 (dd, J=8.1, 0.9 Hz, 1H), 3.35 (s, 3H); $^{13}C$ NMR (101 MHz, $CDCl_3$) δ 190.1, 142.4, 141.5, 138.1, 135.6, 135.1, 133.9, 133.1, 132.2, 131.0, 126.3, 124.7, 98.7, 39.2; LR-MS calcd. for $C_{14}H_{11}INO_3S$ $[M+H]^+$ 399.95, found 399.78.

6-Methyl-3-((trimethylsilyl)ethynyl)dibenzo[c,f][1,2]thiazepin-11(6H)-one 5,5-dioxide (3g)

$Pd_2dba_3$ (20.6 mg, 0.0225 mmol), XPhos (21.5 mg, 0.0450 mmol), and $K_2CO_3$ were combined in anhydrous DMF (3.0 mL) and the dark-brown mixture was stirred at room temperature for 5 min. Ketone 3d (462 mg, 1.50 mmol) and (trimethylsilyl)acetylene (505 μL, 2.25 mmol) were then added and the mixture was heated to 110° C. for 3 h. The mixture was then cooled to room temperature, diluted with water (20 mL), and extracted with $Et_2O$ (3×30 mL). The combined organics were washed with water (2×20 mL) and brine (20 mL), dried over $Na_2SO_4$, and concentrated to give an orange-brown solid. This material was purified by column chromatography (6:4 hexanes:$CH_2Cl_2$, 3 column volumes→1:1 hexanes:$CH_2Cl_2$, 5 column volumes) to provide pure ketone 3g as pale-yellow foam, which, on addition of a little $Et_2O$, formed powdery, pale-yellow crystals (553 mg, 81%). $^1H$ NMR (400 MHz, $CDCl_3$) δ 8.31 (dd, J=8.1, 1.7 Hz, 1H), 8.01 (d, J=1.6 Hz, 1H), 7.91 (d, J=8.0 Hz, 1H), 7.75 (dd, J=8.0, 1.6 Hz, 1H), 7.68-7.61 (m, 1H), 7.38 (ddd, J=8.2, 7.3, 1.2 Hz, 1H), 7.34 (dd, J=8.1, 1.1 Hz, 1H), 3.36 (s, 3H), 1.21-1.10 (m, 21H); $^{13}C$ NMR (101 MHz, $CDCl_3$) 190.1, 141.6, 137.3, 136.4, 135.3, 135.0, 132.2, 131.8, 131.2, 128.6, 128.1, 126.3, 124.8, 104.3, 97.5, 39.2, 18.8, 11.4.

3-Ethynyl-6-methyldibenzo[c,f][1,2]thiazepin-11 (6H)-one 5,5-dioxide (3h)

To a solution of ketone 3g (531 mg, 1.17 mmol) in anhydrous THF (5.0 mL) was added a solution of tetrabutylammonium fluoride (1.0 M in THF, 2.34 mL, 2.34 mmol) at room temperature and the resulting black solution was stirred for 2 h. The reaction mixture was then diluted with $CH_2Cl_2$ (50 mL), washed with water (2×20 mL) and brine (20 mL), dried over $Na_2SO_4$, and concentrated to give a brown solid. This material was purified by column chromatography (1:1 hexanes:$CH_2Cl_2$, 3 column volumes→$CH_2Cl_2$, 3 column volumes) to provide the product contaminated with residual silane. This material was washed 2× with small portions of hexanes and dried to give pure ketone 3h as powdery, off-white crystals (265 mg, 76%). $^1H$ NMR (400 MHz, $CDCl_3$) δ 8.30 (dd, J=8.1, 1.7 Hz, 1H), 8.05 (d, J=1.6 Hz, 1H), 7.92 (d, J=8.0 Hz, 1H), 7.78 (dd, J=8.0, 1.6 Hz, 1H), 7.68-7.62 (m, 1H), 7.38 (ddd, J=8.2, 7.3, 1.1 Hz, 1H), 7.34 (dd, J=8.1, 1.1 Hz, 1H), 3.36 (s, 1H), 3.35 (s, 3H); $^{13}C$ NMR (101 MHz, $CDCl_3$) δ 190.2, 141.7, 137.3, 136.5, 136.0, 135.0, 132.2, 131.9, 130.9, 128.8, 126.7, 126.2, 124.7, 82.2, 81.3, 39.1.

6-Methyl-3-(methylthio)dibenzo[c,f][1,2]thiazepin-11(6H)-one 5,5-dioxide (3i)

To a solution of sodium thiomethoxide (116 mg, 1.65 mmol) in anhydrous DMF (2.0 mL) was added ketone 3d (462 mg, 1.50 mmol) and the resulting yellow suspension was stirred at room temperature for 1 h. Additional sodium thiomethoxide (26.3 mg, 0.375 mmol) was then added and stirring continued for a further 15 min. The reaction was then quenched with water (10 mL) and extracted with $CH_2Cl_2$ (10 mL, 2×5 mL). The combined organics were washed with water (20 mL), dried over $Na_2SO_4$, and concentrated to yield a yellow oil containing residual DMF. This crude was diluted with $Et_2O$ and chilled on ice causing the product to crystallize as pale-yellow needles. These crystals were washed with several small portions of ice-cold $Et_2O$ and dried to give the pure ketone 3i (331 mg, 69%). $^1H$ NMR (500 MHz, $CDCl_3$) δ 8.31 (dd, J=8.1, 1.6 Hz, 1H), 7.92 (d, J=8.3 Hz, 1H), 7.73 (d, J=2.0 Hz, 1H), 7.62 (ddd, J=8.0, 7.4, 1.7 Hz, 1H), 7.48 (dd, J=8.3, 2.0 Hz, 1H), 7.40-7.33 (m, 2H), 3.33 (s, 3H), 2.59 (s, 3H); $^{13}C$ NMR (126 MHz, $CDCl_3$) δ 189.5, 146.5, 141.4, 137.7, 134.7, 132.4, 132.2, 131.8, 131.7, 129.2, 126.4, 125.2, 121.4, 39.3, 15.0. LR-MS calcd. for $C_{15}H_{14}NO_3S_2$$[M+H]^+$ 320.04, found 320.75.

Preparation of Diarylthiazepinyl Chlorides (5)

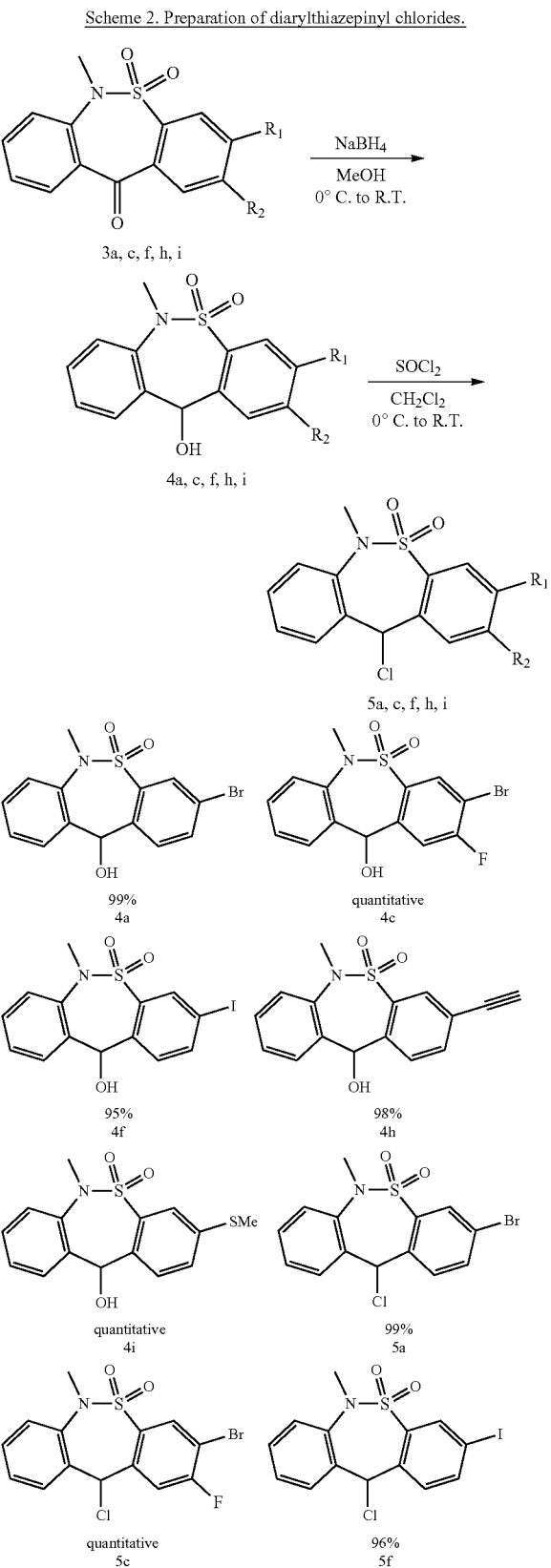

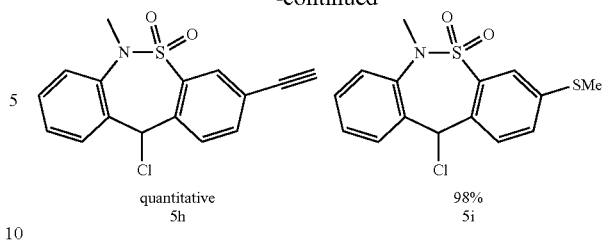

General Procedure for Preparation of Diarylthiazepinyl Alcohols (4)

Sodium borohydride (2 equivalents) was added to an ice-cooled solution (or suspension) of the appropriate ketone 3 (1 equivalent) in MeOH (0.05 M based on 3) and the mixture was allowed to warm to room temperature and stirred until TLC indicated the complete consumption of starting material. The reaction was then quenched with saturated aqueous ammonium chloride (5 mL per mmol 3) and saturated aqueous NaHCO$_3$ (5 mL per mmol 3). The MeOH was evaporated and the precipitate was filtered, washed with water, and dried (alternatively, the residue was extracted with EtOAc and the combined organic layers were washed with water, dried over Na$_2$SO$_4$, filtered, and concentrated). The resulting product 4 was used in the next step without further purification.

3-Bromo-11-hydroxy-6-methyl-6,11-dihydrodibenzo [c,f][1,2]thiazepine 5,5-dioxide (4a)

The product 4a was prepared according to the general procedure and obtained as a white solid (1.85 g, 99%). $^1$H NMR (500 MHz, CDCl$_3$) δ 8.11 (d, J=2.0 Hz, 1H), 7.73 (dd, J=8.2, 2.0 Hz, 1H), 7.61 (dd, J=7.7, 1.0 Hz, 1H), 7.57 (d, J=8.2 Hz, 1H), 7.41 (td, J=7.6, 1.5 Hz, 1H), 7.37-7.30 (m, 2H), 5.93 (d, J=9.7 Hz, 1H), 4.16 (d, J=9.7 Hz, 1H), 3.20 (s, 3H); $^{13}$C NMR (126 MHz, CDCl$_3$) δ 138.9, 138.8, 136.9, 136.4, 135.3, 131.8, 131.5, 131.0, 130.1, 127.9, 127.0, 122.7, 76.2, 39.4; LR-MS calcd. for C$_{14}$H$_{11}$BrNO$_2$S [M-OH]$^+$335.97, found 335.89.

3-Bromo-2-fluoro-11-hydroxy-6-methyl-6,1-dihydrodibenzo [c,f][1,2]thiazepine 5,5-dioxide (4c)

The product 4c was prepared according to the general procedure and obtained as a pale-yellow glass containing minor impurities (21.1 mg, quantitative). $^1$H NMR (400 MHz, CDCl$_3$) δ 8.15 (d, J=6.5 Hz, 1H), 7.63-7.58 (m, 1H), 7.52 (dd, J=9.1, 0.7 Hz, 1H), 7.44-7.32 (m, 4H), 6.06 (br s, 1H), 3.88 (br s, 1H), 3.26 (s, 3H); $^{13}$C NMR (101 MHz, CDCl$_3$) δ 162.8 and 160.3, 140.8 and 140.7, 138.1, 136.5, 134.4 and 134.3, 133.81 and 133.79, 130.1, 129.6, 128.2, 127.1, 117.1 and 116.8, 109.3 and 109.1, 73.6, 38.7.

11-Hydroxy-3-iodo-6-methyl-6,11-dihydrodibenzo [c,f] [1,2] thiazepine 5,5-dioxide (4f)

The product 4f was prepared according to the general procedure and obtained as a white solid (74.8 mg, 95%). $^1$H NMR (500 MHz, CDCl$_3$) (observed as a ~4:1 ratio of 2 conformers, resulting in partial integrals) δ 8.27 (d, J=1.8 Hz, 1H), 7.99 (dd, J=7.7, 1.1 Hz, 0.2H), 7.93 (dd, J=8.1, 1.8 Hz, 0.8H), 7.68 (d, J=7.2 Hz, 0.2H), 7.65-7.58 (m, 1H), 7.53 (td, J=7.6, 1.3 Hz, 0.2H), 7.44-7.37 (m, 1.8H), 7.37-7.29 (m, 1.8H), 5.92 (s, 1H), 4.40 (d, J=9.6 Hz, 0.2H), 4.15 (d, J=7.5 Hz, 0.8H), 3.20 (s, 2.4H), 3.14 (s, 0.6H); $^{13}$C NMR (126 MHz, CDCl$_3$) (additional peaks due to conformers) δ 142.4, 138.8, 138.7, 137.5, 136.5, 135.4, 133.6, 132.1, 131.7, 131.4, 130.6, 130.1, 130.0, 128.9, 128.4, 127.9, 127.6, 127.0, 126.9, 93.6, 76.2, 39.3; LR-MS calcd. for C$_{14}$H$_{11}$INO$_2$S [M-OH]$^+$383.96, found 383.71.

3-Ethynyl-11-hydroxy-6-methyl-6,11-dihydrodibenzo[c,f][1,2]thiazepine 5,5-dioxide (4h)

The product 4h was prepared according to the general procedure and obtained as an off-white solid (very slight yellow tint, 253 mg, 98%). $^1$H NMR (500 MHz, CDCl$_3$) δ 8.09 (d, J=1.6 Hz, 1H), 7.70 (dd, J=7.8, 1.7 Hz, 1H), 7.65 (d, J=7.9 Hz, 1H), 7.62 (dd, J=7.8, 1.6 Hz, 1H), 7.40 (td, J=7.6, 1.7 Hz, 1H), 7.34 (td, J=7.5, 1.4 Hz, 1H), 7.31 (dd, J=7.9, 1.4 Hz, 1H), 5.95 (d, J=9.8 Hz, 1H), 4.27 (d, J=9.9 Hz, 1H), 3.22 (s, 1H), 3.17 (s, 3H); $^{13}$C NMR (126 MHz, CDCl$_3$) δ 139.1, 138.1, 137.4, 136.7, 135.1, 131.74, 131.68, 130.4, 130.1, 127.8, 126.9, 123.3, 81.5, 80.2, 76.6, 39.4.

11-Hydroxy-6-methyl-3-(methylthio)-6,11-dihydrodibenzo[c,f][1,2]thiazepine 5,5-dioxide (4i)

The product 4i was prepared according to the general procedure and obtained as a pale-yellow crystalline solid (323 mg, quantitative). $^1$H NMR (500 MHz, CDCl$_3$) δ 7.75 (d, J=2.0 Hz, 1H), 7.57 (dd, J=7.6, 1.3 Hz, 1H), 7.54 (d, J=8.2 Hz, 1H), 7.37 (ddd, J=9.2, 7.9, 1.9 Hz, 2H), 7.32-7.27 (m, 2H), 5.89 (d, J=9.4 Hz, 1H), 4.44 (d, J=9.4 Hz, 1H), 3.16 (s, 3H), 2.51 (s, 3H); $^{13}$C NMR (126 MHz, CDCl$_3$) δ 140.8, 138.8, 137.4, 136.0, 134.0, 131.2, 130.4, 130.3, 129.7, 127.7, 127.0, 124.8, 75.9, 39.2, 15.4; LR-MS calcd. for C$_{15}$H$_{14}$NO$_2$S$_2$ [M-OH]$^+$ 304.05, found 304.71.

General Procedure for Preparation of Diarylthiazepinyl Chlorides (5)

Thionyl chloride (6 equivalents) was added dropwise to a solution of the appropriate alcohol 4 (1 equivalent) in anhydrous CH$_2$Cl$_2$ (0.065 M based on 4) at 0° C. The reaction mixture was then warmed to room temperature, stirred overnight, and concentrated to provide the corresponding chloride 5, which was used directly in the following reactions without further purification.

3-Bromo-11-chloro-6-methyl-6,11-dihydrodibenzo[c,f][1,2]thiazepine 5,5-dioxide (5a)

The product 5a was prepared according to the general procedure and obtained as a white solid (1.92 g, 99%). $^1$H NMR (400 MHz, CDCl$_3$) δ 8.14 (d, J=2.1 Hz, 1H), 7.66 (dd, J=8.3, 2.1 Hz, 1H), 7.55-7.49 (m, 2H), 7.45-7.40 (m, 2H), 7.39-7.33 (m, 1H), 6.10 (s, 1H), 3.58 (s, 3H); $^{13}$C NMR (101 MHz, CDCl$_3$) δ 142.0, 139.2, 137.6, 135.6, 134.1, 133.0, 131.7, 131.0, 130.2, 129.5, 129.0, 124.3, 63.7, 39.3; LR-MS cald. for C$_{14}$H$_{11}$BrNO$_2$S [M-Cl]$^+$ 335.97, found 335.79.

3-Bromo-11-chloro-2-fluoro-6-methyl-6,11-dihydrodibenzo[c,f][1,2]thiazepine 5,5-dioxide (5c)

The product 5c was prepared according to the general and obtained as an off-white solid (21.3 mg, quantitative). $^1$H NMR (500 MHz, CDCl$_3$) δ 8.21 (d, J=6.6 Hz, 1H), 7.55-7.50 (m, 2H), 7.44 (d, J=7.7 Hz, 1H), 7.40-7.35 (m, 1H), 7.32 (d, J=8.7 Hz, 1H), 6.07 (s, 1H), 3.57 (s, 3H); $^{13}$C NMR (126 MHz, CDCl$_3$) δ 161.7 and 159.6, 139.0, 137.5 and 137.4, 137.04, 136.98, 133.78 and 133.77, 131.8, 130.0, 129.4, 129.1, 118.9 and 118.7, 111.3 and 111.1, 62.7, 39.1.

3,11-Dichloro-6-methyl-6,11-dihydrodibenzo[c,f][1,2]thiazepine 5,5-dioxide (5d)

Chloride 5d was purchased from Ark Pharm Inc. (Libertyville, IL) and used without further purification. 11-Chloro-3-iodo-6-methyl-6,11-dihydrodibenzo[c,f][1,2]thiazepine 5,5-dioxide (5f). The product 5f was prepared according to the general procedure and obtained as a gray solid (73.4 mg, 96%). $^1$H NMR (400 MHz, CDCl$_3$) δ 8.32 (d, J=1.8 Hz, 1H), 7.87 (dd, J=8.2, 1.8 Hz, 1H), 7.57-7.48 (m, 2H), 7.43 (d, J=7.1 Hz, 1H), 7.39-7.33 (m, 1H), 7.27 (d, J=7.1 Hz, 1H), 6.08 (s, 1H), 3.57 (s, 3H); $^{13}$C NMR (101 MHz, CDCl$_3$) δ 141.8, 141.5, 139.3, 137.6, 136.7, 134.7, 132.9, 131.7, 130.1, 129.5, 129.0, 95.4, 63.8, 39.3; LR-MS calcd. for C$_{14}$H$_{11}$INO$_2$S [M-Cl]$^+$ 383.96, found 383.70.

11-Chloro-3-ethynyl-6-methyl-6,11-dihydrodibenzo[c,f][1,2]thiazepine 5,5-dioxide (5h)

The product 5h was prepared according to the general procedure and obtained as an off-white crystalline solid (269 mg, quantitative). $^1$H NMR (400 MHz, CDCl$_3$) δ 8.13 (d, J=1.7 Hz, 1H), 7.62 (dd, J=8.1, 1.7 Hz, 1H), 7.56-7.48 (m, 3H), 7.44 (d, J=7.1 Hz, 1H), 7.36 (ddd, J=7.7, 6.4, 2.1 Hz, 1H), 6.13 (s, 1H), 3.58 (s, 3H), 3.22 (s, 1H); $^{13}$C NMR (101 MHz, CDCl$_3$) 140.7, 139.3, 137.5, 135.6, 135.2, 131.74, 131.67, 131.5, 130.2, 129.4, 128.9, 124.8, 81.3, 80.8, 63.9, 39.2.

11-Chloro-6-methyl-3-(methylthio)-6,11-dihydrodibenzo[c,f][1,2]thiazepine 5,5-dioxide (5i)

The product 5i was prepared according to the general procedure and obtained as an off-white solid (329 mg, 98%) $^1$H NMR (400 MHz, CDCl$_3$) δ 7.78 (s, 1H), 7.56-7.47 (m, 2H), 7.45-7.40 (m, 2H), 7.38-7.32 (m, 2H), 6.12 (s, 1H), 3.58 (s, 3H), 2.53 (s, 3H). $^{13}$C NMR (101 MHz, CDCl$_3$) δ 142.9, 140.9, 139.4, 137.9, 131.9, 131.5, 130.9, 130.1, 129.6, 129.5, 128.9, 124.1, 64.5, 39.3, 15.3; LR-MS calcd. for C$_{15}$H$_{14}$NO$_2$S$_2$[M-Cl]$^+$ 304.05, found 304.74.

Preparation of Amine Side Chains (7)

Scheme 3. Preparation of aminoalkanoic acid esters.

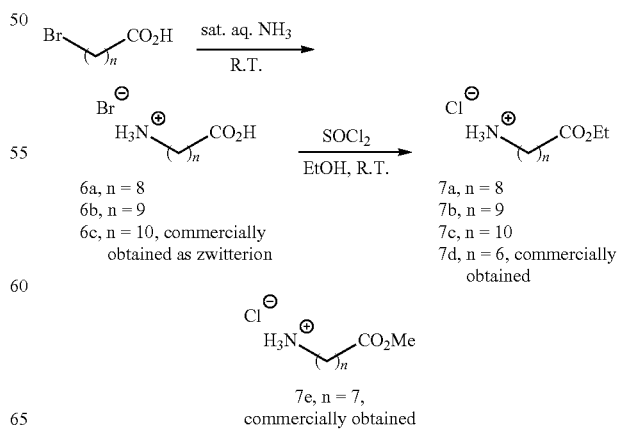

6a, n = 8
6b, n = 9
6c, n = 10, commercially obtained as zwitterion 7a, n = 8
7b, n = 9
7c, n = 10
7d, n = 6, commercially obtained 7e, n = 7, commercially obtained

9-Aminononanoic acid hydrobromide (6a)

Saturated aqueous NH₃ (28-30% NH₃, 30 mL) and 9-bromononanoic acid (949 mg, 4.00 mmol) were combined and the resulting colorless solution was stirred at room temperature for 23 h. The mixture was then boiled for ~15 min open to the atmosphere to remove most of the NH₃ and then fully concentrated in vacuo to give amino acid 6a as a white solid (1.04 g, quantitative). $^1$H NMR (500 MHz, MeOD) δ 2.91 (t, J=7.8 Hz, 2H), 2.20 (t, J=7.4 Hz, 2H), 1.70-1.56 (m, 4H), 1.43-1.32 (m, 8H); $^{13}$C NMR (126 MHz, MeOD) δ 180.9, 40.7, 37.5, 30.3, 30.1, 29.9, 28.5, 27.3, 26.9.

10-Aminodecanoic acid hydrobromide (6b)

Saturated aqueous NH₃ (28-30% NH₃, 60 mL) and 10-bromodecanoic acid (2.01 g, 8.00 mmol) were combined and the resulting colorless solution was stirred at room temperature for 23 h. The mixture was then boiled for 15 min open to the atmosphere to remove most of the NH₃ and then fully concentrated in vacuo to give amino acid 6b as a white solid (2.22 g, quantitative). $^1$H NMR (500 MHz, MeOD) δ 2.92 (t, J=7.5 Hz, 2H), 2.21 (t, J=7.5 Hz, 2H), 1.70-1.56 (m, 4H), 1.43-1.31 (m, 10H); $^{13}$C NMR (126 MHz, MeOD) δ 180.5, 40.8, 37.1, 30.4, 30.20, 30.18, 30.0, 28.5, 27.3, 26.8.

11-Aminoundecanoic acid (6c)

Amino acid 6c was purchased from Thermo Fisher Scientific Inc. in the neutral zwitterion form and used without further purification.

General Procedure for Preparation of Aminoalkanoic Acid Esters (7).

Thionyl chloride (3 equivalents) was slowly added to anhydrous EtOH (0.3 mL per mmol SOCl₂) at room temperature (some warming). This solution was allowed to return to room temperature and added to the appropriate amino acid 6 (in salt or zwitterion form), the resulting suspension was sonicated for ~1 min as needed to break up large particles, and then the mixture was stirred for 24 h at room temperature. The reaction mixture was concentrated in vacuo and the resulting solid was treated with a small quantity of anhydrous EtOH and concentrated again. This procedure was then repeated 2× more to ensure removal of residual HCl. The resulting solid was triturated with boiling hexanes, allowed to cool and settle, and the supernatant was carefully removed by pipet. This procedure was then repeated 1× more and the solids dried to provide the corresponding amino ester 7 as the hydrochloride salt, which was used directly in the following reactions without further purification.

Ethyl 9-aminononanoate hydrochloride (7a)

The product 7a was prepared according to the general procedure and obtained as a pale-yellow solid (1.09 g, quantitative). $^1$H NMR (500 MHz, MeOD) δ 4.11 (q, J=7.1 Hz, 2H), 2.92 (t, J=7.6 Hz, 2H), 2.30 (t, J=7.4 Hz, 2H), 1.71-1.57 (m, 4H), 1.44-1.31 (m, 8H), 1.24 (t, J=7.1 Hz, 3H); 13C NMR (126 MHz, MeOD) δ 175.5, 61.4, 40.8, 35.0, 30.1, 29.98, 29.97, 28.5, 27.4, 26.0, 14.5.

Ethyl 10-aminodecanoate hydrochloride (7b)

The product 7b was prepared according to the general procedure and obtained as an off-white solid (2.38 g, quantitative). $^1$H NMR (400 MHz, MeOD) δ 4.11 (q, J=7.1 Hz, 2H), 2.92 (t, J=7.7 Hz, 2H), 2.30 (t, J=7.4 Hz, 2H), 1.72-1.56 (m, 4H), 1.44-1.28 (m, 10H), 1.24 (t, J=7.1 Hz, 3H); $^{13}$C NMR (101 MHz, MeOD) δ 175.6, 61.4, 40.8, 35.1, 30.24, 30.20, 30.09, 30.08, 28.6, 27.4, 26.0, 14.5.

Ethyl 11-aminoundecanoate hydrochloride (7c)

The product 7c was prepared according to the general procedure but without the hexane wash step and obtained as an off-white solid (2.07 g, 97%). $^1$H NMR (500 MHz, MeOD) δ 4.11 (q, J=7.1 Hz, 2H), 2.92 (t, J=7.6 Hz, 2H), 2.30 (t, J=7.4 Hz, 2H), 1.71-1.55 (m, 4H), 1.42-1.29 (m, 12H), 1.24 (t, J=7.1 Hz, 3H); $^{13}$C NMR (126 MHz, MeOD) δ 175.6, 61.4, 40.8, 35.1, 30.40, 30.38, 30.3, 30.2, 30.1, 28.6, 27.4, 26.0, 14.5.

Ethyl 7-aminoheptanoate hydrochloride (7d)

Amino ester 7d was purchased from Ark Pharm Inc. (Libertyville, IL) as the hydrochloride salt and used without further purification.

Methyl 8-aminooctanoate hydrochloride (7e)

Amino ester 7e was purchased from AURUM Pharmatech LLC (Franklin Park, NJ) as the hydrochloride salt and used without further purification.

Preparation of Diarylthiazepinamine Esters (8)

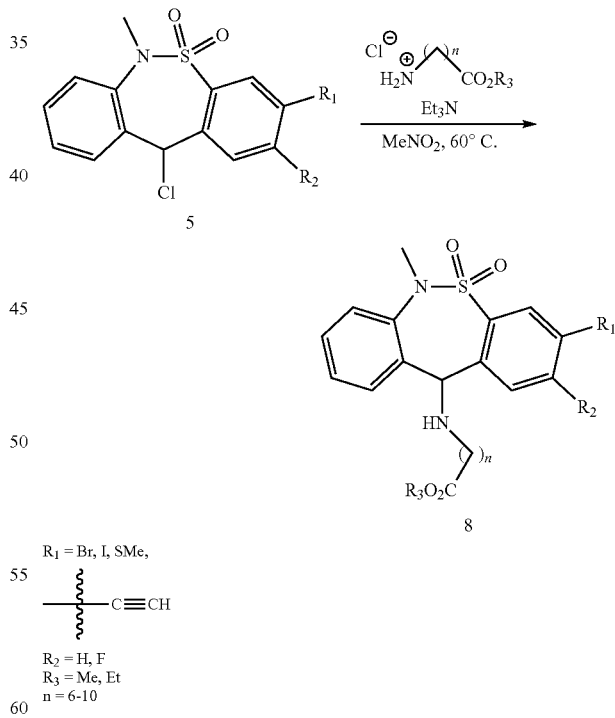

Scheme 4. Preparation of diarylthiazepinamine esters.

R₁ = Br, I, SMe, —C≡CH
R₂ = H, F
R₃ = Me, Et
n = 6-10

General Procedure for Preparation of Diarylthiazepinamines

To a suspension of the appropriate chloride 5 (1 equivalent) in nitromethane (0.5 M based on 5) was added the appropriate aminoalkanoic acid ester hydrochloride (1.2 equivalents) and Et$_3$N (2.4 equivalents) and the mixture was warmed to 60° C. and left to stir until TLC indicated that the reaction was complete (typically <1 h). The reaction mixture was then concentrated in vacuo and purified directly by column chromatography or preparative TLC. Alternatively, the concentrated reaction residue was partitioned between Et$_2$O (20 mL per mmol 5) and water (20 mL per mmol 5). The ethereal layer was separated and the aqueous extracted again with Et$_2$O (20 mL per mmol 5). The combined organics were washed with water (20 mL per mmol 5) and 10% NH$_4$OH (20 mL per mmol 5), dried over Na$_2$SO$_4$, and concentrated to yield the product. If necessary, the product was further purified by column chromatography or preparative TLC.

Ethyl 7-((3-ethynyl-6-methyl-5,5-dioxido-6,11-dihydrodibenzo [c,f][1,2]thiazepin-11-yl)amino)heptanoate (8a)

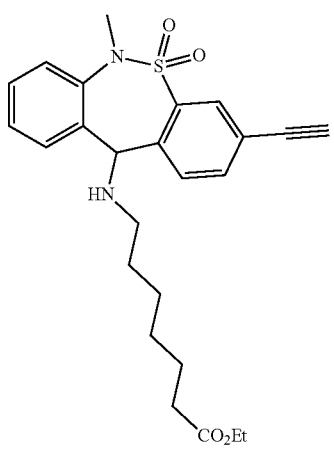

The product 8a was prepared according to the general procedure and purified by preparative TLC (10:1 CH$_2$Cl$_2$:Et$_2$O) to provide a viscous, yellow oil (30.8 mg, 68%). $^1$H NMR (500 MHz, CDCl$_3$) δ 8.09 (d, J=1.7 Hz, 1H), 7.59 (dd, J=7.9, 1.7 Hz, 1H), 7.44 (d, J=8.0 Hz, 1H), 7.41-7.32 (m, 3H), 7.28 (td, J=7.3, 1.8 Hz, 1H), 5.03 (s, 1H), 4.11 (q, J=7.1 Hz, 2H), 3.34 (s, 3H), 3.16 (s, 1H), 2.46 (tq, J=7.3, 4.0 Hz, 2H), 2.26 (t, J=7.5 Hz, 2H), 2.09 (br s, 1H), 1.59 (p, J=7.3 Hz, 2H), 1.53-1.42 (m, 2H), 1.34-1.26 (m, 4H), 1.24 (t, J=7.2 Hz, 3H); $^{13}$C NMR (126 MHz, CDCl$_3$) δ 173.8, 139.2, 139.0, 138.8, 138.7, 135.5, 132.2, 130.2, 129.9, 129.4, 128.1, 127.9, 122.7, 81.6, 79.6, 66.5, 60.3, 48.2, 38.6, 34.4, 30.0, 29.1, 27.0, 25.0, 14.4.

Ethyl 7-((3-bromo-2-fluoro-6-methyl-5,5-dioxido-6,11-dihydrodibenzo[c,f][1,2]thiazepin-11-yl)amino)heptanoate (8b)

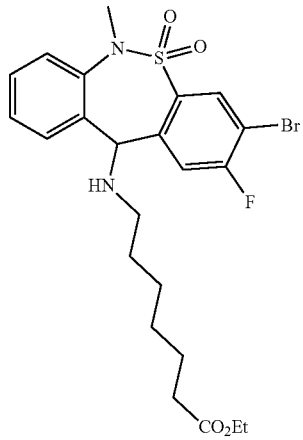

The product 8b was prepared according to the general procedure and purified by column chromatography (CH$_2$Cl$_2$, 2 column volumes→20:1 CH$_2$Cl$_2$:Et$_2$O, 2 column volumes→7:3 CH$_2$Cl$_2$:Et$_2$O, 2 column volumes) to provide a viscous, pale-yellow oil (20.6 mg, 78%). $^1$H NMR (500 MHz, CDCl$_3$) δ 8.16 (d, J=6.6 Hz, 1H), 7.42-7.28 (m, 5H), 5.09 (s, 1H), 4.11 (q, J=7.1 Hz, 2H), 3.39 (s, 3H), 2.57-2.46 (m, 2H), 2.27 (t, J=7.5 Hz, 2H), 1.99 (br s, 1H), 1.66-1.57 (m, 2H), 1.52 (p, J=7.1 Hz, 2H), 1.39-1.28 (m, 4H), 1.24 (t, J=7.1 Hz, 3H); 13C NMR (101 MHz, CDCl$_3$) δ 173.8, 162.2 and 159.7, 141.6, 139.1, 138.3, 135.84 and 135.80, 134.27 and 134.25, 129.5, 128.8, 128.4, 127.9, 116.8 and 116.5, 108.7 and 108.5, 64.3, 60.3, 48.3, 38.2, 34.4, 30.0, 29.1, 27.0, 25.0, 14.4.

Ethyl 7-((6-methyl-3-(methylthio)-5,5-dioxido-6,11-dihydrodibenzo[c,f][1,2]thiazepin-11-yl)amino)heptanoate (8c)

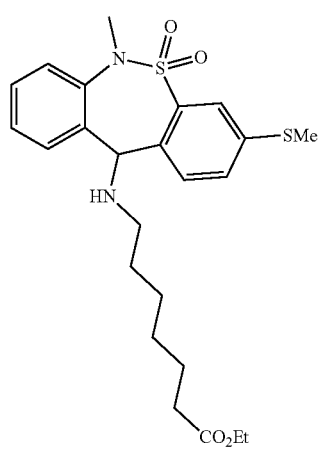

The product 8c was prepared according to the general procedure and obtained as a viscous, pale-yellow oil (44.0 mg, 92%). ¹H NMR (400 MHz, CDCl₃) δ 7.78 (d, J=1.3 Hz, 1H), 7.42-7.31 (m, 5H), 7.31-7.24 (m, 1H), 4.95 (s, 1H), 4.10 (q, J=7.1 Hz, 2H), 3.34 (s, 3H), 2.50 (s, 3H), 2.45 (t, J=7.1 Hz, 2H), 2.25 (t, J=7.5 Hz, 2H), 2.13 (br s, 1H), 1.64-1.53 (m, 2H), 1.52-1.40 (m, 2H), 1.33-1.24 (m, 4H), 1.23 (t, J=7.1 Hz, 4H). ¹³C NMR (101 MHz, CDCl₃) δ 173.8, 140.0, 139.5, 139.0, 138.9, 134.7, 130.5, 130.5, 129.8, 129.3, 128.0, 125.3, 66.8, 60.3, 48.1, 38.9, 34.4, 30.0, 29.1, 27.1, 25.0, 15.6, 14.4; LR-MS calcd. for C₂₄H₃₃N₂O₄S₂ [M+H]⁺ 477.19, found 476.70.

Methyl 8-((3-bromo-6-methyl-5,5-dioxido-6,11-dihydrodibenzo [c,f][1,2]thiazepin-11l-yl)amino)octanoate (8d)

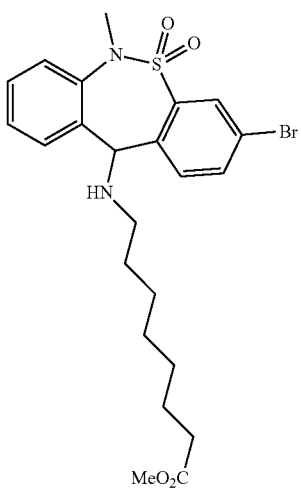

8d

The product 8d was prepared according to the general procedure and purified by column chromatography (CH₂Cl₂, 2 column volumes→28:1 CH₂Cl₂:Et₂O, 3 column volumes→7:3 CH₂Cl₂:Et₂O, 3 column volumes) to provide a viscous, pale-yellow oil (44.8 mg, 88%). ¹H NMR (500 MHz, CDCl₃) δ 8.10 (d, J=2.1 Hz, 1H), 7.62 (dd, J=8.2, 2.1 Hz, 1H), 7.41-7.33 (m, 4H), 7.29 (td, J=7.3, 1.7 Hz, 1H), 4.98 (s, 1H), 3.66 (s, 3H), 3.37 (s, 3H), 2.45 (t, J=7.1 Hz, 2H), 2.28 (t, J=7.5 Hz, 2H), 2.04 (br s, 1H), 1.59 (p, J=7.7 Hz, 2H), 1.51-1.41 (m, 2H), 1.33-1.23 (m, 6H); ¹³C NMR (126 MHz, CDCl₃) δ 174.4, 140.6, 138.9, 138.6, 137.6, 135.3, 131.4, 131.3, 130.1, 129.5, 128.3, 128.1, 122.0, 66.3, 51.6, 48.3, 38.8, 34.2, 30.1, 29.2, 29.1, 27.2, 25.0.

Methyl 8-((3-iodo-6-methyl-5,5-dioxido-6,11-dihydrodibenzo [c,f][1,2]thiazepin-11-yl)amino)octanoate (8e)

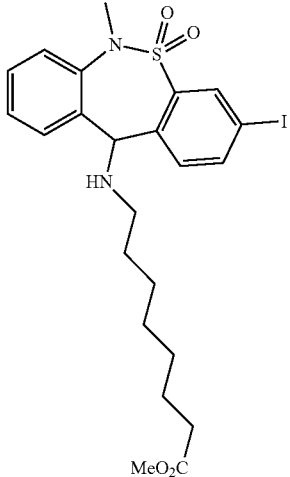

8e

The product 8e was prepared according to the general procedure and purified by column chromatography (CH₂Cl₂, 4 column volumes→20:1 CH₂Cl₂:Et₂O, 2 column volumes→7:3 CH₂Cl₂:Et₂O, 2 column volumes) to provide a viscous, nearly colorless oil (49.0 mg, 88%). ¹H NMR (400 MHz, CDCl₃) δ 8.26 (d, J=1.8 Hz, 1H), 7.81 (dd, J=8.1, 1.8 Hz, 1H), 7.40-7.32 (m, 3H), 7.31-7.26 (m, 1H), 7.21 (d, J=8.2 Hz, 1H), 4.97 (s, 1H), 3.65 (s, 3H), 3.37 (s, 3H), 2.45 (t, J=7.1 Hz, 2H), 2.28 (t, J=7.5 Hz, 2H), 2.01 (br s, 1H), 1.59 (p, J=7.3 Hz, 2H), 1.51-1.41 (m, 2H), 1.34-1.24 (m, 6H); ¹³C NMR (101 MHz, CDCl₃) 174.3, 141.2, 140.6, 139.0, 138.6, 138.3, 136.9, 131.4, 130.0, 129.4, 128.2, 128.1, 92.9, 66.3, 51.6, 48.3, 38.7, 34.2, 30.1, 29.2, 29.1, 27.2, 25.0.

Ethyl 9-((3-iodo-6-methyl-5,5-dioxido-6,11-dihydrodibenzo [c,f][1,2]thiazepin-11-yl)amino)nonanoate (8f)

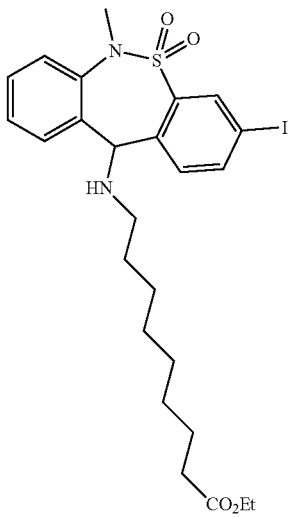

8f

The product 8f was prepared according to the general procedure and purified by column chromatography (CH$_2$Cl$_2$, 2 column volumes→20:1 CH$_2$Cl$_2$:Et$_2$O, 3 column volumes→7:3 CH$_2$Cl$_2$:Et$_2$O, 2 column volumes) to provide a viscous, pale-yellow oil (36.9 mg, 63%). $^1$H NMR (500 MHz, CDCl$_3$) δ 8.26 (d, J=1.8 Hz, 1H), 7.81 (dd, J=8.1, 1.9 Hz, 1H), 7.40-7.33 (m, 3H), 7.28 (td, J=7.4, 1.6 Hz, 1H), 7.21 (d, J=8.1 Hz, 1H), 4.97 (s, 1H), 4.11 (q, J=7.1 Hz, 2H), 3.37 (s, 3H), 2.45 (t, J=7.1 Hz, 2H), 2.27 (t, J=7.5 Hz, 2H), 2.00 (br s, 1H), 1.59 (p, J=7.2 Hz, 2H), 1.51-1.41 (m, 2H), 1.32-1.21 (m, 11H); $^{13}$C NMR (126 MHz, CDCl$_3$) δ 173.94, 141.20, 140.60, 139.02, 138.61, 138.27, 136.90, 131.37, 129.97, 129.40, 128.23, 128.07, 92.84, 66.23, 60.27, 48.29, 38.69, 34.46, 30.17, 29.38, 29.26, 29.15, 27.31, 25.03, 14.39.

Ethyl 9-((3-iodo-6-methyl-5,5-dioxido-6,11-dihydrodibenzo [c,f][1,2]thiazepin-11-yl)amino)decanoate (8g)

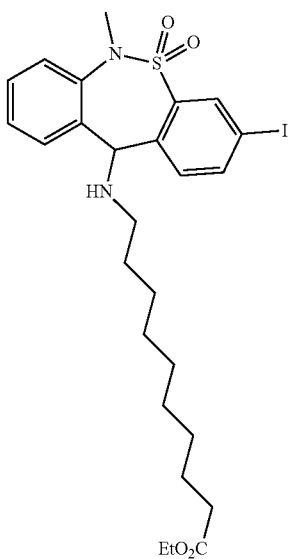

8g

The product 8g was prepared according to the general procedure and purified by column chromatography (CH$_2$Cl$_2$, 2 column volumes→20:1 CH$_2$Cl$_2$:Et$_2$O, 3 column volumes→7:3 CH$_2$C$_2$:Et$_2$O, 2 column volumes) to provide a viscous, colorless oil (42.5 mg, 71%). $^1$H NMR (400 MHz, CDCl$_3$) δ 8.26 (d, J=1.8 Hz, 1H), 7.81 (dd, J=8.1, 1.8 Hz, 1H), 7.40-7.32 (m, 3H), 7.31-7.26 (m, 1H), 7.22 (d, J=8.1 Hz, 1H), 4.98 (s, 1H), 4.12 (q, J=7.1 Hz, 2H), 3.37 (s, 3H), 2.46 (t, J=7.1 Hz, 2H), 2.27 (t, J=7.5 Hz, 2H), 2.01 (br s, 1H), 1.60 (p, J=7.3 Hz, 2H), 1.52-1.40 (m, 2H), 1.33-1.20 (m, 13H); 13C NMR (101 MHz, CDCl$_3$) δ 174.0, 141.2, 140.61, 139.0, 138.6, 138.3, 136.9, 131.4, 130.0, 129.4, 128.2, 128.1, 92.9, 66.2, 60.3, 48.3, 38.7, 34.5, 30.2, 29.5, 29.4, 29.3, 29.2, 27.3, 25.1, 14.4.

Ethyl 9-((3-iodo-6-methyl-5,5-dioxido-6,11-dihydrodibenzo [c,f][1,2]thiazepin-11-yl)amino)undecanoate (8h)

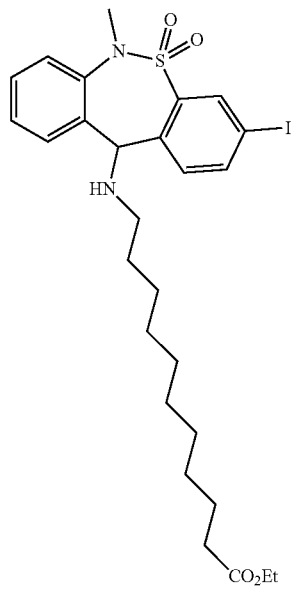

8h

The product 8h was prepared according to the general procedure and purified by column chromatography (CH$_2$Cl$_2$, 2 column volumes→20:1 CH$_2$Cl$_2$:Et$_2$O, 3 column volumes→7:3 CH$_2$Cl$_2$:Et$_2$O, 2 column volumes) to provide a viscous, pale-yellow oil (45.6 mg, 74%). $^1$H NMR (400 MHz, CDCl$_3$) δ 8.26 (d, J=1.9 Hz, 1H), 7.81 (dd, J=8.1, 1.9 Hz, 1H), 7.40-7.32 (m, 3H), 7.31-7.25 (m, 1H), 7.22 (d, J=8.2 Hz, 1H), 4.97 (s, 1H), 4.12 (q, J=7.1 Hz, 2H), 3.37 (s, 3H), 2.46 (t, J=7.1 Hz, 2H), 2.27 (t, J=7.5 Hz, 2H), 2.01 (br s, 1H), 1.66-1.56 (m, 2H), 1.52-1.41 (m, 2H), 1.33-1.20 (m, 15H); $^{13}$C NMR (101 MHz, CDCl$_3$) δ 174.0, 141.2, 140.6, 139.1, 138.6, 138.3, 136.9, 131.4, 129.9, 129.4, 128.2, 128.1, 92.8, 66.2, 60.3, 48.3, 38.7, 34.5, 30.2, 29.6, 29.5, 29.3, 29.2, 27.4, 25.1, 14.4.

Preparation of Diarylthiazepinamine Carboxylic Acids (9)

Scheme 5. Preparation of diarylthiazepinamine carboxylic acids.

A)

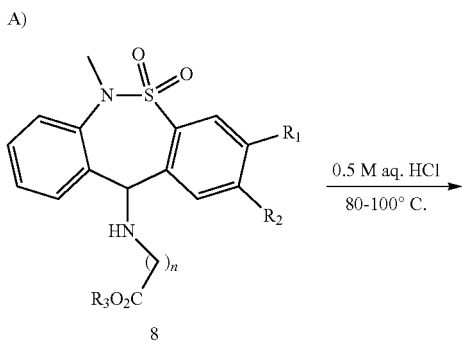

8

-continued

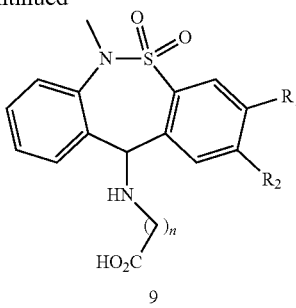

9

R₁ = Br, I, SMe,
R₂ = H, F
R₃ = Me, Et
n = 6-10

B)

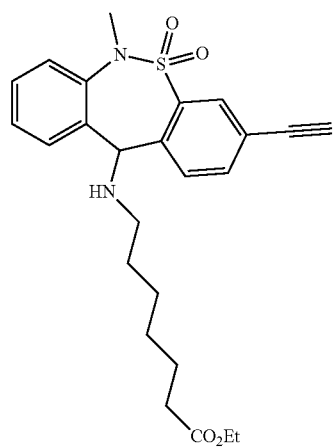

8a $\xrightarrow{\text{LiOH}}_{\substack{\text{THF/H}_2\text{O}\\60° \text{C. to R.T.}}}$

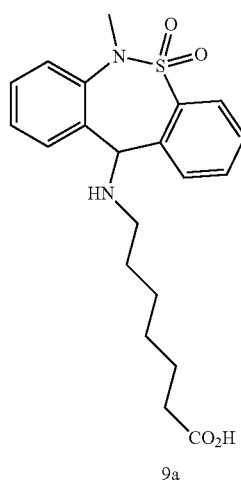

9a

General Procedure for Preparation of Carboxylic Acids (9)

The appropriate ester 8 (0.04 M final concentration) was heated in aqueous HCl (0.5 M) at 80 or 100° C. until TLC indicated the complete consumption of starting material (typically <24 h). The reaction mixture was then concentrated and dried thoroughly in vacuo to provide the pure HCl salt of the corresponding amino carboxylic acid. In some cases, a powdered or crystalline solid resulted directly, but in others, it was necessary to triturate the obtained glass with hexanes and then concentrate to provide a powdered solid if desired.

Note: In some cases, yields below 90% were obtained due to losses while transferring the poorly soluble product between vessels during the concentration process.

7-((3-Ethynyl-6-methyl-5,5-dioxido-6,11-dihydrodibenzo [c,f][1,2]thiazepin-11-yl)amino)heptanoic acid (9a)

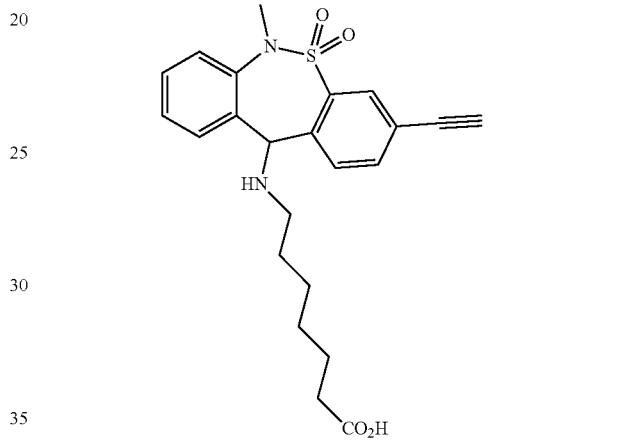

9a

Amino ester 8a (15.7 mg, 0.0345 mmol), aqueous LiOH (0.160 mL of 0.216 M solution, 0.0345 mmol), and THF (0.48 mL) were combined and heated to 60° C. for 30 min. and then stirred for an additional 17 h at room temperature. The THF was then removed in vacuo and the residue was diluted with water (2 mL) and washed with Et₂O (2×2 mL). The aqueous layer was then acidified to ~ph 4 with 10% aqueous HCl, saturated with NaCl, and extracted with CH₂Cl₂ (3×5 mL). The combined organics were washed with brine (1 mL) and concentrated to give a white foam. This material was purified by preparative TLC (20:1 EtOAc: MeOH) to provide the pure product 9a as a white foam (6.7 mg, 46%). $^1$H NMR (500 MHz, CDCl₃) δ 8.10 (d, J=1.6 Hz, 1H), 7.61 (dd, J=7.9, 1.7 Hz, 1H), 7.48 (d, J=8.0 Hz, 1H), 7.44 (d, J=7.6 Hz, 1H), 7.40-7.34 (m, 2H), 7.31-7.26 (m, 1H), 5.15 (s, 1H), 4.98 (br s, 2H), 3.30 (s, 3H), 3.18 (s, 1H), 2.54-2.46 (m, 1H), 2.44-2.36 (m, 1H), 2.26 (t, J=7.3 Hz, 2H), 1.62-1.54 (m, 2H), 1.53-1.42 (m, 2H), 1.32-1.22 (m, 4H); $^{13}$C NMR (126 MHz, CDCl₃) δ 178.1, 139.2, 139.1, 135.8, 132.2, 131.2, 131.0, 129.8, 128.0, 127.6, 123.2, 81.5, 80.0, 66.5, 47.6, 38.8, 34.4, 29.4, 29.0, 27.0, 24.9.

7-((3-Bromo-2-fluoro-6-methyl-5,5-dioxido-6,1-dihydrodibenzo [c,f][1,2]thiazepin-11-yl)amino) heptanoic acid hydrochloride salt (9b)

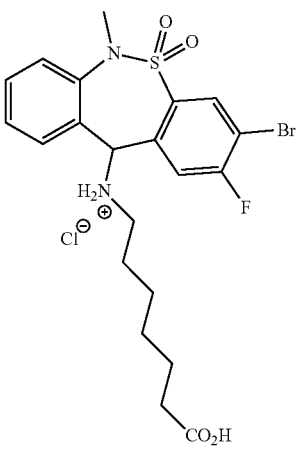

9b

The product 9b was prepared according to the general procedure and obtained as a glassy, white foam (14.1 mg, 95%). $^{1}$H NMR (400 MHz, MeOD) δ 8.32 (d, J=6.6 Hz, 1H), 7.84 (d, J=8.9 Hz, 1H), 7.70 (dd, J=7.8, 1.6 Hz, 1H), 7.62 (ddd, J=8.6, 7.2, 1.5 Hz, 1H), 7.56 (dd, J=8.1, 1.5 Hz, 1H), 7.47 (td, J=7.5, 1.5 Hz, 1H), 5.87 (s, 1H), 3.25 (s, 3H), 3.00-2.90 (m, 1H), 2.87-2.76 (m, 1H), 2.27 (t, J=7.3 Hz, 2H), 1.73-1.52 (m, 4H), 1.38-1.29 (m, 4H); $^{13}$C NMR (101 MHz, MeOD) δ 176.2, 162.9 and 160.3, 140.9, 136.4 and 136.3, 133.89 and 133.88, 133.1, 131.9, 127.9, 127.4, 121.8 and 121.6, 111.5 and 111.3, 65.8, 47.3, 38.5, 33.4, 28.3, 26.0, 25.9, 24.4.

7-((6-Methyl-3-(methylthio)-5,5-dioxido-6,11-dihydrodibenzo [c,f][1,2]thiazepin-11-yl)amino)heptanoic acid (9c)

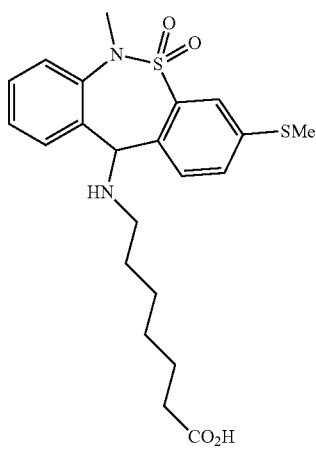

9c

The product 9c was hydrolyzed according to the general procedure and purified by acid-base extraction. Specifically, after concentration of the reaction mixture to give the crude hydrochloride salt, this material was partitioned between saturated aqueous NaHCO$_3$ (with a small amount of NaOH added, 2 mL) and Et$_2$O (2 mL) and the organic layer was removed and discarded. The aqueous layer was washed again with Et$_2$O (2 mL), acidified to ph 6 with 10% aqueous HCl, and extracted with CH$_2$Cl$_2$ (3×5 mL). The combined organics were dried over Na$_2$SO$_4$ and concentrated to provide the neutral, zwitterion form of the product as an off-white solid (10.7 mg, 50%). $^{1}$H NMR (400 MHz, CDCl$_3$) δ 7.79 (d, J=1.9 Hz, 1H), 7.45 (d, J=7.6 Hz, 1H), 7.41 (d, J=8.2 Hz, 1H), 7.38-7.32 (m, 3H), 7.30-7.24 (m, 1H), 6.43 (br s, 2H), 5.12 (s, 1H), 3.28 (s, 3H), 2.52 (s, 3H), 2.53-2.44 (m, 1H), 2.43-2.33 (m, 1H), 2.25 (br s, 2H), 1.56 (br s, 2H), 1.50-1.40 (m, 2H), 1.32-1.20 (m, 4H); $^{13}$C NMR (101 MHz, CDCl$_3$) δ 140.9, 139.5, 139.3, 136.0, 132.6, 131.7, 131.6, 129.9, 129.8, 127.9, 127.7, 125.2, 77.4, 66.6, 47.4, 39.0, 29.3, 29.1, 27.0, 25.2, 15.5.

8-((3-Bromo-6-methyl-5,5-dioxido-6,11-dihydrodibenzo [c,f][1,2]thiazepin-11-yl)amino) octanoic acid hydrochloride salt (9d)

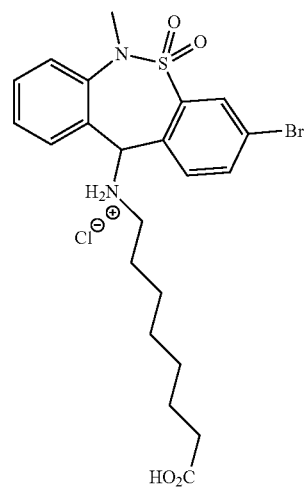

9d

The product 9d was prepared according to the general procedure and obtained as a glassy, white foam (37.0 mg, 97%). $^{1}$H NMR (500 MHz, MeOD) δ 8.19 (d, J=2.1 Hz, 1H), 7.99 (dd, J=8.2, 2.1 Hz, 1H), 7.83 (d, J=8.2 Hz, 1H), 7.74 (dd, J=7.7, 1.5 Hz, 1H), 7.62 (ddd, J=8.7, 7.2, 1.5 Hz, 1H), 7.56 (dd, J=8.1, 1.4 Hz, 1H), 7.47 (td, J=7.5, 1.4 Hz, 1H), 5.90 (s, 1H), 3.25 (s, 3H), 2.92 (ddd, J=12.1, 10.0, 5.7 Hz, 1H), 2.77 (ddd, J=12.1, 9.9, 6.1 Hz, 1H), 2.26 (t, J=7.4 Hz, 2H), 1.72-1.52 (m, 4H), 1.36-1.26 (m, 6H); $^{13}$C NMR (126 MHz, MeOD) δ 177.5, 142.2, 141.8, 138.1, 136.8, 134.5, 133.1, 132.1, 129.5, 129.1, 128.6, 128.4, 126.1, 67.5, 48.3, 39.7, 34.8, 29.8, 29.7, 27.30, 27.26, 25.8.

8-((3-Iodo-6-methyl-5,5-dioxido-6,11-dihydrodibenzo [c,f][1,2]thiazepin-11-yl)amino) octanoic acid hydrochloride salt (9e)

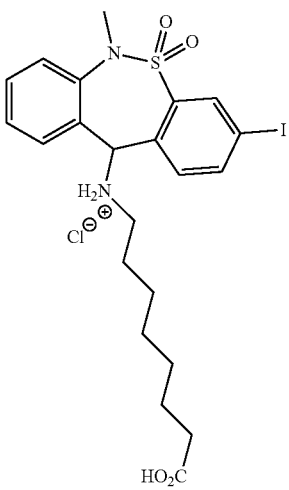

9e

The product 9e was prepared according to the general procedure and obtained as a white solid (117 mg, 98%). $^1$H NMR (400 MHz, MeOD δ 8.36 (d, J=1.9 Hz, 1H), 8.19 (dd, J=8.0, 1.9 Hz, 1H), 7.70 (dd, J=7.8, 1.5 Hz, 1H), 7.65-7.58 (m, 2H), 7.55 (dd, J=8.1, 1.4 Hz, 1H), 7.47 (td, J=7.5, 1.5 Hz, 1H), 5.83 (s, 1H), 3.23 (s, 3H), 2.91 (ddd, J=12.2, 9.8, 5.8 Hz, 1H), 2.77 (ddd, J=12.1, 9.7, 6.2 Hz, 1H), 2.26 (t, J=7.4 Hz, 2H), 1.71-1.51 (m, 4H), 1.36-1.27 (m, 6H); $^{13}$C NMR (101 MHz, MeOD) δ 177.6, 144.3, 142.3, 141.4, 137.9, 136.4, 134.5, 133.1, 129.9, 129.1, 128.6, 128.3, 97.5, 67.8, 48.4, 39.7, 34.8, 29.8, 29.7, 27.3, 27.2, 25.8.

9-((3-Iodo-6-methyl-5,5-dioxido-6,11-dihydrodibenzo [c,f][1,2]thiazepin-11-yl)amino) nonanoic acid hydrochloride salt (9f)

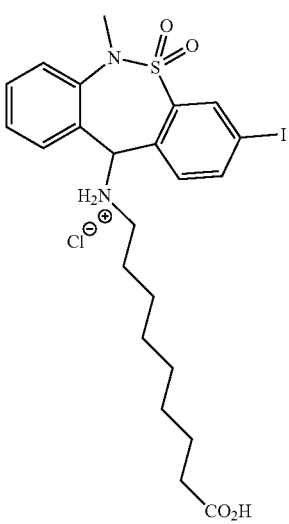

9f

The product 9f was prepared according to the general procedure run under more dilute conditions (0.02 M, because of poor solubility) and obtained as a glassy, white foam (18.7 mg, 76%). $^{13}$C NMR (126 MHz, MeOD) 8.34 (d, J=1.8 Hz, 1H), 8.17 (dd, J=8.0, 1.9 Hz, 1H), 7.68 (dd, J=7.9, 1.5 Hz, 1H), 7.63-7.56 (m, 2H), 7.54 (dd, J=8.2, 1.4 Hz, 1H), 7.45 (td, J=7.5, 1.5 Hz, 1H), 5.75 (s, 3H), 3.24 (s, 3H), 2.86 (ddd, J=12.0, 9.7, 5.6 Hz, 1H), 2.72 (ddd, J=12.0, 9.7, 6.2 Hz, 1H), 2.27 (t, J=7.6 Hz, 2H), 1.68-1.52 (m, 4H), 1.36-1.22 (m, 8H); $^{13}$C NMR (126 MHz, MeOD) δ 177.7, 144.1, 142.1, 141.5, 137.9, 136.2, 134.2, 132.8, 130.9, 129.5, 129.1, 128.6, 97.0, 67.8, 48.4, 39.7, 35.0, 30.0, 29.9, 27.6, 27.5, 26.0.

10-((3-Iodo-6-methyl-5,5-dioxido-6,11-dihydrodibenzo [c,f][1,2]thiazepin-11-yl)amino) decanoic acid hydrochloride salt (9g)

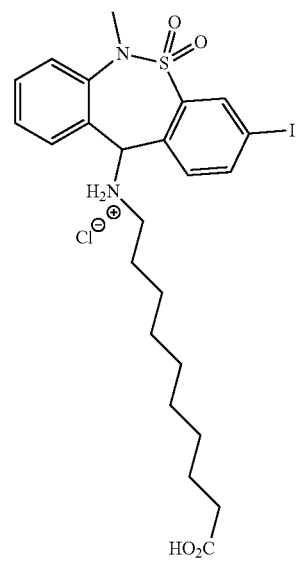

9g

The product 9g was prepared according to the general procedure run under more dilute conditions (0.01 M, because of poor solubility) and obtained as a glassy, white foam (15.6 mg, 70%). $^1$H NMR (500 MHz, MeOD) δ 8.35 (d, J=1.7 Hz, 1H), 8.19 (dd, J=8.0, 1.8 Hz, 1H), 7.71 (dd, J=7.9, 1.4 Hz, 1H), 7.66-7.59 (m, 2H), 7.55 (dd, J=8.1, 1.3 Hz, 1H), 7.47 (td, J=7.6, 1.3 Hz, 1H), 5.84 (s, 1H), 3.23 (s, 3H), 2.91 (ddd, J=12.1, 9.9, 5.6 Hz, 1H), 2.75 (ddd, J=12.1, 9.8, 6.1 Hz, 1H), 2.27 (t, J=7.4 Hz, 2H), 1.70-1.54 (m, 4H), 1.34-1.25 (m, 10H); $^{13}$C NMR (126 MHz, MeOD) δ 177.7, 144.3, 142.3, 141.4, 137.9, 136.5, 134.5, 133.1, 129.9, 129.1, 128.6, 128.3, 97.5, 67.8, 48.3, 39.7, 34.9, 30.18, 30.15, 30.1, 29.9, 27.5, 27.3, 26.0.

11-((3-Iodo-6-methyl-5,5-dioxido-6,11-dihydrodibenzo [c,f][1,2]thiazepin-11-yl)amino)undecanoic acid hydrochloride salt (9h)

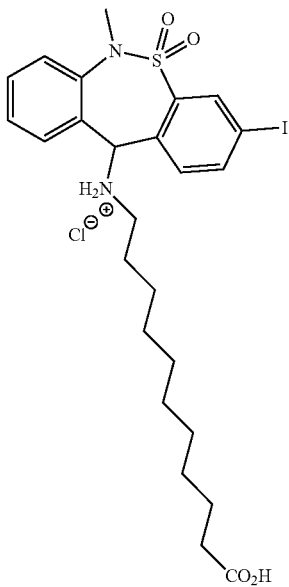

The product 9h was prepared according to the general procedure run under more dilute conditions (0.01 M, because of poor solubility) and obtained as a glassy, white foam (14.0 mg, 51%). $^1$H NMR (500 MHz, MeOD) δ 8.34 (d, J=1.8 Hz, 1H), 8.17 (dd, J=8.0, 1.8 Hz, 1H), 7.68 (dd, J=7.9, 1.5 Hz, 1H), 7.63-7.57 (m, 2H), 7.54 (dd, J=8.1, 1.4 Hz, 1H), 7.45 (td, J=7.5, 1.4 Hz, 1H), 5.75 (s, 1H), 3.23 (s, 3H), 2.87 (ddd, J=12.0, 9.7, 5.7 Hz, 1H), 2.72 (ddd, J=12.1, 9.7, 6.2 Hz, 1H), 2.27 (t, J=7.4 Hz, 2H), 1.69-1.52 (m, 4H), 1.36-1.22 (m, 12H); $^{13}$C NMR (126 MHz, MeOD) δ 177.8, 144.1, 142.1, 141.4, 137.9, 136.2, 134.3, 132.9, 129.1, 128.6, 97.1, 67.8, 48.3, 39.7, 35.0, 30.4, 30.3, 30.2, 30.0, 27.6, 27.5, 26.1.

Example 2. In Vitro Activity at Mu and Delta Opioid Receptors

The diarylthiazepinamine carboxylic acids (9) were tested for agonist activity at the human mu opioid receptor (MOR) and delta opioid receptor (DOR) using bioluminescence resonance energy transfer (BRET) assays measuring G protein activation as previously described (Table 1) (Rives, M.-L. et al. 2012; Negri, A. et al. 2013).

Transfection.

Human MOR cDNA was transfected alongside $G\alpha_{oB}$ with RLuc8 inserted at position 91 ($G\alpha_{oB}$—RLuc8), $G\beta_1$ ($\beta_1$), and $G\gamma_2$ fused to the full-length mVenus at its N terminus (mVenus-γ2) into HEK-293T cells (5×10$^6$ cells/plate) in 10-cm dishes using PEI (Polysciences Inc.; Warrington, PA) in a 1:1 ratio diluted in Opti-MEM (Life Technologies Corp.; Grand Island, NY) to assay for G protein activation as described previously (Rives, M.-L. et al. 2012; Negri, A. et al. 2013). Cells were maintained in Dulbecco's Modified Eagle Medium (high glucose #11965; Life Technologies) supplemented with 10% FBS (Premium Select, Atlanta Biologicals; Atlanta, GA) and 100 U/mL penicillin and 100 μg/mL streptomycin (#15140, Life Technologies). After 24 hours the media was changed, and the experiment was performed 24 hours later (48 hours after transfection).

BRET.

Transfected cells were dissociated and re-suspended in phosphate-buffered saline (PBS). Approximately 200,000 cells/well were added to a black-framed, white well 96-well plate (#60050; Perkin Elmer; Waltham, MA). The microplate was centrifuged and the cells were re-suspended in PBS. Then 5 μM of the luciferase substrate coelenterazine H was added to each well for 5 minutes. Following coelenterazine H addition, ligands were added and the BRET signal was measured at 5 minutes on a PHERAstar FS plate reader. Quantification of the BRET signal required calculating the ratio of the light emitted by the energy acceptor, mVenus (510-540 nm), over the light emitted by the energy donor, RLuc8 (485 nm). This drug-induced BRET signal was normalized using the $E_{max}$ of [D-Ala$^2$, N-MePhe$^4$, Gly-ol]-enkephalin (DAMGO) as the 100% maximal response for G protein activation. Dose response curves were fit using a three-parameter logistics equation in GraphPad Prism 6.

TABLE 1

Functional agonist activity of compounds at human MOR and DOR. Where indicated, error represents ± SEM of 2 or more independent trials. The data shows the trend for increasing DOR potency, but not MOR potency, as the length of the carboxylic acid side chain is increased.

| Compound | Structure | Human MOR (EC$_{50}$) | Human DOR (EC$_{50}$) |
|---|---|---|---|
| Tianeptine | 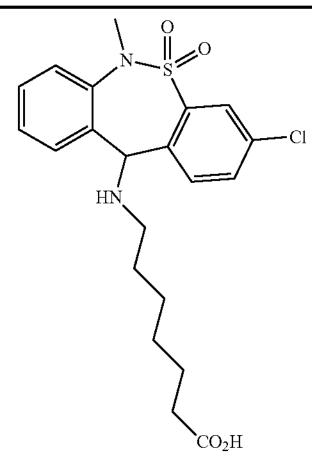 | 194 ± 70 nM | 37.4 ± 11.2 μM |

TABLE 1-continued

Functional agonist activity of compounds at human MOR and DOR. Where indicated, error represents ± SEM of 2 or more independent trials. The data shows the trend for increasing DOR potency, but not MOR potency, as the length of the carboxylic acid side chain is increased.

| Compound | Structure | Human MOR ($EC_{50}$) | Human DOR ($EC_{50}$) |
|---|---|---|---|
| 9a | 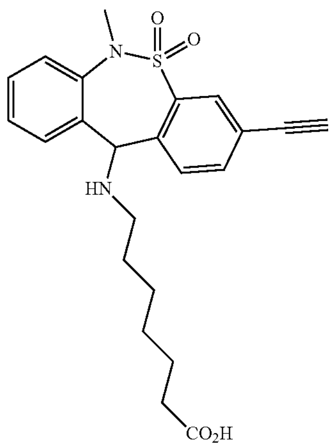 [SMILES: C#Cc1ccc2c(c1)S(=O)(=O)N(C)c1ccccc1C2NCCCCCCC(=O)O] | 53.3 ± 18 nM | 5.9 ± 0.3 µM |
| 9b | 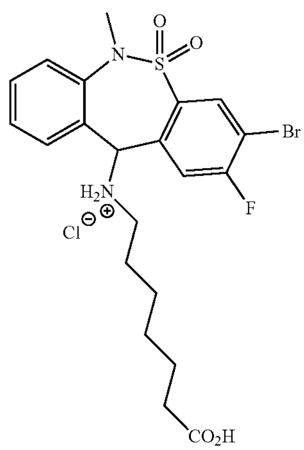 [SMILES: CN1c2ccccc2C([NH2+]CCCCCCC(=O)O)c2cc(F)c(Br)cc2S1(=O)=O ; [Cl-]] | 83.1 ± 5.7 nM | 11.5 ± 2.2 µM |
| 9c | 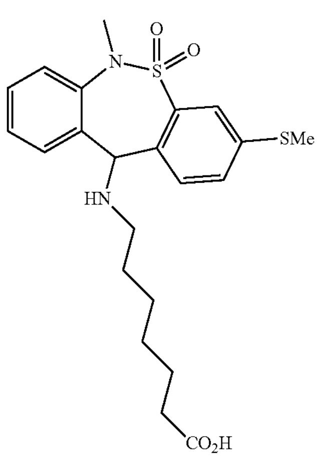 [SMILES: CSc1ccc2c(c1)S(=O)(=O)N(C)c1ccccc1C2NCCCCCCC(=O)O] | 41.8 nM | 2.06 µM ($E_{max}$ = 51%) partial agonist |

TABLE 1-continued

Functional agonist activity of compounds at human MOR and DOR. Where indicated, error represents ± SEM of 2 or more independent trials. The data shows the trend for increasing DOR potency, but not MOR potency, as the length of the carboxylic acid side chain is increased.

| Compound | Structure | Human MOR ($EC_{50}$) | Human DOR ($EC_{50}$) |
|---|---|---|---|
| 9d | 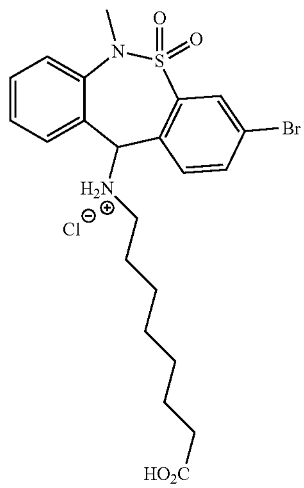 [SMILES: CN1c2ccccc2C([NH2+]CCCCCCCC(=O)O)c2ccc(Br)cc2S1(=O)=O ; [Cl-]] | 56 ± 24 nM | 1.7 ± 0.04 μM |
| 9e | 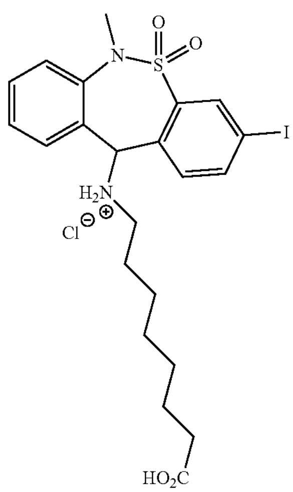 [SMILES: CN1c2ccccc2C([NH2+]CCCCCCCC(=O)O)c2ccc(I)cc2S1(=O)=O ; [Cl-]] | 24.2 ± 11 nM | 724 ± 99 nM |
| 9f | 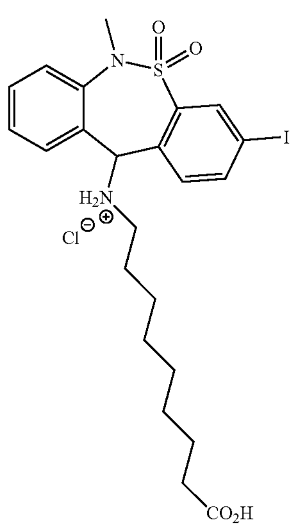 [SMILES: CN1c2ccccc2C([NH2+]CCCCCCCCC(=O)O)c2ccc(I)cc2S1(=O)=O ; [Cl-]] | 22 ± 14 nM | 530 ± 340 nM |

TABLE 1-continued

Functional agonist activity of compounds at human MOR and DOR. Where indicated, error represents ± SEM of 2 or more independent trials. The data shows the trend for increasing DOR potency, but not MOR potency, as the length of the carboxylic acid side chain is increased.

| Compound | Structure | Human MOR ($EC_{50}$) | Human DOR ($EC_{50}$) |
|---|---|---|---|
| 9g | 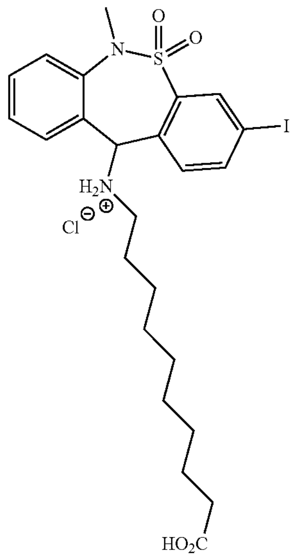 [SMILES: CN1c2ccccc2C([NH2+]CCCCCCCCCC(=O)O)c2ccc(I)cc2S1(=O)=O ; [Cl-]] | 26.6 ± 1.8 nM | 262 ± 25 nM |
| 9h | 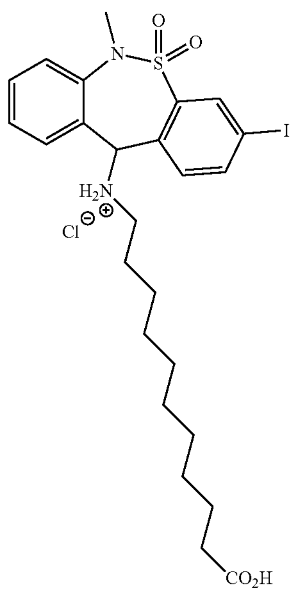 [SMILES: CN1c2ccccc2C([NH2+]CCCCCCCCCCC(=O)O)c2ccc(I)cc2S1(=O)=O ; [Cl-]] | 110 ± 29 nM | 700 ± 305 nM |

Example 3. Preparation of Additional Compounds

General Considerations

Reagents and solvents were obtained from commercial sources and were used without further purification unless otherwise stated. All compounds were prepared in racemic form. All reactions were performed in flame-dried glassware under an argon atmosphere unless otherwise stated, and monitored by TLC using solvent mixtures appropriate to each reaction. All column chromatography was performed on silica gel (40-63 μm). Nuclear magnetic resonance spectra were recorded on Bruker 400 or 500 MHz instruments as indicated. Chemical shifts are reported as δ values in ppm referenced to $CDCl_3$ ($^1$H NMR=7.26 and $^{13}$C NMR=77.16), MeOD ($^1$H NMR=3.31 and $^{13}$C NMR=49.00), or DMSO-$d_6$ ($^1$H NMR=2.50 and $^{13}$C NMR=39.52). Multiplicity is indicated as follows: s (singlet); d (doublet); t (triplet); q (quartet); p (pentet); dd (doublet of doublets); ddd (doublet of doublet of doublets); dt (doublet of triplets); td (triplet of doublets); m (multiplet); br (broad). All carbon peaks are rounded to one decimal place unless such rounding would cause two close peaks to become identical; in these cases, two decimal places are retained. Two carbon peaks joined by "and" in the peak list correspond to a single carbon atom but are split due to F—C coupling.

Preparation of Additional Diarylthiazepinones (3)
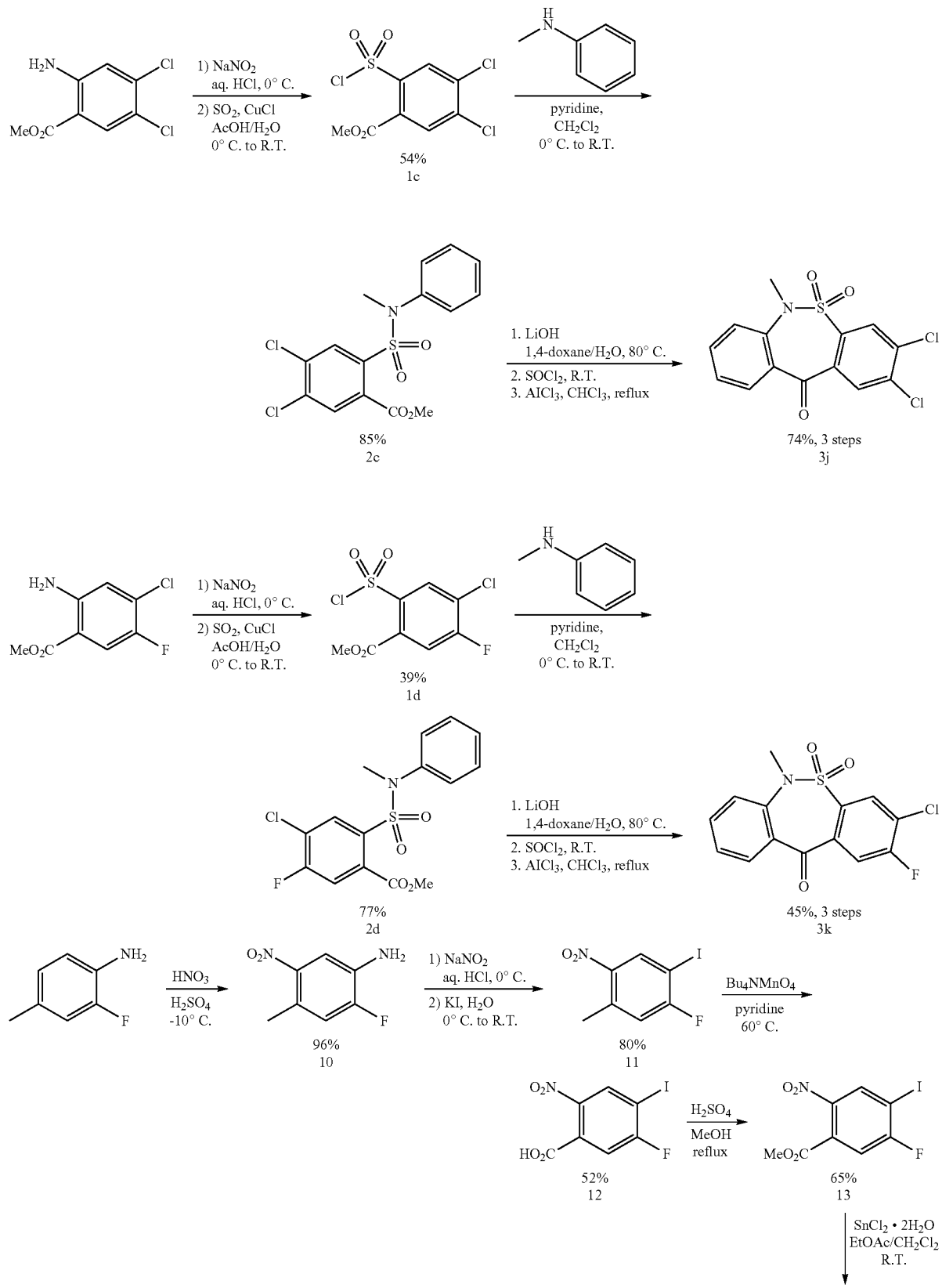
Scheme 6. Preparation of additional diarylthiazepinones.

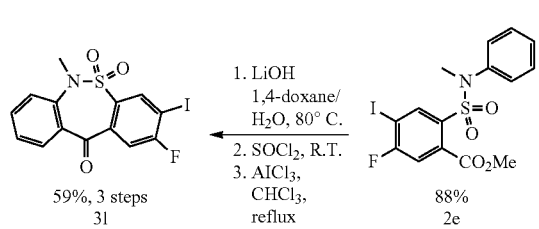 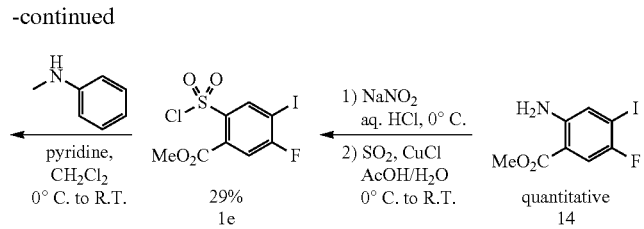

methyl 4,5-dichloro-2-(chlorosulfonyl)benzoate (1c)

A suspension of methyl 2-amino-4,5-dichlorobenzoate (1.92 g, 8.73 mmol) in 20% aqueous HCl (8.7 mL) was sonicated for several minutes and warmed slightly until all clumps were broken up and the mixture was a uniform suspension of fine particles. This mixture was cooled to −5° C., and a solution of $NaNO_2$ (602 mg, 8.73 mmol) in water (1.45 mL) was added dropwise over ~5 minutes, maintaining the internal temperature below −5° C. The resulting mixture was then stirred for 20 minutes at −5° C. Simultaneously, a solution of $SO_2$ (4.47 g, 69.84 mmol) in AcOH (6.98 mL) and water (0.73 mL) was prepared by bubbling the gas though the mixed solvents at 0° C. until the mass had increased by the required amount. To this $SO_2$ solution was then added CuCl (216 mg, 2.18 mmol) followed by the diazonium salt solution portionwise over 15 minutes at 0° C. The resulting mixture was then stirred for 30 minutes at 0° C. and 30 minutes at room temperature, poured into water (50 mL), and extracted with $CH_2Cl_2$ (3×25 mL). The combined organics were poured into water (50 mL), and solid $NaHCO_3$ was added carefully until effervescence ceased. The organic phase was then separated, washed with water (25 mL) and brine (25 mL), dried over $Na_2SO_4$, and concentrated to provide the crude sulfonyl chloride 1c as a waxy, very pale-yellow solid (1.75 g, 82 mass % product by NMR, 54% yield). This material was used in the next step without further purification.

methyl 4,5-dichloro-2-(N-methyl-N-phenylsulfamoyl)benzoate (2c)

To a solution of N-methylaniline (541 μL, 533 mg, 4.97 mmol) in anhydrous $CH_2Cl_2$ (4.4 mL) at 0° C. was added anhydrous pyridine (3.3 mL) followed by a solution of crude methyl 4,5-dichloro-2-(chlorosulfonyl)benzoate 1c (1.68 g, 82% pure, 4.52 mmol) in anhydrous $CH_2Cl_2$ (4.4 mL) over 3 minutes. The resulting orange solution was then allowed to warm to room temperature and stirred for 2.5 h. The reaction mixture was then diluted with $CH_2Cl_2$ (50 mL), washed with 3% aqueous HCl (2×25 mL), brine (25 mL), saturated aqueous $NaHCO_3$ (25 mL), and brine again (25 mL), dried over $Na_2SO_4$, and concentrated to give a viscous orange oil (1.93 g). This material was purified by column chromatography (9:1 hexanes:EtOAc, 3 column volumes→8:2 hexanes:EtOAc, 2 column volumes) to provide sulfonamide 2c as a viscous, pale-yellow oil that slowly crystallized to give a waxy, off-white solid (1.44 g, 85%). $^1$H NMR (500 MHz, $CDCl_3$) δ 7.57 (s, 1H), 7.45 (s, 1H), 7.39-7.30 (m, 3H), 7.22-7.18 (m, 2H), 3.83 (s, 3H), 3.31 (s, 3H); $^{13}$C NMR (126 MHz, $CDCl_3$) δ 166.3, 140.8, 137.4, 135.1, 134.6, 132.7, 131.8, 130.2, 129.4, 128.1, 127.4, 53.6, 39.1.

2,3-dichloro-6-methyldibenzo[c,f][1,2]thiazepin-11(6H)-one 5,5-dioxide (3j)

Sulfonamide 2c (1.43 g, 3.82 mmol) was dissolved in 1,4-dioxane (31 mL), water (16 mL) and $LiOH·H_2O$ (480 mg, 11.46 mmol) were added, and the mixture was heated at 80° C. for 40 minutes. The reaction mixture was diluted with water (125 mL), washed with $Et_2O$ (100 mL), acidified with 10% aqueous HCl, and extracted with $CH_2Cl_2$ (100 mL, 2×50 mL). The combined organics were dried over $Na_2SO_4$ and concentrated to provide the carboxylic acid intermediate as a pale-tan solid (1.33 g), which was used in the next step without further purification. To the carboxylic acid (1.32 g, 3.66 mmol) was added thionyl chloride (5.9 mL), all chunks were broken up by sonication, and the mixture was stirred for 1.5 h at room temperature (solids now dissolved). The volatiles were then removed in vacuo to provide the crude acyl chloride as a viscous yellow oil that slowly crystallized into a waxy yellow solid. This material was dissolved in anhydrous $CHCl_3$ (16 mL), aluminum chloride (1.56 g, 11.71 mmol) was added, and the mixture was refluxed for 1 h. The reaction was then cooled to room temperature, quenched with ice water (75 mL), and extracted with $CH_2Cl_2$ (3×25 mL). The combined organics were washed with water (25 mL), dried over $Na_2SO_4$, and concentrated to give a light-brown solid (1.19 g). This material was purified by column chromatography (hexanes, 1 column volume→1:1 $CH_2Cl_2$:hexanes, 1 column volumes→7:3 $CH_2Cl_2$:hexanes, 2 column volumes) to give ketone 3j as an off-white solid (960 mg, 74% over 3 steps). $^1$H NMR (400 MHz, $CDCl_3$) δ 8.29 (dd, J=8.1, 1.7 Hz, 1H), 8.07 (s, 1H), 8.04 (s, 1H), 7.67 (ddd, J=8.1, 7.3, 1.7 Hz, 1H), 7.40 (ddd, J=8.3, 7.3, 1.2 Hz, 1H), 7.36 (dd, J=8.1, 1.1 Hz, 1H), 3.36 (s, 3H); $^{13}$C NMR (101 MHz, $CDCl_3$) δ 188.3, 141.3, 138.3, 137.1, 136.5, 135.4, 135.3, 133.9, 132.4, 130.8, 127.5, 126.6, 124.9, 39.2.

methyl 4-chloro-2-(chlorosulfonyl)-5-fluorobenzoate (1d)

A suspension of methyl 2-amino-4-chloro-5-fluorobenzoate (4.98 g, 24.46 mmol) in 20% aqueous HCl (15.9 mL) was sonicated for several minutes and warmed slightly until all clumps were broken up and the mixture was a uniform suspension of fine particles. This mixture was cooled to −5° C., and a solution of $NaNO_2$ (1.69 g, 24.46 mmol) in water (4.1 mL) was added dropwise over −10 minutes, maintaining the internal temperature below −5° C. The resulting mixture was then stirred for 20 minutes at −5° C. Simultaneously, a solution of $SO_2$ (12.56 g, 196 mmol) in AcOH (19.6 mL) and water (2.04 mL) was prepared by bubbling the gas though the mixed solvents at 0° C. until the mass had increased by the required amount. To this $SO_2$ solution was then added CuCl (606 mg, 6.12 mmol) followed by the diazonium salt solution portionwise over 25 minutes at 0° C. The resulting mixture was then stirred for 1 h at 0° C. and 1 h at room temperature, poured into ice water (75 mL), and extracted with $CH_2Cl_2$ (3×30 mL). The combined organics were poured into water (100 mL), and solid $NaHCO_3$ was added carefully until effervescence ceased. The organic phase was then separated, washed with water (30 mL) and brine (30 mL), dried over $Na_2SO_4$, and concentrated to provide the crude sulfonyl chloride 1d as a waxy brown solid (3.39 g, 81 mass % product by NMR, 39% yield). This material was used in the next step without further purification.

methyl 4-chloro-5-fluoro-2-(N-methyl-N-phenylsulfamoyl)benzoate (2d)

To a solution of N-methylaniline (1.14 mL, 1.12 g, 10.36 mmol) in anhydrous $CH_2Cl_2$ (9.1 mL) at 0° C. was added anhydrous pyridine (6.9 mL) followed by a solution of crude methyl 4-chloro-2-(chlorosulfonyl)-5-fluorobenzoate 1d (3.35 g, 81% pure, 9.42 mmol) in anhydrous $CH_2Cl_2$ (9.1 mL) over 3 minutes. The resulting yellow-brown solution was then allowed to warm to room temperature and stirred for 1.25 h. The reaction mixture was then diluted with $CH_2Cl_2$ (100 mL), washed with 3% aqueous HCl (2×50 mL), brine (50 mL), saturated aqueous $NaHCO_3$ (50 mL), and brine again (50 mL), dried over $Na_2SO_4$, and concentrated to give a viscous, dark-orange oil (3.77 g). This material was purified by column chromatography (9:1 hexanes:EtOAc, 3 column volumes→8:2 hexanes:EtOAc, 2 column volumes) to provide sulfonamide 2d as a viscous, pale-yellow oil that slowly crystallized to give a waxy, off-white solid (2.60 g, 77%). $^1$H NMR (400 MHz, $CDCl_3$) 7.44 (d, J=6.8 Hz, 1H), 7.39-7.29 (m, 3H), 7.26 (d, J=8.3 Hz, 1H), 7.22-7.17 (m, 2H), 3.83 (s, 3H), 3.30 (s, 3H); $^{13}$C NMR (101 MHz, $CDCl_3$) δ 166.2, 161.1 and 158.6, 140.8, 134.03 and 133.96, 133.0, 132.5 and 132.4, 129.4, 128.1, 127.4, 123.3 and 123.1, 116.9 and 116.7, 53.6, 39.0.

3-chloro-2-fluoro-6-methyldibenzo[c,f][1,2]thiazepin-11(6H)-one 5,5-dioxide (3k)

Sulfonamide 2d (2.55 g, 7.13 mmol) was dissolved in 1,4-dioxane (57 mL), water (29 mL) and $LiOH \cdot H_2O$ (898 mg, 21.39 mmol) were added, and the mixture was heated at 80° C. for 1 h. The reaction mixture was diluted with water (250 mL), washed with $Et_2O$ (200 mL), acidified with 10% aqueous HCl, and extracted with $CH_2Cl_2$ (200 mL, 2×100 mL). The combined organics were dried over $Na_2SO_4$ and concentrated to provide the impure carboxylic acid intermediate as a waxy tan solid (2.48 g), which was used in the next step without further purification. To the crude carboxylic acid (2.45 g) was added thionyl chloride (11.5 mL) and the mixture was stirred for 1.5 h at room temperature (solids now dissolved). The volatiles were then removed in vacuo to provide the crude acyl chloride as a viscous yellow oil that slowly crystallized into a waxy yellow solid. This material was dissolved in anhydrous $CHCl_3$ (31 mL), aluminum chloride (3.04 g, 22.82 mmol) was added, and the mixture was refluxed for 1 h. The reaction was then cooled to room temperature, quenched with ice water (150 mL), and extracted with $CH_2Cl_2$ (3×50 mL). The combined organics were washed with water (50 mL), dried over $Na_2SO_4$, and concentrated to give a brownish-gray solid (1.84 g). This material was purified by column chromatography (7:3 hexanes:$CH_2Cl_2$, 2 column volumes→1:1 hexanes:$CH_2Cl_2$, 4 column volumes) to give ketone 3k as a crystalline, off-white solid (1.04 g, 45% over 3 steps). $^1$H NMR (500 MHz, $CDCl_3$) δ 8.30 (dd, J=8.1, 1.7 Hz, 1H), 8.04 (d, J=6.6 Hz, 1H), 7.78 (d, J=9.0 Hz, 1H), 7.67 (ddd, J=8.1, 7.2, 1.7 Hz, 1H), 7.41 (ddd, J=8.2, 7.2, 1.2 Hz, 1H), 7.36 (dd, J=8.1, 1.1 Hz, 1H), 3.36 (s, 3H); $^{13}$C NMR (126 MHz, $CDCl_3$) δ 188.2, 161.8 and 159.8, 141.4, 136.8 and 136.7, 135.4, 134.11 and 134.08, 132.5, 130.6, 128.6, 126.6, 125.9 and 125.8, 124.9, 120.4 and 120.2, 39.2.

2-fluoro-4-methyl-5-nitroaniline (10)

To $H_2SO_4$ (250 mL) was slowly added 2-fluoro-4-methylaniline (25.03 g, 200 mmol) while cooling the mixture on ice to prevent excessive warming, and the resulting mixture was stirred until all precipitated solids dissolved to give a transparent brown solution. This aniline solution was then cooled to −10° C. A second solution was prepared by careful addition of 68-70% m/m $HNO_3$ (20.0 g, 14.1 mL, 220 mmol) to $H_2SO_4$ (28 mL) while cooling the mixture on ice to maintain the temperature at room temperature or below. The $HNO_3/H_2SO_4$ solution was then added to the cooled aniline solution dropwise over 3 h, taking care not to allow the internal temperature to rise above −5° C. At the end of the addition, the reaction mixture was carefully poured into ice water (1.5 L) and the resulting mixture was carefully basified by slow addition of an NaOH solution (~450 g dissolved in 600 mL water), cooling the mixture in an ice bath to maintain the internal temperature below 60° C. at all times. The resulting precipitate was collected by filtration, washed thoroughly with water (4×), and dried to provide the pure product 10 as a yellow solid (32.65 g, 96%). $^1$H NMR (500 MHz, $CDCl_3$) δ 7.49 (d, J=8.2 Hz, 1H), 6.92 (d, J=11.2 Hz, 1H), 3.89 (br s, 2H), 2.48 (s, 3H); $^{13}$C NMR (126 MHz, $CDCl_3$) δ 154.5 and 152.5, 145.0, 133.5 and 133.3, 125.1 and 125.0, 119.0 and 118.8, 113.2 and 113.1, 20.21.

1-fluoro-2-iodo-5-methyl-4-nitrobenzene (11)

Aniline 10 (10.21 g, 60.00 mmol) was suspended in 36% m/m aqueous HCl (120 mL) and the mixture cooled to <0° C. To this mixture was added a solution of $NaNO_2$ (4.55 g, 66.00 mmol) in water (24 mL) dropwise over 10 minutes, maintaining the internal temperature at <0° C., and the resulting mixture was stirred for 30 minutes at −10° C. This diazonium salt solution was then added portionwise over 20 minutes to a solution of KI (19.92 g, 120 mmol) in water (36 mL) at 0° C., making sure to maintain the internal temperature of the KI solution below 10° C. during the addition. The resulting very dark-brown mixture was then allowed to warm to room temperature and stirred for 2 h. To the reaction mixture was then added water (300 mL), saturated aqueous $Na_2S_2O_3$ (50 mL), and $Et_2O$ (200 mL), and the mixture was shaken until the dark color was dissipated. The organic layer was separated and the remaining aqueous extracted with additional $Et_2O$ (2×200 mL). The combined organics were washed with water (100 mL) and brine (100 mL), dried over $Na_2SO_4$, and concentrated to give a dark-orange oil mixed with yellow solids (15.85 g). This material was purified by column chromatography (hexanes, 2 column volumes→25:1 hexanes:$Et_2O$, 3 column volumes) to give the pure product 11 as a crystalline, pale-yellow solid (13.53 g, 80%). $^1$H NMR (400 MHz, $CDCl_3$) δ 8.42 (d, J=5.8 Hz, 1H), 7.03 (dd, J=8.0, 0.8 Hz, 1H), 2.59 (s, 3H); $^{13}$C NMR (101 MHz, $CDCl_3$) δ 165.3 and 162.7, 145.8, 137.5 and 137.4, 136.4 and 136.3, 119.4 and 119.1, 77.8 and 77.5, 20.9.

5-fluoro-4-iodo-2-nitrobenzoic acid (12)

Tetrabutylammonium permanganate was prepared fresh according to the literature procedure (Vincent, J. et al. 1987) and dried for 21 h under high vacuum before immediate use. Compound 11 (10.07 g, 35.83 mmol) was dissolved in anhydrous pyridine (170 mL) and the solution was heated to 60° C. To this solution was slowly added a second solution of tetrabutylammonium permanganate (27.19 mmol, 75.24 mmol) in anhydrous pyridine (170 mL) over 19 minutes. Details of addition: +3.5 minutes, +10° C. exotherm, stopped addition for ~1 minute and removed external heating; +3.5-16.5 minutes, addition continued without external heating, maintaining stable internal temperature at 65-70° C.; +16.5-19 minutes, temperature began dropping, so external heating resumed, final third of addition completed more rapidly over 2.5 minutes. After the addition was complete, the reaction mixture was stirred for 30 minutes at 60° C. and then concentrated in vacuo to give a dark-brown residue. To this material was added EtOAc (270 mL) and 10% aqueous HCl (270 mL), followed by solid $Na_2S_2O_5$ to reduce residual oxidant (color dissipated). The organic layer was separated and the remaining aqueous was extracted with additional EtOAc (2×135 mL). The combined organics were washed with water (2×135 mL) and then extracted with 5% aqueous NaOH (270 mL, 2×135 mL). The basic aqueous extracts were washed with EtOAc (2×135 mL), acidified with concentrated aqueous HCl, and extracted with EtOAc (270 mL, 2×135 mL). The combined organics were washed with brine (135 mL), dried over $Na_2SO_4$, and concentrated to give carboxylic acid 12 containing minor impurities as an orange-brown solid (5.80 g, 52%). $^1$H NMR (400 MHz, DMSO-$d_6$) δ 8.52 (d, J=5.2 Hz, 1H), 7.72 (d, J=7.6 Hz, 1H); 13C NMR (101 MHz, DMSO-$d_6$) δ 164.4, 164.3 and 161.9, 144.74 and 144.70, 134.81 and 134.77, 129.8 and 129.7, 116.6 and 116.3, 87.0 and 86.7.

methyl 5-fluoro-4-iodo-2-nitrobenzoate (13)

To a solution of carboxylic acid 12 (5.76 g, 18.52 mmol) in MeOH (49 mL) was added $H_2SO_4$ (4.85 mL) and the mixture was refluxed for 21 h. The reaction mixture was then concentrated in vacuo and the resulting oil was diluted with EtOAc (200 mL), washed with saturated aqueous $NaHCO_3$ (200 mL) and brine (100 mL), dried over $Na_2SO_4$, and concentrated to give a viscous, dark orange-brown oil (5.36 g). This material was purified by column chromatography (hexanes, 1 column volume→20:1 hexanes:$Et_2O$, 2 column volumes→9:1 hexanes:$Et_2O$, 3 column volumes) to give ester 13 as a crystalline, pale-yellow solid (3.93 g, 65%). $^1$H NMR (400 MHz, CDCl$_3$) δ 8.35 (d, J=5.2 Hz, 1H), 7.37 (d, J=7.0 Hz, 1H), 3.93 (s, 3H); $^{13}$C NMR (101 MHz, CDCl$_3$) δ 165.3 and 162.8, 164.3, 144.4, 135.70 and 135.66, 130.2 and 130.1, 116.8 and 116.5, 84.5 and 84.2, 53.8.

methyl 2-amino-5-fluoro-4-iodobenzoate (14)

To a solution of ester 13 (3.92 g, 12.06 mmol) in EtOAc (90 mL) and $CH_2Cl_2$ (30 mL) was added $SnCl_2.2H_2O$ (13.61 g, 60.30 mmol) and the mixture was stirred for 21 h. The reaction mixture was then diluted with water (300 mL), solid $NaHCO_3$ was added with stirring until bubbling stopped, and the mixture was extracted with EtOAc (3×150 mL). The combined organics were washed with water (150 mL) and brine (150 mL), dried over $Na_2SO_4$, and concentrated to provide aniline 14 as a crystalline yellow solid (3.55 g, quantitative). $^1$H NMR (500 MHz, CDCl$_3$) δ 7.46 (d, J=8.8 Hz, 1H), 7.07 (d, J=5.1 Hz, 1H), 5.57 (br s, 2H), 3.85 (s, 3H); $^{13}$C NMR (126 MHz, CDCl$_3$) δ 167.4, 154.0 and 152.2, 147.4, 126.7, 115.9 and 115.7, 111.04 and 111.00, 90.0 and 89.8, 52.0.

methyl 2-(chlorosulfonyl)-5-fluoro-4-iodobenzoate (1e)

A suspension of aniline 14 (3.49 g, 11.83 mmol) in 20% aqueous HCl (7.7 mL) was sonicated for several minutes and warmed slightly until all clumps were broken up and the mixture was a uniform suspension of fine particles. This mixture was cooled to <0° C., and a solution of $NaNO_2$ (816 mg, 11.83 mmol) in water (2.0 mL) was added dropwise over ~10 minutes, maintaining the internal temperature below 0° C. The resulting mixture was then stirred for 25 minutes at −5° C. Simultaneously, a solution of $SO_2$ (6.06 g, 94.64 mmol) in AcOH (9.5 mL) and water (0.99 mL) was prepared by bubbling the gas though the mixed solvents at 0° C. until the mass had increased by the required amount. To this $SO_2$ solution was then added CuCl (293 mg, 2.96 mmol) followed by the diazonium salt solution portionwise over 10 minutes at 0° C. The resulting mixture was then stirred for 30 minutes at 0° C. and 30 minutes at room temperature, poured into water (50 mL), and extracted with $CH_2Cl_2$ (3×25 mL). The combined organics were poured into water (50 mL), and solid $NaHCO_3$ was added carefully until effervescence ceased. The organic phase was then separated, washed with water (25 mL) and brine (25 mL), dried over $Na_2SO_4$, and concentrated to provide the crude sulfonyl chloride 1e as a waxy, pale-yellow solid (2.12 g, 61 mass % product by NMR, 29% yield). This material was used in the next step without further purification.

methyl 5-fluoro-4-iodo-2-(N-methyl-N-phenylsulfamoyl)benzoate (2e)

To a solution of N-methylaniline (401 μL, 395 mg, 3.69 mmol) in anhydrous $CH_2Cl_2$ (3.2 mL) at 0° C. was added anhydrous pyridine (2.5 mL) followed by a solution of crude methyl 2-(chlorosulfonyl)-5-fluoro-4-iodobenzoate 1e (2.07 g, 61% pure, 3.35 mmol) in anhydrous $CH_2Cl_2$ (3.2 mL) over ~3 minutes. The resulting orange solution was then allowed to warm to room temperature and stirred for 30 minutes. The reaction mixture was then diluted with $CH_2Cl_2$ (30 mL), washed with 3% aqueous HCl (2×15 mL), brine (15 mL), saturated aqueous $NaHCO_3$ (15 mL), and brine again (15 mL), dried over $Na_2SO_4$, and concentrated to give a viscous orange oil (2.07 g). This material was purified by column chromatography (9:1 hexanes:EtOAc, 4 column volumes→8:2 hexanes:EtOAc, 2 column volumes) to provide sulfonamide 2e as a viscous yellow oil (1.33 g, 88%). $^1$H NMR (500 MHz, CDCl$_3$) δ 7.72 (d, J=5.8 Hz, 1H), 7.39-7.30 (m, 3H), 7.21-7.16 (m, 2H), 7.14 (d, J=7.3 Hz, 1H), 3.83 (s, 3H), 3.29 (s, 3H); $^{13}$C NMR (126 MHz, CDCl$_3$) δ 166.41 and 166.40, 164.6 and 162.6, 141.7 and 141.6, 140.9, 135.9 and 135.8, 132.48 and 132.45, 129.4, 128.1, 127.4, 115.5 and 115.3, 82.9 and 82.7, 53.6, 38.9.

2-fluoro-3-iodo-6-methyldibenzo[c,f][1,2]thiazepin-11(6H)-one 5,5-dioxide (31)

Sulfonamide 2e (1.31 g, 2.91 mmol) was dissolved in 1,4-dioxane (23 mL), water (12 mL) and LiOH·H$_2$O (366 mg, 8.73 mmol) were added, and the mixture was heated at 80° C. for 45 minutes. The reaction mixture was diluted with water (125 mL), washed with $Et_2O$ (100 mL), acidified with 10% aqueous HCl, and extracted with $CH_2Cl_2$ (100 mL, 2×50 mL). The combined organics were dried over $Na_2SO_4$ and concentrated to provide the impure carboxylic acid intermediate as a viscous orange oil that slowly crystallized to a pale-orange solid (1.10 g), which was used in the next step without further purification. To the crude carboxylic acid (1.08 g) was added thionyl chloride (4.0 mL) and the mixture was stirred for 5 h at room temperature (solids now dissolved). The volatiles were then removed in vacuo to provide the crude acyl chloride as a viscous yellow oil. This material was dissolved in anhydrous CHCl$_3$ (11 mL), aluminum chloride (1.06 g, 7.94 mmol) was added, and the mixture was refluxed for 1 h. The reaction was then cooled to room temperature, quenched with ice water (75 mL), and extracted with CH$_2$Cl$_2$ (3×25 mL). The combined organics were washed with water (25 mL), dried over Na$_2$SO$_4$, and concentrated to give a tan solid (0.90 g). This material was purified by column chromatography (hexanes, 1 column volume→7:3 hexanes:CH$_2$Cl$_2$, 1 column volume→1:1 hexanes:CH$_2$Cl$_2$, 1 column volume→3:7 hexanes:CH$_2$Cl$_2$, 3 column volumes) to give ketone 31 as an off-white solid (717 mg, 59% over 3 steps). $^1$H NMR (500 MHz, CDCl$_3$) δ 8.37 (d, J=5.6 Hz, 1H), 8.29 (dd, J=8.2, 1.7 Hz, 1H), 7.69-7.65 (m, 1H), 7.63 (d, J=7.9 Hz, 1H), 7.40 (td, J=7.8, 1.2 Hz, 1H), 7.35 (dd, J=8.1, 1.2 Hz, 1H), 3.36 (s, 3H); $^{13}$C NMR (126 MHz, CDCl$_3$) δ 188.6, 165.7 and 163.7, 141.5, 138.74 and 138.68, 137.11 and 137.08, 135.4, 134.3 and 134.2, 132.4, 130.6, 126.5, 124.9, 118.8 and 118.6, 86.4 and 86.2, 39.2.

Preparation of Additional Diarylthiazepinyl Chlorides (5)

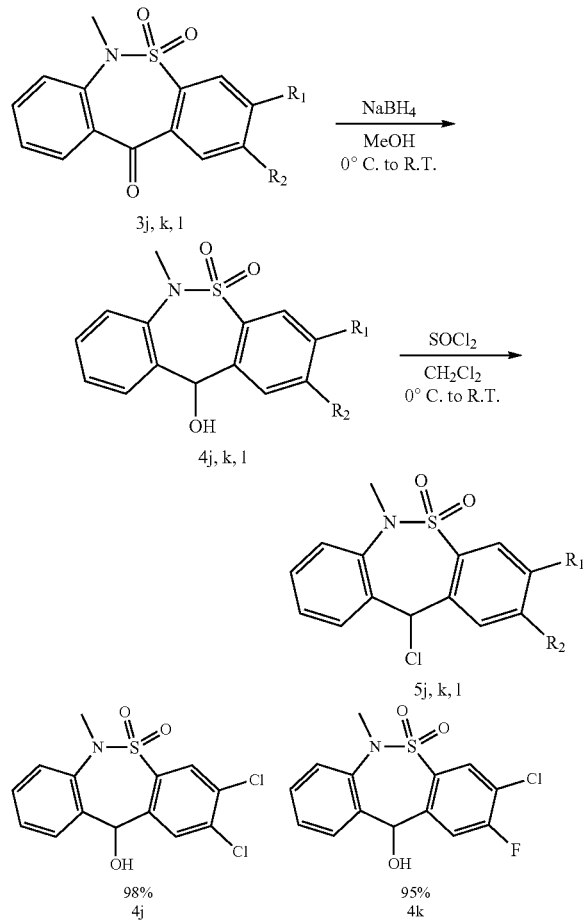

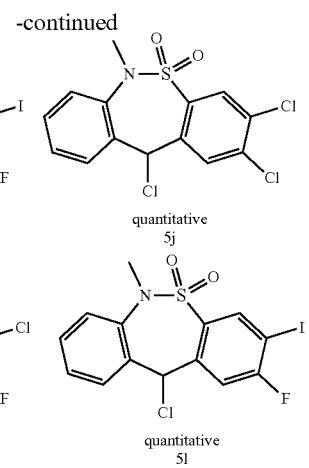

2,3-dichloro-11-hydroxy-6-methyl-6,11-dihydrodibenzo [c,f][1,2]thiazepine 5,5-dioxide (4j)

The product 4j was prepared according to the general procedure described in Example 1 and obtained as an off-white solid (935 mg, 98%). $^1$H NMR (400 MHz, CDCl$_3$) δ 8.02 (s, 1H), 7.84 (s, 1H), 7.63-7.57 (m, 1H), 7.44-7.31 (m, 3H), 6.02 (d, J=8.0 Hz, 1H), 3.95 (d, J=8.4 Hz, 1H), 3.25 (s, 3H); $^{13}$C NMR (101 MHz, CDCl$_3$) δ 138.2, 138.0, 137.7, 136.8, 136.2, 133.2, 131.0, 130.13, 130.12, 130.0, 128.2, 127.1, 74.1, 38.9.

3-chloro-2-fluoro-11-hydroxy-6-methyl-6,11-dihydrodibenzo [c,f][1,2]thiazepine 5,5-dioxide (4k)

The product 4k was prepared according to the general procedure described in Example 1 and obtained as an off-white solid (973 mg, 95%). $^1$H NMR (500 MHz, CDCl$_3$) δ 8.01 (d, J=6.9 Hz, 1H), 7.63-7.58 (m, 1H), 7.55 (d, J=9.5 Hz, 1H), 7.41 (td, J=7.3, 1.7 Hz, 1H), 7.38-7.32 (m, 2H), 6.07 (d, J=6.8 Hz, 1H), 3.91 (d, J=7.8 Hz, 1H), 3.26 (s, 3H); $^{13}$C NMR (126 MHz, CDCl$_3$) δ 161.5 and 159.4, 140.0 and 139.9, 138.0, 136.6, 134.1 and 134.0, 131.0, 130.1, 129.7, 128.2, 127.1, 121.6 and 121.5, 117.3 and 117.1, 73.6, 38.7.

2-fluoro-11-hydroxy-3-iodo-6-methyl-6,11-dihydrodibenzo [c,f][1,2]thiazepine 5,5-dioxide (4l)

The product 4l was prepared according to the general procedure described in Example 1 and obtained as an extremely pale-pink solid (669 mg, 94%). $^1$H NMR (400 MHz, CDCl$_3$) δ 8.31 (d, J=5.9 Hz, 1H), 7.64-7.57 (m, 1H), 7.45-7.38 (m, 2H), 7.37-7.32 (m, 2H), 6.04 (d, J=8.4 Hz, 1H), 3.89 (d, J=8.5 Hz, 1H), 3.25 (s, 3H); $^{13}$C NMR (101 MHz, CDCl$_3$) δ 165.7 and 163.1, 141.9 and 141.8, 139.48 and 139.45, 138.2, 136.4, 134.63 and 134.60, 130.1, 129.7, 128.2, 127.0, 116.2 and 115.9, 80.8 and 80.5, 73.8, 38.7.

Modified Procedure for Preparation of Diarylthiazepinyl Chlorides (5)

Thionyl chloride (12 equivalents) was added dropwise to a solution of the appropriate alcohol 4 (1 equivalent) in anhydrous CH$_2$Cl$_2$ (0.126 M based on 4) at 0° C. The reaction mixture was then warmed to room temperature, stirred overnight, and concentrated to provide the corresponding chloride 5, which was used directly in the following reactions without further purification.

2,3,11-trichloro-6-methyl-6,11-dihydrodibenzo [c,f][1,2]thiazepine 5,5-dioxide (5j)

The product 5j was prepared according to the modified procedure and obtained as an off-white solid (973 mg, quantitative). $^1$H NMR (500 MHz, CDCl$_3$) δ 8.08 (s, 1H), 7.67 (s, 1H), 7.55-7.49 (m, 2H), 7.43 (d, J=7.6 Hz, 1H), 7.41-7.34 (m, 1H), 6.06 (s, 1H), 3.57 (s, 3H); $^{13}$C NMR (126 MHz, CDCl$_3$) δ 139.9, 139.0, 137.1, 136.7, 134.9, 134.79, 132.8, 131.9, 130.1, 130.0, 129.5, 129.1, 62.7, 39.3.

3,11-dichloro-2-fluoro-6-methyl-6,11-dihydrodibenzo [c,f][1,2]thiazepine 5,5-dioxide (5k)

The product 5k was prepared according to the modified procedure and obtained as a white solid (1.01 g, quantitative). $^1$H NMR (500 MHz, CDCl$_3$) δ 8.07 (d, J=7.1 Hz, 1H), 7.55-7.48 (m, 2H), 7.44 (d, J=7.4 Hz, 1H), 7.40-7.33 (m, 2H), 6.08 (s, 1H), 3.57 (s, 3H); $^{13}$C NMR (126 MHz, CDCl$_3$) δ 160.6 and 158.5, 139.0, 137.28 and 137.25, 137.1, 136.3 and 136.2, 131.8, 131.0, 130.0, 129.4, 129.1, 123.5 and 123.4, 119.2 and 119.0, 62.7, 39.1.

11-chloro-2-fluoro-3-iodo-6-methyl-6,11-dihydrodibenzo [c,f][1,2]thiazepine 5,5-dioxide (5l)

The product 5l was prepared according to the modified procedure and obtained as a white solid (695 mg, quantitative). $^1$H NMR (500 MHz, CDCl$_3$) δ 8.38 (d, J=6.0 Hz, 1H), 7.55-7.48 (m, 2H), 7.44 (d, J=7.5 Hz, 1H), 7.40-7.33 (m, 1H), 7.24 (d, J=8.2 Hz, 1H), 6.07 (s, 1H), 3.57 (s, 3H); $^{13}$C NMR (126 MHz, CDCl$_3$) δ 164.5 and 162.5, 139.53 and 139.50, 139.0, 138.14 and 138.08, 137.64 and 137.61, 137.1, 131.8, 130.0, 129.4, 129.1, 117.8 and 117.6, 83.1 and 82.9, 62.8, 39.1.

Preparation of Additional Diarylthiazepinamine Esters (8)

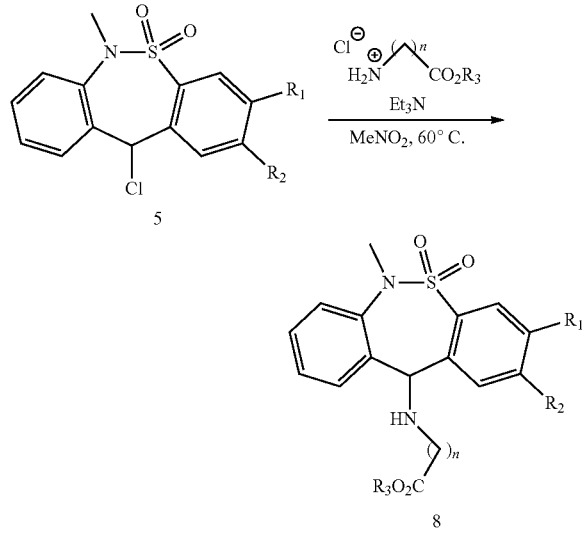

Scheme 8. Preparation of additional diarylthiazepinamine esters.

$R_1$ = Cl, Br, I
$R_2$ = F, Cl
$R_3$ = Me, Et
n = 4, 6 ethyl 7-((2,3-dichloro-6-methyl-5,5-dioxido-6,11-dihydrodibenzo [c,f][1,2]thiazepin-11-yl)amino) heptanoate (8i)

The product 8i was prepared according to the general procedure described in Example 1 and purified by column chromatography (CH$_2$Cl$_2$, 2 column volumes→20:1 CH$_2$Cl$_2$:Et$_2$O, 4 column volumes) to provide a viscous, pale-yellow oil (90.2 mg, 90%). $^1$H NMR (400 MHz, CDCl$_3$) δ 8.02 (s, 1H), 7.62 (s, 1H), 7.42-7.33 (m, 3H), 7.33-7.27 (m, 1H), 5.03 (s, 1H), 4.11 (q, J=7.1 Hz, 2H), 3.39 (s, 3H), 2.50 (t, J=7.0 Hz, 2H), 2.27 (t, J=7.5 Hz, 2H), 1.97 (br s, 1H), 1.60 (p, J=7.3 Hz, 2H), 1.51 (p, J=6.9 Hz, 2H), 1.40-1.27 (m, J=5.5, 5.0 Hz, 4H), 1.24 (t, J=7.1 Hz, 3H); $^{13}$C NMR (101 MHz, CDCl$_3$) δ 173.8, 139.0, 138.8, 138.6, 138.3, 136.7, 132.6, 130.8, 130.4, 129.6, 129.3, 128.5, 128.1, 65.0, 60.3, 48.3, 38.5, 34.4, 30.0, 29.1, 27.0, 24.9, 14.4.

ethyl 7-((3-chloro-2-fluoro-6-methyl-5,5-dioxido-6,11-dihydrodibenzo[c,f][1,2]thiazepin-11-yl)amino) heptanoate (8j)

The product 8j was prepared according to the general procedure described in Example 1 and purified by column chromatography (CH$_2$Cl$_2$, 2 column volumes→20:1 CH$_2$Cl$_2$:Et$_2$O, 2 column volumes→7:3 CH$_2$Cl$_2$:Et$_2$O, 2 column volumes) to provide a viscous, pale-yellow oil (433 mg, 90%). $^1$H NMR (500 MHz, CDCl$_3$) δ 8.00 (d, J=7.0 Hz, 1H), 7.41-7.32 (m, 4H), 7.29 (td, J=7.3, 1.5 Hz, 1H), 5.09 (s, 1H), 4.10 (q, J=7.1 Hz, 2H), 3.38 (s, 3H), 2.51 (td, J=7.2, 1.8 Hz, 2H), 2.27 (t, J=7.5 Hz, 2H), 1.98 (br s, 1H), 1.60 (p, J=7.4 Hz, 2H), 1.51 (p, J=7.1 Hz, 2H), 1.38-1.26 (m, 4H), 1.23 (t, J=7.1 Hz, 3H); $^{13}$C NMR (126 MHz, CDCl$_3$) δ 173.8, 160.8 and 158.7, 140.9 and 140.8, 139.2, 138.2, 135.54 and 135.51, 131.3, 129.4, 128.7, 128.4, 127.9, 121.0 and 120.8, 116.9 and 116.7, 64.2, 60.3, 48.3, 38.1, 34.3, 30.0, 29.0, 27.0, 24.9, 14.3.

ethyl 7-((2-fluoro-3-iodo-6-methyl-5,5-dioxido-6,11-dihydrodibenzo[c,f][1,2]thiazepin-11-yl)amino) heptanoate (8k)

The product 8k was prepared according to the general procedure described in Example 1 and purified by column chromatography (8:2 hexanes:EtOAc, 4 column volumes→7:3 hexanes:EtOAc, 2 column volumes) to provide a viscous, pale-yellow oil (240 mg, 84%). $^1$H NMR (500 MHz, CDCl$_3$) δ 8.30 (d, J=6.0 Hz, 1H), 7.41-7.32 (m, 3H), 7.29 (td, J=7.4, 1.5 Hz, 1H), 7.24 (d, J=8.6 Hz, 1H), 5.08 (s, 1H), 4.11 (q, J=7.1 Hz, 2H), 3.38 (s, 3H), 2.56-2.46 (m, 2H), 2.27 (t, J=7.5 Hz, 2H), 1.99 (br s, 1H), 1.60 (p, J=7.4 Hz, 2H), 1.51 (p, J=7.2 Hz, 2H), 1.38-1.26 (m, 4H), 1.24 (t, J=7.1 Hz, 3H); $^{13}$C NMR (126 MHz, CDCl$_3$) δ 173.8, 164.7 and 162.7, 142.9 and 142.8, 139.82 and 139.79, 139.1, 138.2, 136.04 and 136.01, 129.4, 128.7, 128.3, 127.8, 115.7 and 115.5, 80.0 and 79.8, 64.2, 60.3, 48.3, 38.1, 34.3, 30.0, 29.0, 27.0, 24.9, 14.4.

methyl 5-((3-bromo-2-fluoro-6-methyl-5,5-dioxido-6,11-dihydrodibenzo[c,f][1,2]thiazepin-11-yl)amino)pentanoate (8l)

The product 8l was prepared according to the general procedure described in Example 1 and purified by column chromatography (8:2 hexanes:EtOAc, 3 column volumes→7:3 hexanes:EtOAc, 4 column volumes) to provide a viscous, pale-yellow oil (196 mg, 81%). $^1$H NMR (500 MHz, CDCl$_3$) δ 8.15 (d, J=6.6 Hz, 1H), 7.40-7.27 (m, 5H), 5.08 (s, 1H), 3.65 (s, 3H), 3.37 (s, 3H), 2.54 (td, J=7.0, 2.1 Hz, 2H), 2.31 (t, J=7.3 Hz, 2H), 2.02 (br s, 1H), 1.72-1.63 (m, 2H), 1.59-1.50 (m, 2H); $^{13}$C NMR (126 MHz, CDCl$_3$) δ 173.9, 161.9 and 159.9, 141.54 and 141.49, 138.9, 138.3, 135.82 and 135.80, 134.2, 129.5, 128.9, 128.4, 127.9, 116.8 and 116.6, 108.7 and 108.5, 64.3, 51.6, 47.8, 38.2, 33.8, 29.6, 22.7.

Preparation of Additional Diarylthiazepinamine Carboxylic Acids (9)

Scheme 9. Preparation of additional diarylthiazepinamine carboxylic acids.

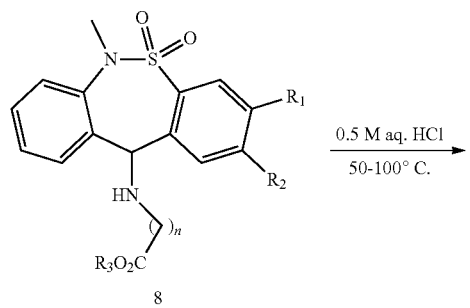

R$_1$ = Cl, Br, I
R$_2$ = F, Cl
R$_3$ = Me, Et
n = 4, 6

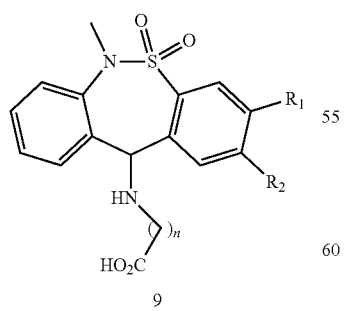

7-((2,3-dichloro-6-methyl-5,5-dioxido-6,11-dihydrodibenzo [c,f][1,2]thiazepin-11-yl)amino)heptanoic acid hydrochloride salt (9i)

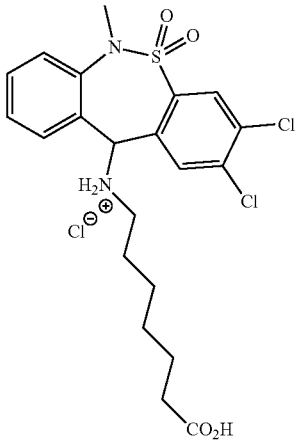

The product 9i was prepared according to the general procedure described in Example 1 and obtained as an off-white foam (78.5 mg, 88%, Note: some spilled during workup). $^1$H NMR (500 MHz, MeOD) δ 8.23 (s, 1H), 8.19 (s, 1H), 7.72 (dd, J=7.9, 1.5 Hz, 1H), 7.66 (ddd, J=8.7, 7.3, 1.5 Hz, 1H), 7.59 (dd, J=8.2, 1.3 Hz, 1H), 7.50 (td, J=7.5, 1.4 Hz, 1H), 5.96 (s, 1H), 2.99 (ddd, J=12.2, 10.1, 5.7 Hz, 1H), 2.88 (ddd, J=12.2, 10.1, 6.1 Hz, 1H), 2.27 (t, J=7.3 Hz, 2H), 1.75-1.62 (m, 2H), 1.62-1.53 (m, 2H), 1.40-1.28 (m, 4H); $^{13}$C NMR (126 MHz, MeOD) δ 177.4, 142.4, 140.1, 139.1, 137.0, 137.0, 134.8, 133.6, 131.3, 129.4, 129.2, 128.6, 67.0, 39.8, 34.6, 29.5, 27.1, 26.8, 25.6.

7-((3-chloro-2-fluoro-6-methyl-5,5-dioxido-6,11-dihydrodibenzo [c,f][1,2]thiazepin-11-yl)amino)heptanoic acid hydrochloride salt (9j)

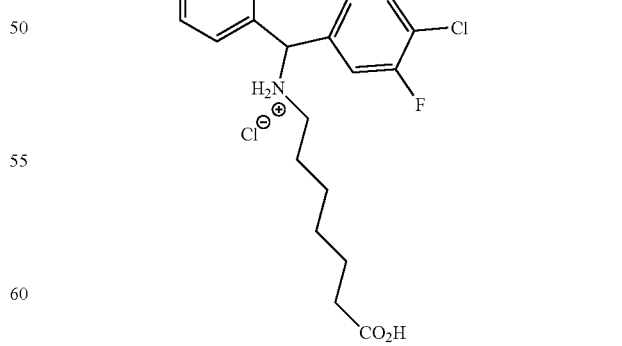

The product 9j was prepared according to the general procedure described in Example 1 and obtained as an off-white foam (396 mg, 92%). $^1$H NMR (400 MHz, MeOD) δ 8.23 (d, J=7.0 Hz, 1H), 7.94 (d, J=9.2 Hz, 1H), 7.74 (dd, J=7.8, 1.5 Hz, 1H), 7.65 (ddd, J=8.5, 7.3, 1.5 Hz, 1H), 7.58 (dd, J=8.2, 1.3 Hz, 1H), 7.49 (td, J=7.5, 1.4 Hz, 1H), 5.98 (s, 1H), 3.24 (s, 3H), 3.01 (ddd, J=12.1, 9.9, 5.9 Hz, 1H), 2.87 (ddd, J=12.2, 9.9, 6.2 Hz, 1H), 2.27 (t, J=7.3 Hz, 2H), 1.77-1.63 (m, 2H), 1.63-1.52 (m, 2H), 1.40-1.27 (m, 4H); $^{13}$C NMR (101 MHz, MeOD) δ 177.4, 163.0 and 160.4, 142.5, 137.50 and 137.46, 134.8, 133.6, 132.4, 130.9 and 130.8, 129.2, 128.6, 126.7, 125.4 and 125.2, 124.0 and 123.7, 67.1, 48.5, 39.9, 34.6, 29.5, 27.1, 26.9, 25.6.

7-((2-fluoro-3-iodo-6-methyl-5,5-dioxido-6,11-dihydrodibenzo [c,f][1,2]thiazepin-11-yl)amino) heptanoic acid hydrochloride salt (9k)

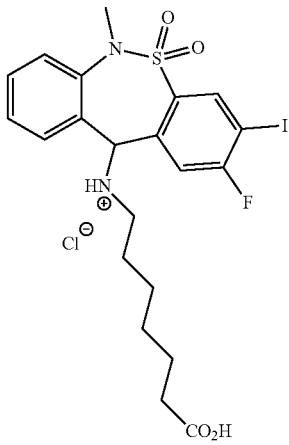

9k

The product 9k was prepared according to the general procedure described in Example 1 and obtained as a white solid (210 mg, 91%) containing a minor impurity (~5 mol %, introduced during preparation of intermediate 41 and carried through following steps). A portion of this material was further purified by recrystallization. A quantity (199 mg) was re-dissolved in $CH_2Cl_2$ and concentrated in vacuo to give a white foam. To this was added minimal $CH_2Cl_2$, causing the product to first dissolve and then crystallize. The product was allowed to settle, the supernatant removed by pipet, and the residue dried in vacuo to give a crystallized sample of product 9k (176 mg). $^1$H NMR (400 MHz, MeOD) δ 8.47 (d, J=6.0 Hz, 1H), 7.78-7.70 (m, 2H), 7.65 (ddd, J=8.7, 7.2, 1.6 Hz, 1H), 7.57 (dd, J=8.1, 1.4 Hz, 1H), 7.49 (td, J=7.5, 1.5 Hz, 1H), 5.95 (s, 1H), 3.23 (s, 3H), 3.00 (ddd, J=12.2, 10.0, 5.8 Hz, 1H), 2.85 (ddd, J=12.2, 9.9, 6.2 Hz, 1H), 2.27 (t, J=7.3 Hz, 2H), 1.76-1.62 (m, 2H), 1.62-1.53 (m, 2H), 1.39-1.28 (m, 4H); $^{13}$C NMR (101 MHz, MeOD) δ 177.4, 167.4 and 164.8, 142.6, 141.1 and 141.0, 137.44 and 137.40, 134.9, 133.5, 132.3 and 132.2, 129.1, 128.6, 126.6, 122.4 and 122.1, 85.7 and 85.5, 67.3, 48.4, 39.9, 34.6, 29.5, 27.1, 26.8, 25.6.

5-((3-bromo-2-fluoro-6-methyl-5,5-dioxido-6,11-dihydrodibenzo [c,f][1,2]thiazepin-11-yl)amino) pentanoic acid hydrochloride salt (91)

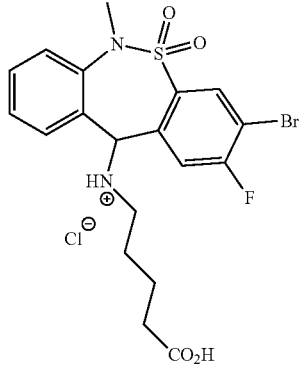

91

The product 91 was prepared according to the general procedure described in Example 1 and obtained as a crystalline white solid (195 mg, 99%). $^1$H NMR (500 MHz, MeOD) δ 8.35 (d, J=6.6 Hz, 1H), 7.87 (d, J=8.7 Hz, 1H), 7.73 (dd, J=7.9, 1.5 Hz, 1H), 7.66 (ddd, J=8.8, 7.4, 1.5 Hz, 1H), 7.58 (dd, J=8.2, 1.4 Hz, 1H), 7.49 (td, J=7.6, 1.3 Hz, 1H), 5.96 (s, 1H), 3.24 (s, 3H), 3.03 (ddd, J=12.3, 9.6, 5.9 Hz, 1H), 2.90 (ddd, J=12.3, 9.6, 6.2 Hz, 1H), 2.32 (t, J=7.0 Hz, 2H), 1.81-1.66 (m, 2H), 1.61 (p, J=7.0 Hz, 2H); $^{13}$C NMR (126 MHz, MeOD) δ 176.7, 164.0 and 162.0, 142.5, 137.7 and 137.6, 135.2, 134.8, 133.6, 131.3, 129.2, 128.6, 126.6, 123.7 and 123.4, 113.3 and 113.1, 67.3, 48.2, 39.8, 33.8, 26.5, 22.7.

Example 4. In Vitro Activity of Additional Compounds at Mu Opioid Receptors

The additional diarylthiazepinamine carboxylic acids (9i, 9j, 9k, and 91) were tested for agonist activity at the human mu opioid receptor (MOR) using bioluminescence resonance energy transfer (BRET) assays measuring G protein activation (Table 2) as previously described (Rives, M.-L. et al. 2012; Negri, A. et al. 2013; Example 2 of the present application).

TABLE 2

Functional agonist activity of compounds at human MOR. All compounds are full agonists relative to the reference agonist DAMGO with potency equal to or higher than tianeptine.

| Compound | Structure | Human MOR $EC_{50}$ [95% CI] |
|---|---|---|
| 9i | 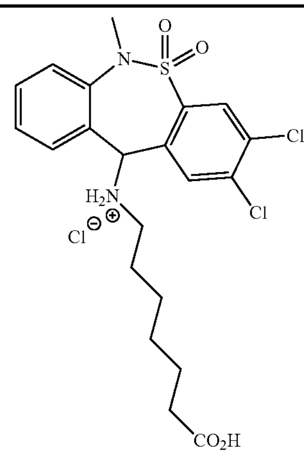 | 172 nM [120, 229] |

TABLE 2-continued

Functional agonist activity of compounds at human MOR. All compounds are full agonists relative to the reference agonist DAMGO with potency equal to or higher than tianeptine.

| Compound | Structure | Human MOR EC$_{50}$ [95% CI] |
|---|---|---|
| 9j | 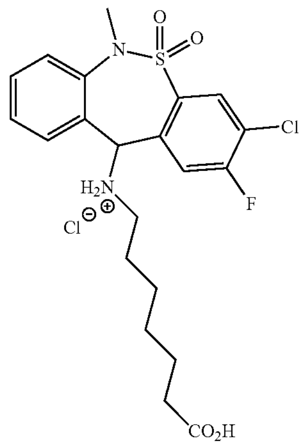 [SMILES: CN1c2ccccc2C([NH2+]CCCCCCC(=O)O)c2cc(F)c(Cl)cc2S1(=O)=O ; [Cl-]] | 129 nM |
| 9k | 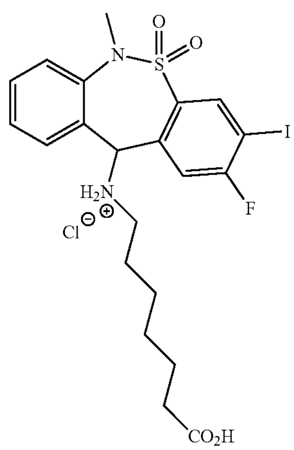 [SMILES: CN1c2ccccc2C([NH2+]CCCCCCC(=O)O)c2cc(F)c(I)cc2S1(=O)=O ; [Cl-]] | 4.6 nM [3.2, 6.7] |
| 9l | 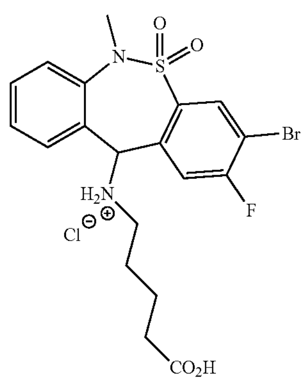 [SMILES: CN1c2ccccc2C([NH2+]CCCCC(=O)O)c2cc(F)c(Br)cc2S1(=O)=O ; [Cl-]] | 45 nM [33, 60] |

Example 5. Preparation of Additional Compounds

Additional compounds active as agonists of the MOR or DOR are synthesized according to the synthetic methods described in Example 1 and Example 3. For instance, such additional compounds include 9m, 9n, and 9o (Scheme 10), which are active metabolites of compounds 9i, 9j, and 9k, respectively. The ester precursors of these compounds, 8m, 8n, and 8o, are active themselves and also act as prodrugs for compounds 9m, 9n, and 9o, respectively.

Scheme 10. Additional diarylthiazepinamine esters and carboyxlic acids.

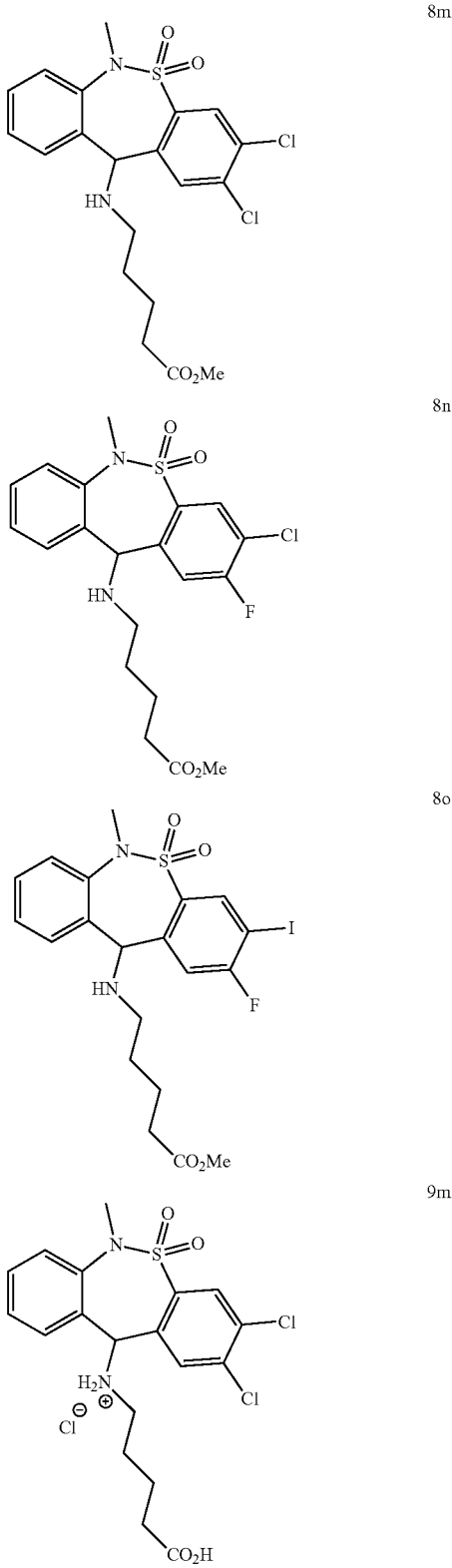

9n

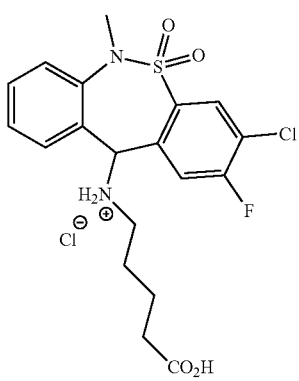

9o

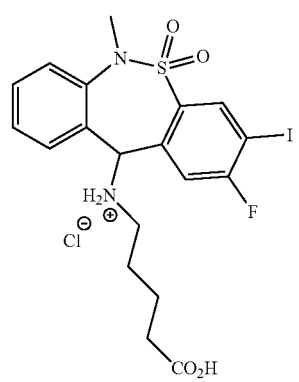

Example 6. Administration of MOR/DOR Agonists

An amount of any one of compounds 8a, 8b, 8c, 8d, 8e, 8f, 8g, 8h, 8i, 8j, 8k, 8l, 8m, 8n, 8o, 9a, 9b, 9c, 9d, 9e, 9f, 9g, 9h, 9i, 9j, 9k, 9l, 9m, 9n, or 9o is administered to a subject afflicted with depression. The amount of the compound is effective to treat the subject afflicted with depression.

An amount of any one of compounds 8a, 8b, 8c, 8d, 8e, 8f, 8g, 8h, 8i, 8j, 8k, 8l, 8m, 8n, 8o, 9a, 9b, 9c, 9d, 9e, 9f, 9g, 9h, 9i, 9j, 9k, 9l, 9m, 9n, or 9m is administered to a subject afflicted with a mood disorder. The amount of the compound is effective to treat the subject afflicted with the mood disorder.

An amount of any one of compounds 8a, 8b, 8c, 8d, 8e, 8f, 8g, 8h, 8i, 8j, 8k, 8l, 8m, 8n, 8o, 9a, 9b, 9c, 9d, 9e, 9f, 9g, 9h, 9i, 9j, 9k, 9l, 9m, 9n, or 9o is administered to a subject afflicted with an anxiety disorder. The amount of the compound is effective to treat the subject afflicted with the anxiety disorder.

An amount of any one of compounds 8a, 8b, 8c, 8d, 8e, 8f, 8g, 8h, 8i, 8j, 8k, 8l, 8m, 8n, 8o, 9a, 9b, 9c, 9d, 9e, 9f, 9g, 9h, 9i, 9j, 9k, 9l, 9m, 9n, or 9o is administered to a subject afflicted with borderline personality disorder. The amount of the compound is effective to treat the subject afflicted with borderline personality disorder.

An amount of any one of compounds 8a, 8b, 8c, 8d, 8e, 8f, 8g, 8h, 8i, 8j, 8k, 8l, 8m, 8n, 8o, 9a, 9b, 9c, 9d, 9e, 9f, 9g, 9h, 9i, 9j, 9k, 9l, 9m, 9n, or 9o is administered to a subject afflicted with pain. The amount of the compound is effective to treat the subject afflicted with pain.

An amount of any one of compounds 8a, 8b, 8c, 8d, 8e, 8f, 8g, 8h, 8i, 8j, 8k, 8l, 8m, 8n, 8o, 9a, 9b, 9c, 9d, 9e, 9f, 9g, 9h, 9i, 9j, 9k, 9l, 9m, 9n, or 9o is administered to a subject afflicted with opioid addiction. The amount of the compound is effective to treat the subject afflicted with the opioid addiction.

An amount of any one of compounds 8a, 8b, 8c, 8d, 8e, 8f, 8g, 8h, 8i, 8j, 8k, 8l, 8m, 8n, 8o, 9a, 9b, 9c, 9d, 9e, 9f, 9g, 9h, 9i, 9j, 9k, 9l, 9m, 9n, or 9o is administered to a subject afflicted with opioid withdrawal symptoms. The amount of the compound is effective to treat the subject afflicted with the opioid withdrawal symptoms.

Example 7. Solubility Modulation Via Dihalogenation

Dihalo substitution of the tricyclic core provides compounds that are more water soluble than their analogous monohalo counterparts. For example, compound 9b is more soluble than the analogous compound bromotianeptine (Table 3). Likewise, compound 9k is more soluble than the analogous compound iodotianeptine (Table 4). Increased solubility is useful for optimizing pharmacokinetic and formulation properties, for example by reducing variability in pharmacokinetics following oral administration of solid dose forms (increased solubility decreases the dependence of absorption rate on particle size).

Solubility Determination (Method A).

A quantity of the appropriate compound sufficient to saturate the resulting solution was added to distilled water (0.50 mL) and the mixture was stirred vigorously for 24 h at room temperature (20° C.). The mixture was then centrifuged for 3 min. at 21,000×g and the stir bar was carefully removed. The mixture was then centrifuged again for 5 min. at 21,000×g and the supernatant was carefully removed by syringe and passed through a 0.45 µM syringe filter. An aliquot (300 µL) of the filtered supernatant was concentrated in vacuo and the mass of the residual solids determined in order to calculate the solubility.

TABLE 3

Solubility of compounds in neutral water at room temperature (20° C.) determined using Method A. Data points represent the average of 2 independent trials.

| Compound | Structure | Aqueous Solubility (mg/mL @ 20° C.) |
|---|---|---|
| bromotianeptine | 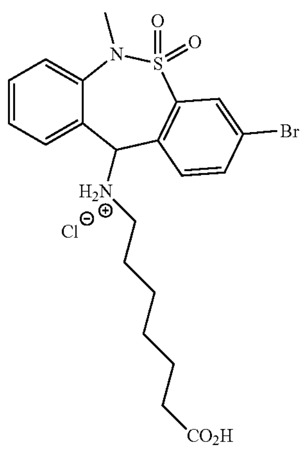 [SMILES: CN1c2ccccc2C([NH2+]CCCCCCC(=O)O)c2ccc(Br)cc2S1(=O)=O ; [Cl-]] | 4.5 |
| 9b | 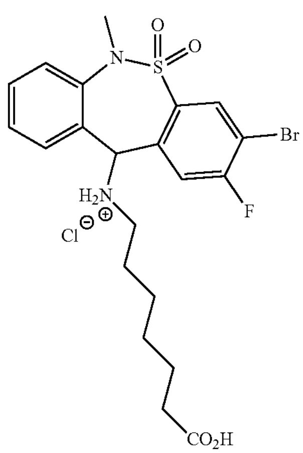 [SMILES: CN1c2ccccc2C([NH2+]CCCCCCC(=O)O)c2cc(F)c(Br)cc2S1(=O)=O ; [Cl-]] | 9.8 |

TABLE 4

Solubility of compounds in neutral water at room temperature (20° C.) determined using Method B.

| Compound | Structure | Aqueous Solubility (mg/mL @ 20° C.) |
|---|---|---|
| iodotianeptine | 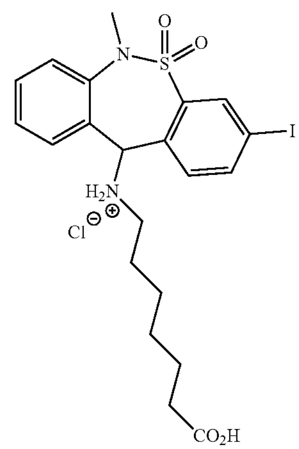 [SMILES: CN1c2ccccc2C([NH2+]CCCCCCC(=O)O)c2ccc(I)cc2S1(=O)=O ; [Cl-]] | 2.3 |
| 9k | 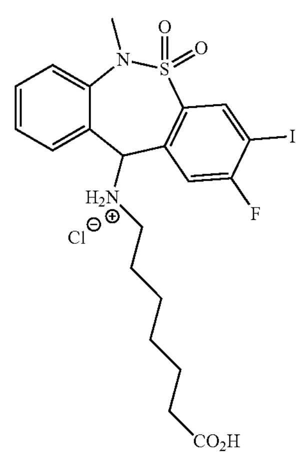 [SMILES: CN1c2ccccc2C([NH2+]CCCCCCC(=O)O)c2cc(F)c(I)cc2S1(=O)=O ; [Cl-]] | 5.7 |

Solubility Determination (Method B).

A quantity of the appropriate compound sufficient to saturate the resulting solution was added to distilled water (0.50 mL) and the mixture agitated on an orbital shaker for 2 h at room temperature (20° C.). The mixture was then centrifuged for 5 min. at 21,000×g and the supernatant was carefully removed by syringe and passed through a 0.45 μM syringe filter. An aliquot (300 μL) of the filtered supernatant was concentrated in vacuo and the mass of the residual solids determined in order to calculate the solubility.

Example 8. Methylthio Substitution Yields Partial Agonists of DOR

In contrast to all other compounds in this class, which are full agonists of DOR, methylthio substitution of the tricyclic core yields compounds with partial agonist activity at this receptor. For example, compound 9c is a partial agonist at DOR (FIG. 1). Compound 9c is also more potent at MOR and DOR than both its corresponding ethyl ester analog and tianeptine (Table 5).

TABLE 5

Functional agonist activity of compounds at human MOR and DOR. Where indicated, error represents ± SEM of 2 or more independent trials. The data shows that compound 9c is more potent at MOR and DOR than both its corresponding ethyl ester analog and tianeptine.

| Compound | Structure | Human MOR ($EC_{50}$) | Human DOR ($EC_{50}$) |
| --- | --- | --- | --- |
| Tianeptine | (structure with Cl, $CO_2H$) | 194 ± 70 nM | 37.4 ± 11.2 µM |
| Ester Analog of 9c | (structure with SMe, $CO_2Et$) | 222 nM | 7.0 µM ($E_{max}$ = 70%) partial agonist |
| 9c | (structure with SMe, $CO_2H$) | 41.8 nM | 2.06 µM ($E_{max}$ = 51%) partial agonist |

Example 9. Ethynyl Substitution Increases Potency

Introduction of an ethynyl group at position 3 of the aryl ring system provides compounds of higher MOR and DOR potency than the corresponding analogs with chloro or methyl substituents at this position (Table 6).

TABLE 6

Functional agonist activity of compounds at human MOR and DOR. Where indicated, error represents ± SEM of 2 or more independent trials. The data shows that compound 9a is more potent at MOR and DOR than both its corresponding 3-methyl-substituted analog and tianeptine.

| Compound | Structure | Human MOR ($EC_{50}$) | Human DOR ($EC_{50}$) |
|---|---|---|---|
| Tianeptine | 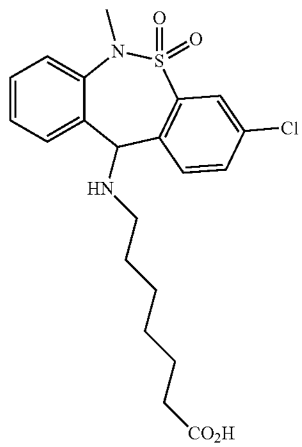 [SMILES: CN1c2ccccc2C(NCCCCCCC(=O)O)c2ccc(Cl)cc2S1(=O)=O] | 194 ± 70 nM | 37.4 ± 11.2 μM |
| 3-Methyl-substituted Analog | 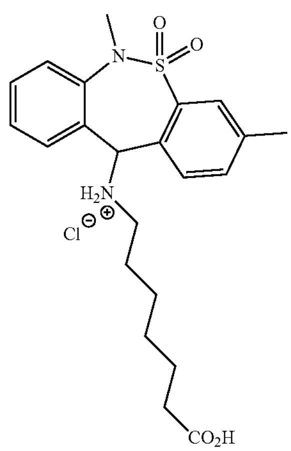 [SMILES: Cc1ccc2c(c1)S(=O)(=O)N(C)c1ccccc1C2[NH2+]CCCCCCC(=O)O ; [Cl-]] | 890 nM | >10 μM |
| 9a | 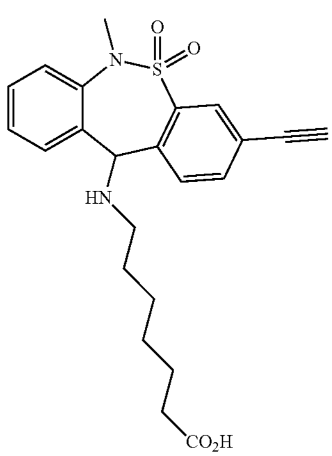 [SMILES: C#Cc1ccc2c(c1)S(=O)(=O)N(C)c1ccccc1C2NCCCCCCC(=O)O] | 53.3 ± 18 nM | 5.9 ± 0.3 μM |

Example 10. Esters as Prodrugs

Carboxylate esters are well known as prodrugs for the corresponding carboxylic acids obtained by hydrolysis (Beaumont, K. et al. 2003). Such ester prodrugs may show improved oral bioavailability, better brain penetration, or longer duration of action compared to their carboxylic acid counterparts. Accordingly, compounds of this application having an ester side chain (8), although biologically active on their own, may also act as prodrugs for the corresponding carboxylic acids (9). Further, one skilled in the art will be able to apply the methods and knowledge of this application to prepare additional prodrugs. For example, the type of ester (e.g. methyl, ethyl, propyl, isopropyl, tert-butyl, phenyl) or the length of the side chain may be varied to adjust the activity and pharmacokinetic properties of the prodrugs and their corresponding carboxylic acid hydrolysis products.

Example 11. Conversion to Active Metabolites Via Beta-Oxidation In Vivo

Tianeptine is known to be metabolized primarily via beta-oxidation of the carboxylic acid side chain in a manner similar to fatty acids (Grislain, L. et al. 1990). This results in metabolites with carboxylic acid side chains shortened sequentially by 2-carbon units. Other carboxylic acid analogs, including the compounds described in the present disclosure, are expected to be metabolized in a similar manner. Therefore, the extended chain analogs of this application (8 carbons or longer), in addition to their higher DOR potency, serve as prodrugs of analogous compounds with shorter side chains, which are in many cases also agonists of the MOR and/or DOR. For example, compound 9e, with an 8-carbon side chain, is metabolized into active metabolite 1, with a six-carbon side chain (Scheme 11A). Similarly, compound 9f, with a 9-carbon side chain, is metabolized sequentially into active metabolite 2 and active metabolite 3, with 7- and 5-carbon side chains respectively (Scheme 11B). Similarly, compounds 9l, 9m, 9n, and 9o are active metabolites of compounds 9b, 9i, 9j, and 9k, respectively. Thus, the specific length of the side chain selected is useful for fine control of the pharmacokinetic and pharmacodynamic profile in this genus.

Scheme 11. Conversion to active metabolites via beta-oxidation.

A)

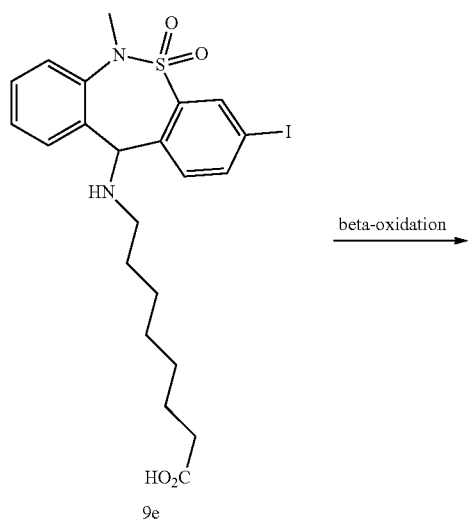
9e

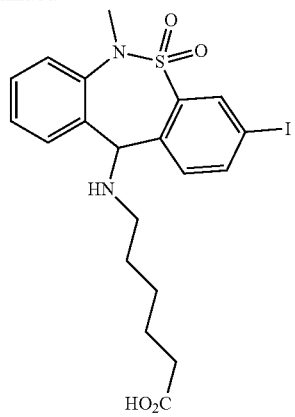
active metabolite 1

B)

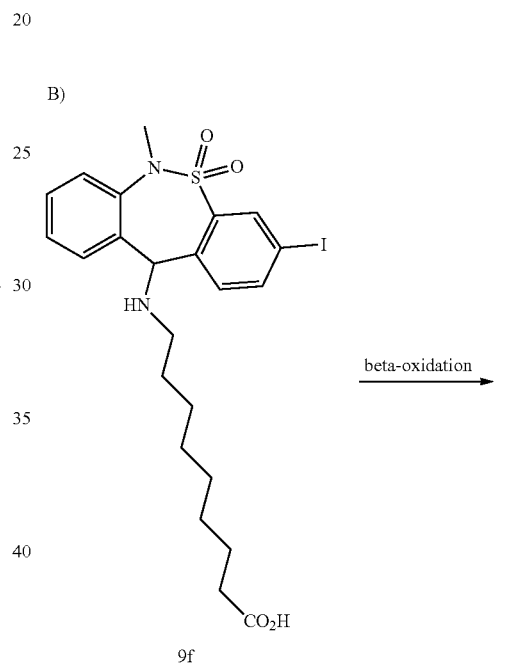
9f active metabolite 2

-continued

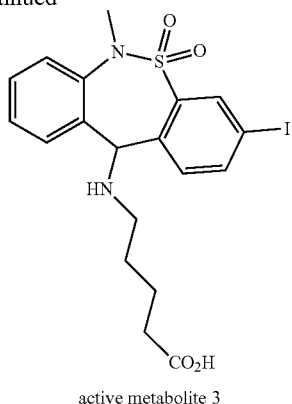

active metabolite 3

Example 12. Potent Activity of Dihalo-Substituted Compounds is Unexpected

Our previous work has found that placement of a chlorine substituent at position 2 of the diarylthiazepine core of compounds of the type described in this invention is detrimental to agonist activity at MOR. For example, in Table 7, compare compound 15a to compounds 15b and 15c or compound 16a to compounds 16b and 16c. In each case, translocation of the chlorine substituent from position 3 to position 2, or introduction of a chlorine substituent at position 2 of unsubstituted compounds, results in a 6-fold or greater loss of activity at MOR. Accordingly, it was surprising to find that compounds 9b, 9i, 9j, 9k, and 9l of the present invention, which each bear a fluorine or chlorine substituent at position 2 within their dihalo-substituted core structures, are equipotent or more potent than their analogs lacking such substitution at position 2. Accordingly, in this class of compounds, the structure-activity relationship at MOR of disubstituted compounds is different from that of monosubstituted compounds.

TABLE 7

Functional agonist activity of compounds at human MOR. Where indicated, error represents ± SEM of 2 or more independent trials. The data shows that placement of a chlorine substituent at position 2 of the diarylthiazepine core of compounds of the type described in this invention is generally detrimental to activity at MOR.

| Compound | Structure | Human MOR ($EC_{50}$) |
|---|---|---|
| 15a | | 4.15 ± 0.93 μM |
| 15b | 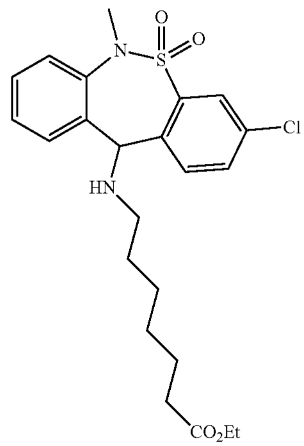 | 657 ± 366 nM |
| 15c | 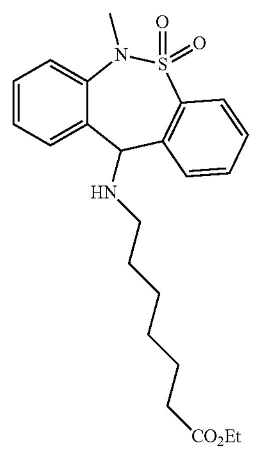 [SMILES: CCOC(=O)CCCCCCNC1c2ccccc2N(C)S(=O)(=O)c2ccccc21] | 156 ± 84.7 nM |
| 16a | 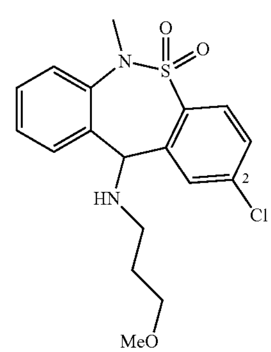 [SMILES: COCCCNC1c2ccccc2N(C)S(=O)(=O)c2ccc(Cl)cc21] | 16.9 ± 5.22 μM |

TABLE 7-continued

Functional agonist activity of compounds at human MOR. Where indicated, error represents ± SEM of 2 or more independent trials. The data shows that placement of a chlorine substituent at position 2 of the diarylthiazepine core of compounds of the type described in this invention is generally detrimental to activity at MOR.

| Compound | Structure | Human MOR (EC$_{50}$) |
|---|---|---|
| 16b | [structure: tricyclic diarylthiazepine with N-Me, S(=O)$_2$, Cl substituent, HN-CH$_2$CH$_2$CH$_2$-, MeO] | 264 ± 85.3 nM |
| 16c | [structure: tricyclic diarylthiazepine with N-Me, S(=O)$_2$, HN-CH$_2$CH$_2$CH$_2$-, MeO] | 2.011 ± 0.7 μM |

Example 13. pH Dependence of Solubility

Since compounds of type 9 of the present invention are zwitterionic, their aqueous solubility depends on pH. Interestingly, fluoro substitution at position 2 of the tricyclic core provides compounds that are more water soluble than their analogous monohalo counterparts, especially at low pH. As previously described in Example 7, 2-fluoro compounds 9b and 9k are 2-3-fold more soluble than their analogous monohalo counterparts, bromotianeptine and iodotianeptine, respectively, in neutral unbuffered water. However, at pH 1, the difference in solubility is dramatically enhanced, with compounds 9b and 9k being at least 10-fold more soluble than their monohalo counterparts (Table 8). This trend also holds for compound 9j, which is 8-fold more soluble than tianeptine at pH 1. In contrast, in Na phosphate buffer at pH 7, compounds 9b and 9k are of similar or modestly higher solubility than bromotianeptine and iodotianeptine, respectively (Table 8).

The ability to modulate the pH dependence of solubility is useful for optimizing pharmacokinetic and formulation properties, since the pH of the gastrointestinal tract changes from ~1.5 in the fasted stomach to 6-8 in the intestines. Accordingly, compounds that change solubility at different pH may also change their rate of dissolution and/or absorption in different compartments of the gastrointestinal tract. For example, 2-fluoro compounds 9j, 9b, and 9k are likely to be more rapidly absorbed from solid dosage forms than their monohalo counterparts tianeptine, bromotianeptine, and iodotianeptine, respectively, given their much higher solubility at low pH, as would be found in the stomach.

Solubility Determination.

Test compounds (4 mg) were added to 200 μL of one of the tested aqueous solutions (hereinafter—buffer): 100 mM aqueous HCl (pH 1) or 100 mM Na-phosphate buffer (pH 7). The obtained suspensions/solutions with the theoretical concentration of 20 mg/mL were further allowed to equilibrate at 25° C. on a thermostatic orbital shaker for 24 hours and then centrifuged at 6000 rpm for 4 minutes and filtered through HTS filter plates using a vacuum manifold. In parallel, compound dilutions in 50% acetonitrile/HCl and 30% acetonitrile/Na-phosphate buffer mixes were prepared to theoretical concentrations of 0 mg/mL (blank), 0.1 mg/mL, 0.2 mg/mL, and 0.4 mg/mL in duplicates to generate calibration curves falling within the optimum UV absorption range. The filtrates of test compounds were diluted 100-fold with acetonitrile-buffer mixtures before measuring. The filtered supernatant test samples were transferred to 96-well plates and measured for absorbance in the 200-550 nm range with 5 nm step increment. The concentrations of compounds in supernatants were calculated using the measured absorbance and the previously determined calibration curve. Proper absorbance wavelengths for calculations were selected for each compound manually based on absorbance maxima (absolute absorbance unit values for the minimum and maximum concentration points within 0-2.5 OD range).

TABLE 8

Solubility of compounds at pH 1 and 7 at room temperature (25° C.). Data points represent the average of 2 independent trials.

| Compound | Structure | 100 mM HCl, pH 1 (mg/mL) | 100 mM Na phosphate buffer, pH 7 (mg/mL) |
| --- | --- | --- | --- |
| tianeptine (HCl salt) | 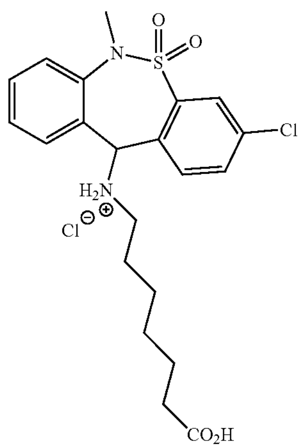 [SMILES: CN1c2ccccc2C([NH2+]CCCCCCC(=O)O)c2ccc(Cl)cc2S1(=O)=O ; [Cl-]] | 0.68 | 0.26 |
| 9j | 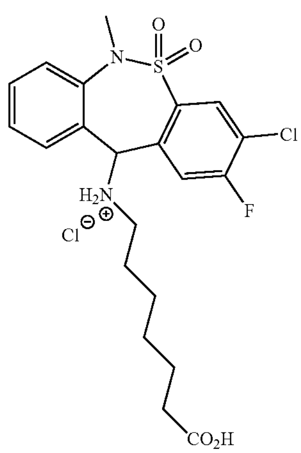 [SMILES: CN1c2ccccc2C([NH2+]CCCCCCC(=O)O)c2cc(F)c(Cl)cc2S1(=O)=O ; [Cl-]] | 5.3 | 0.07 |
| bromotianeptine | 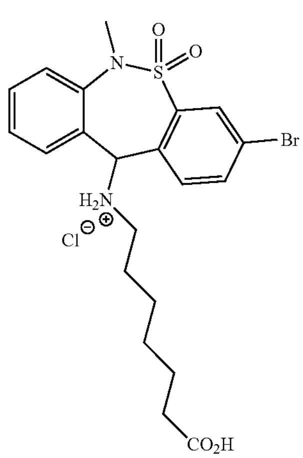 [SMILES: CN1c2ccccc2C([NH2+]CCCCCCC(=O)O)c2ccc(Br)cc2S1(=O)=O ; [Cl-]] | <0.1 | 0.62 |

TABLE 8-continued

Solubility of compounds at pH 1 and 7 at room temperature (25° C.). Data points represent the average of 2 independent trials.

| Compound | Structure | 100 mM HCl, pH 1 (mg/mL) | 100 mM Na phosphate buffer, pH 7 (mg/mL) |
| --- | --- | --- | --- |
| 9b | 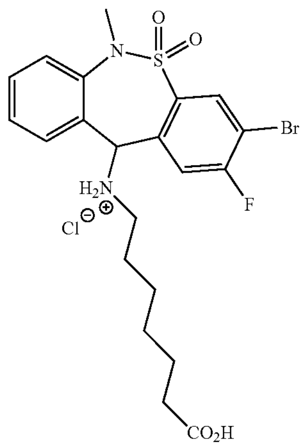 [SMILES: CN1c2ccccc2C([NH2+]CCCCCCC(=O)O)c2cc(F)c(Br)cc2S1(=O)=O ; [Cl-]] | 1.1 | 0.84 |
| iodotianeptine | 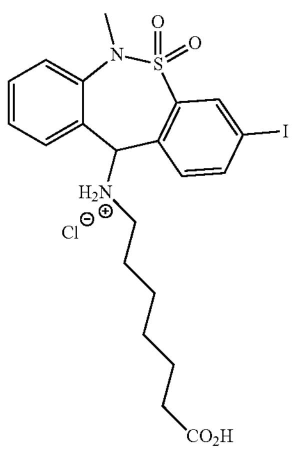 [SMILES: CN1c2ccccc2C([NH2+]CCCCCCC(=O)O)c2ccc(I)cc2S1(=O)=O ; [Cl-]] | <0.1 | 0.15 |
| 9k | 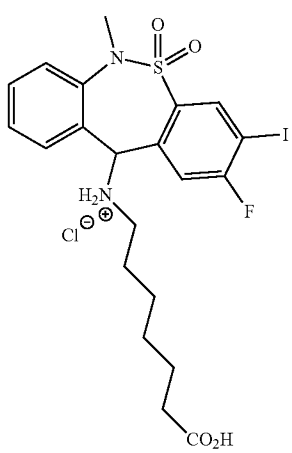 [SMILES: CN1c2ccccc2C([NH2+]CCCCCCC(=O)O)c2cc(F)c(I)cc2S1(=O)=O ; [Cl-]] | 2.7 | 0.39 |

Example 14. Analgesic Activity of Compounds

Figure 2:
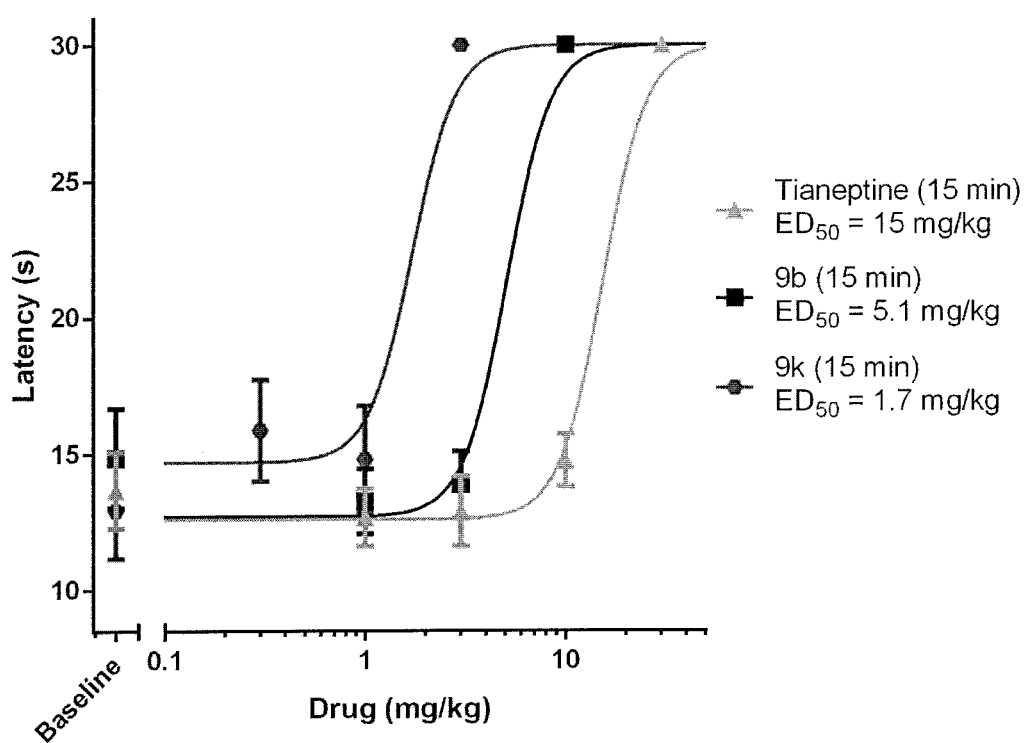
FIG. 2: Dose-response curves of analgesic activity of tianeptine, 9b and 9k in the hot plate assay.

Compounds 9b and 9k are potent analgesics in the mouse hot plate assay, with much higher potency than tianeptine (Table 9 and FIG. 2).

Analgesic Activity in Hot Plate Assay.

Male C57BL/6 mice were timed for latency to jump on a hot-plate apparatus set to 55° C., using a 30 s cutoff to prevent tissue damage. Following a baseline test, animals were injected subcutaneously (s.c.) with escalating doses of drug and tested at 15 post-injection (time of maximal effect). Dose-response curves were fit via nonlinear regression using GraphPad Prism (La Jolla, CA).

TABLE 9

$ED_{50}$ for analgesic activity in the hot plate assay in male C57BL/6 mice.

| Compound | Structure | Analgesic $ED_{50}$ (mg/kg, s.c.) |
|---|---|---|
| Tianeptine (Na salt) | 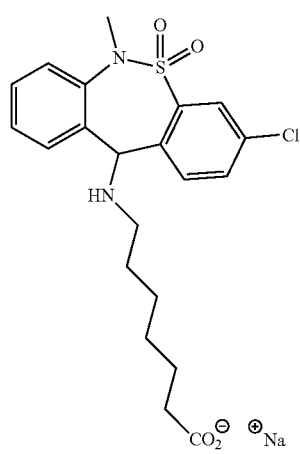 | 15 |
| 9b | 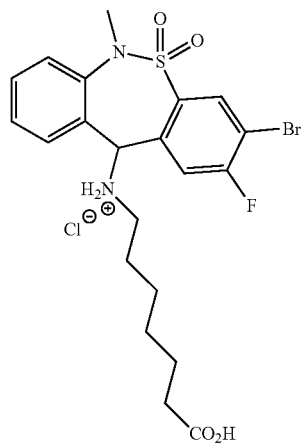 [SMILES: CN1c2ccccc2C([NH2+]CCCCCCC(=O)O)c2cc(F)c(Br)cc2S1(=O)=O ; [Cl-]] | 5.1 |

TABLE 9-continued $ED_{50}$ for analgesic activity in the hot plate assay in male C57BL/6 mice.

| Compound | Structure | Analgesic $ED_{50}$ (mg/kg, s.c.) |
|---|---|---|
| 9k | (structure shown) | 1.7 |

Example 15. Combinations with NMDA Receptor Antagonists

Antagonists of the N-methyl-D-aspartate receptor (NMDAR) are known to potentiate the beneficial effects of opioid receptor agonists in the treatment of pain and to prevent development of tolerance to those effects (Trujillo, K. A. et al. 1994; Mao, J. et al. 1996). Therefore, pharmaceutical compositions of the compounds of the present invention, combined with NMDAR antagonists, may be useful in the treatment of, depression, mood disorders, anxiety disorders, borderline personality disorder, pain, opioid addiction, or opioid withdrawal symptoms, where the NMDAR antagonist serves as an adjunct to prevent the development of tolerance to the compounds of the present invention with chronic use. NMDAR antagonists are also known to be effective in the treatment of depression (Murrough, J. W. et al. 2013; Zarate, C. A. Jr et al. 2006). Therefore, pharmaceutical compositions of the compounds of the present invention, combined with NMDAR antagonists, may treat depression or other mood disorders with enhanced efficacy compared to the compounds of the present invention alone. Alternatively, the opioid modulator and NMDAR antagonist may be dosed separately, as a novel method for treating the conditions described above.

Non-Limiting Examples of NMDA Receptor Antagonists:

Dextromorphinans—dextromethorphan, dextrorphan, dextrallorphan

Adamantanes—memantine, amantadine, rimantadine, nitromemantine (YQW-36)

Arylcyclohexylamines—ketamine (and its analogs, e.g. tiletamine), phencyclidine (and its analogs, e.g. tenocyclidine, eticyclidine, rolicyclidine), methoxetamine (and its analogs), gacyclidine (GK-11);

Miscellaneous—neramexane, lanicemine (AZD6765), diphenidine, dizocilpine (MK-801), 8a-phenyldecahydroquinoline (8A-PDHQ), remacemide, ifenprodil, traxoprodil (CP-101,606), eliprodil (SL-82.0715), etoxadrol (CL-1848C), dexoxadrol, WMS-2539, NEFA, delucemine (NPS-1506), aptiganel (Cerestat; CNS-1102), midafotel (CPPene; SDZ EAA 494), dexanabinol (HU-211 or ETS2101), selfotel (CGS-19755), 7-chlorokynurenic acid (7-CKA), 5,7-dichlorokynurenic acid (5,7-DCKA), L-683344, L-689560, L-701324, GV150526A, GV196771A, CERC-301 (formerly MK-0657), atomoxetine, LY-235959, CGP 61594, CGP 37849, CGP 40116 (active enantiomer of CG 37849), LY-233536, PEAQX (NVP-AAM077), ibogaine, noribogaine, Ro 25-6981, GW468816, EVT-101, indantadol, perzinfotel (EAA-090), SSR240600, 2-MDP (U-23807A), AP-7

Example 16. Combinations with NMDA Receptor Partial Agonists

Weak partial agonists of NMDAR are also known (Moskal, J. R. et al. 2005), and may be expected to produce beneficial or synergistic effects similar to an antagonist when intrinsic glutamate signaling activity is high or over-activated (e.g. during opioid withdrawal). Therefore, pharmaceutical compositions of the compounds of the present invention, combined with NMDAR partial agonists, may be useful in the treatment of depression, mood disorders, anxiety disorders, borderline personality disorder, pain, opioid addiction, or opioid withdrawal symptoms, where the NMDAR partial agonist serves as an adjunct to prevent the development of tolerance to the compounds of the present invention with chronic use. Similarly, pharmaceutical compositions of the compounds of the present invention, combined with NMDAR partial agonists, may treat depression or other mood disorders with enhanced efficacy compared to the compounds of the present invention alone. Alternatively, the opioid modulator and NMDAR partial agonist may be dosed separately, as a novel method for treating the conditions described above.

Non-Limiting Examples of NMDA Receptor Partial Agonists:
NRX-1074, rapastinel (GLYX-13)

Example 17. Combinations with Neurokinin 1 Receptor Antagonists

Antagonists of the neurokinin 1 receptor (NK-1) are known to modulate the effects of opioid agonists, specifically in reward and self-administration protocols. More specifically, NK-1 antagonists attenuate opioid reward and self-administration in animal models (Robinson, J. E. et al. 2012; Barbier, E. et al. 2013). Therefore, pharmaceutical compositions of the compounds of the present invention, combined with NK-1 antagonists, may be useful in the treatment of depression, mood disorders, anxiety disorders, borderline personality disorder, pain, opioid addiction, or opioid withdrawal, where the NK-1 antagonist serves as an adjunct to reduce the abuse potential of the compounds of the present invention. NK-1 antagonists are also known to be effective in the treatment of depression (Kramer, M. S. et al. 2004). Therefore, pharmaceutical compositions of the compounds of the present invention, combined with NK-1 antagonists, may treat depression or other mood disorders with enhanced efficacy compared to the compounds of the present invention alone. Alternatively, the opioid modulator and NK-1 antagonist may be dosed separately, as a novel method for treating the conditions described above.

Non-Limiting Examples of Neurokinin 1 Receptor Antagonists:
aprepitant, fosaprepitant, casopitant, maropitant, vestipitant, vofopitant, lanepitant, orvepitant, ezlopitant, netupitant, rolapitant, L-733060, L-703606, L-759274, L-822429, L-760735, L-741671, L-742694, L-732138, CP-122721, RPR-100893, CP-96345, CP-99994, TAK-637, T-2328, CJ-11974, RP 67580, NKP608, VPD-737, GR 205171, LY686017, AV608, SR140333B, SSR240600C, FK 888, GR 82334

Example 18. Combinations with Neurokinin 2 Receptor Antagonists

Antagonists of the neurokinin 2 receptor (NK-2) are known to show antidepressant effects and to synergize with tricyclic antidepressants (Overstreet, D. H. et al. 2010). Therefore, pharmaceutical compositions of the compounds of the present invention, combined with NK-2 antagonists, may be useful in the treatment of depression or other mood disorders with increased efficacy compared to the compounds of the present invention alone. Alternatively, the opioid modulator and NK-2 antagonist may be dosed separately, as a novel method for treating depression or other mood disorders.

Non-Limiting Examples of Neurokinin 2 Receptor Antagonists:
saredutant, ibodutant, nepadutant, GR-159897, MEN-10376

Example 19. Combinations with Neurokinin 3 Receptor Antagonists

Antagonists of the neurokinin 3 receptor (NK-3) are known to show antidepressant effects (Salome, et al. 2006). Further, the actions of NK-3 modulators show a dependency on the opioid receptor system (Panocka, I. et al. 2001). Therefore, pharmaceutical compositions of the compounds of the present invention, combined with NK-3 antagonists, may be useful in the treatment of depression or other mood disorders with increased efficacy compared to the compounds of the present invention alone. Alternatively, the opioid modulator and NK-3 antagonist may be dosed separately, as a novel method for treating depression or other mood disorders.

Non-Limiting Examples of Neurokinin 3 Receptor Antagonists:
osanetant, talnetant, SB-222200, SB-218795

Example 20. Combinations with DOR Agonists

DOR Agonists have been shown to elicit antidepressant and anxiolytic effects (Saitoh, A. et al. 2004; Torregrossa, et al. 2005; Jutkiewicz, E. M. 2006) and are analgesic (Vanderah, T. W. 2010; Peppin, J. F. and Raffa, R. B. 2015). They have also been shown to reverse the respiratory depression induced by MOR agonists (Su, Y-F. et al. 1998). Therefore, pharmaceutical compositions of the compounds of the present invention, combined with DOR agonists, may be useful in the treatment of depression, mood disorders, anxiety disorders, borderline personality disorder, or pain with increased efficacy or reduced side effects compared to the compounds of the present invention alone. Alternatively, the opioid modulator and DOR agonist may be dosed separately, as a novel method for treating the conditions described above.

Non-Limiting Examples of DOR Agonists:
tianeptine, (+)BW373U86, SNC-80, SNC-121, SNC-162, DPI-287, DPI-3290, DPI-221, TAN-67, KN-127, AZD2327, JNJ-20788560, NIH11082, RWJ-394674, ADL5747, ADL5859, UFP-512, AR-M100390, SB-235863, 7-spiroindanyloxymorphone.

Example 21. Combinations with Naloxone

Naloxone is an MOR antagonist that is effective in blockading all behavioral effects induced by classical MOR agonists and is the standard treatment for opioid overdose. It is highly bioavailable by parenteral routes of administration but not by the oral route (Smith, K. et al. 2012). Accordingly, pharmaceutical compositions containing mixtures of an MOR agonist and naloxone remain effective agonists when given by the oral route but the naloxone component inhibits the effects of the MOR agonist component when the mixture is administered parenterally. Thus, addition of naloxone to pharmaceutical compositions containing MOR agonists is useful for preventing their misuse or abuse by parenteral routes of administration. Therefore, pharmaceutical compositions of the compounds of the present invention, combined with naloxone, may be useful in providing the therapeutic benefits of the compounds of the present invention while having diminished potential for abuse.

Example 22. Combinations With SSRI or SNRIs

Selective serotonin reuptake inhibitors (SSRIs) and serotonin-norepinephrine reuptake inhibitors (SNRIs) are the standard of care for a many depressive disorders and mood disorders (Thase, M. E. 2008; Vaswani, M. et al. 2003). They are also useful in the treatment of chronic pain (Marks, D. M. et al. 2009). Therefore, pharmaceutical compositions of the compounds of the present invention, combined with SSRIs or SNRIs, are useful in the treatment of depressive disorders, mood disorders, borderline personality disorder, or pain with increased efficacy compared to the compounds of the present invention alone. Alternatively, the opioid modulator and SSRI or SNRI may be dosed separately, as a novel method for treating the conditions described above. Further, the compound of the present invention may be used as an add-on therapy to enhance the efficacy of preexisting SSRI or SNRI therapy for the conditions described above.

Non-Limiting Examples of SSRIs:
citalopram, escitalopram, fluoxetine, fluvoxamine, paroxetine, sertraline, dapoxetine Non-Limiting Examples of SNRIs:
venlafaxine, desvenlafaxine

Example 23. Combinations with Methylnaltrexone

Constipation is a frequent, unpleasant side effect of MOR agonists resulting from inhibition of intestinal smooth muscle contractions via activation of MORs located in this tissue. Methylnaltrexone (Relistor) is a clinically approved quaternary ammonium salt of the opioid receptor antagonist naltrexone that does not cross the blood brain barrier. Accordingly, this compound is capable of inhibiting MORs in the gastrointestinal tract and preventing opioid-induced constipation while avoiding simultaneous inhibition of centrally mediated therapeutic effects. Therefore, pharmaceutical compositions of the compounds of the present invention, combined with methylnaltrexone, are useful in the treatment of depressive disorders, mood disorders, borderline personality disorder, pain, opioid addiction, or opioid withdrawal symptoms with reduced constipation compared to the compounds of the present invention alone. Alternatively, the opioid modulator and methylnaltrexone may be dosed separately, as a novel method for treating the conditions described above with less constipation.

Example 24. Use of Fluoro-Substituted Compounds as PET Radiotracers

Positron emission tomography (PET) is a noninvasive in vivo imaging technique that uses radiotracers to characterize, visualize, and quantify physiological processes at the molecular level (Miller, P. W. et al. 2008). Fluorine-18 is the preferred positron-emitting isotope for use in positron emission tomography (PET). However, placement of a fluorine substituent at an inappropriate position may abolish the activity of a compound at its target of interest. Accordingly, drug compounds containing a fluorine substituent and retaining activity at the target of interest are useful for PET imaging of target engagement and/or drug localization in the body. In the case of the present invention, compounds bearing a fluorine substituent at position 2 of the diarylthiazepine core (e.g. compounds 9b, 9j, 9k, 9l, 9n, and 9o) are particularly well suited for this purpose since they are equipotent or more potent as agonists of MOR than their non-fluorinated analogs. In any such compound, fluorine-18 is substituted in place of fluorine-19 to provide a PET radiotracer of MOR.

A PET radiotracer of MOR is useful to determine the occupancy of MOR achieved following administration of different doses of compounds binding to MOR, for example the compounds of the present invention, to a subject. Information on the relationship between dosing and MOR occupancy is useful for setting the appropriate dose for use in clinical trials or in the treatment of disease. It is also useful for defining the pharmacodynamic effect of a compound acting at MOR, since a particular degree of receptor occupancy may be related to effects on physiology (e.g. breath rate) or behavior (e.g. analgesia or antidepressant effects).

A radiotracer of MOR is also useful for studying release of endogenous opioid peptides, the natural ligands for MOR in the brain. When an external stimulus induces release of endogenous opioid peptides in a subject, such release can be detected by displacement of an MOR PET radiotracer from MOR binding sites in the brain, demonstrating that the endogenous ligand is competing for binding to these same sites. Accordingly, endogenous opioid peptide release and activation of MOR signaling pathways in response to physiological or psychological stimuli may be studied in vivo. Such study and quantification of endogenous opioid signaling is useful in the diagnosis of disease states or as a biomarker of treatment response. For example, using such MOR PET imaging techniques, it has been shown that in healthy individuals, there is a robust decrease in availability of MOR binding sites in multiple brain regions following social rejection, presumably demonstrating a release of endogenous opioid peptides, which displace the radiotracer (Hsu, D. T. et al. 2013). Accordingly, activation of MOR signaling pathways appears to serve as a natural coping mechanism that attenuates the negative feelings associated with rejection.

Interestingly, similar MOR activation is observed in response to social acceptance events, suggesting that this signaling system also acts as a positive reinforcer (Hsu, D. T. et al. 2013). In contrast, patients with major depressive disorder display almost no change in MOR neurotransmission following identical rejection and acceptance events, suggesting that their natural MOR signaling pathways are dysfunctional (Hsu, D. T. et al. 2013; Hsu, D. T. et al. 2015).

Discussion

The present invention provides a number of diarylthiazepinamine carboxylic acids related to the antidepressant tianeptine that are useful opioid modulators with a number of improved properties compared to other compounds in this structural class. In addition to its primary activity at the MOR, tianeptine also exhibits low potency agonist activity at the DOR (Gassaway, M. M. et al. 2014). Literature reports suggest that simultaneous activation of DOR, in addition to MOR, will provide therapeutic benefits in treating a number of conditions. For example, DOR agonists alone are known to be efficacious antidepressants and anxiolytics in animal models (Saitoh, A. et al. 2004; Torregrossa, et al. 2005; Jutkiewicz, E. M. 2006). Accordingly, simultaneous activation of DOR is expected to enhance the MOR-dependent antidepressant and anxiolytic effects of compounds in the tianeptine class. Similarly, DOR agonists possess analgesic properties (Vanderah, T. W. 2010; Peppin, J. F. and Raffa, R. B. 2015). Thus, the addition of a DOR agonist component to the activity profile of tianeptine analogs is also expected to enhance their analgesic activity. Lastly, DOR agonists have been shown to inhibit the respiratory depression evoked by MOR agonists (Su, Y-F. et al. 1998). Therefore, dual MOR/DOR agonists are expected to limit the magnitude of this side effect. The present invention provides tianeptine analogs with increased DOR agonist potency compared to the parent compound. Specifically, increasing the length of the carboxylic acid side chain to 8 or more carbons increases the potency of this class as DOR agonists without analogous shifts in MOR potency, such that the DOR:MOR potency ratio is shifted in favor of DOR. Notably, varying the length of this side chain is also useful for modulating the pharmacokinetic properties within this class and longer chain analogs are expected to produce a number of active metabolites with shorter carboxylic acid side chains following beta-oxidation in vivo.

This invention also provides alternative substitution patterns on the aryl ring system (dihalo, alkynyl, and methylthio substituents) that are sufficient to maintain similar or improved opioid activity compared to the monohalo substitution pattern (and improved potency relative to tianeptine itself). These alternative substitution patterns also provide other unique properties. For example, the methylthio substitution yields compounds with partial agonist activity at DOR, a contrast to all other compounds in this class, which are full agonists. Further, dihalo substitution provides compounds that are more water soluble than their analogous monohalo counterparts, at both neutral pH and in particular, at low pH. Increased solubility is useful for optimizing pharmacokinetic and formulation properties, for example by reducing variability in pharmacokinetics following oral administration of solid dose forms (increased solubility decreases the dependence of absorption rate on particle size). Similarly, compounds that are more soluble at low pH, as found in the stomach, are expected to be absorbed more rapidly from solid dosage forms following oral administration due to their increased rate or extent of dissolution. Therefore, the alternative substitution patterns described herein may be combined with any appropriate side chain modification to generate additional opioid-active compounds with pharmacological and physical properties tuned as desired for optimal activity in any particular pharmaceutical composition or mode of medical treatment.

As an adjunct to the novel compositions of matter described above, the present invention also provides uses of the described compounds, either alone or in combination with drugs having synergistic pharmacological properties, for treating a number of medical conditions. These indications include, but are not limited to, depression and related mood disorders, anxiety disorders, borderline personality disorder, pain, and opioid dependence (as a maintenance therapy).

Lastly, an additional aspect of the invention provides synthetic methods and chemical intermediates that may be used to encompass chemical space around the diarythiazepinamine core structure.

REFERENCES

Barbier, E. et al. *Neuropsychopharmacology* 2013, 38, 976-984.
Bart, G. *J. Addict. Dis.* 2012, 31, 207-25.
Beaumont, K.; Webster, R.; Gardner, I.; Dack, K. *Curr. Drug Metab.* 2003, 4, 461-485.
Berrocoso, E.; Sanchez-Blazquez, P.; Garzón, J.; Mico, J. A. *Curr. Pharm. Des.* 2009, 15, 1612-1622.
Besson, A.; Privat, A. M.; Eschalier, A.; Fialip, J. *Psychopharmacology* 1996, 123, 71-78.
Bodkin, J. A.; Zornberg, G. L.; Lukas, S. E.; Cole, J. O. *J. Clin. Psychopharmacol.* 1995, 15, 49-57.
Corbett, A. D.; Henderson, G.; McKnight, A. T.; Paterson, S. J.; *Brit. J. Pharmacol.* 2006, 147, S153-S162.
Fujimoto, T.; Ritter, T. *Org. Lett.*, 2015, 17, 544-547.
Gassaway, M. M.; Rives, M-L.; Kruegel A. C.; Javitch, J. A.; Sames, D. *Transl. Psychiatry* 2014, 4, e411.
Grislain, L.; Gele, P.; Bertrand, M.; Luijten, W.; Bromet, N.; Salvadori, C.; Kamoun, A. *Drug Metab. Dispos.* 1990, 18, 804-808.
Hsu, D. T. et al. *Mol. Psychiatry* 2013, 18, 1211-1217.
Hsu, D. T. et al. *Mol. Psychiatry* 2015, 20, 193-200.
Jutkiewicz, E. M. *Mol. Interv.* 2006, 6, 162-169.
Kramer, M. S. et al. *Neuropsychopharmacology* 2004, 29, 385-392.
Mao, J.; Price, D. D.; Caruso, F. S.; Mayer, D. J. *Pain* 1996, 67, 361-368.
Marks, D. M. et al. *Curr. Neuropharmacol.* 2009, 7, 331-336.
McNeill, E.; Barder, T. E.; Buchwald, S. L. *Org. Lett.* 2007, 99, 3785-3788.
Miller, P. W. et al. *Angew. Chem., Int. Ed.* 2008, 47, 8998-9033.
Moskal, J. R.; et al. *Neuropharmacology* 2005, 49, 1077-1087.
Murrough, J. W. et al. *Am. J. Psychiatry* 2013, 170, 1134-1142.
Negri, A.; Rives, M.-L.; Caspers, M. J.; Prisinzano, T. E.; Javitch, J. A.; Filizola, M. *J. Chem. Inf. Model.* 2013, 53 (3), 521-526.
Overstreet, D. H.; Naimoli, V. M.; Griebel, G. *Pharmacol. Biochem. Behav.* 2010, 96, 206-210.
Peppin, J. F.; Raffa, R. B. *J. Clin. Pharm. Ther.* 2015, 40, 155-166.
Rives, M.-L.; Rossillo, M.; Liu-Chen, L.-Y.; Javitch, J. A. *J. Biol. Chem.* 2012, 287 (32), 27050-27054.
Robinson, J. E.; Fish, E. W.; Krouse, M. C.; Thorsell, A.; Heilig, M.; Malanga, C. J. *Psychopharmacology* 2012, 220, 215-224.
Panocka, I.; Massi, M.; Lapo, I.; Swiderski, T.; Kowalczyk M.; Sadowski, B. *Peptides* 2001, 22, 1037-1042.
Paul, I. A.; Skolnick, P. *Ann. N. Y. Acad. Sci.* 2003, 1003, 250-272.
Prossin, A. R.; Love, T. M.; Koeppe, R. A.; Zubieta, J-K.; Silk, K. R. *Am. J. Psychiatry* 2010, 167, 925-933.
Saitoh, A. et al. *J. Pharmacol. Sci.* 2004, 95, 374-380.
Salomé, N. et al. *Pharmacol. Biochem. Behav.* 2006, 83, 533-539.

Sansone, R. A. et al. *Int. J. Psychiatry Med.* 2008, 38, 217-226.
Smith, K.; Hopp, M.; Mundin, G.; Bond, S.; Bailey, P.; Woodward, J.; Bell, D. *Int. J. Clin. Pharmacol. Ther.* 2012, 50, 360-367.
Su, Y. F.; McNutt, R. W.; Chang, K. J. *J. Pharmacol. Exp. Ther.* 1998, 287, 815-823.
Svoboda, K. R. et al. *J. Neurosci.* 1999, 19, 85-95.
Thase, M. E. *Psychopharmacol. Bull.* 2008, 41, 58-85.
Torregrossa, M. M. et al. *Psychopharmacology* (Berl). 2005, 183, 31-40.
Trujillo, K. A.; Akil, H. *Brain Res.* 1994, 633, 178-188.
Vanderah, T. W. *Clin. J. Pain.* 2010, 26 Suppl, S10-15.
Vaswani, M. et al. *Prog. Neuropsychopharmacol. Biol. Psychiatry* 2003, 27, 85-102.
Vincent, J. et al. *J. Am. Chem. Soc.* 1987, 109, 5703-5711
Williams, J. T. et al. *Pharmacol. Rev.* 2013, 65, 223-254.
Xie, C. W., Lewis D. V. *J. Neurophysiol.* 1997, 78: 759-766.
Zarate, C. A. Jr et al. *Arch. Gen. Psychiatry* 2006, 63, 856-864.

What is claimed is:

1. A compound having the structure:

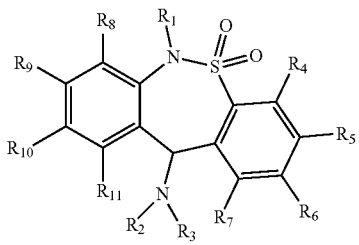

wherein
$R_1$ is —H or -(alkyl);
$R_2$ is —($C_3$-$C_{20}$ alkyl)-$CO_2$H or —($C_3$-$C_{20}$ alkyl)-$CO_2$-(alkyl);
$R_3$ is —H or -(alkyl);
$R_4$, $R_5$, $R_6$ and $R_7$ are each independently —H, —Cl, —Br, —F, —I, —CN, —$CF_3$, —$OCF_3$, -(alkyl), -(alkenyl), -(alkynyl), -(aryl), —$NH_2$, —NH-(alkyl), —NH-(alkenyl), —NH-(alkynyl) —NH-(aryl), —NH-(heteroaryl), —OH, —OAc, —O—C(O) (alkyl), —O-(alkyl), —O-(alkylaryl), —O-(alkenyl), —O-(alkynyl), —O-(aryl), —O-(heteroaryl), —S-(alkyl), —S-(alkenyl), —S-(alkynyl), —S-(aryl), —S-(heteroaryl), —S(O)-(alkyl), —S(O)-(aryl), —S(O)-(heteroaryl), —$SO_2$-(alkyl), —$SO_2$-(aryl), or —$SO_2$-(heteroaryl);
$R_8$, $R_9$, —$R_{10}$ and —$R_{11}$ are each independently —H, —Cl, —Br, —F, —I, —CN, —$CF_3$, —$OCF_3$, -(alkyl), -(aryl), -(heteroaryl) -(alkenyl), -(alkynyl), —$NH_2$, —NH-(alkyl), —NH-(alkenyl), —NH-(alkynyl) —NH-(aryl), —NH-(heteroaryl), —OH, —OAc, —O—C(O)(alkyl), —O-(alkyl), —O-(alkenyl), —O-(alkynyl), —O-(aryl), —O-(heteroaryl), —S-(alkyl), —S-(alkenyl), —S-(alkynyl), —S-(aryl), —S-(heteroaryl), —S(O)-(alkyl), —S(O)-(aryl), —S(O)-(heteroaryl), —$SO_2$-(alkyl), —$SO_2$-(aryl), or —$SO_2$-(heteroaryl);
wherein when $R_2$ is —($C_{3-6}$ alkyl)-$CO_2$H, then one of $R_5$ or $R_6$ is -(alkynyl) or —S-(alkyl), or $R_5$ and $R_6$ are each independently —Cl, —Br, —F, or —I,
wherein when $R_2$ is —($C_{3-6}$ alkyl)-$CO_2$-(alkyl), then one of $R_5$ or $R_6$ is -(alkynyl), or $R_5$ and $R_6$ are each independently —Cl, —Br, —F, or —I, and
wherein when $R_1$ is —$CH_3$, $R_3$, $R_4$, $R_6$, $R_7$, $R_8$, $R_9$, —$R_{10}$ and —$R_{11}$ are each —H, and $R_5$ is Cl, then $R_2$ is other than —($CH_2$)$_7CO_2$H, —($CH_2$)$_{10}CO_2$H, —CH($CH_3$)($CH_2$)$_5CO_2$H or —($CH_2$)$_2CH(CH_3$)($CH_2$)$_3CO_2$H, and
wherein when $R_1$ is —$CH_3$, $R_3$, $R_4$, $R_6$, $R_7$, $R_8$, $R_9$, —$R_{10}$ and —$R_{11}$ are each —H, and $R_5$ is $SCH_3$, then $R_2$ is other than —($CH_2$)$_6CO_2$H, or a pharmaceutically acceptable salt or ester thereof.

2. The compound of claim 1 having the structure:

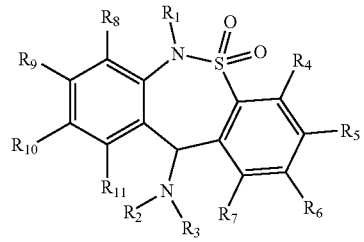

wherein
$R_1$ is —H or -(alkyl);
$R_2$ is —($C_6$-$C_{20}$ alkyl)-$CO_2$H or —($C_6$-$C_{20}$ alkyl)-$CO_2$-(alkyl);
$R_3$ is —H or -(alkyl);
$R_4$, $R_5$, $R_6$ and $R_7$ are each independently —H, —Cl, —Br, —F, —I, —CN, —$CF_3$, —$OCF_3$, -(alkyl), -(alkenyl), -(alkynyl), -(aryl), —$NH_2$, —NH-(alkyl), —NH-(alkenyl), —NH-(alkynyl) —NH-(aryl), —NH-(heteroaryl), —OH, —OAc, —O—C(O) (alkyl), —O-(alkyl), —O-(alkylaryl), —O-(alkenyl), —O-(alkynyl), —O-(aryl), —O-(heteroaryl), —S-(alkyl), —S-(alkenyl), —S-(alkynyl), —S-(aryl), —S-(heteroaryl), —S(O)-(alkyl), —S(O)-(aryl), —S(O)-(heteroaryl), —$SO_2$-(alkyl), —$SO_2$-(aryl), or —$SO_2$-(heteroaryl);
$R_8$, $R_9$, —$R_{10}$ and —$R_{11}$ are each independently —H, —Cl, —Br, —F, —I, —CN, —$CF_3$, —$OCF_3$, -(alkyl), -(aryl), -(heteroaryl) -(alkenyl), -(alkynyl), —$NH_2$, —NH-(alkyl), —NH-(alkenyl), —NH-(alkynyl) —NH-(aryl), —NH-(heteroaryl), —OH, —OAc, —O—C(O)(alkyl), —O-(alkyl), —O-(alkenyl), —O-(alkynyl), —O-(aryl), —O-(heteroaryl), —S-(alkyl), —S-(alkenyl), —S-(alkynyl), —S-(aryl), —S-(heteroaryl), —S(O)-(alkyl), —S(O)-(aryl), —S(O)-(heteroaryl), —$SO_2$-(alkyl), —$SO_2$-(aryl), or —$SO_2$-(heteroaryl);
wherein when $R_2$ is —($C_6$ alkyl)-$CO_2$H, then one of $R_5$ or $R_6$ is -(alkynyl) or —S-(alkyl), or $R_5$ and $R_6$ are each independently —Cl, —Br, —F, or —I,
wherein when $R_2$ is —($C_6$ alkyl)-$CO_2$-(alkyl), then one of $R_5$ or $R_6$ is -(alkynyl), or $R_5$ and $R_6$ are each independently —Cl, —Br, —F, or —I, and
wherein when $R_1$ is —$CH_3$, $R_3$, $R_4$, $R_6$, $R_7$, $R_8$, $R_9$, —$R_{10}$ and —$R_{11}$ are each —H, and $R_5$ is Cl, then $R_2$ is other than —($CH_2$)$_7CO_2$H, —($CH_2$)$_{10}CO_2$H, —CH($CH_3$)($CH_2$)$_5CO_2$H or —($CH_2$)$_2CH(CH_3$)($CH_2$)$_3CO_2$H, and
wherein when $R_1$ is —$CH_3$, $R_3$, $R_4$, $R_6$, $R_7$, $R_8$, $R_9$, —$R_{10}$ and —$R_{11}$ are each —H, and $R_5$ is $SCH_3$, then $R_2$ is other than —($CH_2$)$_6CO_2$H, or a pharmaceutically acceptable salt or ester thereof.

3. The compound of claim 2 having the structure:

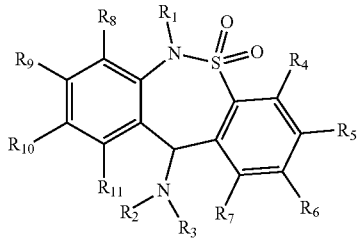

wherein $R_1$ is —H or -(alkyl);

$R_2$ is —($C_7$-$C_{20}$ alkyl)-$CO_2$H or —($C_2$-$C_{20}$ alkyl)-$CO_2$-(alkyl);

$R_3$ is —H or -(alkyl);

$R_4$, $R_5$, $R_6$ and $R_7$ are each independently —H, —Cl, —Br, —F, —I, —CN, —$CF_3$, —$OCF_3$, -(alkyl), -(alkenyl), -(alkynyl), -(aryl), —$NH_2$, —NH-(alkyl), —NH-(alkenyl), —NH-(alkynyl) —NH-(aryl), —NH-(heteroaryl), —OH, —OAc, —O—C(O) (alkyl), —O-(alkyl), —O-(alkylaryl), —O-(alkenyl), —O-(alkynyl), —O-(aryl), —O-(heteroaryl), —S-(alkyl), —S-(alkenyl), —S-(alkynyl), —S-(aryl), —S-(heteroaryl), —S(O)-(alkyl), —S(O)-(aryl), —S(O)-(heteroaryl), —$SO_2$-(alkyl), —$SO_2$-(aryl), or —$SO_2$-(heteroaryl);

$R_8$, $R_9$, —$R_{10}$ and —$R_{11}$ are each independently —H, —Cl, —Br, —F, —I, —CN, —$CF_3$, —$OCF_3$, -(alkyl), -(aryl), -(heteroaryl) -(alkenyl), -(alkynyl), —$NH_2$, —NH-(alkyl), —NH-(alkenyl), —NH-(alkynyl) —NH-(aryl), —NH-(heteroaryl), —OH, —OAc, —O—C(O)(alkyl), —O-(alkyl), —O-(alkenyl), —O-(alkynyl), —O-(aryl), —O-(heteroaryl), —S-(alkyl), —S-(alkenyl), —S-(alkynyl), —S-(aryl), —S-(heteroaryl), —S(O)-(alkyl), —S(O)-(aryl), —S(O)-(heteroaryl), —$SO_2$-(alkyl), —$SO_2$-(aryl), or —$SO_2$-(heteroaryl);

wherein when $R_1$ is —$CH_3$, $R_3$, $R_4$, $R_6$, $R_2$, $R_8$, $R_9$, —$R_{10}$ and —$R_{11}$ are each —H, and $R_5$ is Cl, then $R_2$ is other than —$(CH_2)_2CO_2H$, —$(CH_2)_{10}CO_2H$, —$CH(CH_3)(CH_2)_5CO_2H$ or —$(CH_2)_2CH(CH_3)(CH_2)_3CO_2H$, or a pharmaceutically acceptable salt or ester thereof.

4. The compound of claim 3, wherein $R_2$ is —($C_8$-$C_{20}$ alkyl)-$CO_2$H or —($C_8$-$C_{20}$ alkyl)-$CO_2$-(alkyl); or $R_2$ is —($C_9$-$C_{20}$ alkyl)-$CO_2$H or —($C_9$-$C_{20}$ alkyl)-$CO_2$-(alkyl); or $R_2$ is —($C_8$-$C_{20}$ alkyl)-$CO_2$H or —($C_8$-$C_{20}$ alkyl)-$CO_2CH_3$; or $R_2$ is —($C_9$-$C_{20}$ alkyl)-$CO_2$H or —($C_9$-$C_{20}$ alkyl)-$CO_2CH_2CH_3$.

5. The compound of claim 3, wherein $R_5$ is —Br, —I, -(alkenyl), -(alkynyl) or —S-(alkyl); or one of $R_5$ or $R_6$ is -(alkynyl); or one of $R_5$ or $R_6$ is —S-(alkyl); or $R_5$ and $R_6$ are each independently —Cl, —Br, —F, or —I.

6. The compound of claim 3 having the structure

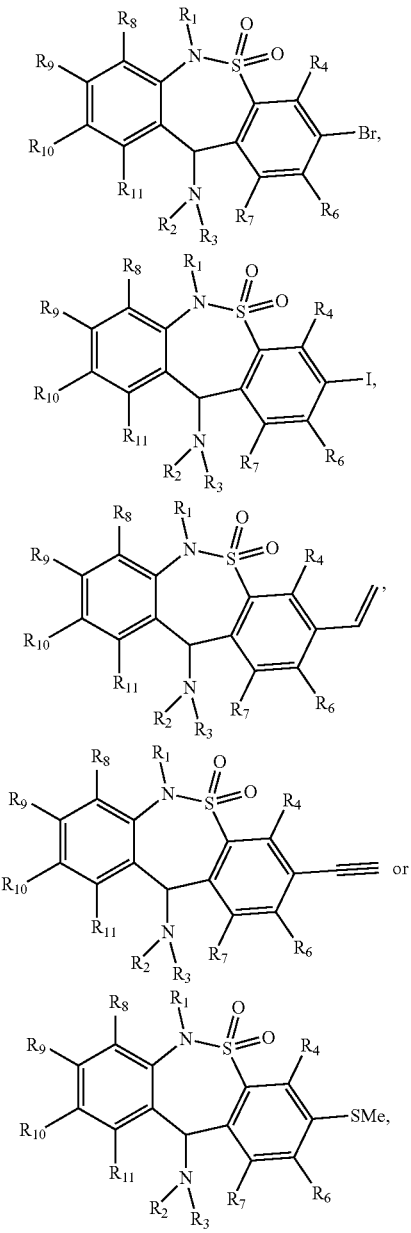

wherein $R_1$ is —H or -(alkyl);

$R_2$ is —($C_7$-$C_{20}$ alkyl)-$CO_2$H or —($C_7$-$C_{20}$ alkyl)-$CO_2$-(alkyl);

$R_3$ is —H or -(alkyl);

$R_4$, $R_6$ and $R_7$ are each independently —H, —Cl, —Br, —F, —I, —CN, —$CF_2$, —$OCF_3$, -(alkyl), -(alkenyl), -(alkynyl), -(aryl), —$NH_2$, —NH-(alkyl), —NH-(alkenyl), —NH-(alkynyl) —NH-(aryl), —NH-(heteroaryl), —OH, —OAc, —O—C(O)(alkyl), —O-(alkyl), —O-(alkylaryl), —O-(alkenyl), —O-(alkynyl), —O-(aryl), —O-(heteroaryl), —S-(alkyl), —S-(alkenyl), —S-(alkynyl), —S-(aryl), —S-(heteroaryl), —S(O)-(alkyl), —S(O)-(aryl), —S(O)-(heteroaryl), —$SO_2$-(alkyl), —$SO_2$-(aryl), or —$SO_2$-(heteroaryl);

$R_8$, $R_9$, —$R_{10}$ and —$R_{11}$ are each independently —H, —Cl, —Br, —F, —I, —CN, —$CF_3$, —$OCF_3$, -(alkyl), -(aryl), -(heteroaryl) -(alkenyl), -(alkynyl), —NH₂, —NH-(alkyl), —NH-(alkenyl), —NH-(alkynyl) —NH-(aryl), —NH-(heteroaryl), —OH, —OAc, —O—C(O)(alkyl), —O-(alkyl), —O-(alkenyl), —O-(alkynyl), —O-(aryl), —O-(heteroaryl), —S-(alkyl), —S-(alkenyl), —S-(alkynyl), —S-(aryl), —S-(heteroaryl), —S(O)-(alkyl), —S(O)-(aryl), —S(O)-(heteroaryl), —SO₂-(alkyl), —SO₂-(aryl), or —SO₂-(heteroaryl); or

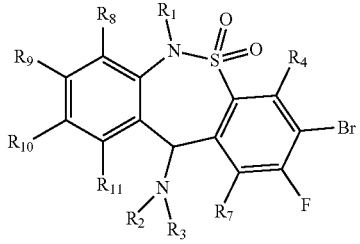

wherein $R_1$ is —H or -(alkyl);

$R_2$ is —($C_7$-$C_{20}$ alkyl)-$CO_2$H or —($C_2$-$C_{20}$ alkyl)-$CO_2$-(alkyl);

$R_3$ is —H or -(alkyl);

$R_4$ and $R_7$ are each independently —H, —Cl, —Br, —F, —I, —CN, —CF₃, —OCF₃, -(alkyl), -(alkenyl), -(alkynyl), -(aryl), —NH₂, —NH-(alkyl), —NH-(alkenyl), —NH-(alkynyl) —NH-(aryl), —NH-(heteroaryl), —OH, —OAc, —O—C(O) (alkyl), —O-(alkyl), —O-(alkylaryl), —O-(alkenyl), —O-(alkynyl), —O-(aryl), —O-(heteroaryl), —S-(alkyl), —S-(alkenyl), —S-(alkynyl), —S-(aryl), —S-(heteroaryl), —S(O)-(alkyl), —S(O)-(aryl), —S(O)-(heteroaryl), —SO₂-(alkyl), —SO₂-(aryl), or —SO₂-(heteroaryl);

$R_8$, $R_9$, $R_{10}$ and $R_{11}$ are each independently —H, —Cl, —Br, —F, —I, —CN, —CF₃, —OCF₃, -(alkyl), -(aryl), -(heteroaryl) -(alkenyl), -(alkynyl), —NH₂, —NH-(alkyl), —NH-(alkenyl), —NH-(alkynyl) —NH-(aryl), —NH-(heteroaryl), —OH, —OAc, —O—C(O)(alkyl), —O-(alkyl), —O-(alkenyl), —O-(alkynyl), —O-(aryl), —O-(heteroaryl), —S-(alkyl), —S-(alkenyl), —S-(alkynyl), —S-(aryl), —S-(heteroaryl), —S(O)-(alkyl), —S(O)-(aryl), —S(O)-(heteroaryl), —SO₂-(alkyl), —SO₂-(aryl), or —SO₂-(heteroaryl); or

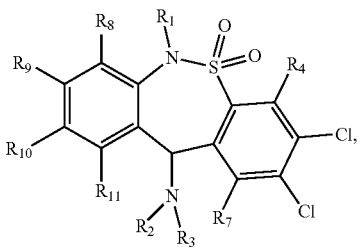

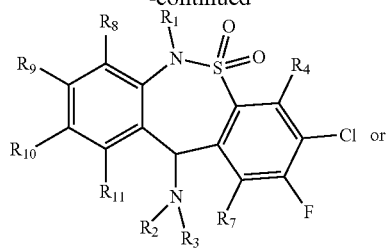

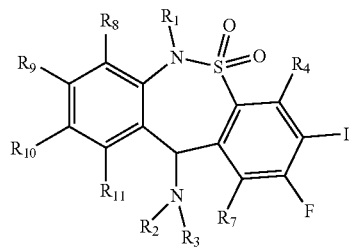

wherein $R_1$ is —H or -(alkyl);

$R_2$ is —($C_7$-$C_{20}$ alkyl)-$CO_2$H or —($C_2$-$C_{20}$ alkyl)-$CO_2$-(alkyl);

$R_3$ is —H or -(alkyl);

$R_4$ and $R_7$ are each independently —H, —Cl, —Br, —F, —I, —CN, —CF₃, —OCF₃, -(alkyl), -(alkenyl), -(alkynyl), -(aryl), —NH₂, —NH-(alkyl), —NH-(alkenyl), —NH-(alkynyl) —NH-(aryl), —NH-(heteroaryl), —OH, —OAc, —O—C(O) (alkyl), —O-(alkyl), —O-(alkylaryl), —O-(alkenyl), —O-(alkynyl), —O-(aryl), —O-(heteroaryl), —S-(alkyl), —S-(alkenyl), —S-(alkynyl), —S-(aryl), —S-(heteroaryl), —S(O)-(alkyl), —S(O)-(aryl), —S(O)-(heteroaryl), —SO₂-(alkyl), —SO₂-(aryl), or —SO₂-(heteroaryl);

$R_8$, $R_9$, $R_{10}$ and $R_{11}$ are each independently —H, —Cl, —Br, —F, —I, —CN, —CF₃, —OCF₃, -(alkyl), -(aryl), -(heteroaryl) -(alkenyl), -(alkynyl), —NH₂, —NH-(alkyl), —NH-(alkenyl), —NH-(alkynyl) —NH-(aryl), —NH-(heteroaryl), —OH, —OAc, —O—C(O)(alkyl), —O-(alkyl), —O-(alkenyl), —O-(alkynyl), —O-(aryl), —O-(heteroaryl), —S-(alkyl), —S-(alkenyl), —S-(alkynyl), —S-(aryl), —S-(heteroaryl), —S(O)-(alkyl), —S(O)-(aryl), —S(O)-(heteroaryl), —SO₂-(alkyl), —SO₂-(aryl), or —SO₂-(heteroaryl), or a pharmaceutically acceptable salt or ester thereof.

7. The compound of claim 3 having the structure
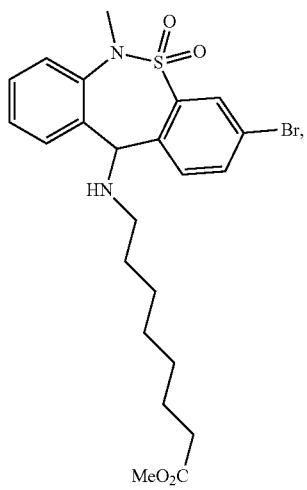
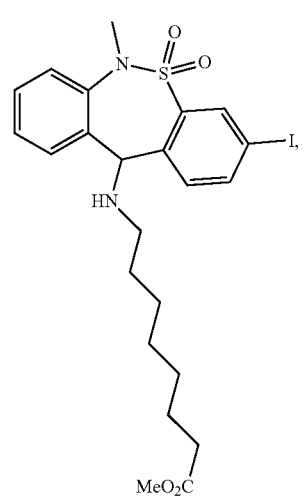
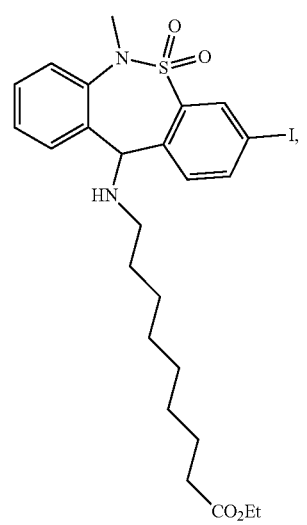
-continued
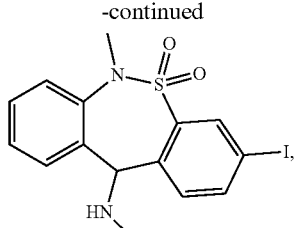
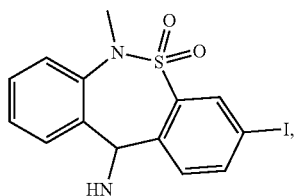
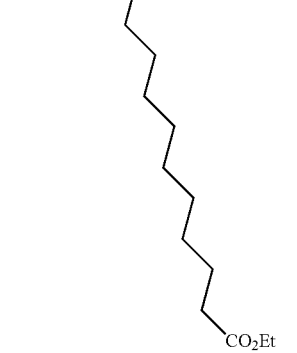
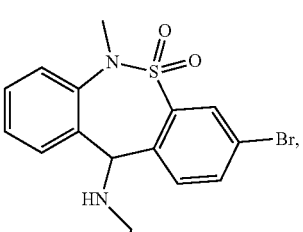

173
-continued
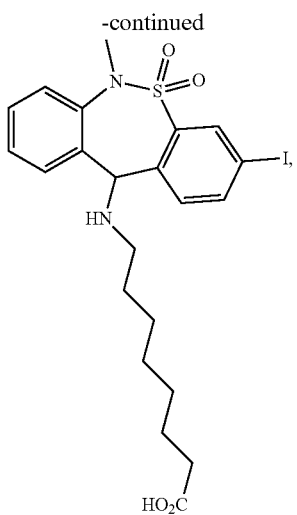
174
-continued
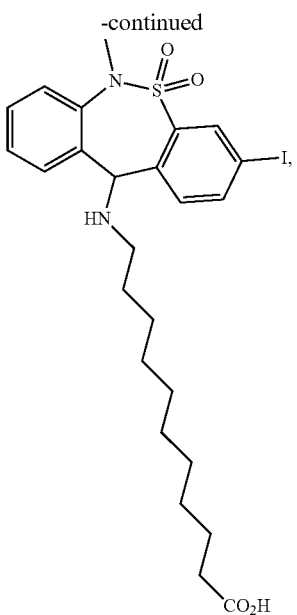
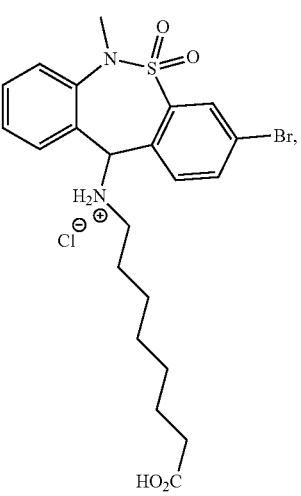
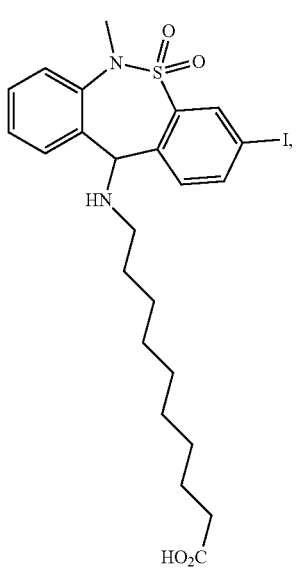
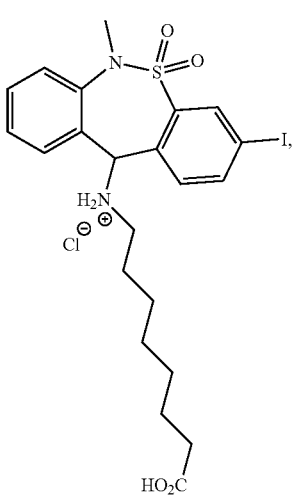

-continued

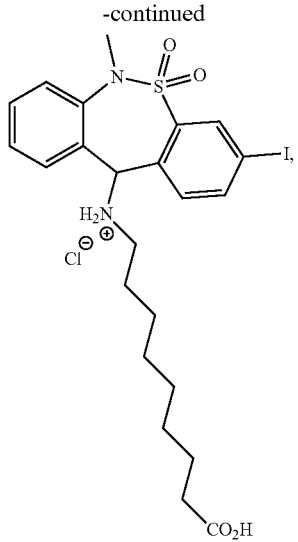
I,

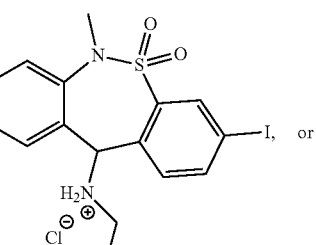
I, or

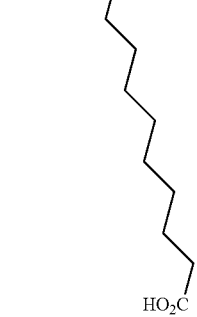
I,

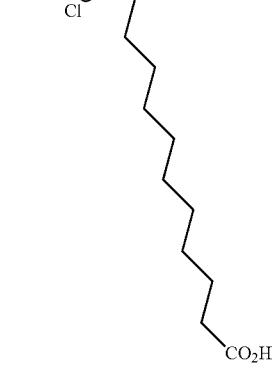

or a pharmaceutically acceptable salt or ester thereof.

8. The compound of claim 2 having the structure:

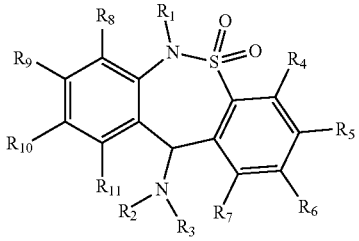

wherein
$R_1$ is —H or -(alkyl);
$R_2$ is —($C_6$ alkyl)-$CO_2H$;
$R_3$ is —H or -(alkyl);
$R_4$, $R_5$, $R_6$ and $R_7$ are each independently —H, —Cl, —Br, —F, —I, —CN, —$CF_3$, —$OCF_3$, -(alkyl), -(alkenyl), -(alkynyl), -(aryl), —$NH_2$, —NH-(alkyl), —NH-(alkenyl), —NH-(alkynyl) —NH-(aryl), —NH-(heteroaryl), —OH, —OAc, —O—C(O) (alkyl), —O-(alkyl), —O-(alkylaryl), —O-(alkenyl), —O-(alkynyl), —O-(aryl), —O-(heteroaryl), —S-(alkyl), —S-(alkenyl), —S-(alkynyl), —S-(aryl), —S-(heteroaryl), —S(O)-(alkyl), —S(O)-(aryl), —S(O)-(heteroaryl), —$SO_2$-(alkyl), —$SO_2$-(aryl), or —$SO_2$-(heteroaryl);
$R_8$, $R_9$, —$R_{10}$ and —$R_{11}$ are each independently —H, —Cl, —Br, —F, —I, —CN, —$CF_3$, —$OCF_3$, -(alkyl), -(aryl), -(heteroaryl) -(alkenyl), -(alkynyl), —$NH_2$, —NH-(alkyl), —NH-(alkenyl), —NH-(alkynyl) —NH-(aryl), —NH-(heteroaryl), —OH, —OAc, —O—C(O)(alkyl), —O-(alkyl), —O-(alkenyl), —O-(alkynyl), —O-(aryl), —O-(heteroaryl), —S-(alkyl), —S-(alkenyl), —S-(alkynyl), —S-(aryl), —S-(heteroaryl), —S(O)-(alkyl), —S(O)-(aryl), —S(O)-(heteroaryl), —$SO_2$-(alkyl), —$SO_2$-(aryl), or —$SO_2$-(heteroaryl);
wherein one of $R_5$ or $R_6$ is -(alkynyl) or —S-(alkyl), or $R_5$ and $R_6$ are each independently —Cl, —Br, —F, or —I, and
wherein when $R_1$ is —$CH_3$, $R_3$, $R_4$, $R_6$, $R_2$, $R_8$, $R_9$, —$R_{10}$ and $R_{11}$ are each —H, and $R_5$ is $SCH_3$, then $R_2$ is other than —$(CH_2)_6CO_2H$,
or a pharmaceutically acceptable salt or ester thereof.

9. The compound of claim 8 having the structure

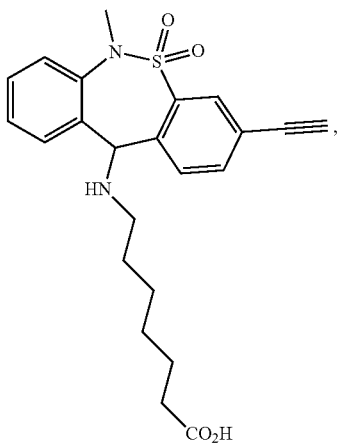

177
-continued
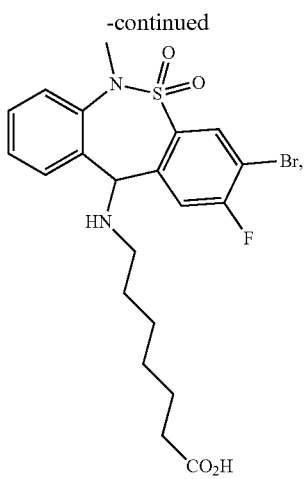
178
-continued
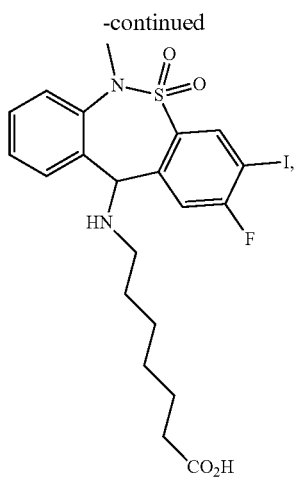
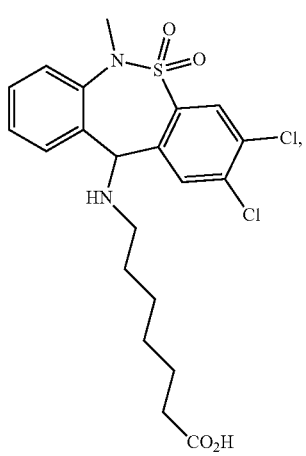
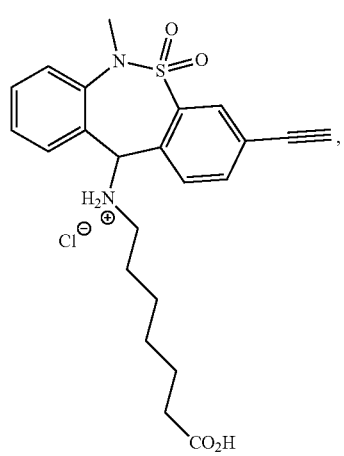
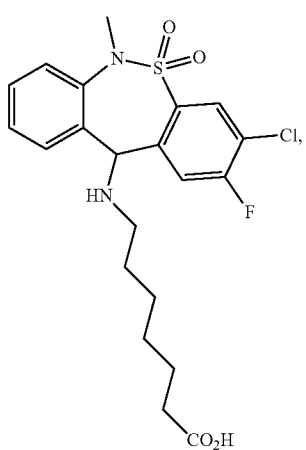
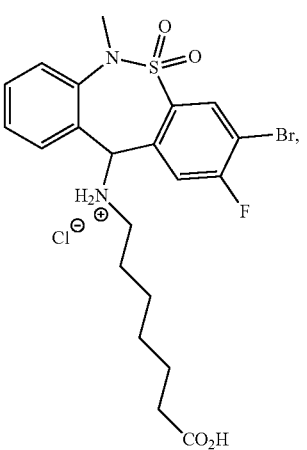

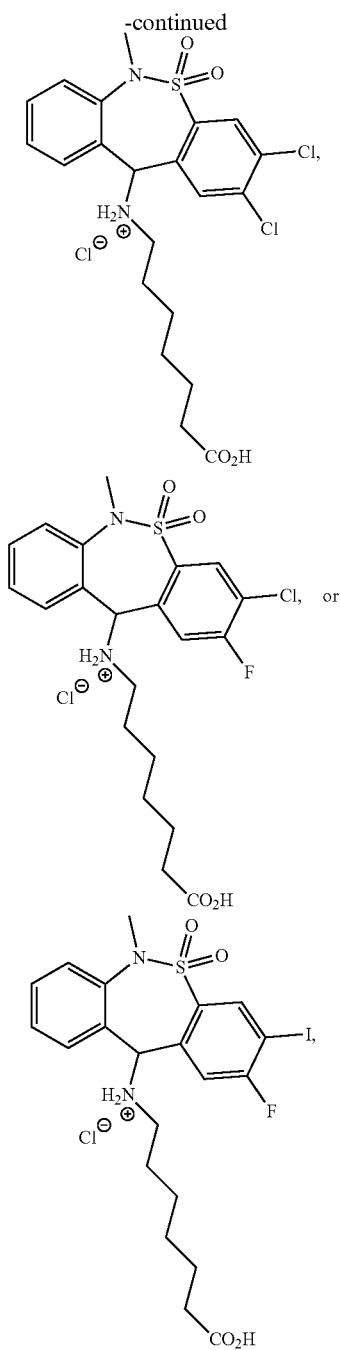

or a pharmaceutically acceptable salt or ester thereof.
10. The compound of claim 2 having the structure:

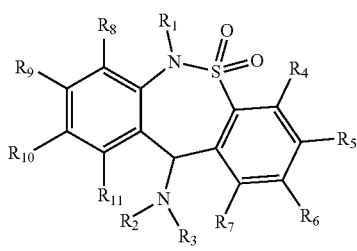

wherein
R₁ is —H or -(alkyl);
R₂ is —(C₆ alkyl)-CO₂-(alkyl);
R₃ is —H or -(alkyl);
R₄, R₅, R₆ and R₇ are each independently —H, —Cl, —Br, —F, —I, —CN, —CF₃, —OCF₃, -(alkyl), -(alkenyl), -(alkynyl), -(aryl), —NH₂, —NH-(alkyl), —NH-(alkenyl), —NH-(alkynyl) —NH-(aryl), —NH-(heteroaryl), —OH, —OAc, —O—C(O)(alkyl), —O-(alkyl), —O-(alkylaryl), —O-(alkenyl), —O-(alkynyl), —O-(aryl), —O-(heteroaryl), —S-(alkyl), —S-(alkenyl), —S-(alkynyl), —S-(aryl), —S-(heteroaryl), —S(O)-(alkyl), —S(O)-(aryl), —S(O)-(heteroaryl), —SO₂-(alkyl), —SO₂-(aryl), or —SO₂-(heteroaryl);

R₈, R₉, R₁₀ and R₁₁ are each independently —H, —Cl, —Br, —F, —I, —CN, —CF₃, —OCF₃, -(alkyl), -(aryl), -(heteroaryl) -(alkenyl), -(alkynyl), —NH₂, —NH-(alkyl), —NH-(alkenyl), —NH-(alkynyl) —NH-(aryl), —NH-(heteroaryl), —OH, —OAc, —O—C(O)(alkyl), —O-(alkyl), —O-(alkenyl), —O-(alkynyl), —O-(aryl), —O-(heteroaryl), —S-(alkyl), —S-(alkenyl), —S-(alkynyl), —S-(aryl), —S-(heteroaryl), —S(O)-(alkyl), —S(O)-(aryl), —S(O)-(heteroaryl), —SO₂-(alkyl), —SO₂-(aryl), or —SO₂-(heteroaryl);

wherein one of R₅ or R₆ is -(alkynyl), or R₅ and R₆ are each independently —Cl, —Br, —F, or —I, and
or a pharmaceutically acceptable salt or ester thereof.

11. The compound of claim 10 having the structure

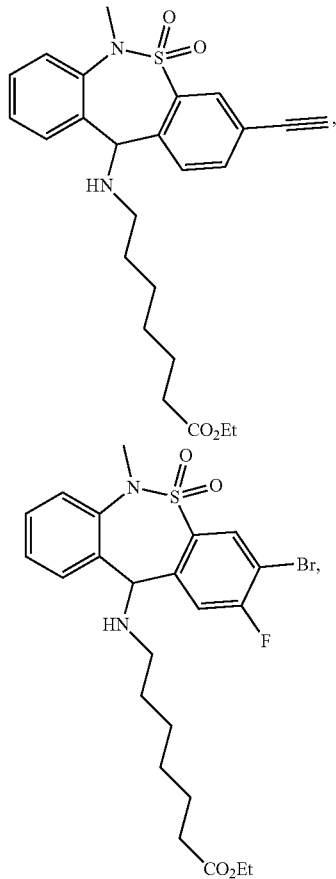

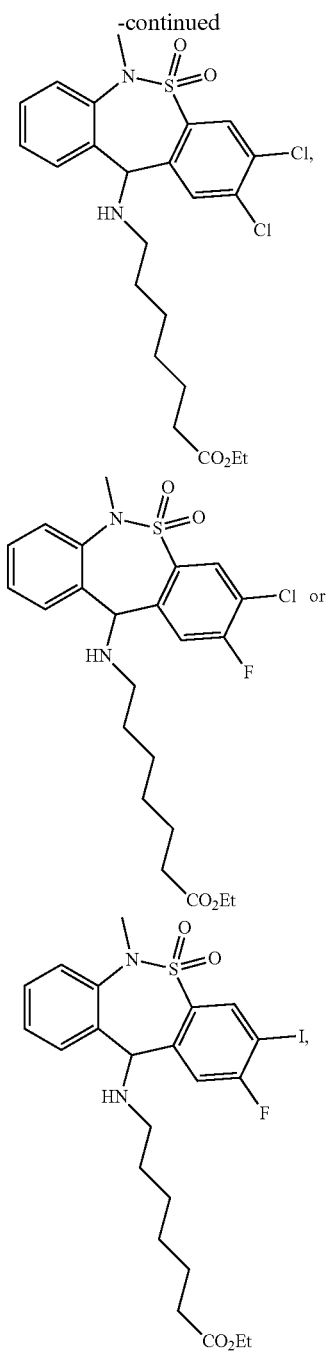

or a pharmaceutically acceptable salt thereof.

12. The compound of claim 1 having the structure:

wherein
R$_1$ is —H or -(alkyl);
R$_2$ is —(C$_{3-5}$ alkyl)-CO$_2$H or —(C$_{2-8}$ alkyl)-CO$_2$(alkyl);
R$_3$ is —H or -(alkyl);
R$_4$, R$_5$, R$_6$ and R$_7$ are each independently —H, —Cl, —Br, —F, —I, —CN, —CF$_3$, —OCF$_3$, -(alkyl), -(alkenyl), -(alkynyl), -(aryl), —NH$_2$, —NH-(alkyl), —NH-(alkenyl), —NH-(alkynyl) —NH-(aryl), —NH-(heteroaryl), —OH, —OAc, —O—C(O) (alkyl), —O-(alkyl), —O-(alkylaryl), —O-(alkenyl), —O-(alkynyl), —O-(aryl), —O-(heteroaryl), —S-(alkyl), —S-(alkenyl), —S-(alkynyl), —S-(aryl), —S-(heteroaryl), —S(O)-(alkyl), —S(O)-(aryl), —S(O)-(heteroaryl), —SO$_2$-(alkyl), —SO$_2$-(aryl), or —SO$_2$-(heteroaryl);
R$_8$, R$_9$, R$_{10}$ and R$_{11}$ are each independently —H, —Cl, —Br, —F, —I, —CN, —CF$_3$, —OCF$_3$, -(alkyl), -(aryl), -(heteroaryl) -(alkenyl), -(alkynyl), —NH$_2$, —NH-(alkyl), —NH-(alkenyl), —NH-(alkynyl) —NH-(aryl), —NH-(heteroaryl), —OH, —OAc, —O—C(O)(alkyl), —O-(alkyl), —O-(alkenyl), —O-(alkynyl), —O-(aryl), —O-(heteroaryl), —S-(alkyl), —S-(alkenyl), —S-(alkynyl), —S-(aryl), —S-(heteroaryl), —S(O)-(alkyl), —S(O)-(aryl), —S(O)-(heteroaryl), —SO$_2$-(alkyl), —SO$_2$-(aryl), or —SO$_2$-(heteroaryl);
wherein R$_5$ and R$_6$ are each independently —Cl, —Br, —F, or —I,
or a pharmaceutically acceptable salt or ester thereof.

13. The compound of claim 12 having the structure

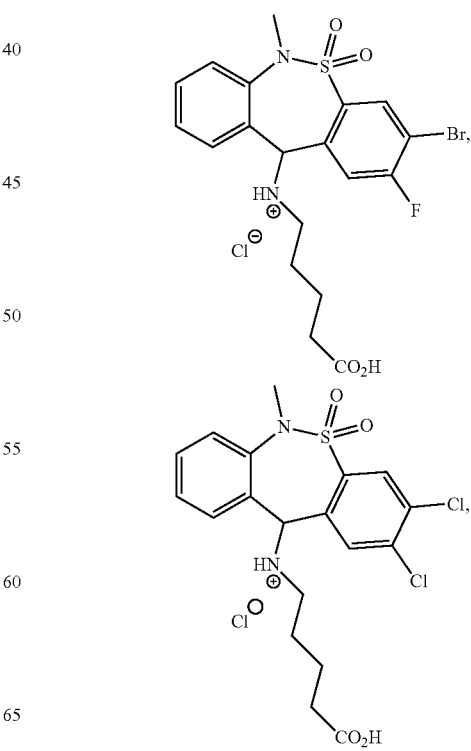

183
-continued
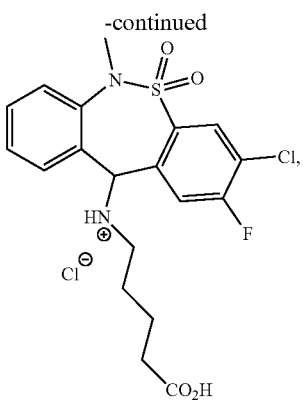
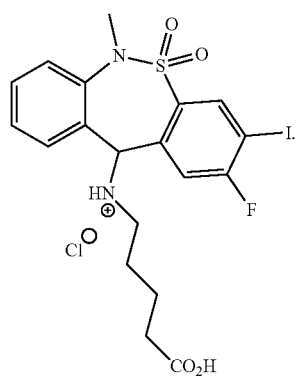
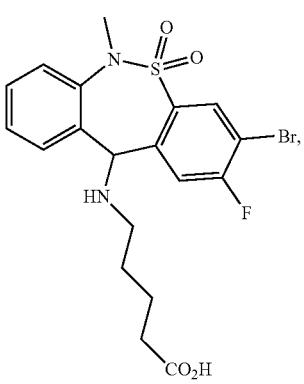
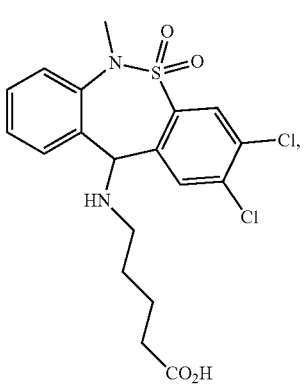
184
-continued
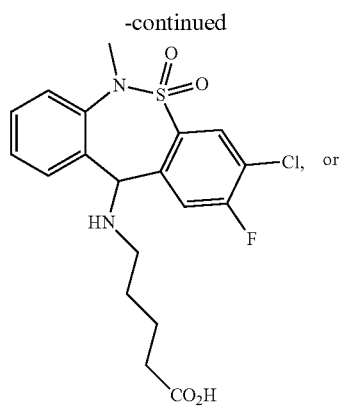
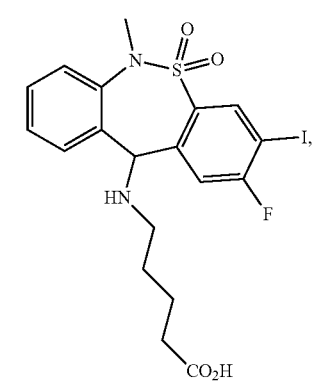
or a pharmaceutically acceptable salt or ester thereof; or
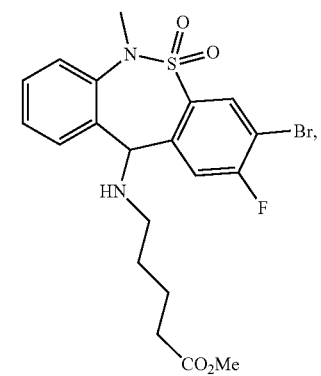
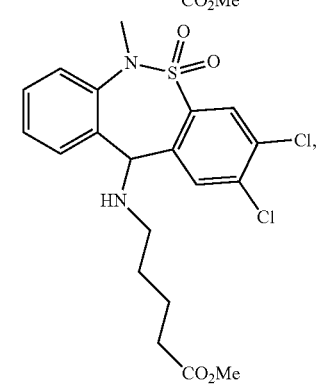

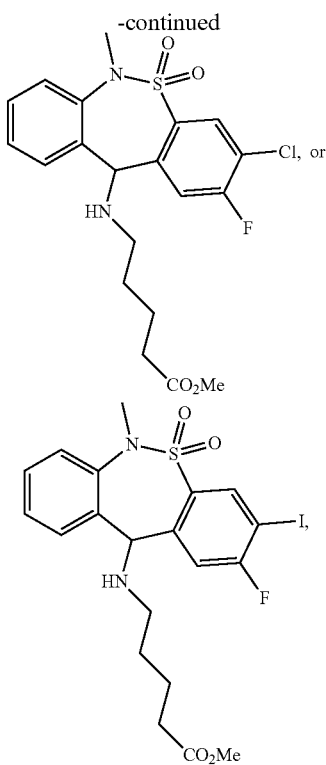

or a pharmaceutically acceptable salt thereof.

14. The compound of claim 1 wherein when an F is present, the F is $^{18}$F, or when an F is present at $R_6$, the F is $^{18}$F.

15. A pharmaceutical composition comprising the compound of claim 14 and a pharmaceutically acceptable carrier.

16. A method of detecting the presence of mu-opioid receptors in the brain of a subject which comprises determining if an amount of the compound of claim 14 is present in the brain of the subject at a period of time after administration of the compound or salt thereof to the subject, thereby detecting the presence of the mu-opioid receptors based on the amount of the compound determined to be present in the brain of the subject; or a method of detecting the location of mu-opioid receptors in the brain of a subject which comprises determining where an amount of the compound is present in the subject at a period of time after administration of the compound or salt thereof to the subject, thereby detecting the location of the mu-opioid receptors based on the location of the compound determined to be present in the subject; or a method of quantifying the occupancy of mu-opioid receptors by a compound binding to mu-opioid receptors in the brain of a subject, which comprises determining the binding competition between said compound and the compound at a period of time after administration of the compounds or salts thereof to the subject, thereby detecting the occupancy of the mu-opioid receptors based on the displacement of the compound binding to mu-opioid receptors in the brain of a subject; or a method of quantifying the occupancy of mu-opioid receptors by endogenous opioid peptides in the brain of a subject, which comprises determining the binding competition between said endogenous opioid peptides and the compound at a period of time after administration of the compound to the subject, thereby detecting the occupancy of the mu-opioid receptors based on the displacement of the compound by the endogenous opioid peptides.

17. A pharmaceutical composition comprising the compound of claim 1 and a pharmaceutically acceptable carrier; or a pharmaceutical composition comprising the compound and, an NMDA receptor antagonist, an NMDA receptor partial agonist, a neurokinin 1 receptor antagonist, a neurokinin 2 receptor antagonist, a neurokinin 3 receptor antagonist, a DOR agonist, naloxone, methylnaltrexone, a selective serotonin reuptake inhibitor or a serotonin-norepinephrine reuptake inhibitor, and a pharmaceutically acceptable carrier.

18. A method of activating a mu-opioid receptor or delta-opioid receptor comprising contacting the mu-opioid receptor or delta-opioid receptor with the compound of claim 1.

19. A method of treating a subject afflicted with a depressive disorder, a mood disorder, pain, an anxiety disorder, borderline personality disorder, opioid addiction or opioid withdrawal symptoms comprising administering an effective amount of the compound of claim 1 to the subject so as to treat the subject.

20. A method of treating a subject afflicted with, a depressive disorder or a mood disorder comprising administering to the subject an effective amount of an NMDA receptor antagonist, an NMDA receptor partial agonist, a neurokinin 1 receptor antagonist, a neurokinin 2 receptor antagonist, a neurokinin 3 receptor antagonist, or a DOR agonist, and an effective amount of the compound of claim 1 so as to thereby treat the subject afflicted with the depressive disorder or the mood disorder; or a method of treating a subject afflicted with pain, an anxiety disorder, or borderline personality disorder comprising administering to the subject an effective amount of an NMDA receptor antagonist, an NMDA receptor partial agonist, a neurokinin 1 receptor antagonist, or a DOR agonist, and an effective amount of the compound so as to thereby treat the subject afflicted with pain, the anxiety disorder, or borderline personality disorder; or a method of treating a subject afflicted with opioid addiction or opioid withdrawal symptoms comprising administering to the subject an effective amount of an NMDA receptor antagonist, an NMDA receptor partial agonist, or a neurokinin 1 receptor antagonist and an effective amount of the compound so as to thereby treat the subject afflicted with the opioid addiction or opioid withdrawal symptoms; or a method of treating a subject afflicted with opioid addiction or opioid withdrawal symptoms comprising administering to the subject an effective amount of naloxone or methylnaltrexone and an effective amount of the compound so as to thereby treat the subject afflicted with the opioid addiction or opioid withdrawal symptoms; or a method of treating a subject afflicted with pain, a depressive disorder, a mood disorder, an anxiety disorder, or borderline personality disorder, comprising administering to the subject an effective amount of naloxone or methylnaltrexone and an effective amount of the compound so as to thereby treat the subject afflicted with pain, the depressive disorder, the mood disorder, the anxiety disorder, or borderline personality disorder; or a method of treating of treating a subject afflicted with a depressive disorder, a mood disorder, an anxiety disorder, or borderline personality disorder, comprising administering to the subject an effective amount of a selective serotonin reuptake inhibitor or a serotonin-norepinephrine reuptake inhibitor and an effective amount of the compound so as to thereby treat the subject afflicted with the depressive disorder, mood disorder, anxiety disorder, or borderline personality disorder.

21. The pharmaceutical composition of claim 17, wherein the NMDA receptor antagonist is ibogaine or noribogaine.

22. The method of claim 20, wherein the NMDA receptor antagonist is ibogaine or noribogaine.

23. The compound of claim 8 having the structure

[Chemical structure with CO₂H group, I, F substituents]

or

[Chemical structure with H₂N⁺, Cl⁻, CO₂H, I, F substituents]

or a pharmaceutically acceptable salt or ester thereof; or

[Chemical structure with CO₂Et, I, F substituents]

or a pharmaceutically acceptable salt thereof.

* * * * *